United States Patent
Bhattacharya et al.

(10) Patent No.: US 11,649,289 B2
(45) Date of Patent: *May 16, 2023

(54) ANTI-ICOS AND ANTI-PD-1 ANTIBODY COMBINATION THERAPY

(71) Applicant: GlaxoSmithKline Intellectual Property Development Limited, Middlesex (GB)

(72) Inventors: Sabyasachi Bhattacharya, Collegeville, PA (US); Paul M. Bojczuk, Collegeville, PA (US); Heather L. Jackson, Collegeville, PA (US); Mili Mandal, Lawrenceville, NJ (US); Hong Shi, Collegeville, PA (US); Sapna Yadavilli, Collegeville, PA (US); Niranjan Yanamandra, Collegeville, PA (US)

(73) Assignee: GlaxoSmithKline Intellectual Property Development Limited, Middlesex (GB)

( * ) Notice: Subject to any disclaimer, the term of this patent is extended or adjusted under 35 U.S.C. 154(b) by 812 days.

This patent is subject to a terminal disclaimer.

(21) Appl. No.: 16/322,538

(22) PCT Filed: Aug. 3, 2017

(86) PCT No.: PCT/IB2017/054764
§ 371 (c)(1),
(2) Date: Feb. 1, 2019

(87) PCT Pub. No.: WO2018/025221
PCT Pub. Date: Feb. 8, 2018

(65) Prior Publication Data
US 2019/0256599 A1 Aug. 22, 2019

Related U.S. Application Data

(60) Provisional application No. 62/370,891, filed on Aug. 4, 2016, provisional application No. 62/400,344, filed on Sep. 27, 2016, provisional application No. 62/438,464, filed on Dec. 23, 2016, provisional application No. 62/479,558, filed on Mar. 31, 2017.

(51) Int. Cl.
*C07K 16/28* (2006.01)
*A61K 39/395* (2006.01)
*A61P 35/00* (2006.01)
*A61K 39/00* (2006.01)

(52) U.S. Cl.
CPC .......... *C07K 16/2818* (2013.01); *A61P 35/00* (2018.01); *A61K 2039/505* (2013.01); *A61K 2039/507* (2013.01); *A61K 2039/545* (2013.01); *C07K 2317/24* (2013.01); *C07K 2317/30* (2013.01); *C07K 2317/33* (2013.01); *C07K 2317/732* (2013.01); *C07K 2317/74* (2013.01); *C07K 2317/75* (2013.01); *C07K 2317/92* (2013.01)

(58) Field of Classification Search
None
See application file for complete search history.

(56) References Cited

U.S. PATENT DOCUMENTS

| | | | | |
|---|---|---|---|---|
| 6,632,927 | B2 * | 10/2003 | Adair ................... | C07K 16/18 424/133.1 |
| 7,595,048 | B2 * | 9/2009 | Honjo ................ | A61K 38/1774 424/142.1 |
| 9,738,718 | B2 * | 8/2017 | Liu ..................... | C07K 16/3069 |
| 9,771,424 | B2 * | 9/2017 | Liu ..................... | C07K 16/3015 |
| 11,130,811 | B2 * | 9/2021 | Liu ..................... | C07K 16/30 |
| 2015/0125463 | A1 * | 5/2015 | Cogswell ............. | A61P 35/04 424/142.1 |
| 2016/0215059 | A1 | 7/2016 | Liu et al. | |
| 2017/0174767 | A1 * | 6/2017 | Liu ..................... | C07K 16/2803 |
| 2020/0123257 | A1 * | 4/2020 | Liu ..................... | C07K 16/30 |
| 2020/0181275 | A1 * | 6/2020 | Hopson ............... | C07K 16/30 |
| 2020/0190194 | A1 * | 6/2020 | Bi ....................... | C07K 16/2818 |

FOREIGN PATENT DOCUMENTS

WO WO 2017/025871 A1 2/2017

OTHER PUBLICATIONS

Angevin et al. (2020) Journal of Clinical Oncology 38, No. 15_suppl (May 20, 2020) 6517-6517.*
Rudikoff et al. 1982, Proc. Natl. Acad. Sci. USA, , 79: 1979-1983.*
Panka et al., 1988, Proc. Natl. Acad. Sci. USA, 85: 3080-3084.*
Beiboer et al., J. Mol. Biol. (2000), 296: 833-849.*
Klimka et al., British Journal of Cancer (2000), 83: 252-260.*
Rader et al., Proc. Natl. Acad. Sci. USA (1998), 95: 8910-8915.*
Xu et al., Immunity (2000), 13: 37-45.*
Clinical Trials NCT02723955, 2016; https://clinicaltrials.gov/ct2/show/NCT02723955.
Harvey, et al., *Journal for ImmunoTherapy of Cancer*, 3(Suppl 2):09 (2015).
Brodsky, et al., "*CICON16: The Power of Combinations*," Internet Citation, XP009501318, 1-6 (2016), URL:https://www.cancerresearch.org/blog/september-2016/cicon16-the-power-of-combinations.

(Continued)

*Primary Examiner* — Ilia I Ouspenski
(74) *Attorney, Agent, or Firm* — Carly A. Shanahan; Nicole Ginanni

(57) ABSTRACT

The present invention provides methods for increasing expression of ICOS on an effector T cell comprising contacting said effector T cell with an anti-PD-1 antibody. The present invention also provides methods for decreasing expression of ICOS on a regulatory T cell comprising contacting said regulatory T cell with an anti-PD-1 antibody. The present invention provides methods for increasing sensitivity to an agent directed to ICOS in a human comprising administering to the human an anti-PD1 antibody. The present invention also provides methods of treating cancer in a human in need thereof comprising administering an anti-PD-1 antibody and an anti-ICOS antibody to said human, wherein the anti-PD-1 antibody increases T cell sensitivity to the ICOS antibody.

10 Claims, 103 Drawing Sheets

Specification includes a Sequence Listing.

(56) References Cited

OTHER PUBLICATIONS

Curran, et al., "PD-1 and CTLA-4 combination blockade expands infiltrating T cells and reduces regulatory T and myeloid cells within B16 melanoma tumors," *Proceedings of the Natl Academy of Sciences*, 107(9):4275-4280 (2010).

Liakou, et al., "CTLA-4 blockade increases IFN Gamma producing CD4(+)ICOS(HI) cells to shift the ratio of effector to regulatory T cells in cancer patients," *Proceedings Natl Academy Sciences PNAS*, 105(39):14987-14992 (2008).

Mayes, et al., "Abstract IA22: Targeting inducible T cell co-stimulator (ICOS) prootes effector T cell function and antitumor response," *Cancer Immunology Research*, 4(11):IA22-IA22, 2326-6066 (2016).

Roussey, et al., "Targeted Blockade of the Programmed Cell Death-1 Receptor Improves Fungal Clearance in a Murine Model of Persistent Cryptococcal Lung Infection," *Am. J. Respiratory and Critical Care Medicine*, Online: URL:http://www.atsjournals.org/doi/abs/10.1164/ajrccm-conference.2017.195.1_MeetingAbstracts.A5255_XP009501216, Jan. 1, 2017.

Yadavilli, et al., "ICOS agonist induces potent immune activation and anti-tumor response in non-clinical models," *Cancer Research*, XP009501353 (2017).

* cited by examiner

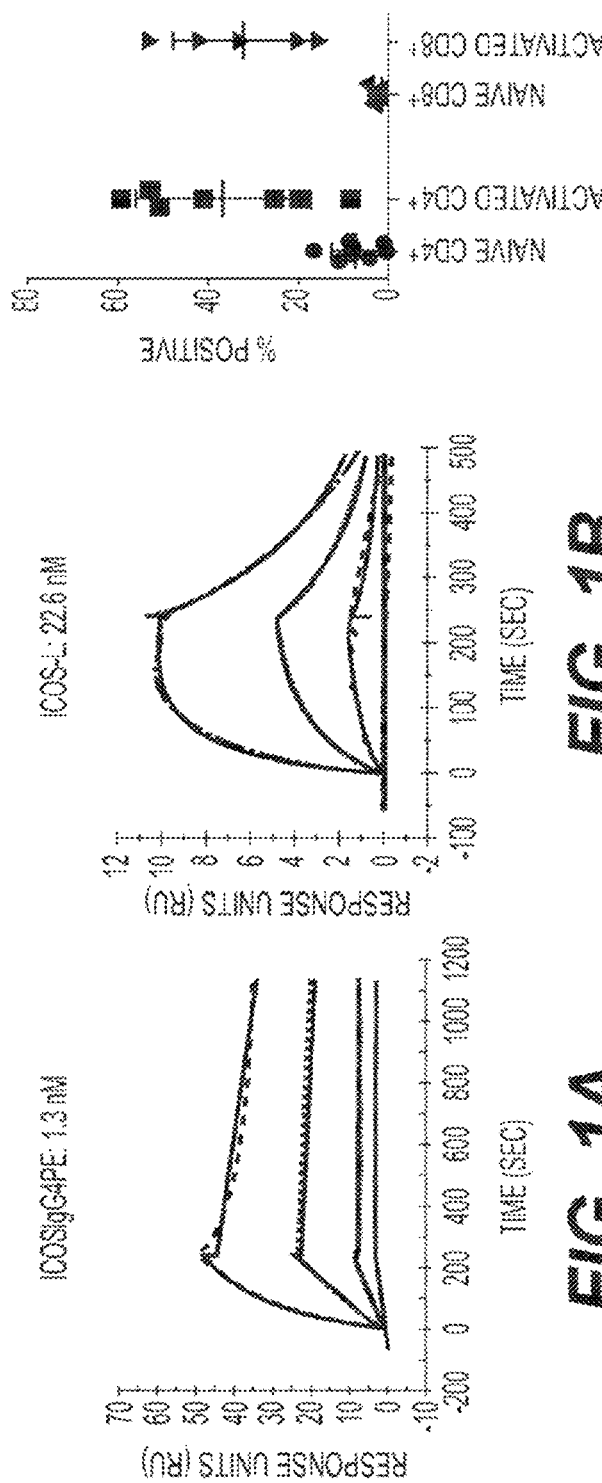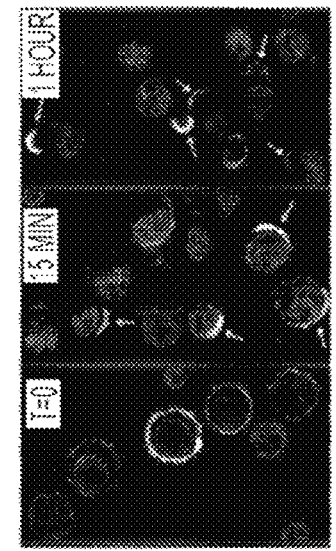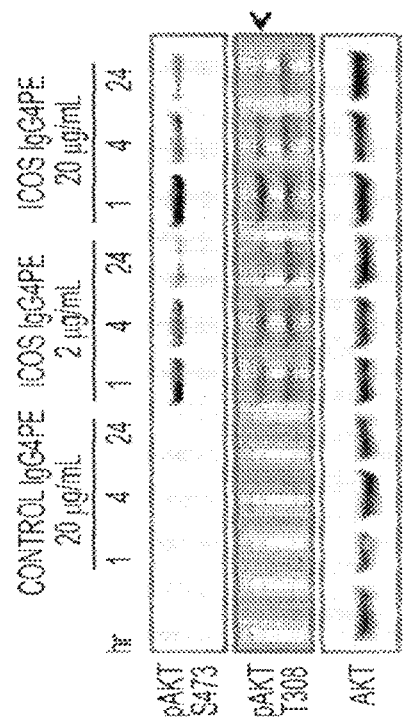

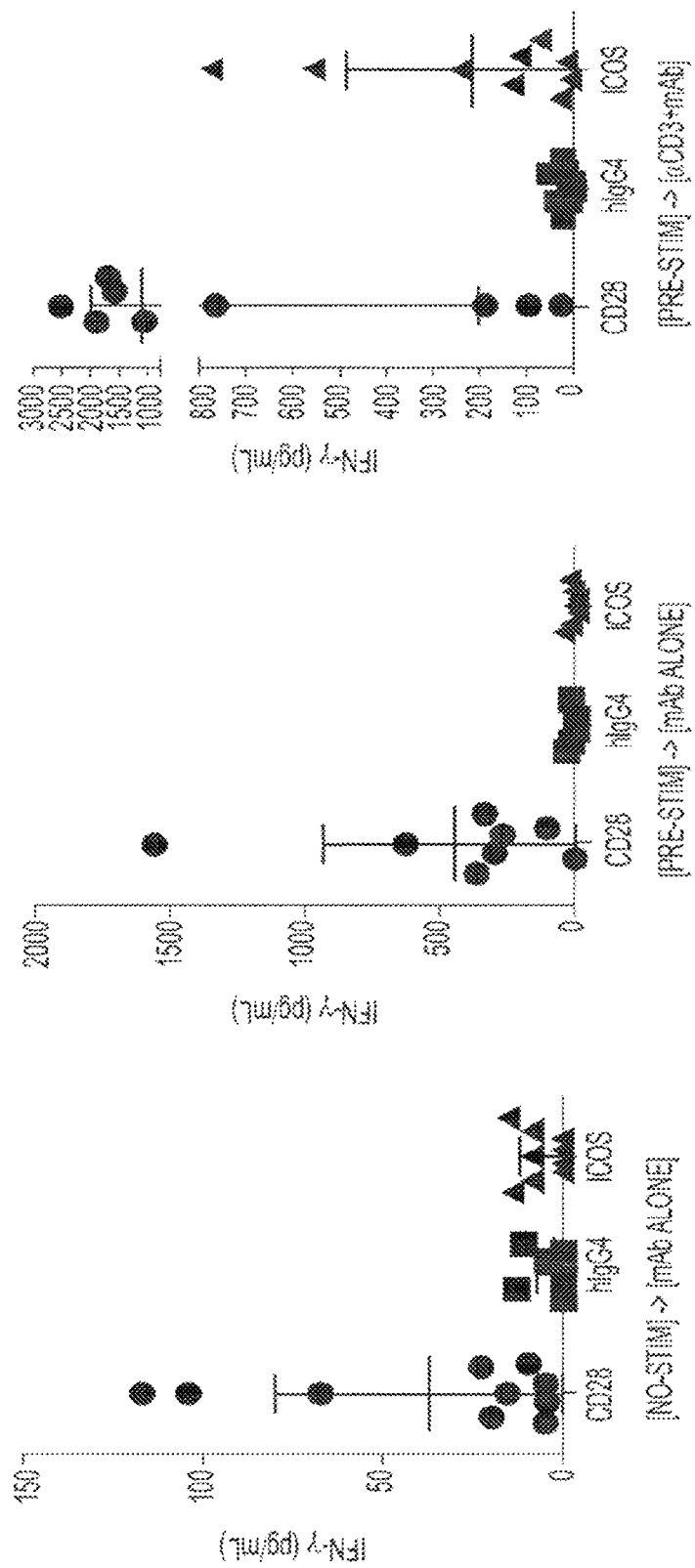

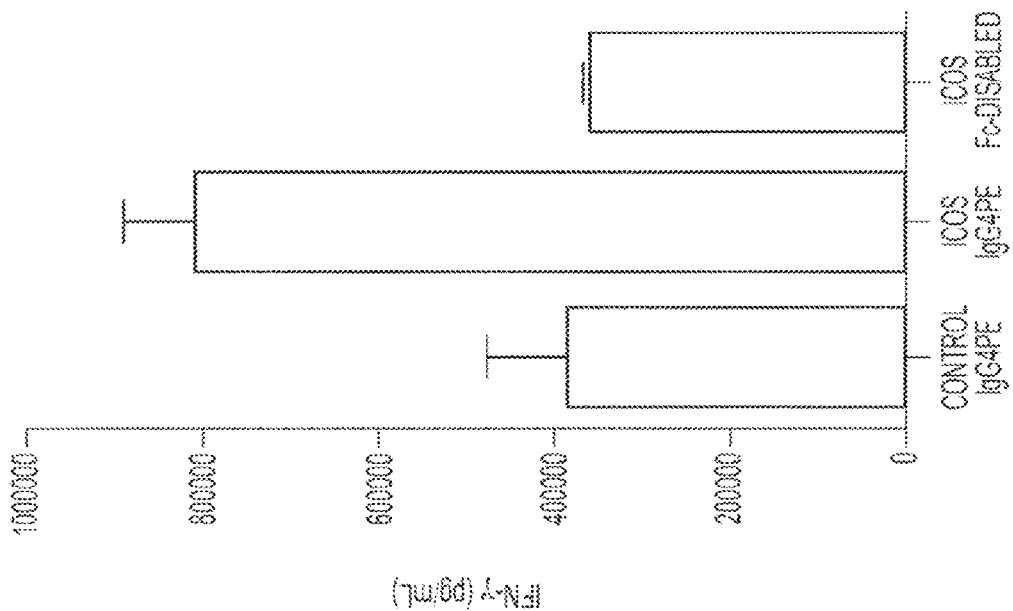
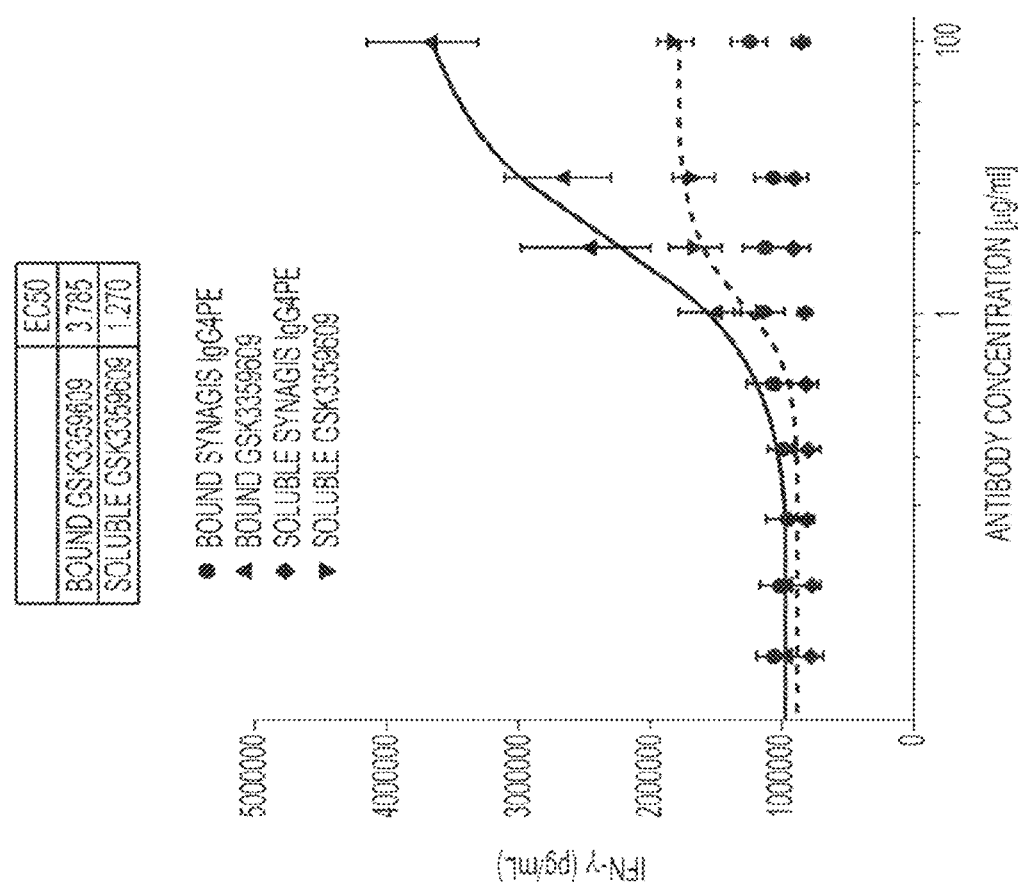
FIG. 3A
FIG. 3B

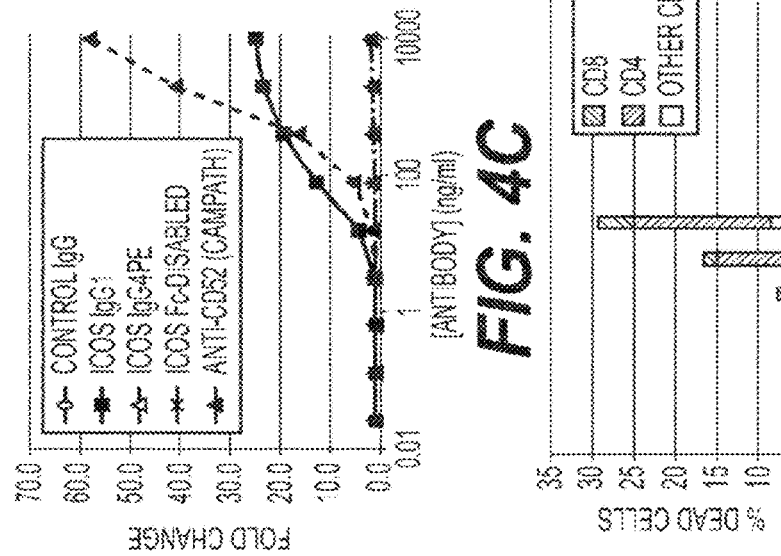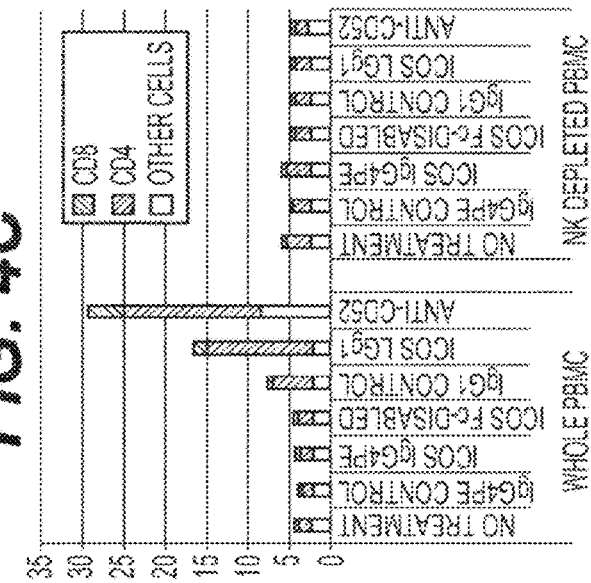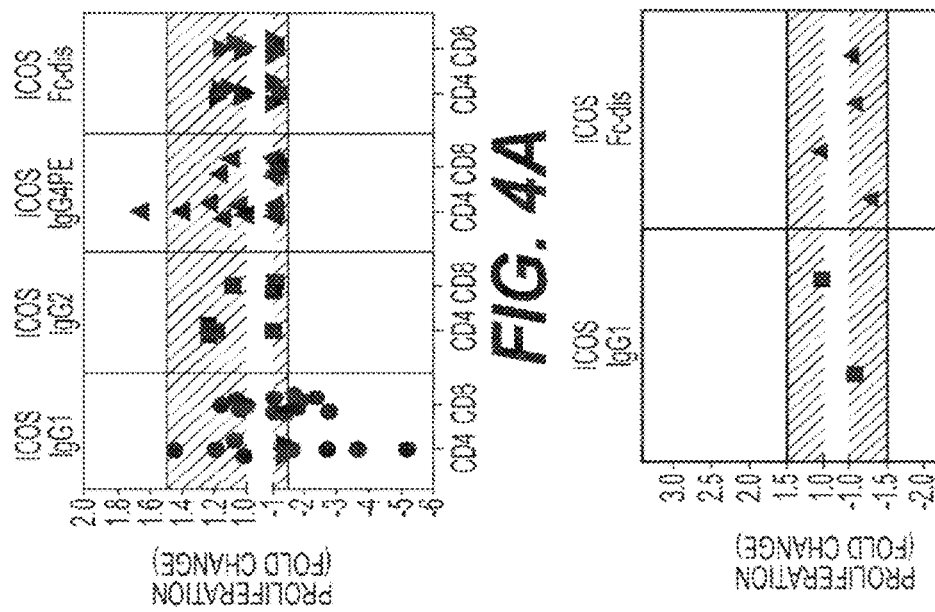

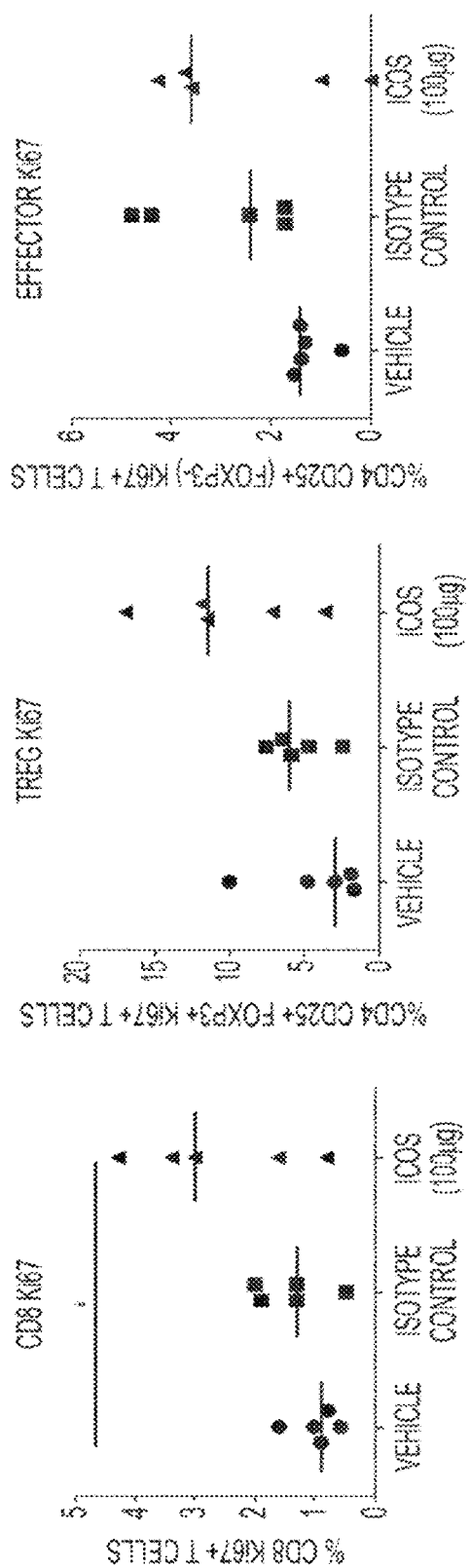

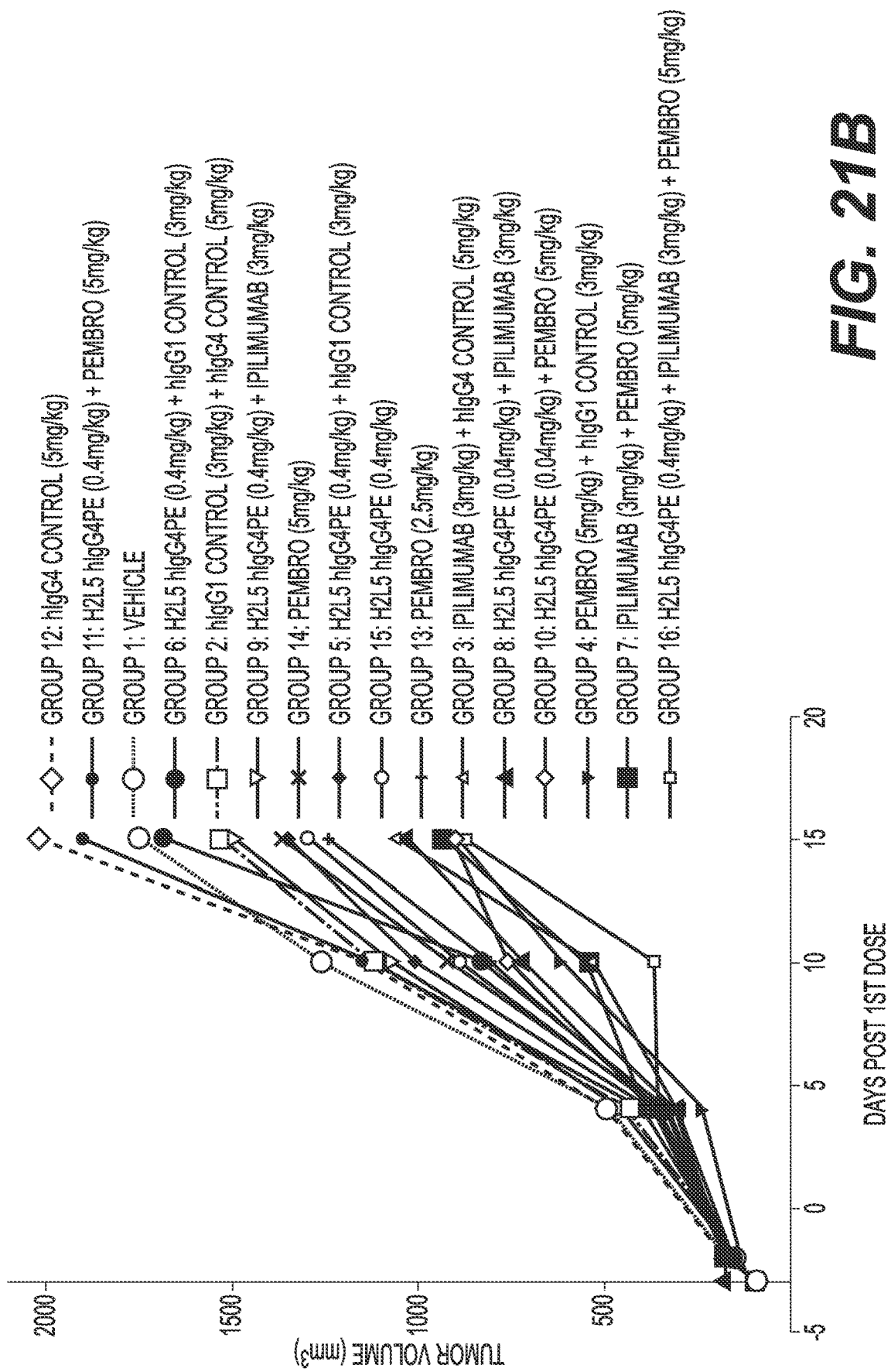

(CONT. 1)

(CONT. 2)

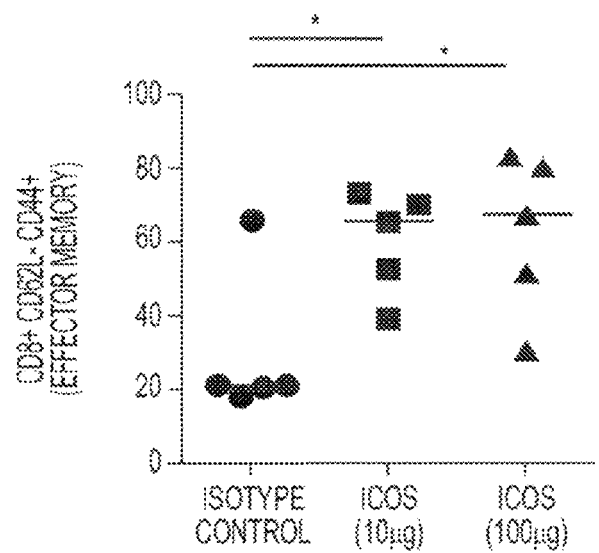
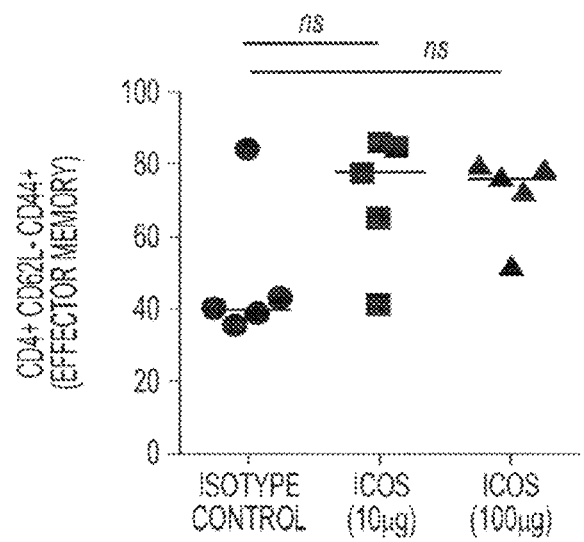
FIG. 24A

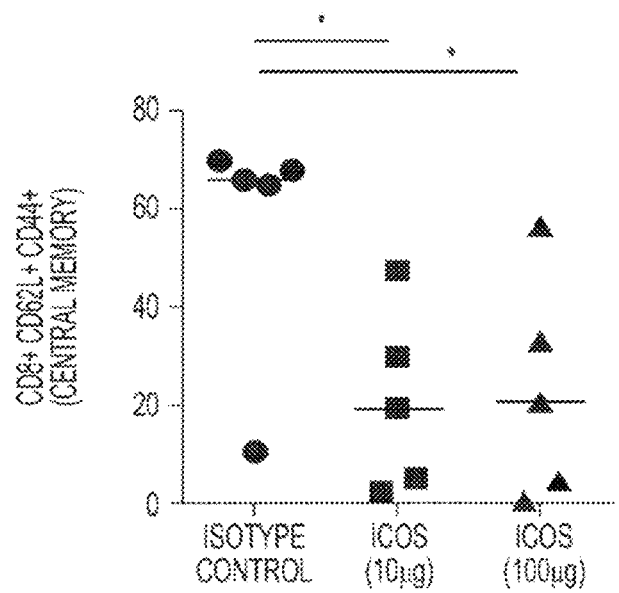
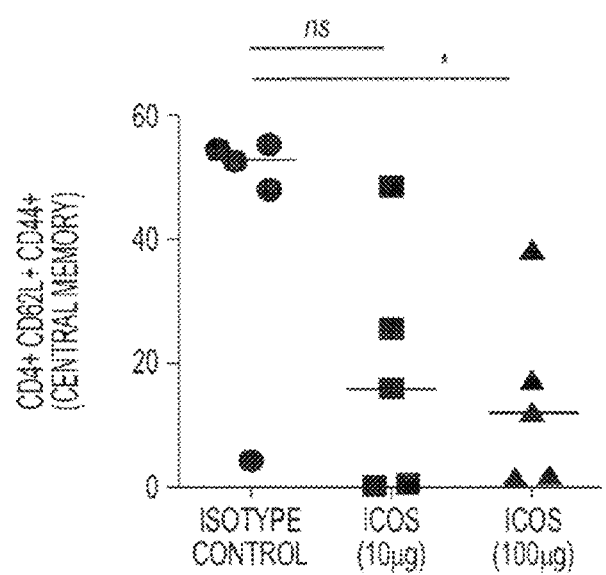
FIG. 24B

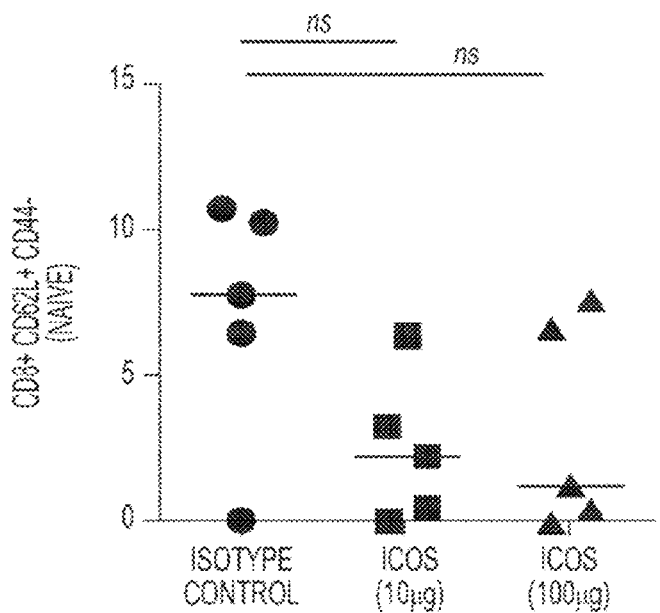
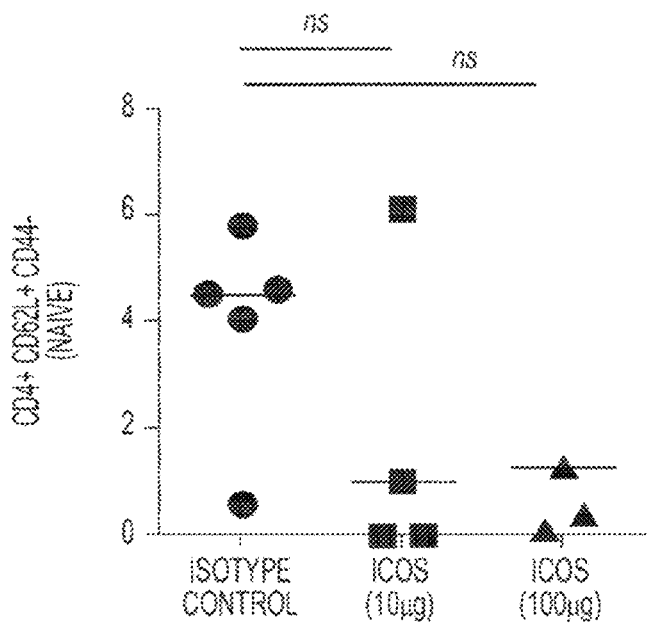
FIG. 24C

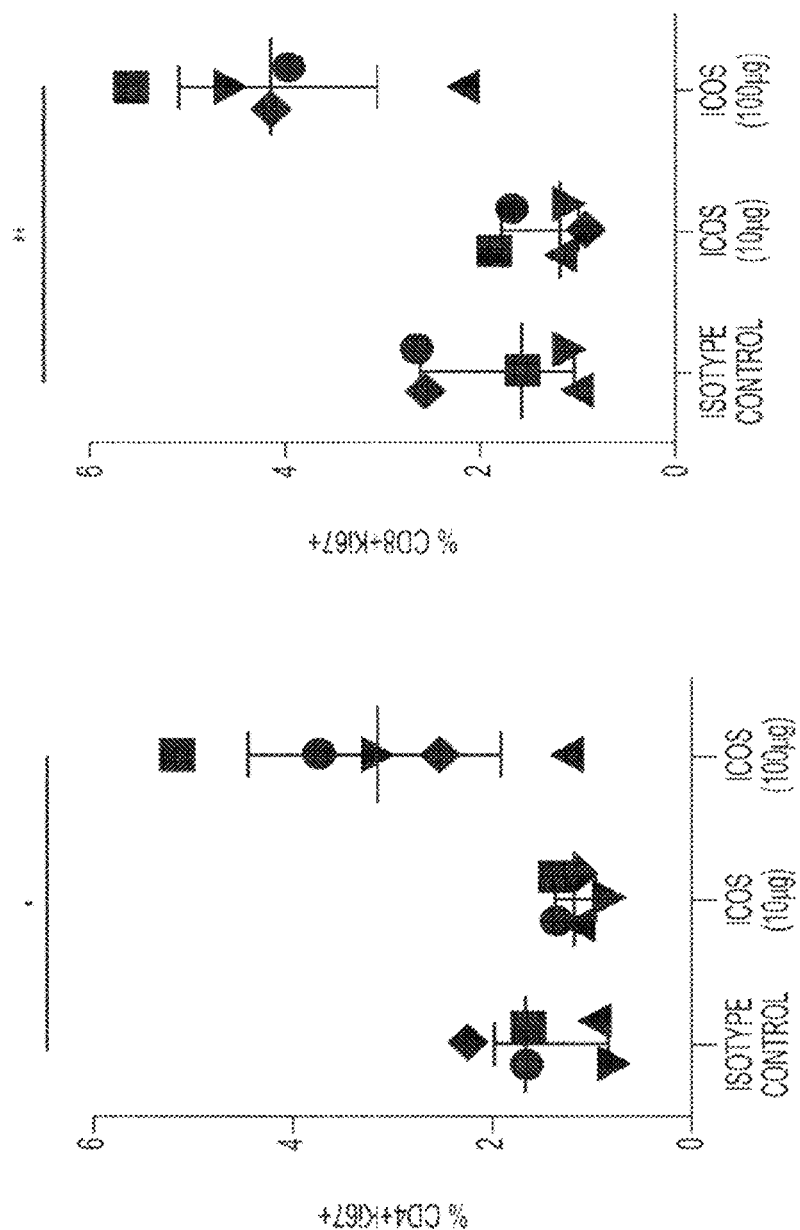

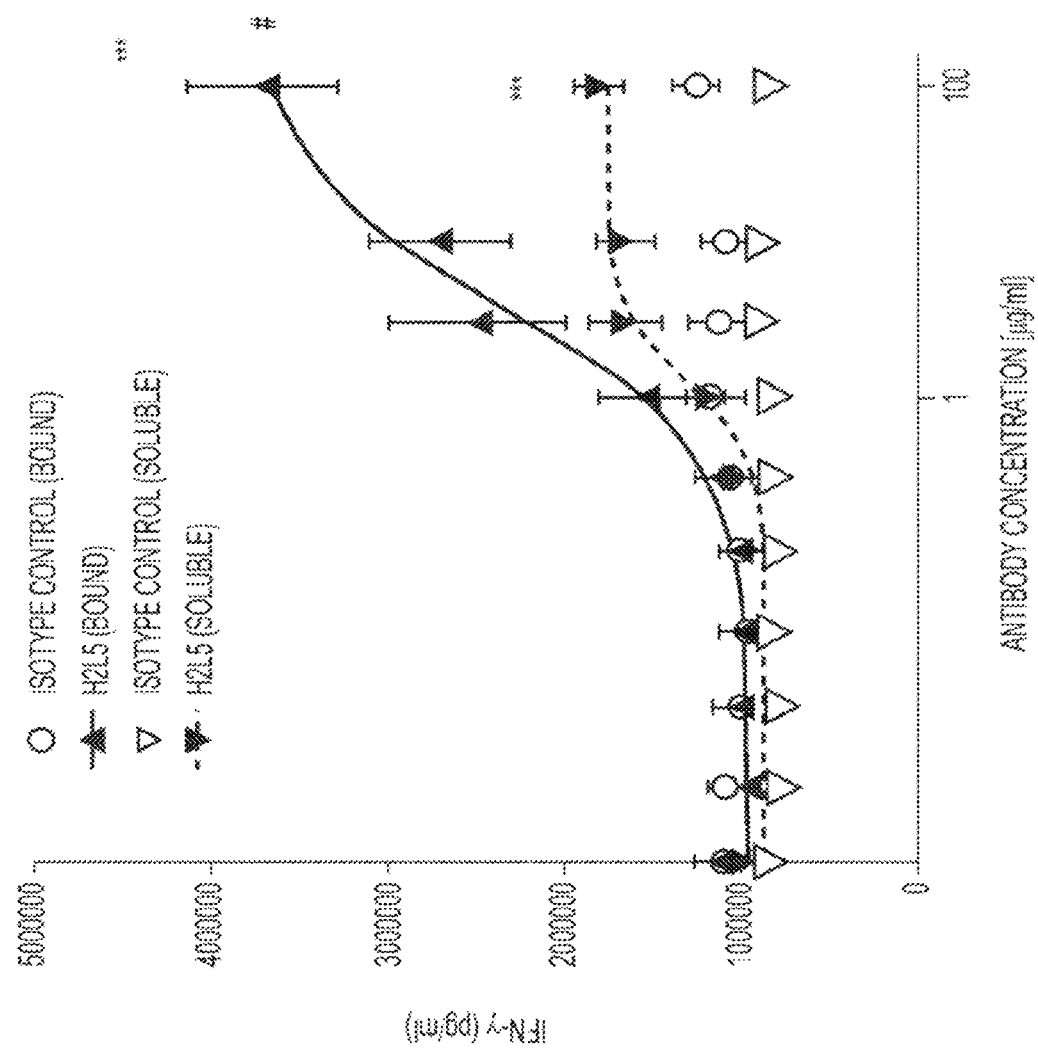

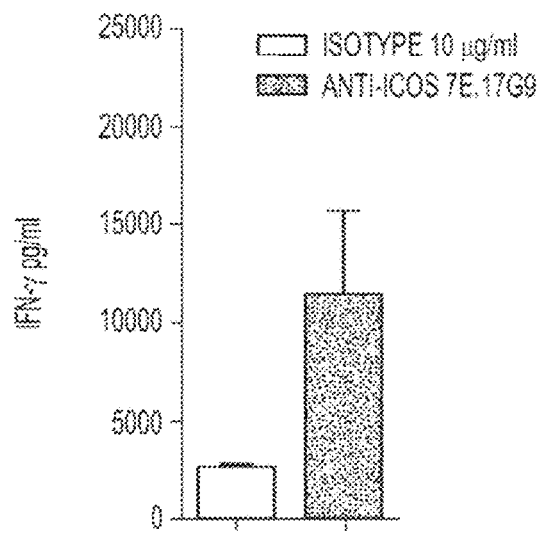

FIG. 30A

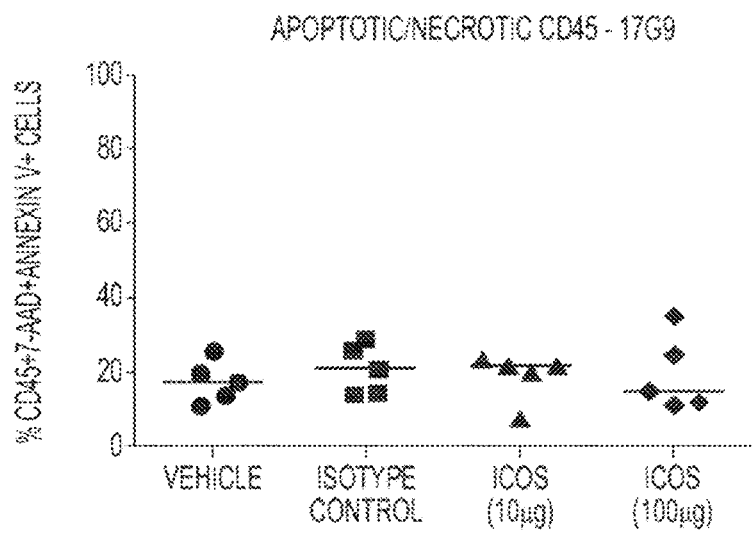

FIG. 30B

CHARACTERIZATION OF AN ANTI-MOUSE ICOS ANTIBODY. (A) ANTI-MOUSE ICOS AGONIST ANTIBODY (7E.17G9) INDUCES IFNγ PRODUCTION IN DISSEMINATED MOUSE SPLENOCYTES CULTURED EX VIVO (B) PERCENTAGE OF APOPTOTIC / NECROTIC BLOOD CD45+ CELLS 48 HOURS AFTER THE $3^{RD}$ DOSE OF 7E.17G9 IN MICE WITH EMT-6 TUMORS. BARS REPRESENT MEAN AND ERROR BARS STANDARD DEVIATION. HORIZONTAL LINES REPRESENT MEAN VALUES. EACH SYMBOL REPRESENTS AN INDIVIDUAL MOUSE

ANTI-MOUSE ICOS AGONIST ANTIBODY 7E.17G9 DOES NOT SIGNIFICANTLY INDUCE OTHER CYTOKINES IN VIVO. (A) LEVELS OF TNFα (B) IL-2 AND (C) IL-10 IN THE BLOOD OF MICE WITH EMT-6 TUMORS 48 HOURS AFTER THE 3RD DOSE OF 7E.17G9. EACH SYMBOL REPRESENTS AN INDIVIDUAL MOUSE AND HORIZONTAL BARS REPRESENT THE MEAN VALUES. N=5 MICE PER GROUP.

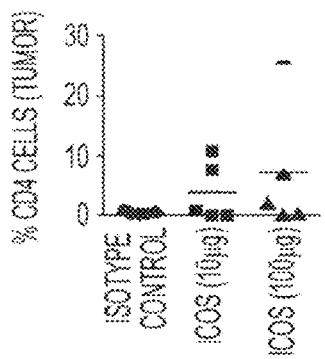
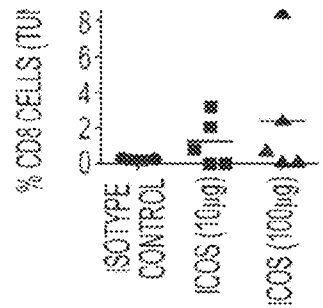

FIG. 32A  FIG. 32B

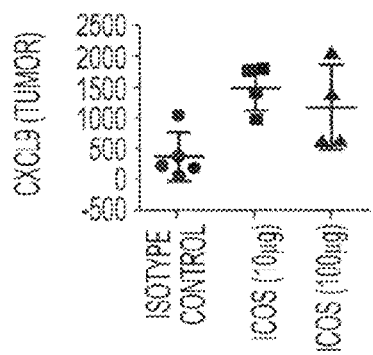
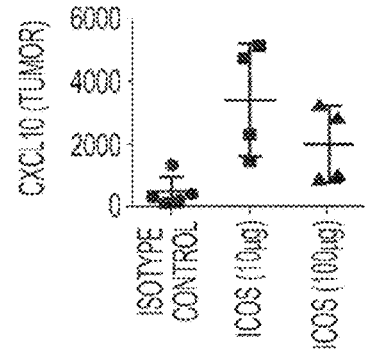
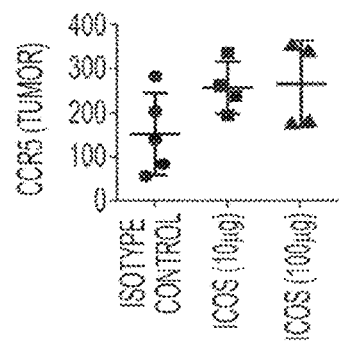

FIG. 32C  FIG. 32D  FIG. 32E

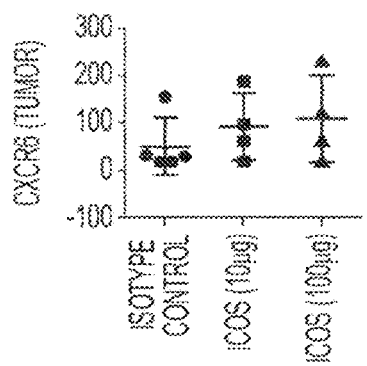
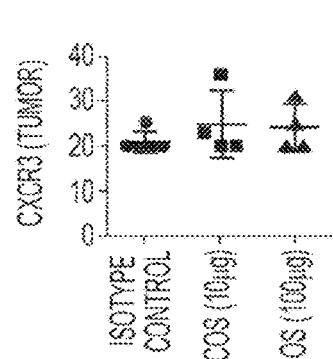
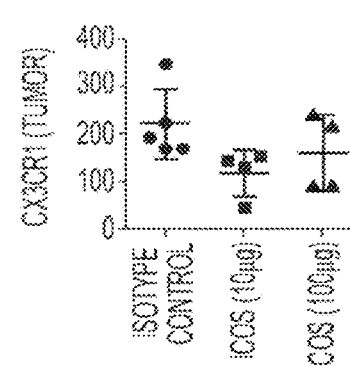

FIG. 32F  FIG. 32G  FIG. 32H

ANTI-MOUSE ICOS AGONIST ANTIBODY 7E.17G9 INDUCES T CELL INFILTRATION AND INDUCTION OF CHEMOKINES. (A) QUANTIFICATION OF THE PERCENTAGE OF CD4+ AND (B) CD8+ CELLS RELATIVE TO ALL LIVE CELLS WITHIN EMT6 TUMORS TREATED WITH 7E.17G9 (C-H) QUANTIFICATION OF RNA EXPRESSION OF THE INDICATED CHEMOKINE OR CHEMOKINE RECEPTOR IN CT26 TUMORS FOLLOWING INDICATED TREATMENTS. EACH SYMBOL REPRESENTS AN INDIVIDUAL MOUSE TUMOR; N=5 MICE PER TREATMENT GROUP, AND IN INSTANCES WHERE <5 TUMORS ARE REPRESENTED THERE WAS NOT SUFFICIENT TUMOR MATERIAL AND/OR RNA QUALITY AVAILABLE TO PERFORM NANOSTRING ANALYSIS. HORIZONTAL LINES REPRESENT MEAN VALUES, ERROR BARS REPRESENT STANDARD DEVIATION.

H2L5 IgG4PE INDUCES PHOSPHO-AKT (A) TREATMENT WITH H2L5 IgG4PE ANTIBODY AT (20 µg/mL) FOR 1 HR IN BaF3 CELLS WITH AND WITHOUT EXPRESSION OF HUMAN ICOS RECEPTOR (B) TREATMENT WITH H2L5 IgG4PE AT (10 µg/mL) IN PRIMARY CD4+ T CELLS

HUMAN IgG1 ISTOYPE ANTI-ICOS AGONIST RESULTS IN T CELL DEPLETION THROUGH ADCC. (A) PBMCS FROM HEALTHY SUBJECTS TREATED WITH SOLUBLE H2L5 OF VARYING ISOTYPES AT 5 μg/mL FOR 6 DAYS. (B) PROLIFERATION AS MEASURED BY CFSE DILUTION RELATIVE TO ISOTYPE CONTROL (FOLD CHANGE).

PBMCS FROM HEALTHY SUBJECTS, WITH OR WITHOUT DEPLETION OF NK CELLS; TREATED WITH SOLUBLE H2L5 OF VARYING ISOTYPES AT (5 μg/mL) FOR 6 DAYS. (C) TREATMENT WITH SOLUBLE H2L5 OF VARYING ISOTYPES FOR 6 HRS. FOLD CHANGE RELATIVE TO ISOTYPE CONTROL (D) PBMCS FROM HEALTHY SUBJECTS WITH OR WITHOUT NK CELL DEPLETION TREATED WITH SOLUBLE H2L5 OF VARYING ISOTYPES (10 μg/mL) FOR 24 HRS.

MEMBRANE TRAFFICKING OF H2L5 IgG4PE FOLLOWING BINDING. H2L5 IgG4PE AFTER BINDING TO PRIMARY CD4+ T CELLS. TIMECOURSE INDICATES TIME FOLLOWING ADDITION OF H2L5 IgG4PE TO CELLS. GREEN IS ALEXA488 LABELED H2L5 ANTIBODY AND BLUE IT NUCLEAR DAPI STAIN.

| SAMPLE GROUP | TEMPLATE MOLECULES | UNIQUE TCRs | CLONALITY | MAX. FREQUENCY | AVG INPUT DNA (ng) |
|---|---|---|---|---|---|
| WB PREBLEED (PBS) | 49986 (17993-77555) | 42357 (14735-65268) | 0.009 (0.005-0.012) | 0.136 (0.089-0.186) | 1153 (874-1434) |
| WB PREBLEED (ISOTYPE CONTROL) | 72389 (49679-101121) | 59836 (38111-89729) | 0.009 (0.006-0.016) | 0.116 (0.051-0.209) | 1320 (1109-1756) |
| WB PREBLEED (ICOS 100µg) | 55067 (41318-66650) | 44117 (34406-57132) | 0.011 (0.008-0.016) | 0.181 (0.06-0.443) | 1193 (1008-1564) |
| WB PREBLEED (ICOS 10µg) | 59662 (42828-93487) | 46634 (32868-69916) | 0.011 (0.006-0.018) | 0.185 (0.083-0.321) | 1230 (1010-1466) |
| WB (PBS) | 227658 (167139-280034) | 186082 (144515-233792) | 0.021 (0.01-0.065) | 0.548 (0.067-3.345) | 7044 (4826-7997) |
| WB (ISOTYPE CONTROL) | 218691 (111797-401031) | 168493 (94953-274102) | 0.017 (0.007-0.027) | 0.207 (0.095-0.778) | 7174 (5025-7997) |
| WB (ICOS 100µg) | 206011 (108054-287713) | 162492 (91153-213917) | 0.025 (0.01-0.052) | 0.824 (0.178-3.776) | 6150 (3418-7997) |
| WB (ICOS 10µg) | 224655 (139477-359612) | 175393 (122527-245519) | 0.02 (0.009-0.029) | 0.426 (0.146-0.851) | 6871 (4895-7997) |
| TUMOR (PBS) | 10692 (5174-14568) | 2508 (1146-4649) | 0.267 (0.149-0.439) | 16.308 (5.122-38.906) | 2666 (2665-2666) |
| TUMOR (ISOTYPE CONTROL) | 13032 (1849-24153) | 5784 (798-13018) | 0.179 (0.063-0.416) | 12.266 (2.998-34.837) | 2666 (2665-2666) |
| TUMOR (ICOS 100µg) | 43268 (22046-67816) | 13849 (1784-34813) | 0.344 (0.081-0.604) | 18.343 (2.939-41.943) | 2408 (1466-2666) |
| TUMOR (ICOS 10µg) | 29429 (8926-43462) | 8112 (1315-19125) | 0.36 (0.187-0.548) | 19.46 (11.293-29.598) | 2380 (1139-2666) |

*FIG. 38*

| PHOSPHO PROTEIN | WESTERN BLOT | ANTIBODY | OBSERVATIONS UPON H2L5 IgG4PE |
|---|---|---|---|
| AKT (T308) | Y | Y | INCREASE UP TO 48 HOURS (WB ONLY) |
| AKT (S473) | Y | Y | INCREASE FROM 1-6 HOUR |
| ERK1/2 (T202/Y204) | Y | Y | NO EFFECT |
| p70 S6K (T389) | N | Y | NO EFFECT |
| S6 (S235/236) | Y | Y | INCREASE AT 1 HOUR ONLY |
| S6 (S240/244) | Y | N | NO EFFECT |
| GSK3a (S21) | Y | N | MODEST INCREASE FROM 1-6 HOUR |
| GSK3β (S9) | Y | Y | NO EFFECT |
| PRAS40 (T246) | Y | Y | NO EFFECT |
| 4EBP1 (T37/46) | Y | N | NO EFFECT |
| FOXO1/FOXO3a | Y | N | NO EFFECT |
| mTOR (S2448) | N | Y | NO EFFECT |
| NDRG1 (T346) | Y | N | NO EFFECT |
| RSK1/2 (S221/227) | N | N | NO EFFECT |
| STAT1 (Y701) | N | Y | NO EFFECT |
| STAT3 (Y705) | N | Y | NO EFFECT |
| AMPKα (T172) | N | Y | NO EFFECT |
| HSP27 (S78) | N | Y | NO EFFECT |
| Bad (S112) | N | Y | NO EFFECT |
| p53 (S15) | N | Y | NO EFFECT |
| p38 (T180/Y182) | N | Y | MODEST INCREASE AT 48 HOUR ONLY |
| SAPK/JNK | N | Y | NO EFFECT |
| PARP (D214) | N | Y | NO EFFECT |
| Caspase-3 (D175) | | | |

*FIG. 39*

| METHOD (BIACORE) | HUMAN | | | MONKEY | | |
|---|---|---|---|---|---|---|
| | ka (1/Ms) | kd (1/s) | $K_D$ (nM) | ka (1/Ms) | kd (1/s) | $K_D$ (nM) |
| H2L5 IgG4PE | $2.97 \times 10^5$ | $3.96 \times 10^{-4}$ | 1.34 | $3.91 \times 10^5$ | $3.71 \times 10^{-4}$ | 0.95 |

KEY:
ka = ASSOCIATION RATE CONSTANT.
kd = DISSOCIATION RATE CONSTANT.
$K_D$ = EQUILIBRIUM DISSOCIATION CONSTANT.
BLI = BIOLAYER INTERFEROMETRY; ICOS = INDUCIBLE T CELL CO-STIMULATOR; T = NOT TESTED.

FIG. 40

| CYTOKINES [pg/mL] 48hr TIMEPOINT | ISOTYPE CONTROL (12.5 μg/mL) | | | | | H2L5 IgG4PE (12.5 μg/mL) | | | | | |
|---|---|---|---|---|---|---|---|---|---|---|---|
| | DONOR 1 | DONOR 2 | DONOR 3 | DONOR 4 | MEAN OF DONORS ISOTYPE CONTROL | DONOR 1 | DONOR 2 | DONOR 3 | DONOR 4 | MEAN OF DONORS (H2L5) | MEAN FOLD CHANGE |
| IL-17a | 17.0 | 88.3 | 24.7 | 224.2 | 88.5 | 7217.7 | 12558.5 | 19137.9 | 37021.5 | 18983.9 | 376.6 |
| IL-6 | 47.6 | 40.9 | 7.2 | 49.9 | 36.4 | 1473.7 | 705.2 | 435.5 | 1430.3 | 1011.2 | 34.4 |
| TNFa | 5245.8 | 1765.4 | 1109.6 | 798.5 | 2229.3 | 30755.1 | 8506.9 | 10951.5 | 7590.0 | 14450.9 | 7.5 |
| IL-10 | 160.0 | 45.0 | 5.3 | 19.0 | 58.1 | 4457.5 | 1686.6 | 519.0 | 3449.3 | 2528.1 | 86.1 |
| IL-4 | 1.6 | 0.7 | 0.2 | 0.3 | 0.7 | 27.9 | 19.4 | 4.2 | 74.2 | 31.4 | 78.1 |
| IL-5 | 40.8 | 25.6 | 1.2 | 21.8 | 22.4 | 503.8 | 340.1 | 294.8 | 687.0 | 466.4 | 73.3 |
| IL-13 | 93.6 | 44.1 | 18.6 | 34.6 | 47.7 | 368.0 | 158.7 | 225.0 | 357.0 | 282.2 | 7.5 |
| IFNγ | 70.4 | 786.9 | 1022.4 | 1053.2 | 733.2 | 7927.0 | 26598.6 | 50383.9 | 199174.6 | 71021.0 | 96.2 |

*FIG. 41*

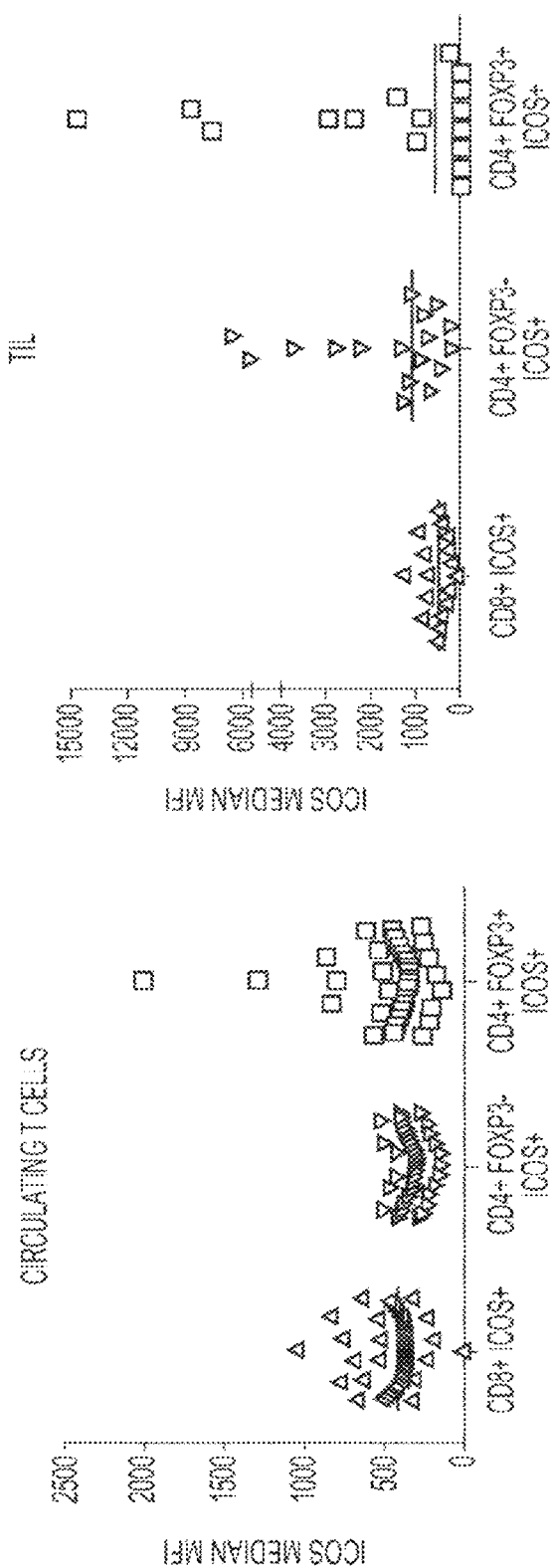

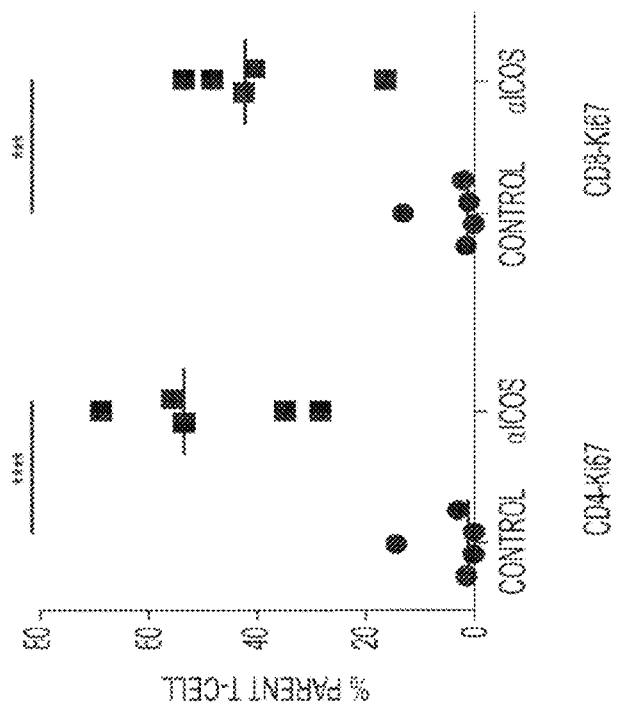
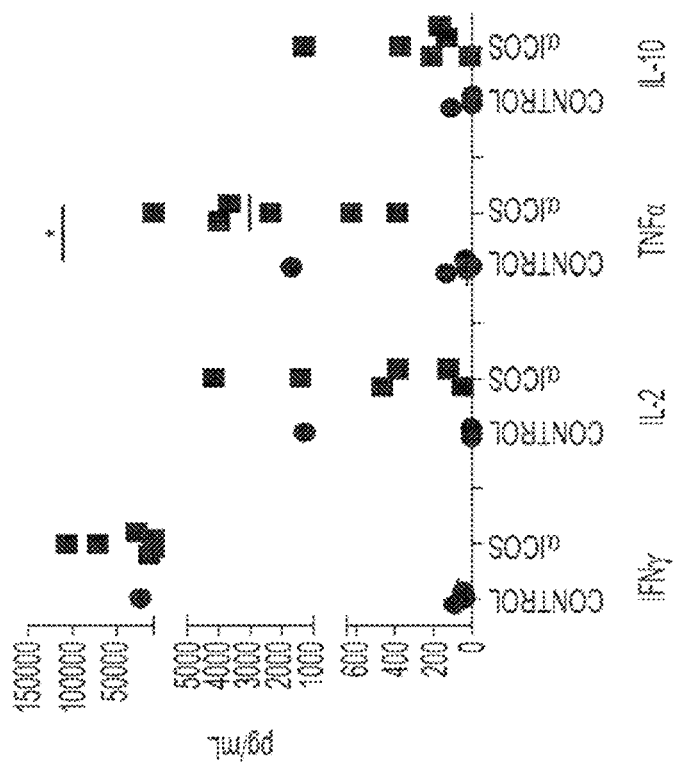
FIG. 45A
FIG. 45B

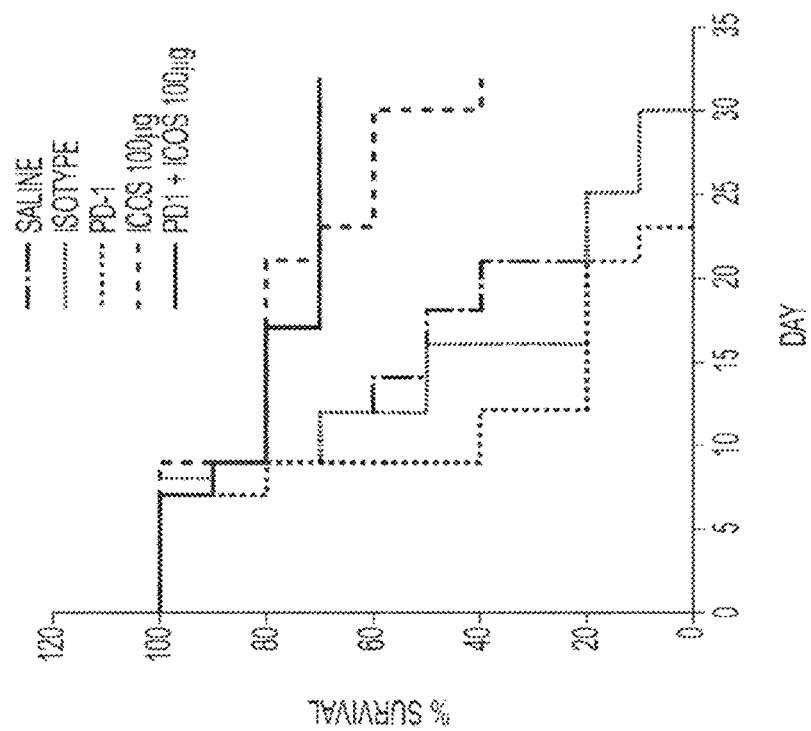
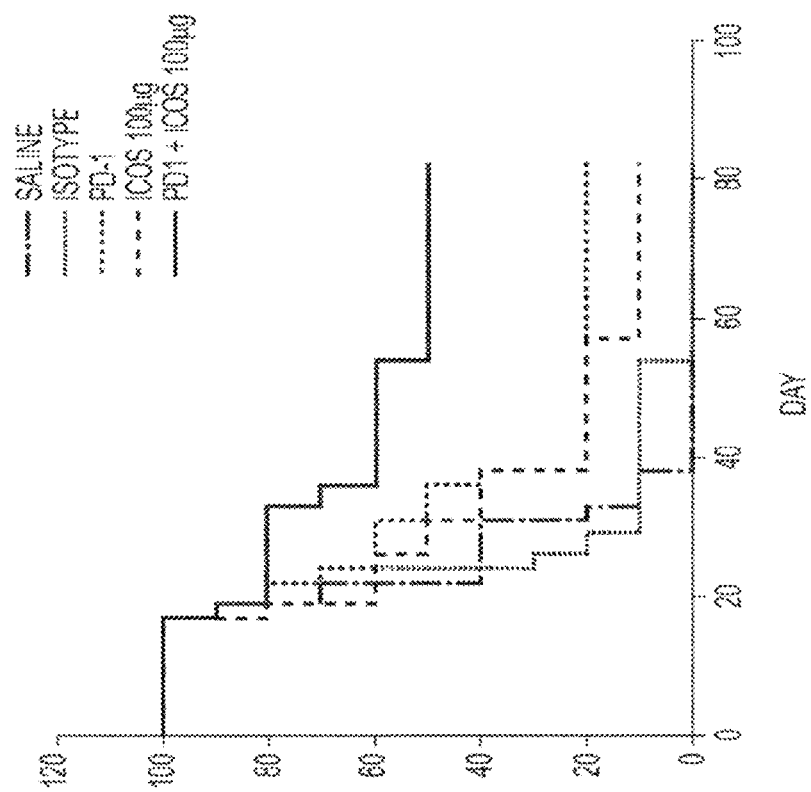
FIG. 50A
FIG. 50B

ANTI-ICOS AND ANTI-PD-1 ANTIBODY COMBINATION THERAPY

This application is a 371 of International Application No. PCT/IB2017/054764, filed 3 Aug. 2017, which claims priority to U.S. 62/370,891 filed 4 Aug. 2016, U.S. 62/400,344 filed 27 Sep. 2016, U.S. 62/438,464 filed 23 Dec. 2016, and U.S. 62/479,558 filed 31 Mar. 2017.

FIELD OF THE INVENTION

The present invention relates generally to immunotherapy in the treatment of human disease. More specifically, the present invention relates to the use of immunomodulators in the treatment of cancer.

BACKGROUND OF THE INVENTION

Cancer immunity is a multistep process that is tightly regulated by a series of negative immune checkpoint and positive co-stimulatory receptors that when effectively triggered can achieve antitumor response (Mellman, I., et al. (2011) Cancer Immunotherapy Comes of Age. Nature 480(7378), 480-489). However, tumors have established various mechanisms to circumvent immune clearance by altering the responsiveness of the immune infiltrate. In some instances, tumors will be highly dependent on a single mechanism, and in these cases, there is the potential to achieve significant clinical activity with single agent immunomodulatory therapy (Hoos, A. (2016). Development of immuno-oncology drugs—from CTLA4 to PD1 to the next generations. Nat Rev Drug Discov. 15(4), 235-47). However, as tumors often utilize multiple, overlapping and redundant mechanisms to block antitumor immune response, combination therapy will likely be required for durable efficacy across a wide range of tumor types. Therefore, new immune targeted therapies are needed to improve the treatment of all cancers.

Thus, there is a need for combination treatments of immunomodulators for the treatment of disease, in particular cancer.

BRIEF DESCRIPTION OF THE DRAWINGS

FIG. 1: H2L5 IgG4PE is a potent anti-ICOS agonist antibody (A) H2L5 IgG4PE binding to dimeric human ICOS (B) native ICOS-L binding to dimeric human ICOS (C) Binding of H2L5 IgG4PE (20 ug/mL) to CD4$^+$ and CD8$^+$ T cells from healthy donor PBMCs (D) Induction of AKT signaling in Ba/F3-ICOS expressing cell line after treatment with H2L5 IgG4PE (E) Binding of H2L5 IgG4PE (green) to isolated and activated CD4$^+$ T cells as imaged by confocal microscopy.

FIG. 4: H2L5 isotype is critical to avoid FcγR-mediated ICOS$^+$ cell depletion (A) PBMCs from healthy subjects treated with soluble H2L5 of varying isotypes at 5 ug/mL for 6 days. Proliferation as measured by CFSE dilution relative to isotype control (Fold change). (B) PBMCs from healthy subjects, with or without depletion of NK cells; treated with soluble H2L5 of varying isotypes at (5 ug/mL) for 6 days. (C) Treatment with soluble H2L5 of varying isotypes for 6 hrs. Fold change relative to isotype control (D) PBMCs from healthy subjects with or without NK cell depletion treated with soluble H2L5 of varying isotypes (10 ug/mL) for 24 hrs.

FIG. 14: Anti-mouse ICOS agonist antibody 7E.17G9 induces T cell proliferation in vivo. (A) Percentage of proliferating CD8+ (B) CD4+ Tregs and (C) CD4+ effector cells 48 hours after the 3$^{rd}$ dose of 7E.17G9 in mice with EMT-6 tumors

Figure 2E:
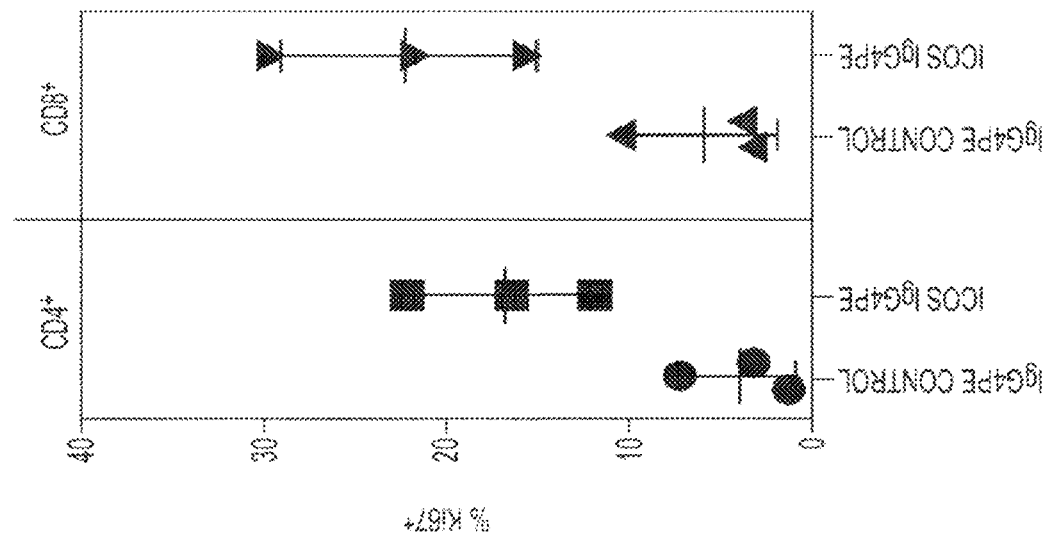
FIG. 2: H2L5 IgG4PE induces potent T cell activation, proliferation and function in a TCR-dependent manner (A) PBMCs from healthy subjects treated with either anti-CD28, IgG4PE isotype control or H2L5 IgG4PE (ICOS) alone in bound format at (10pg/mL) for 24 hrs (B) PBMCs prestimulated with anti-CD3 antibody followed by treatment with soluble anti-CD28, IgG4PE isotype control or H2L5 IgG4PE (ICOS) alone in bound format at (10pg/mL) for 24 hrs (C) PBMCs prestimulated with anti-CD3 antibody followed by treatment with anti-CD28, IgG4PE isotype control or H2L5 IgG4PE (ICOS) in bound format at (10pg/mL) for 24 hrs (D) PBMCs from healthy subjects treated with (12.5 ug/mL) of bound H2L5 IgG4PE and anti-CD3 for 48 hrs (E) PBMCs from healthy subjects treated with (12.5 ug/mL) of bound H2L5 IgG4PE and anti-CD3 for 48 hrs (F) Soluble IFNγ from the supernatant of healthy donor PBMCs treated with (12.5 ug/mL) of bound H2L5 IgG4PE and anti-CD3 (G) Soluble IFNγ from the supernatant of cancer patient PBMCs treated with (10 ug/mL) of bound H2L5 IgG4PE and anti-CD3 for 72 hrs.

FIG. 29: H2L5 induces T cell mobilization and effector memory T cell redistribution in vivo (a) Human T cells pre-stimulated with anti-CD3 for 48 hrs and added to a co-culture with human dendritic cells. AlexaFlour488-labeled H2L5 IgG4PE added at 3 μg/mL to co-culture cells on ice then moved to 37 deg C. for indicated timepoints. Arrows indicate T cell activated in response to H2L5 treatment, polarization and mobilization towards neighbouring dendritic cell. (b) quantification of RNA expression of L-Selectin (SELL) (*P=0.0161, t=2.955 df=9) two-tailed, unpaired t-test (c) quantification of human CD45+CD3+ cells in the blood of mice H2L5 treatments as compared to isotype control IgG4PE all significant (****P=<0.0001, F=33.57, df=24) (d) Quantification of human CD45+CD3+ CD69+ cells from the blood of mice H2L5 IgG4PE (1.2 mg/kg) vs. isotype control IgG4PE (*P=0.0119, F=4.179, df=24) (e) Percentage of human naïve CD4+ T cells (**P=0.<0001, F=20.82, df=20) (f) CD4+ $T_{CM}$ (0.04 mg/kg P=0.0038, 0.4 mg/kg *P=0.0002, 1.2 mg/kg *P=0.0005, F=8.172, df=20) (g) CD4+$T_{EM}$ (****P=<0.0001, F=15.85, df=20) (h) naïve CD8+ (0.004 mg/kg*P=0.0367, 1.2 mg/kg *P=0.0434, F=5.193, df=20) (i) CD8+ $T_{CM}$ (0.04 mg/kg *P=0.0003, 0.4 mg/kg P=0.0044, 1.2 mg/kg P=0.0031, F=6.070, df=20) and (j) CD8+ $T_{EM}$ (0.004 mg/kg P=0.0036, 0.04 mg/kg and 0.4 mg/kg **P=<0.0001, mg/kg P=0.0072, F=13.78, df=20) in the spleen of mice (c-j) horizontal lines represent median values, error bars represent interquartile range. All statistical tests were one-way ANOVA with square root transformed data to stabilize variances.

FIG. 30: Characterization of an anti-mouse ICOS antibody. (A) Anti-mouse ICOS agonist antibody (7E.17G9) induces IFNγ production in disseminated mouse splenocytes cultured ex vivo (B) Percentage of apoptotic/necrotic blood CD45+ cells 48 hours after the 3rd dose of 7E.17G9 in mice with EMT-6 tumors. Bars represent mean and error bars standard deviation. Horizontal lines represent mean values. Each symbol represents an individual mouse.

FIG. 31: Anti-mouse ICOS agonist antibody 7E.17G9 does not significantly induce other cytokines in vivo. (A) Levels of TNFα (B) IL-2 and (C) IL-10 in the blood of mice with EMT-6 tumors 48 hours after the 3rd dose of 7E.17G9. Each symbol represents an individual mouse and horizontal bars represent the mean values. N=5 mice per group.

FIG. 32: Anti-mouse ICOS agonist antibody 7E.17G9 induces T cell infiltration and induction of chemokines. (a) quantification of the percentage of CD4+ and (b) CD8+ cells relative to all live cells within EMT6 tumors treated with 7E.17G9 (c-h) quantification of RNA expression of the indicated chemokine or chemokine receptor in CT26 tumors following indicated treatments. Each symbol represents an individual mouse tumor; n=5 mice per treatment group, and in instances where <5 tumors are represented there was not sufficient tumor material and/or RNA quality available to perform Nanostring analysis. Horizontal lines represent mean values, error bars represent standard deviation.

Figure 33:
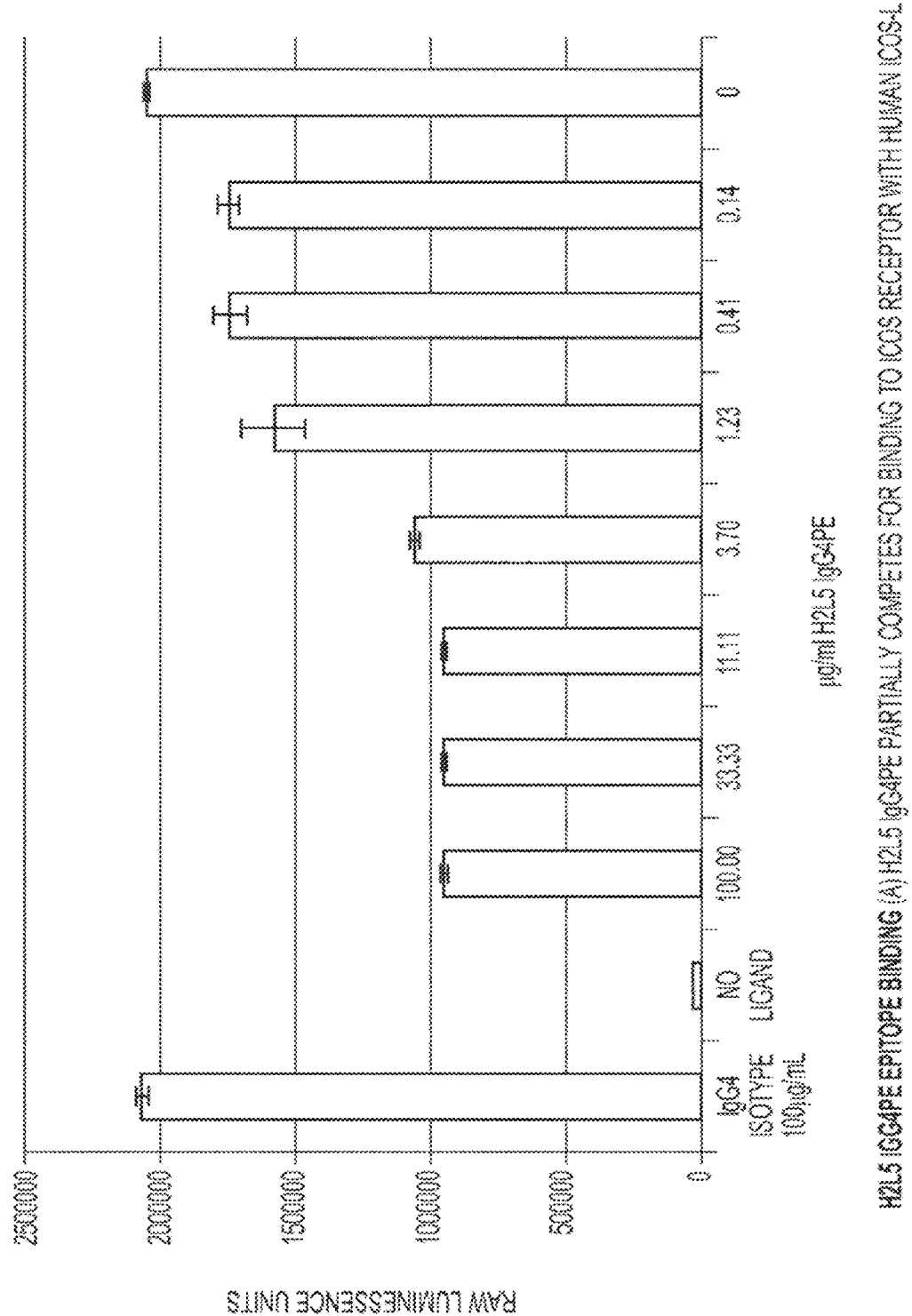

FIG. 33: H2L5 IgG4PE epitope binding (a) H2L5 IgG4PE partially competes for binding to ICOS receptor with human ICOS-L.

FIG. 34: H2L5 IgG4PE induces phospho-AKT (a) Treatment with H2L5IgG4PE antibody at (20 ug/mL) for 1 hr in Ba/F3 cells with and without expression of human ICOS receptor (b) Treatment with H2L5 IgG4PE at (10 ug/mL) in primary CD4+ Tcells.

FIG. 35: Human IgG1 istoype anti-ICOS agonist results in T cell depletion through ADCC. (a) PBMCs from healthy subjects treated with soluble H2L5 of varying isotypes at 5 ug/mL for 6 days. (b) Proliferation as measured by CFSE dilution relative to isotype control (Fold change). PBMCs from healthy subjects, with or without depletion of NK cells; treated with soluble H2L5 of varying isotypes at (5 ug/mL) for 6 days. (c) Treatment with soluble H2L5 of varying isotypes for 6 hrs. Fold change relative to isotype control (d) PBMCs from healthy subjects with or without NK cell depletion treated with soluble H2L5 of varying isotypes (10 ug/mL) for 24 hrs.

Figure 36:
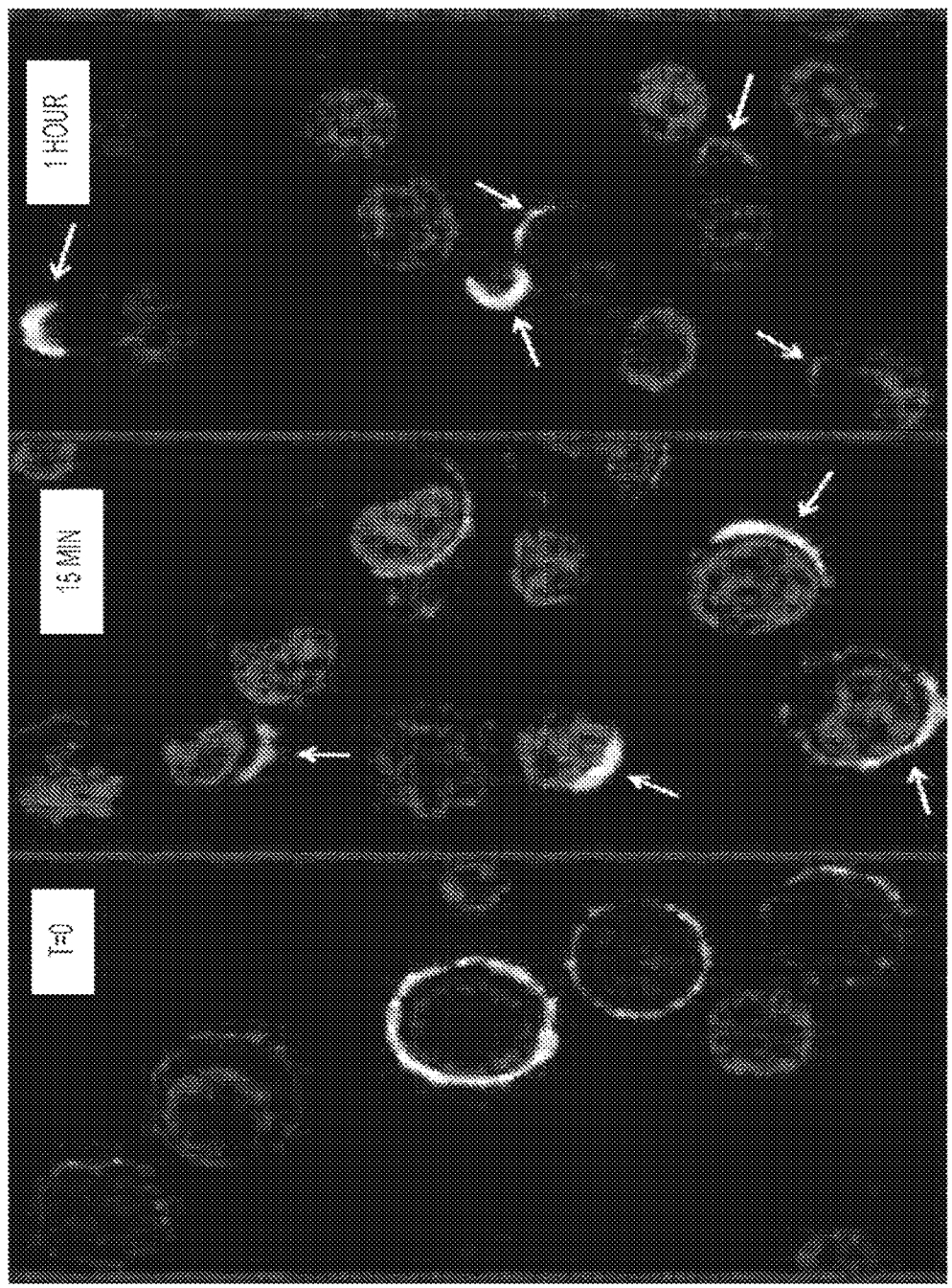

FIG. 36: Membrane trafficking of H2L5 IgG4PE following binding. H2L5 IgG4PE after binding to primary CD4+ T cells. Timecourse indicates time following addition of H2L5 IgG4PE to cells. Green is Alex488 labeled H5L5 antibody and blue it nuclear DAPI stain.

Figure 37:
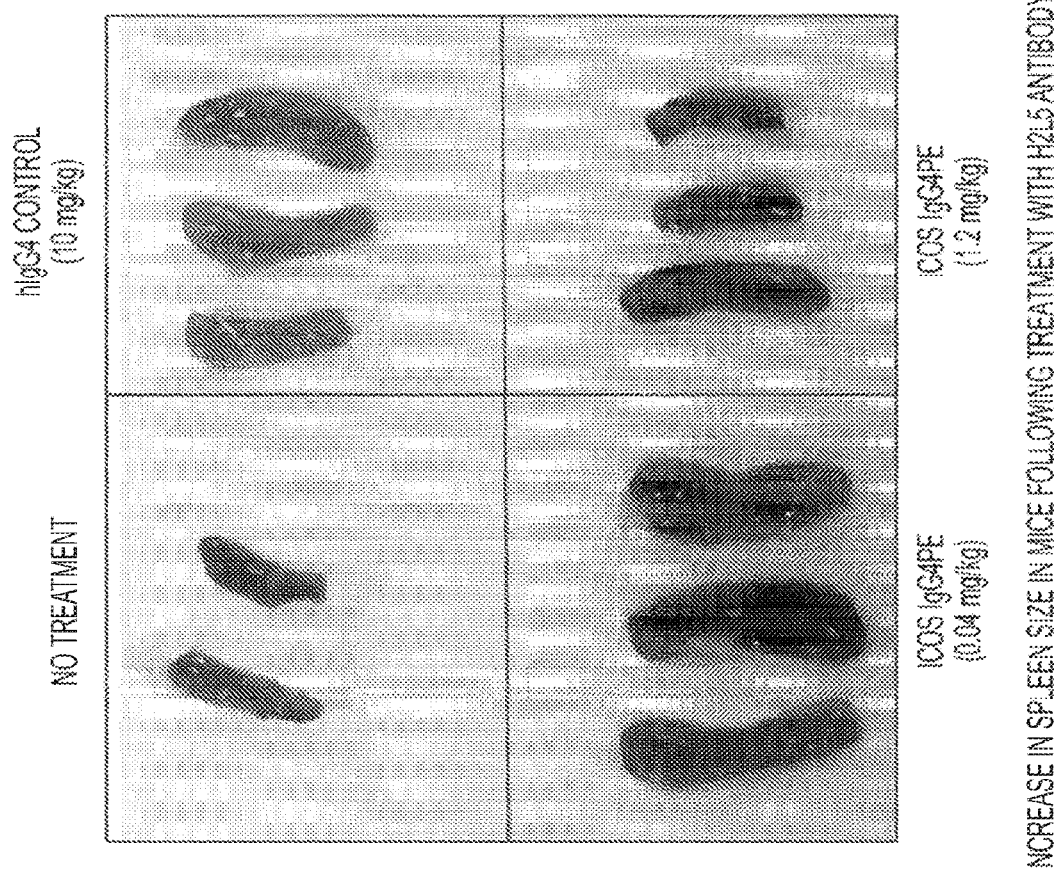

FIG. 37: Increase in spleen size in mice following treatment with H2L5antibody.

FIG. 38: T Cell Receptor (TCR) Sequencing data from mice with EMT6tumors (WB)=whole blood. Values shown are mean of n=8 mice per group with range (min-max)

FIG. 39: Summary of phospho-proteins (n=24) investigated in Ba/F3-ICOS cells treated with H2L5 IgG4PE antibody at 20 ug/mL.

FIG. 40: H2L5 IgG4PE binding to human and cynomolgus monkey ICOS.

FIG. 41: Changes in cytokine levels from healthy human donor PBMC in response to treatment with anti-CD3 mAb plus indicated treatments below.

Figure 42A:
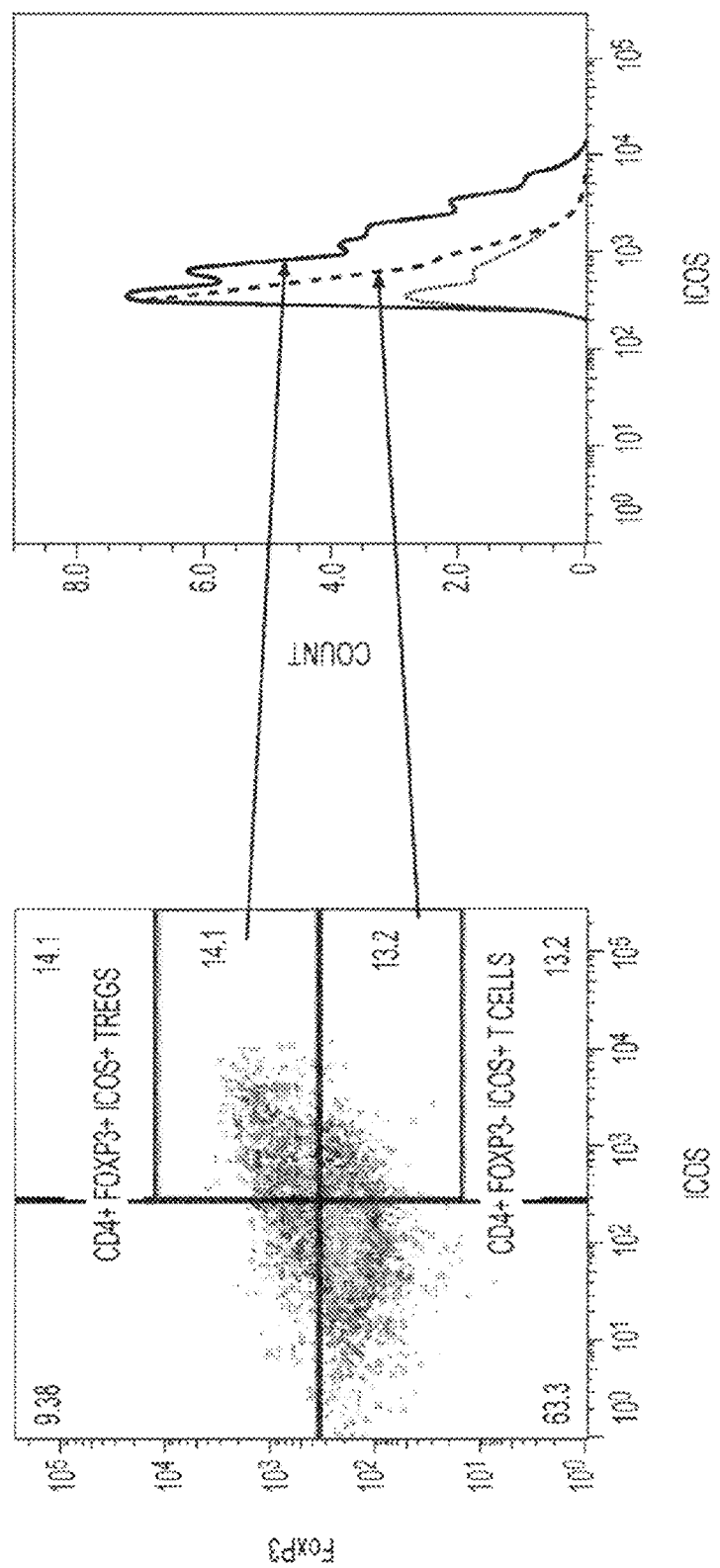

FIGS. 42A-42C: ICOS expression in whole blood and tumor.

Figure 43B:
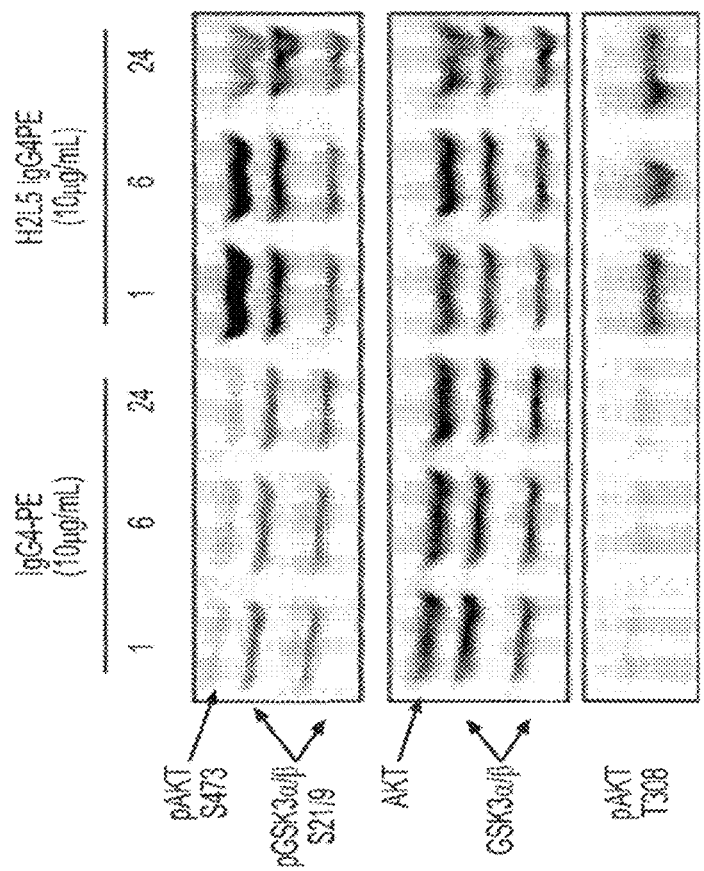
Figure 43A:
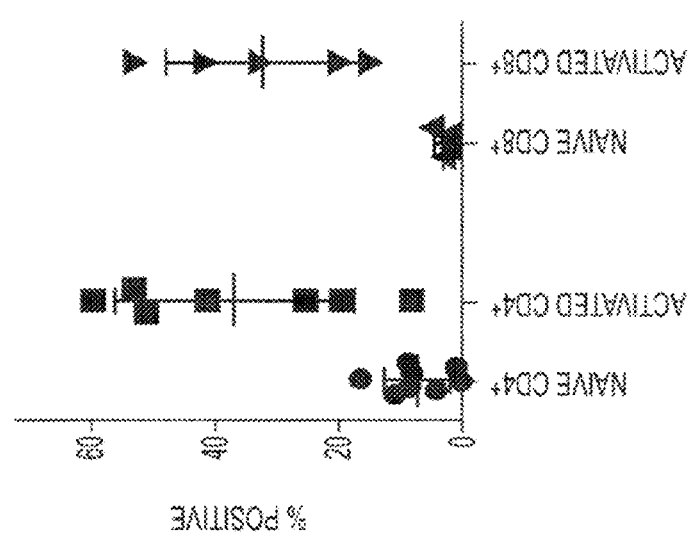

FIGS. 43A-43B: H2L5 hIgG4PE binds to ICOS and induces signaling via AKT phosphorylation.

Figure 44A:
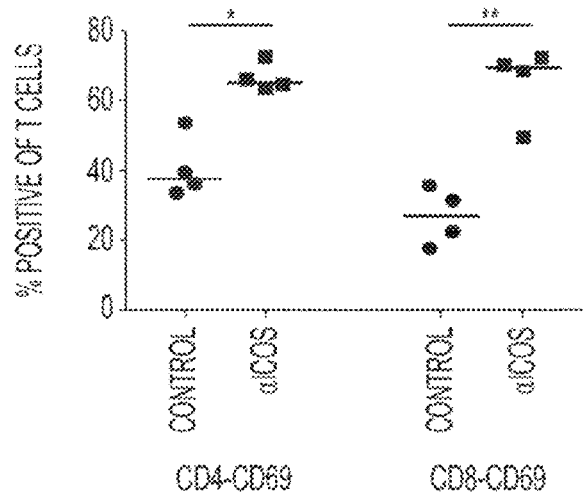
Figure 44B:
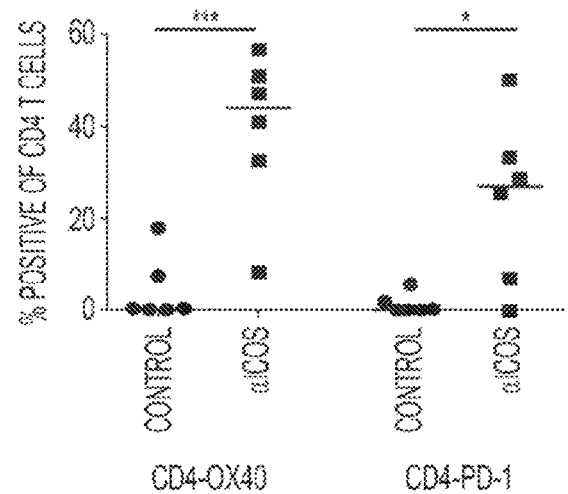
Figure 44C:
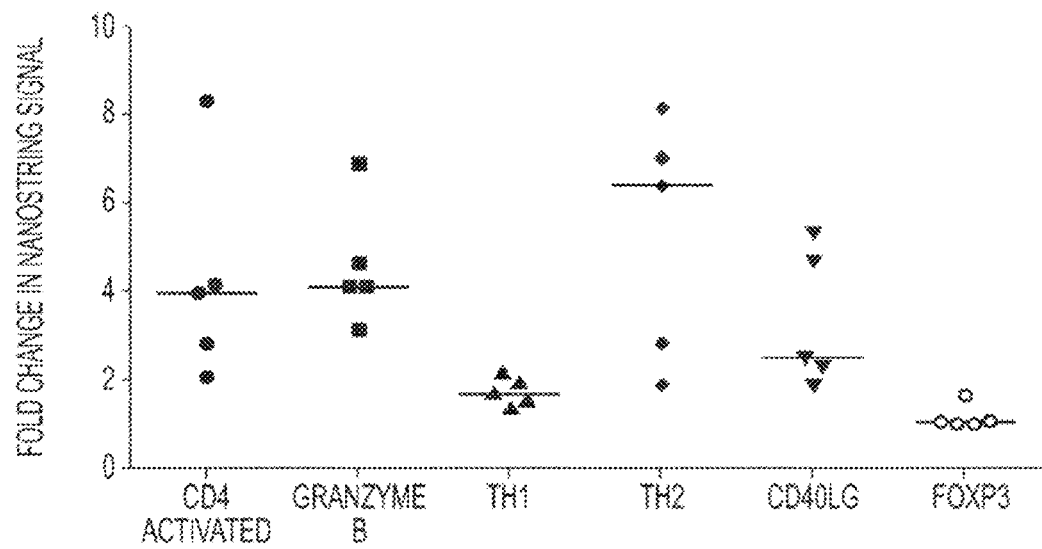

FIGS. 44A-44C: H2L5 hIgG4PE induces T cell activation and Th differentiation in vitro.

FIGS. 45A-45B: Induction of cytokine secretion and increased T cell proliferation by H2L5 hIgG4PE.

Figure 46A:
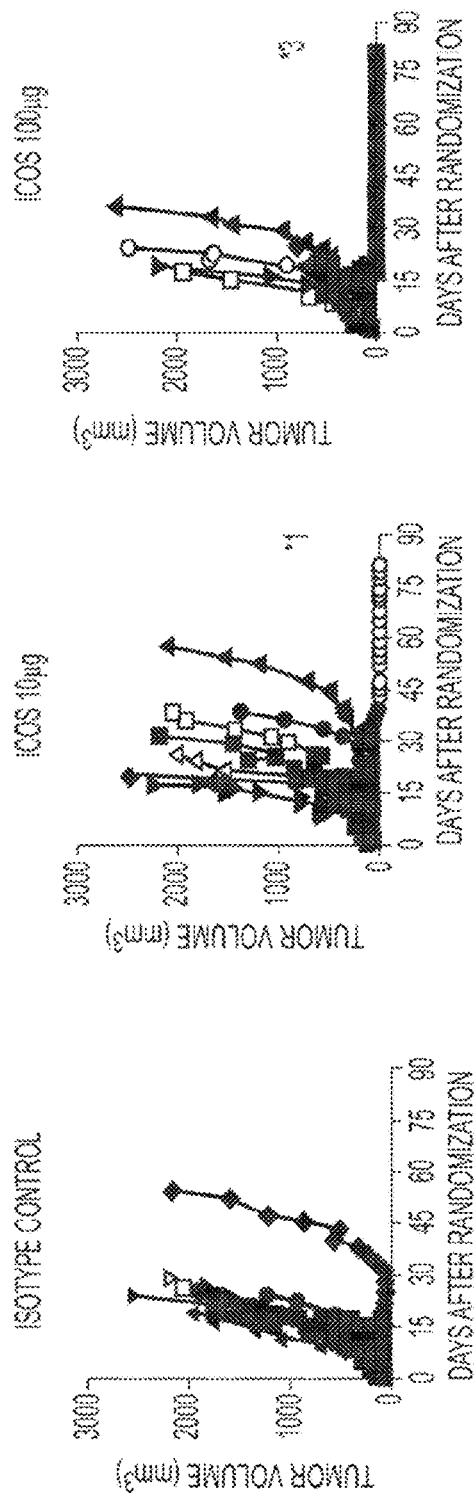
Figure 46B:
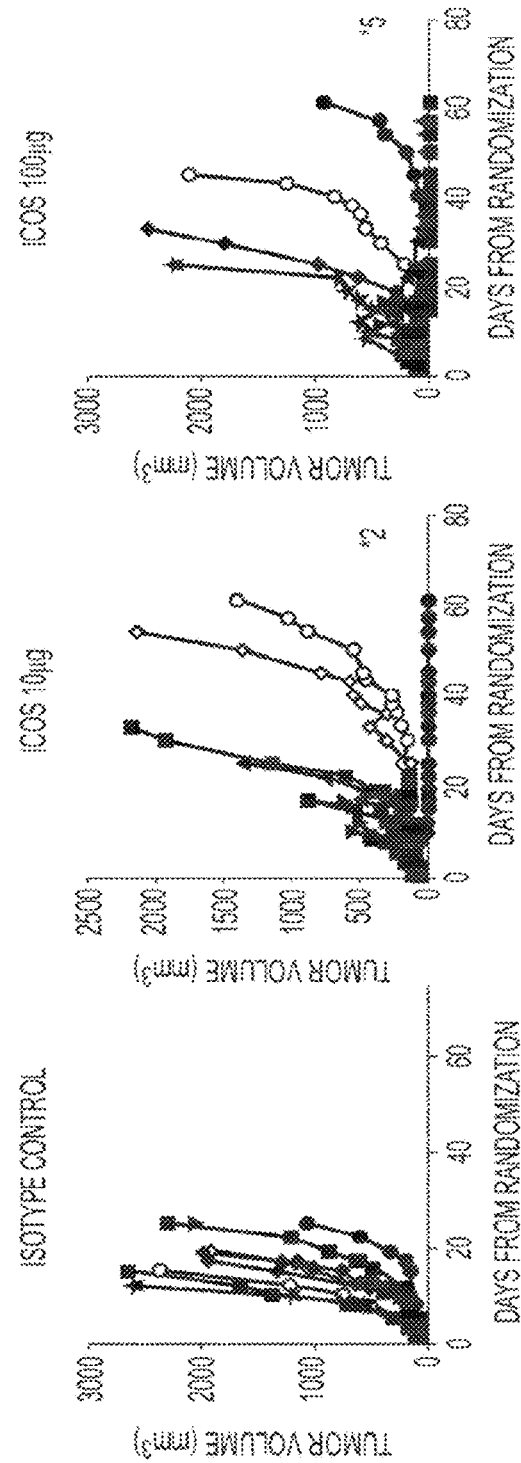

FIGS. 46A-46B: Anti-tumor activity with mouse anti-ICOS antibody.

FIGS. 47A-47D: ICOS induces T cell activation, proliferation and memory changes in vivo.

Figure 48A:
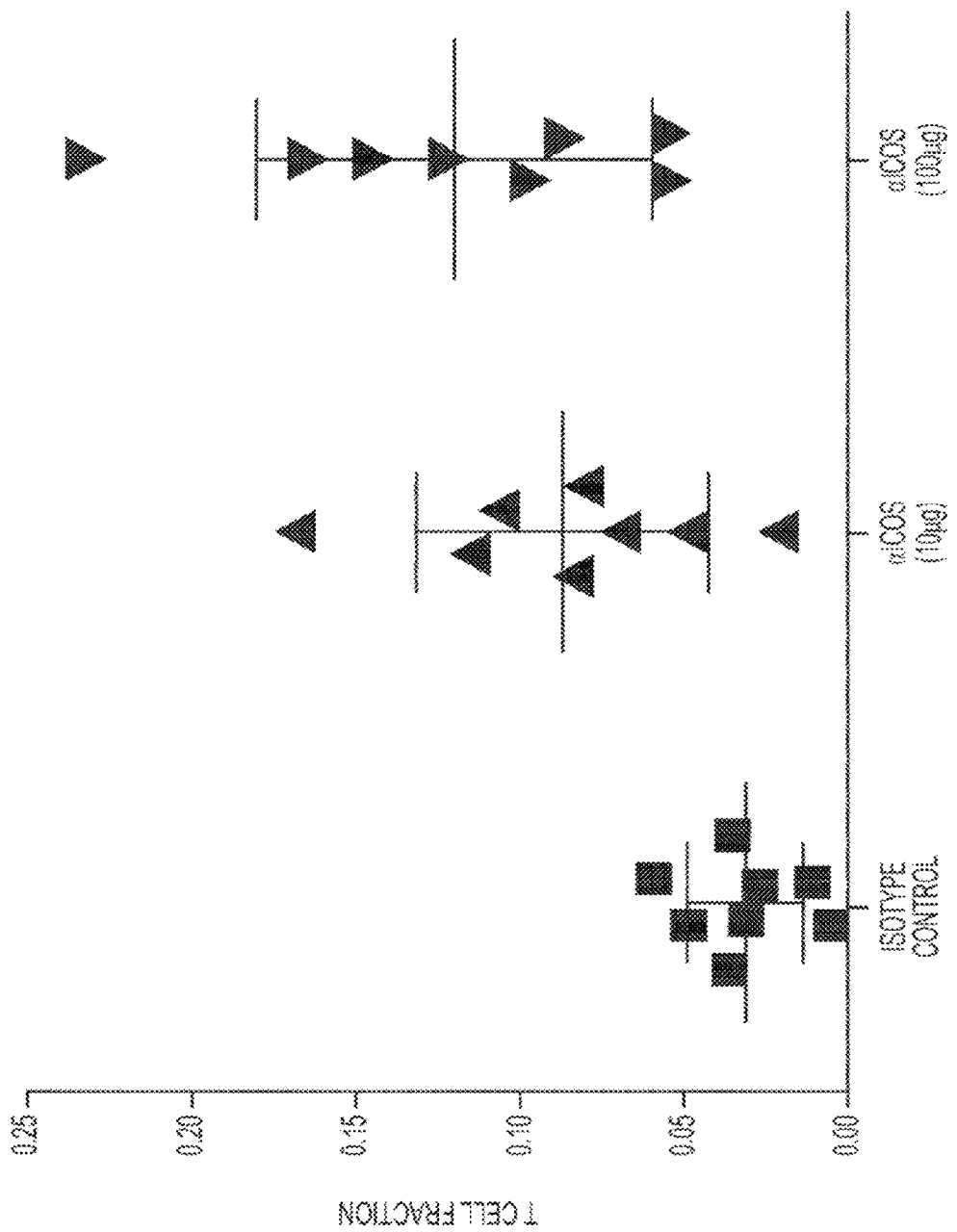
Figure 48B:
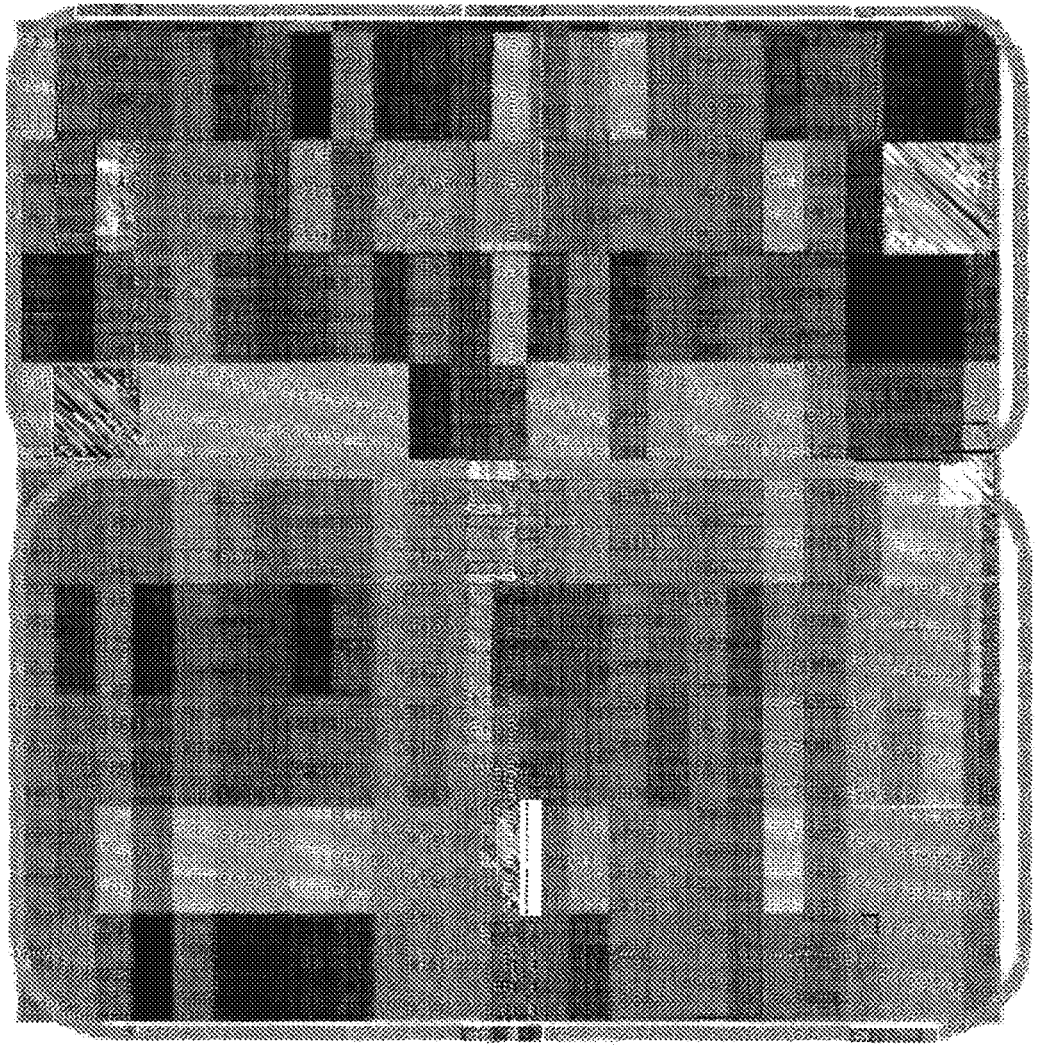

FIGS. 48A-48B: Increase in TIL, IFN-γ gene signature, higher PD-L1 expression with ICOS mAb in vivo.

Figure 49B:
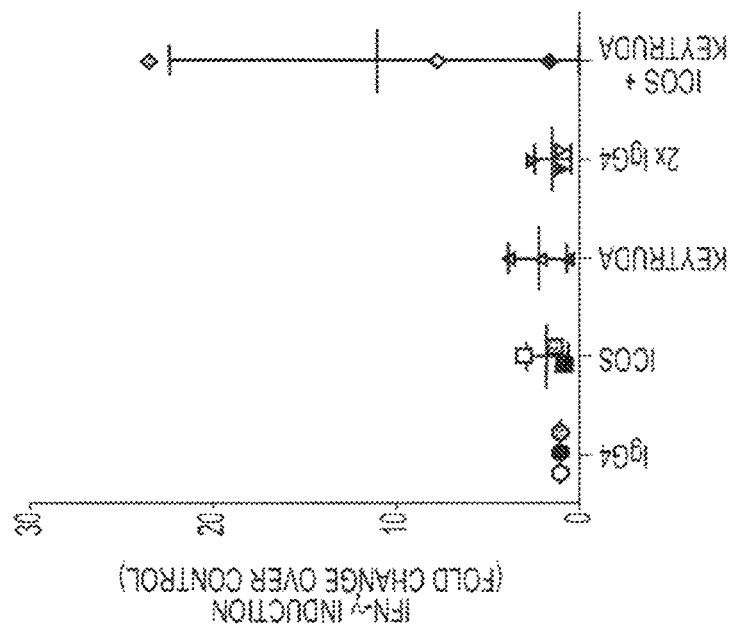
Figure 49A:
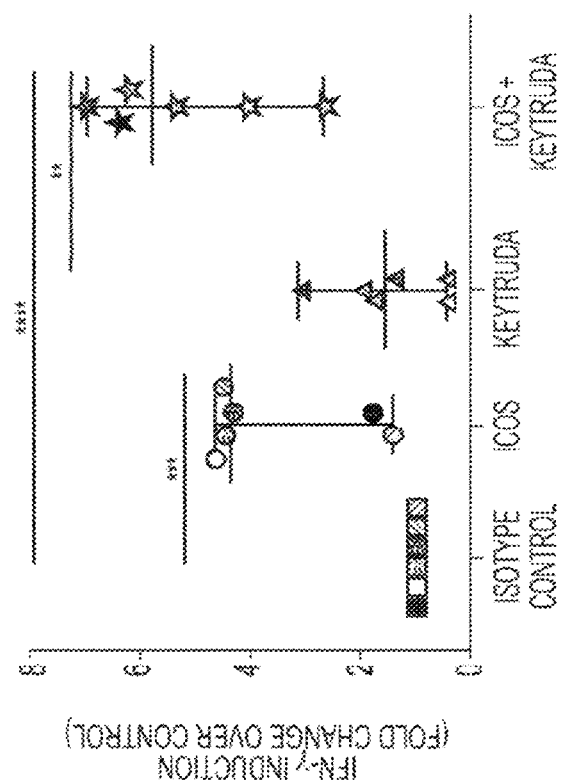

FIGS. 49A-49B: Significant increase in IFNγ secretion with H2L5 hIgG4PE and pembrolizumab combination.

FIGS. 50A-50B: Synergistic anti-tumor activity of ICOS+ PD1 combination.

Figure 51A:
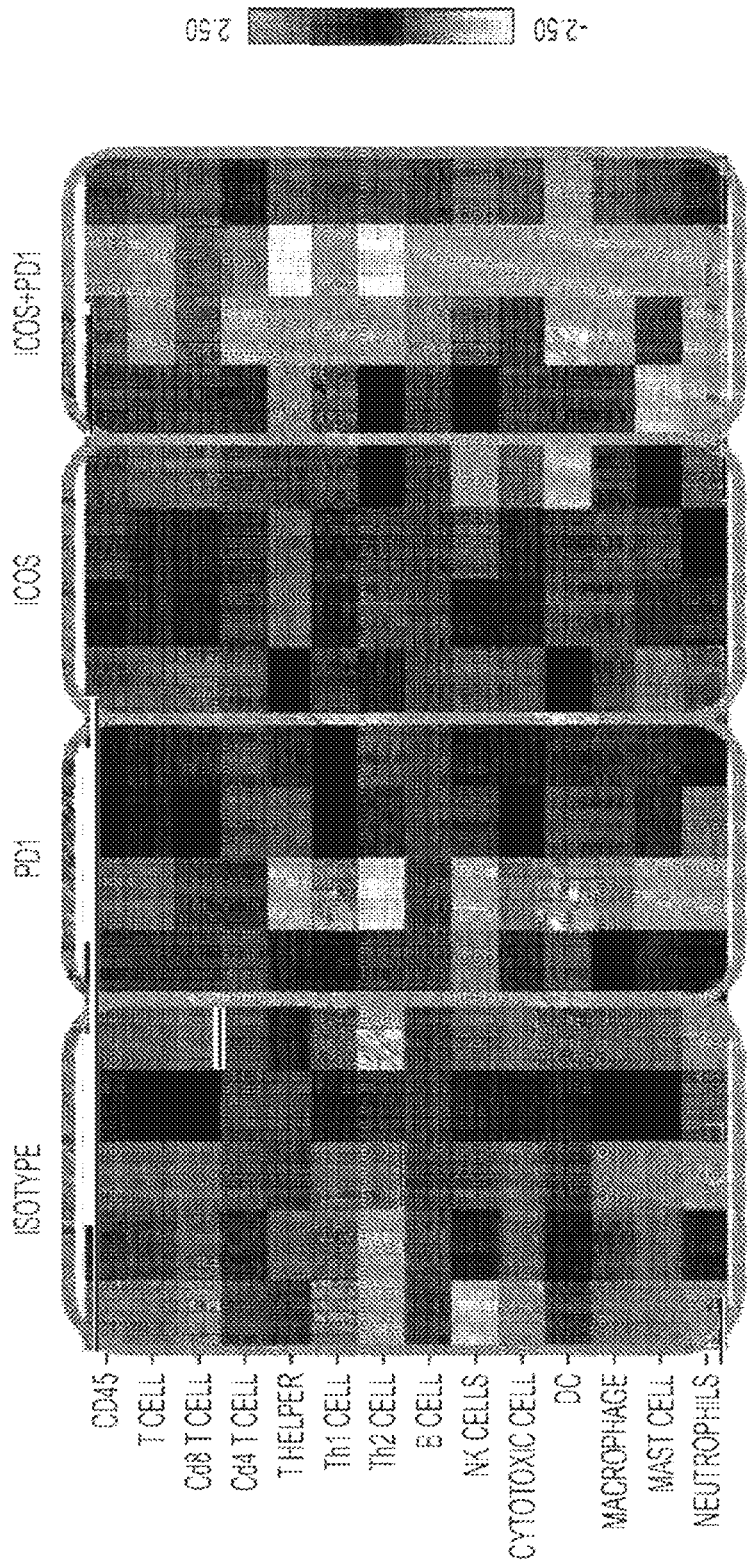
Figures 51B, 51C:
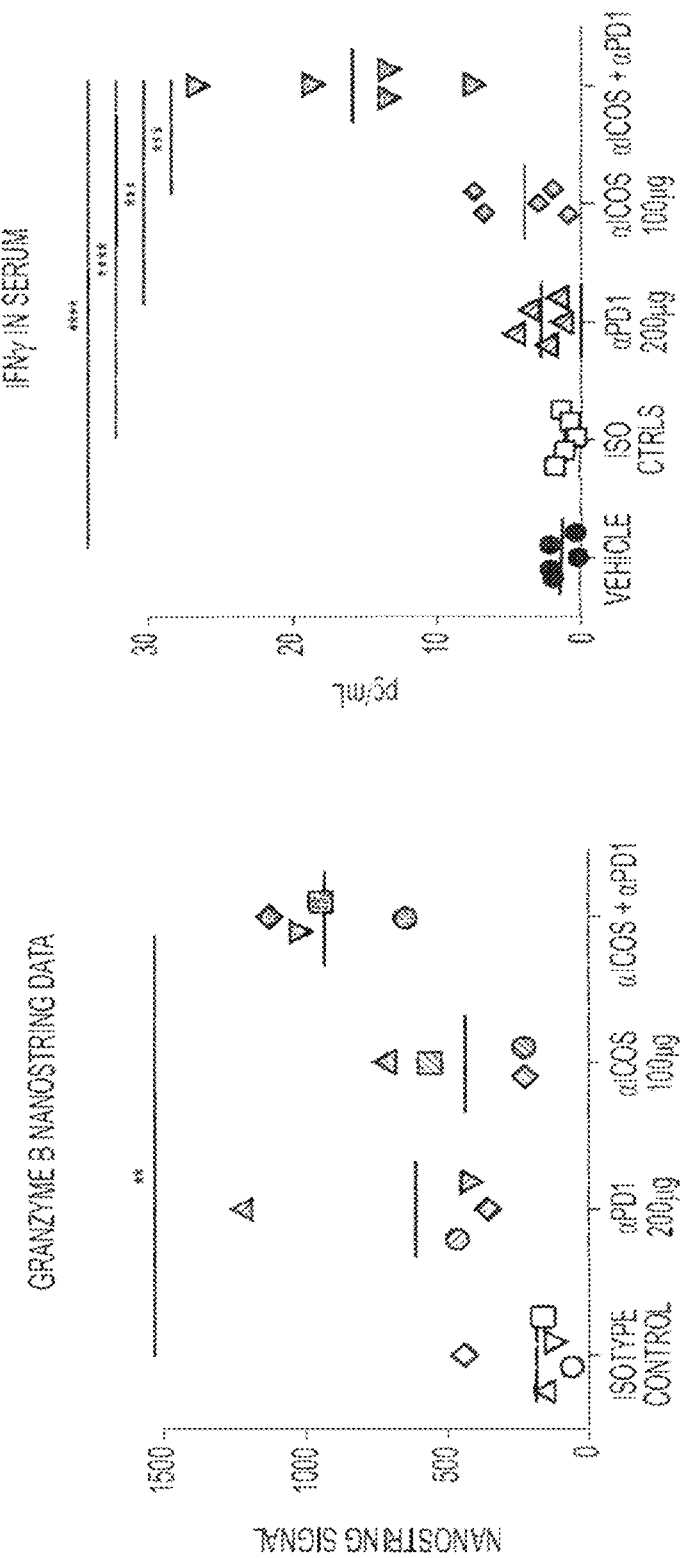

FIGS. 51A-51C: Increase in immune cells, cytotoxicity and IFNγ levels with ICOS+PD1 in vivo.

Figure 52A:
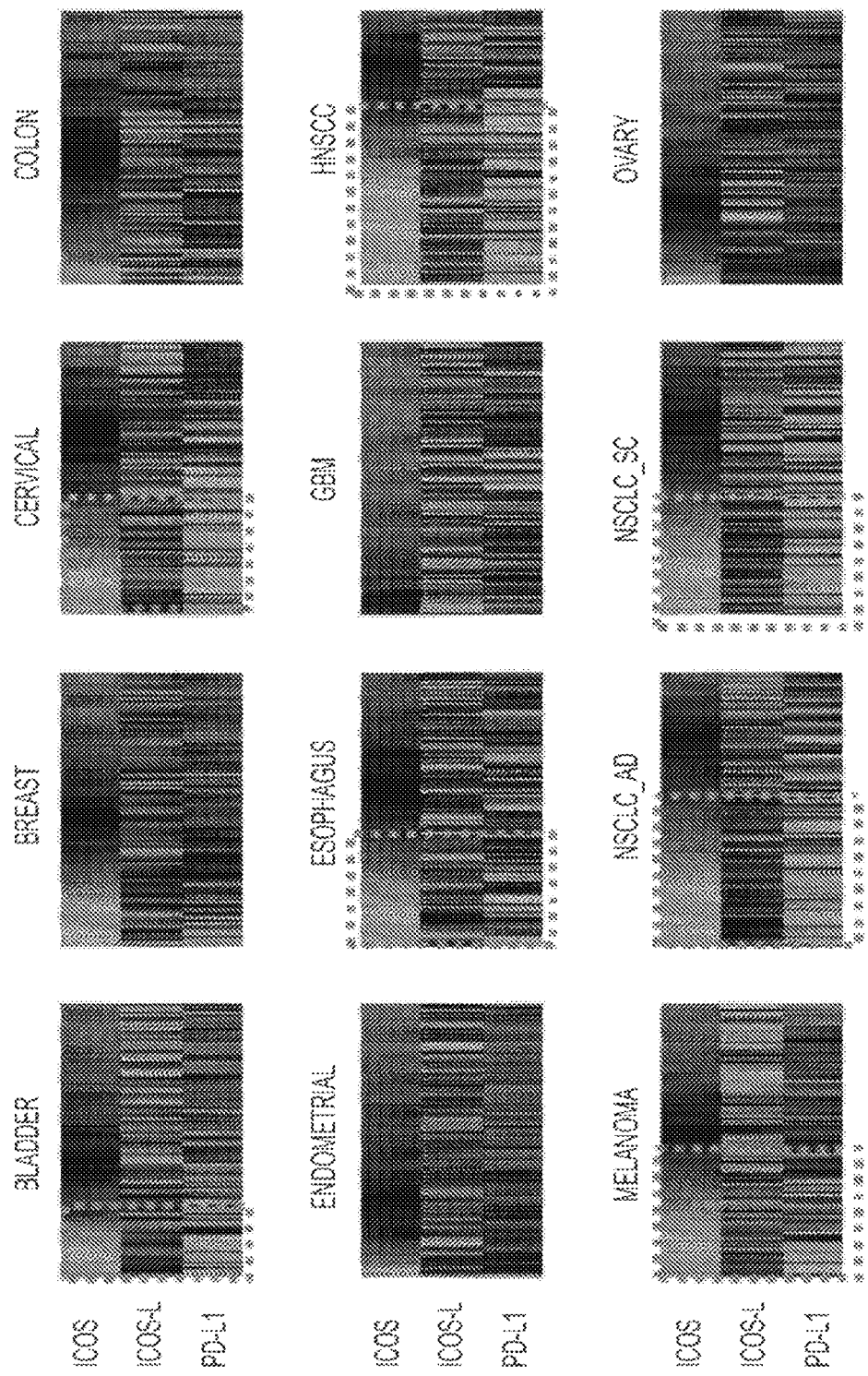
Figure 52B:
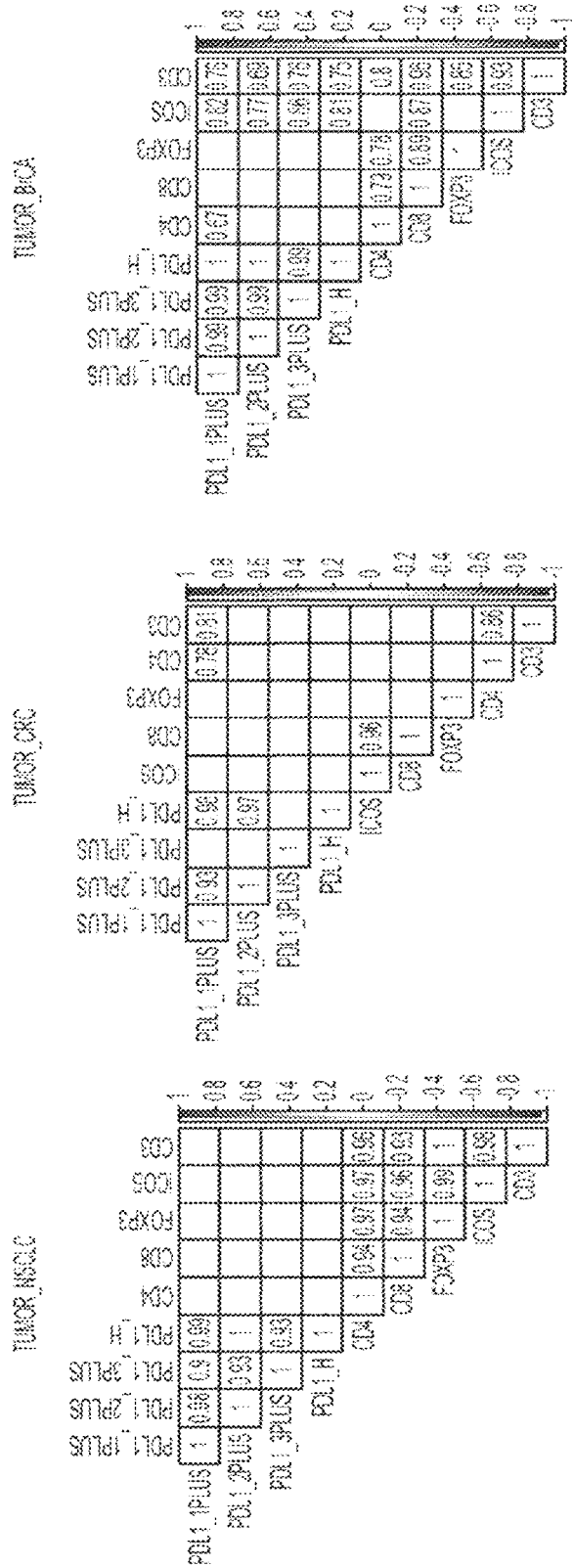

FIGS. 52A-52B: ICOS, ICOS-L and PD-L1 abundance in tumors.

SUMMARY OF THE INVENTION

In one embodiment, the present invention provides methods for increasing expression of ICOS an effector T cell comprising contacting said efffector T cell with an anti-PD-1 antibody.

In one embodiment, the present invention provides methods for decreasing expression of ICOS on a regulatory T cell comprising contacting said regulatory T cell with an anti-PD-1 antibody.

In one embodiment, the present invention provides methods for increasing sensitivity to an agent directed to ICOS in a human, the methods comprising administering to the human an anti-PD1 antibody.

In one embodiment, methods are provided for treating cancer in a human in need thereof comprising administering an anti-PD-1 antibody and an anti-ICOS antibody to said human, wherein the anti-PD-1 antibody increases T cell sensitivity to the ICOS antibody.

In one embodiment, in vitro methods are provided for increasing expression of ICOS on an effector T cell, the method comprising contacting the effector T cell with an anti-PD-1 antibody, thereby increasing the expression of said ICOS on said effector T cell.

In one embodiment, in vitro methods are provided for decreasing expression of ICOS on a regulatory T cell, the method comprising contacting the regulatory T cell with an anti-PD-1 antibody, thereby decreasing expression of said ICOS on said regulatory T cell.

In one embodiment, an anti-PD-1 antibody is provided for use in treating cancer in a human in need thereof, wherein the anti-PD-1 antibody is administered with an anti-ICOS antibody in said human. In one aspect, administration of the anti-PD-1 antibody increases T cell sensitivity to the ICOS antibody in said human.

In one embodiment, an anti-ICOS antibody is provided for use in treating cancer in a human in need thereof, wherein the anti-ICOS antibody is administered with an anti-PD-1 antibody in said human. In one aspect, administration of the anti-PD-1 antibody increases T cell sensitivity to the ICOS antibody in said human.

In one embodiment, an anti-PD-1 antibody and an anti-ICOS antibody are provided for use in treating cancer in a human. In one aspect, administration of the anti-PD-1 antibody increases T cell sensitivity to the ICOS antibody in said human.

In one embodiment, an anti-PD-1 antibody and an anti-ICOS antibody are provided for use in treating sepsis in a human.

In one embodiment, an anti-PD-1 antibody and an anti-ICOS antibody are provided for use in treating chronic infection in a human.

DETAILED DESCRIPTION OF THE INVENTION

Definitions

As used herein "ICOS" means any Inducible T-cell costimulator protein. Pseudonyms for ICOS (Inducible T-cell COStimulator) include AILIM; CD278; CVID1, JTT-1 or JTT-2, MGC39850, or 8F4. ICOS is a CD28-superfamily costimulatory molecule that is expressed on activated T cells. The protein encoded by this gene belongs to the CD28 and CTLA-4 cell-surface receptor family. It forms homodimers and plays an important role in cell-cell signaling, immune responses, and regulation of cell proliferation. Human ICOS is a 199 amino acid protein (Accession No.: UniProtKB-Q9Y6W8 (ICOS_HUMAN).

As used herein "increasing expression of ICOS" means increasing the number of ICOS expressed on a single T cell and/or increasing the number of ICOS-expressing or ICOS-positive T cells in a population of cells. As used herein "decreasing expression of ICOS" means decreasing the number of ICOS expressed on a single T cell and/or decreasing the number of ICOS-expressing or ICOS-positive T cells in a population of cells. In some embodiments, the T cell is an effector T cell. In some embodiments, the T cell is a regulatory T cell.

Activation of ICOS occurs through binding by ICOS-L (B7RP-1/B7-H2). Neither B7-1 nor B7-2 (ligands for CD28 and CTLA4) bind or activate ICOS. However, ICOS-L has been shown to bind weakly to both CD28 and CTLA-4 (Yao S et al., "B7-H2 is a costimulatory ligand for CD28 in human", Immunity, 34(5); 729-40 (2011)). Expression of ICOS appears to be restricted to T cells. ICOS expression levels vary between different T cell subsets and on T cell activation status. ICOS expression has been shown on resting TH17, T follicular helper (TFH) and regulatory T (Treg) cells; however, unlike CD28; it is not highly expressed on naïve $T_H1$ and $T_H2$ effector T cell populations (Paulos C M et al., "The inducible costimulator (ICOS) is critical for the development of human Th17 cells", Sci Transl Med, 2(55); 55ra78 (2010)). ICOS expression is highly induced on CD4+ and CD8+ effector T cells following activation through TCR engagement (Wakamatsu E, et al., "Convergent and divergent effects of costimulatory molecules in conventional and regulatory CD4+ T cells", Proc Natal Acad Sci USA, 110(3); 1023-8 (2013)). Co-stimulatory signalling through ICOS receptor only occurs in T cells receiving a concurrent TCR activation signal (Sharpe A H and Freeman G J. "The B7-CD28 Superfamily", Nat. Rev Immunol, 2(2); 116-26 (2002)). In activated antigen specific T cells, ICOS regulates the production of both $T_H1$ and $T_H2$ cytokines including IFN-γ, TNF-α, IL-10, IL-4, IL-13 and others. ICOS also stimulates effector T cell proliferation, albeit to a lesser extent than CD28 (Sharpe A H and Freeman G J. "The B7-CD28 Superfamily", Nat. Rev Immunol, 2(2); 116-26 (2002)). Antibodies to ICOS and methods of using in the treatment of disease are described, for instance, in WO 2012/131004, US20110243929, and US20160215059. US20160215059 is incorporated by reference herein. Combination treatment of anti-CTLA4 antibodies and ICOS-ligand and anti-ICOS antibodies are described in US 2012251556.

In one embodiment, the ICOS antibodies of the present invention comprise any one or a combination of the following CDRs:

```
                                           (SEQ ID NO: 1)
CDRH1: DYAMH (SEQ ID NO: 2)
CDRH2: LISIYSDHTNYNQKFQG (SEQ ID NO: 3)
CDRH3: NNYGNYGWYFDV
```

```
                                         (SEQ ID NO: 4)
    CDRL1: SASSSVSYMH (SEQ ID NO: 5)
    CDRL2: DTSKLAS (SEQ ID NO: 6)
    CDRL3: FQGSGYPYT
```

In some embodiments, the anti-ICOS antibodies of the present invention comprise a heavy chain variable region having at least 90% sequence identity to SEQ ID NO:7. Suitably, the ICOS binding proteins of the present invention may comprise a heavy chain variable region having about 85%, 86%, 87%, 88%, 89%, 90%, 91%, 92%, 93%, 94%, 95%, 96%, 97%, 98%, 99%, or 100% sequence identity to SEQ ID NO:7.

Humanized Heavy Chain ($V_H$) Variable Region (H2):

```
                                         (SEQ ID NO: 7)
    QVQLVQSGAE VKKPGSSVKV SCKASGYTFT DYAMHWVRQA

PGQGLEWMGL ISIYSDHTNY NQKFQGRVTI TADKSTSTAY

MELSSLRSED TAVYYCGRNN YGNYGWYFDV WGQGTTVTVS

S
```

In one embodiment of the present invention the ICOS antibody comprises CDRL1 (SEQ ID NO:4), CDRL2 (SEQ ID NO:5), and CDRL3 (SEQ ID NO:6) in the light chain variable region having the amino acid sequence set forth in SEQ ID NO:8. ICOS binding proteins of the present invention comprising the humanized light chain variable region set forth in SEQ ID NO:8 are designated as "L5." Thus, an ICOS binding protein of the present invention comprising the heavy chain variable region of SEQ ID NO:7 and the light chain variable region of SEQ ID NO:8 can be designated as H2L5 herein.

In some embodiments, the ICOS binding proteins of the present invention comprise a light chain variable region having at least 90% sequence identity to the amino acid sequence set forth in SEQ ID NO:8. Suitably, the ICOS binding proteins of the present invention may comprise a light chain variable region having about 85%, 86%, 87%, 88%, 89%, 90%, 91%, 92%, 93%, 94%, 95%, 10 96%, 97%, 98%, 99%, or 100% sequence identity to SEQ ID NO:8.

Humanized Light Chain ($V_L$) Variable Region (L5)

```
                                         (SEQ ID NO: 8)
    EIVLTQSPAT LSLSPGERAT LSCSASSSVS YMHWYQQKPG

QAPRLLIYDT SKLASGIPAR FSGSGSGTDY TLTISSLEPE

DFAVYYCFQG SGYPYTFGQG TKLEIK
```

CDRs or minimum binding units may be modified by at least one amino acid substitution, deletion or addition, wherein the variant antigen binding protein substantially retains the biological characteristics of the unmodified protein, such as an antibody comprising SEQ ID NO:7 and SEQ ID NO:8.

It will be appreciated that each of CDR H1, H2, H3, L1, L2, L3 may be modified alone or in combination with any other CDR, in any permutation or combination. In one embodiment, a CDR is modified by the substitution, deletion or addition of up to 3 amino acids, for example 1 or 2 amino acids, for example 1 amino acID Typically, the modification is a substitution, particularly a conservative substitution, for example as shown in Table 1 below.

TABLE 1

| Side chain | Members |
| --- | --- |
| Hydrophobic | Met, Ala, Val, Leu, Ile |
| Neutral hydrophilic | Cys, Ser, Thr |
| Acidic | Asp, Glu |
| Basic | Asn, Gln, His, Lys, Arg |
| Residues that influence chain orientation | Gly, Pro |
| Aromatic | Trp, Tyr, Phe |

The subclass of an antibody in part determines secondary effector functions, such as complement activation or Fc receptor (FcR) binding and antibody dependent cell cytotoxicity (ADCC) (Huber, et al., Nature 229(5284): 419-20 (1971); Brunhouse, et al., Mol Immunol 16(11): 907-17 (1979)). In identifying the optimal type of antibody for a particular application, the effector functions of the antibodies can be taken into account. For example, hIgG1 antibodies have a relatively long half life, are very effective at fixing complement, and they bind to both FcγRI and FcγRII. In contrast, human IgG4 antibodies have a shorter half life, do not fix complement and have a lower affinity for the FcRs. Replacement of serine 228 with a proline (S228P) in the Fc region of IgG4 reduces heterogeneity observed with hIgG4 and extends the serum half life (Kabat, et al., "Sequences of proteins of immunological interest" 5.sup.th Edition (1991); Angal, et al., Mol Immunol 30(1): 105-8 (1993)). A second mutation that replaces leucine 235 with a glutamic acid (L235E) eliminates the residual FcR binding and complement binding activities (Alegre, et al., J Immunol 148(11): 3461-8 (1992)). The resulting antibody with both mutations is referred to as IgG4PE. The numbering of the hIgG4 amino acids was derived from EU numbering reference: Edelman, G. M. et al., Proc. Natl. Acad. USA, 63, 78-85 (1969). PMID: 5257969. In one embodiment of the present invention the ICOS antibody is an IgG4 isotype. In one embodiment, the ICOS antibody comprises an IgG4 Fc region comprising the replacement S228P and L235E may have the designation IgG4PE.

As used herein "ICOS-L" and "ICOS Ligand" are used interchangeably and refer to the membrane bound natural ligand of human ICOS. ICOS ligand is a protein that in humans is encoded by the ICOSLG gene. ICOSLG has also been designated as CD275 (cluster of differentiation 275). Pseudonyms for ICOS-L include B7RP-1 and B7-H2.

The protein Programmed Death 1 (PD-1) is an inhibitory member of the CD28 family of receptors, that also includes CD28, CTLA-4, ICOS and BTLA. PD-1 is expressed on activated B cells, T cells, and myeloid cells (Agata et al., supra; Okazaki et al. (2002) Curr. Opin. Immunol 14:391779-82; Bennett et al. (2003) J Immunol 170:711-8) The initial members of the family, CD28 and ICOS, were discovered by functional effects on augmenting T cell proliferation following the addition of monoclonal antibodies (Hutloff et al. (1999) Nature 397:263-266; Hansen et al. (1980) Immunogenics 10:247-260). PD-1 was discovered through screening for differential expression in apototic cells (Ishida et al. (1992) EMBO J 11:3887-95) The other members of the family, CTLA-4, and BTLA were discovered through screening for differential expression in cytotoxic T lymphocytes and TH1 cells, respectively. CD28, ICOS and CTLA-4 all have an unpaired cysteine residue allowing for homodimerization. In contrast, PD-1 is suggested to exist as a monomer, lacking the unpaired cysteine residue characteristic in other CD28 family members. PD-1 antibodies and methods of using in treatment of disease are described in U.S. Pat. Nos. 7,595,048; 8,168,179; 8,728,474; 7,722,868; 8,008,449; 7,488,802; 7,521,051; 8,088,905; 8,168,757; 8,354,509; and US Publication Nos. US20110171220; US20110171215; and US20110271358. Combinations of CTLA-4 and PD-1 antibodies are described in U.S. Pat. No. 9,084,776.

Opdivo/nivolumab is a fully human monoclonal antibody marketed by Bristol Myers Squibb directed against the negative immunoregulatory human cell surface receptor PD-1 (programmed death-1 or programmed cell death-1/PCD-1) with immunopotentiation activity. Nivolumab binds to and blocks the activation of PD-1, an Ig superfamily transmembrane protein, by its ligands PD-L1 and PD-L2, resulting in the activation of T-cells and cell-mediated immune responses against tumor cells or pathogens. Activated PD-1 negatively regulates T-cell activation and effector function through the suppression of P13k/Akt pathway activation. Other names for nivolumab include: BMS-936558, MDX-1106, and ONO-4538. The amino acid sequence for nivolumab and methods of using and making are disclosed in U.S. Pat. No. 8,008,449.

KEYTRUDA/pembrolizumab is an anti-PD-1 antibodies marketed for the treatment of lung cancer by Merck. The amino acid sequence of pembrolizumab and methods of using are disclosed in U.S. Pat. No. 8,168,757.

CD134, also known as OX40, is a member of the TNFR-superfamily of receptors which is not constitutively expressed on resting naïve T cells, unlike CD28. OX40 is a secondary costimulatory molecule, expressed after 24 to 72 hours following activation; its ligand, OX40L, is also not expressed on resting antigen presenting cells, but is following their activation. Expression of OX40 is dependent on full activation of the T cell; without CD28, expression of OX40 is delayed and of fourfold lower levels. OX40/OX40-ligand (OX40 Receptor)/(OX40L) are a pair of costimulatory molecules critical for T cell proliferation, survival, cytokine production, and memory cell generation. Early in vitro experiments demonstrated that signaling through OX40 on $CD4^+$ T cells lead to TH2, but not TH1 development. These results were supported by in vivo studies showing that blocking OX40/OX40L interaction prevented the induction and maintenance of TH2-mediated allergic immune responses. However, blocking OX40/OX40L interaction ameliorates or prevents TH1-mediated diseases. Furthermore, administration of soluble OX40L or gene transfer of OX40L into tumors were shown to strongly enhance anti-tumor immunity in mice. Recent studies also suggest that OX40/OX40L may play a role in promoting CD8 T cell-mediated immune responses. As discussed herein, OX40 signaling blocks the inhibitory function of $CD4^+$ $CD25^+$ naturally occurring regulatory T cells and the OX40/OX40L pair plays a critical role in the global regulation of peripheral immunity versus tolerance. OX-40 antibodies, OX-40 fusion proteins and methods of using them are disclosed in U.S. Pat. Nos. 7,504,101; 7,758,852; 7,858,765; 7,550,140; 7,960,515; and 9,006,399 and international publications: WO 2003082919; WO 2003068819; WO 2006063067; WO 2007084559; WO 2008051424; WO2012027328; and WO2013028231.

T cell immunoglobulin and mucin domain-containing molecule 3 (TIM3) is an immunoglobulin (Ig) superfamily member, expressed on Th1 cells. TIM3 has been shown to play a role in modulating the immune response of Th1 cells, and reducing inflammation in a number of conditions. TIM3 is also expressed on cancer cells, and on cancer stem cells (CSCs), which are cells that can give rise to additional cancer cells. Antibodies to TIM3 and methods of using in the treatment of disease are described in U.S. Pat. Nos. 7,470,428 and 8,101,176.

CTLA-4 is a T cell surface molecule that was originally identified by differential screening of a murine cytolytic T cell cDNA library (Brunet et al., Nature 328:267-270 (1987)). CTLA-4 is also a member of the immunoglobulin (Ig) superfamily; CTLA-4 comprises a single extracellular Ig domain. CTLA-4 transcripts have been found in T cell populations having cytotoxic activity, suggesting that CTLA-4 might function in the cytolytic response (Brunet et al., supra; Brunet et al., Immunol. Rev. 103-(21-36 (1988)). Researchers have reported the cloning and mapping of a gene for the human counterpart of CTLA-4 (Dariavach et al., Eur. J. Immunol. 18:1901-1905 (1988)) to the same chromosomal region (2q33-34) as CD28 (Lafage-Pochitaloff et al., Immunogenetics 31:198-201 (1990)). Sequence comparison between this human CTLA-4 DNA and that encoding CD28 proteins reveals significant homology of sequence, with the greatest degree of homology in the juxtamembrane and cytoplasmic regions (Brunet et al., 1988, supra; Dariavach et al., 1988, supra). Yervoy (ipilimumab) is a fully human CTLA-4 antibody marketed by Bristol Myers Squibb. The protein structure of ipilimumab and methods are using are described in U.S. Pat. Nos. 6,984,720 and 7,605,238.

Suitable anti-CTLA4 antibodies for use in the methods of the invention, include, without limitation, anti-CTLA4 antibodies, human anti-CTLA4 antibodies, mouse anti-CTLA4 antibodies, mammalian anti-CTLA4 antibodies, humanized anti-CTLA4 antibodies, monoclonal anti-CTLA4 antibodies, polyclonal anti-CTLA4 antibodies, chimeric anti-CTLA4 antibodies, ipilimumab, tremelimumab, anti-CD28 antibodies, anti-CTLA4 adnectins, anti-CTLA4 domain antibodies, single chain anti-CTLA4 fragments, heavy chain anti-CTLA4 fragments, light chain anti-CTLA4 fragments, inhibitors of CTLA4 that agonize the co-stimulatory pathway, the antibodies disclosed in PCT Publication No. WO 2001/014424, the antibodies disclosed in PCT Publication No. WO 2004/035607, the antibodies disclosed in U.S. Published Application No. US 2005/0201994, and the antibodies disclosed in granted European Patent No. EP1212422B1. Additional CTLA-4 antibodies are described in U.S. Pat. Nos. 5,811,097, 5,855,887, 6,051,227, and 6,984,720; in PCT Publication Nos. WO 01/14424 and WO 00/37504; and in U.S. Publication Nos. US 2002/0039581 and US 2002/086014. Other anti-CTLA-4 antibodies that can be used in a method of the present invention include, for example, those disclosed in: WO 98/42752; U.S. Pat. Nos. 6,682,736 and 6,207,156; Hurwitz et al., Proc. Natl. Acad. Sci. USA, 95(17):10067-10071 (1998); Camacho et al., J. Clin. Oncology, 22(145):Abstract No. 2505 (2004) (antibody CP-675206); Mokyr et al., Cancer Res., 58:5301-5304 (1998), and U.S. Pat. Nos. 5,977,318, 6,682,736, 7,109,003, and 7,132,281.

As used herein the term "agonist" refers to an antigen binding protein including but not limited to an antibody, which upon contact with a co-signalling receptor causes one or more of the following (1) stimulates or activates the receptor, (2) enhances, increases or promotes, induces or prolongs an activity, function or presence of the receptor and/or (3) enhances, increases, promotes or induces the expression of the receptor. Agonist activity can be measured in vitro by various assays know in the art such as, but not limited to, measurement of cell signalling, cell proliferation, immune cell activation markers, cytokine production. Agonist activity can also be measured in vivo by various assays that measure surrogate end points such as, but not limited to the measurement of T cell proliferation or cytokine production.

As used herein the term "antagonist" refers to an antigen binding protein including but not limited to an antibody, which upon contact with a co-signalling receptor causes one or more of the following (1) attenuates, blocks or inactivates the receptor and/or blocks activation of a receptor by its natural ligand, (2) reduces, decreases or shortens the activity, function or presence of the receptor and/or (3) reduces, decrease, abrogates the expression of the receptor. Antagonist activity can be measured in vitro by various assays know in the art such as, but not limited to, measurement of an increase or decrease in cell signalling, cell proliferation, immune cell activation markers, cytokine production. Antagonist activity can also be measured in vivo by various assays that measure surrogate end points such as, but not limited to the measurement of T cell proliferation or cytokine production.

As used herein the term "cross competes for binding" refers to any agent such as an antibody that will compete for binding to a target with any of the agents of the present invention. Competition for binding between two antibodies can be tested by various methods known in the art including Flow cytometry, Meso Scale Discovery and ELISA. Binding can be measured directly, meaning two or more binding proteins can be put in contact with a co-signalling receptor and bind may be measured for one or each. Alternatively, binding of molecules or interest can be tested against the binding or natural ligand and quantitatively compared with each other.

The term "binding protein" as used herein refers to antibodies and other protein constructs, such as domains, which are capable of binding to and antigen.

The term "antibody" is used herein in the broadest sense to refer to molecules with an immunoglobulin-like domain (for example IgG, IgM, IgA, IgD or IgE) and includes monoclonal, recombinant, polyclonal, chimeric, human, humanized, multispecific antibodies, including bispecific antibodies, and heteroconjugate antibodies; a single variable domain (e.g., $V_H$, $V_{HH}$, $V_L$, domain antibody (dAb™)), antigen binding antibody fragments, Fab, F(ab')$_2$, Fv, disulphide linked Fv, single chain Fv, disulphide-linked scFv, diabodies, TANDABS™, etc. and modified versions of any of the foregoing.

Alternative antibody formats include alternative scaffolds in which the one or more CDRs of the antigen binding protein can be arranged onto a suitable non-immunoglobulin protein scaffold or skeleton, such as an affibody, a SpA scaffold, an LDL receptor class A domain, an avimer or an EGF domain.

The term "domain" refers to a folded protein structure which retains its tertiary structure independent of the rest of the protein. Generally domains are responsible for discrete functional properties of proteins and in many cases may be added, removed or transferred to other proteins without loss of function of the remainder of the protein and/or of the domain.

The term "single variable domain" refers to a folded polypeptide domain comprising sequences characteristic of antibody variable domains. It therefore includes complete antibody variable domains such as $V_H$, $V_{HH}$ and $V_L$ and modified antibody variable domains, for example, in which one or more loops have been replaced by sequences which are not characteristic of antibody variable domains, or antibody variable domains which have been truncated or comprise N- or C-terminal extensions, as well as folded fragments of variable domains which retain at least the binding activity and specificity of the full-length domain. A single variable domain is capable of binding an antigen or epitope independently of a different variable region or domain. A "domain antibody" or "dAb(™)" may be considered the same as a "single variable domain". A single variable domain may be a human single variable domain, but also includes single variable domains from other species such as rodent nurse shark and Camelid $V_{HH}$ dAbs™. Camelid $V_{HH}$ are immunoglobulin single variable domain polypeptides that are derived from species including camel, llama, alpaca, dromedary, and guanaco, which produce heavy chain antibodies naturally devoid of light chains. Such $V_{HH}$ domains may be humanized according to standard techniques available in the art, and such domains are considered to be "single variable domains". As used herein $V_H$ includes camelid $V_{HH}$ domains.

An antigen binding fragment may be provided by means of arrangement of one or more CDRs on non-antibody protein scaffolds. "Protein Scaffold" as used herein includes but is not limited to an immunoglobulin (Ig) scaffold, for example an IgG scaffold, which may be a four chain or two chain antibody, or which may comprise only the Fc region of an antibody, or which may comprise one or more constant regions from an antibody, which constant regions may be of human or primate origin, or which may be an artificial chimera of human and primate constant regions.

The protein scaffold may be an Ig scaffold, for example an IgG, or IgA scaffold. The IgG scaffold may comprise some or all the domains of an antibody (i.e. CH1, CH2, CH3, $V_H$, $V_L$). The antigen binding protein may comprise an IgG scaffold selected from IgG1, IgG2, IgG3, IgG4 or IgG4PE. For example, the scaffold may be IgG1. The scaffold may consist of, or comprise, the Fc region of an antibody, or is a part thereof.

Affinity is the strength of binding of one molecule, e.g. an antigen binding protein of the invention, to another, e.g. its target antigen, at a single binding site. The binding affinity of an antigen binding protein to its target may be determined by equilibrium methods (e.g. enzyme-linked immunoabsorbent assay (ELISA) or radioimmunoassay (RIA)), or kinetics (e.g. BIACORE™ analysis). For example, the Biacore™ methods described in Example 5 may be used to measure binding affinity.

Avidity is the sum total of the strength of binding of two molecules to one another at multiple sites, e.g. taking into account the valency of the interaction.

By "isolated" it is intended that the molecule, such as an antigen binding protein or nucleic acid, is removed from the environment in which it may be found in nature. For example, the molecule may be purified away from substances with which it would normally exist in nature. For example, the mass of the molecule in a sample may be 95% of the total mass.

The term "expression vector" as used herein means an isolated nucleic acid which can be used to introduce a nucleic acid of interest into a cell, such as a eukaryotic cell or prokaryotic cell, or a cell free expression system where the nucleic acid sequence of interest is expressed as a peptide chain such as a protein. Such expression vectors may be, for example, cosmids, plasmids, viral sequences, transposons, and linear nucleic acids comprising a nucleic acid of interest. Once the expression vector is introduced into a cell or cell free expression system (e.g., reticulocyte lysate) the protein encoded by the nucleic acid of interest is produced by the transcription/translation machinery. Expression vectors within the scope of the disclosure may provide necessary elements for eukaryotic or prokaryotic expression and include viral promoter driven vectors, such as CMV promoter driven vectors, e.g., pcDNA3.1, pCEP4, and their derivatives, Baculovirus expression vectors, Drosophila expression vectors, and expression vectors that are driven by mammalian gene promoters, such as human Ig gene promoters. Other examples include prokaryotic expression vectors, such as T7 promoter driven vectors, e.g., pET41, lactose promoter driven vectors and arabinose gene promoter driven vectors. Those of ordinary skill in the art will recognize many other suitable expression vectors and expression systems.

The term "recombinant host cell" as used herein means a cell that comprises a nucleic acid sequence of interest that was isolated prior to its introduction into the cell. For example, the nucleic acid sequence of interest may be in an expression vector while the cell may be prokaryotic or eukaryotic. Exemplary eukaryotic cells are mammalian cells, such as but not limited to, COS-1, COS-7, HEK293, BHK21, CHO, BSC-1, HepG2, 653, SP2/0, NS0, 293, HeLa, myeloma, lymphoma cells or any derivative thereof. Most preferably, the eukaryotic cell is a HEK293, NS0, SP2/0, or CHO cell. E. coli is an exemplary prokaryotic cell. A recombinant cell according to the disclosure may be generated by transfection, cell fusion, immortalization, or other procedures well known in the art. A nucleic acid sequence of interest, such as an expression vector, transfected into a cell may be extrachromasomal or stably integrated into the chromosome of the cell.

A "chimeric antibody" refers to a type of engineered antibody which contains a naturally-occurring variable region (light chain and heavy chains) derived from a donor antibody in association with light and heavy chain constant regions derived from an acceptor antibody.

A "humanized antibody" refers to a type of engineered antibody having its CDRs derived from a non-human donor immunoglobulin, the remaining immunoglobulin-derived parts of the molecule being derived from one or more human immunoglobulin(s). In addition, framework support residues may be altered to preserve binding affinity (see, e.g., Queen et al. Proc. Natl Acad Sci USA, 86:10029-10032 (1989), Hodgson, et al., Bio/Technology, 9:421 (1991)). A suitable human acceptor antibody may be one selected from a conventional database, e.g., the KABAT™ database, Los Alamos database, and Swiss Protein database, by homology to the nucleotide and amino acid sequences of the donor antibody. A human antibody characterized by a homology to the framework regions of the donor antibody (on an amino acid basis) may be suitable to provide a heavy chain constant region and/or a heavy chain variable framework region for insertion of the donor CDRs. A suitable acceptor antibody capable of donating light chain constant or variable framework regions may be selected in a similar manner. It should be noted that the acceptor antibody heavy and light chains are not required to originate from the same acceptor antibody. The prior art describes several ways of producing such humanized antibodies—see, for example, EP-A-0239400 and EP-A-054951.

The term "fully human antibody" includes antibodies having variable and constant regions (if present) derived from human germline immunoglobulin sequences. The human sequence antibodies of the invention may include amino acid residues not encoded by human germline immunoglobulin sequences (e.g., mutations introduced by random or site-specific mutagenesis in vitro or by somatic mutation in vivo). Fully human antibodies comprise amino acid sequences encoded only by polynucleotides that are ultimately of human origin or amino acid sequences that are identical to such sequences. As meant herein, antibodies encoded by human immunoglobulin-encoding DNA inserted into a mouse genome produced in a transgenic mouse are fully human antibodies since they are encoded by DNA that is ultimately of human origin. In this situation, human immunoglobulin-encoding DNA can be rearranged (to encode an antibody) within the mouse, and somatic mutations may also occur. Antibodies encoded by originally human DNA that has undergone such changes in a mouse are fully human antibodies as meant herein. The use of such transgenic mice makes it possible to select fully human antibodies against a human antigen. As is understood in the art, fully human antibodies can be made using phage display technology wherein a human DNA library is inserted in phage for generation of antibodies comprising human germline DNA sequence.

The term "donor antibody" refers to an antibody that contributes the amino acid sequences of its variable regions, CDRs, or other functional fragments or analogs thereof to a first immunoglobulin partner. The donor, therefore, provides the altered immunoglobulin coding region and resulting expressed altered antibody with the antigenic specificity and neutralising activity characteristic of the donor antibody.

The term "acceptor antibody" refers to an antibody that is heterologous to the donor antibody, which contributes all (or any portion) of the amino acid sequences encoding its heavy and/or light chain framework regions and/or its heavy and/or light chain constant regions to the first immunoglobulin partner. A human antibody may be the acceptor antibody.

The terms "$V_H$" and "$V_L$" are used herein to refer to the heavy chain variable region and light chain variable region respectively of an antigen binding protein.

"CDRs" are defined as the complementarity determining region amino acid sequences of an antigen binding protein. These are the hypervariable regions of immunoglobulin heavy and light chains. There are three heavy chain and three light chain CDRs (or CDR regions) in the variable portion of an immunoglobulin. Thus, "CDRs" as used herein refers to all three heavy chain CDRs, all three light chain CDRs, all heavy and light chain CDRs, or at least two CDRs.

Throughout this specification, amino acid residues in variable domain sequences and full length antibody sequences are numbered according to the Kabat numbering convention. Similarly, the terms "CDR", "CDRL1", "CDRL2", "CDRL3", "CDRH1", "CDRH2", "CDRH3" used in the Examples follow the Kabat numbering convention. For further information, see Kabat et al., Sequences of Proteins of Immunological Interest, 5th Ed., U.S. Department of Health and Human Services, National Institutes of Health (1991).

It will be apparent to those skilled in the art that there are alternative numbering conventions for amino acid residues in variable domain sequences and full length antibody sequences. There are also alternative numbering conventions for CDR sequences, for example those set out in Chothia et al. (1989) Nature 342: 877-883. The structure and protein folding of the antibody may mean that other residues are considered part of the CDR sequence and would be understood to be so by a skilled person.

Other numbering conventions for CDR sequences available to a skilled person include "AbM" (University of Bath) and "contact" (University College London) methods. The minimum overlapping region using at least two of the Kabat, Chothia, AbM and contact methods can be determined to provide the "minimum binding unit". The minimum binding unit may be a sub-portion of a CDR.

In one embodiment, methods are provided for increasing expression of ICOS on an effector T cell comprising contacting said effector T cell with an anti-PD-1 antibody. In one aspect the anti-PD-1 antibody is selected from selected from pembrolizumab and nivolumab. In one aspect, the effector T cell is CD4+ and/or CD8+.

In one embodiment, methods are provided for decreasing expression of ICOS on a regulatory T cell comprising contacting said regulatory T cell with an anti-PD-1 antibody. In one aspect the anti-PD-1 antibody is selected from selected from pembrolizumab and nivolumab. In one aspect, the regulatory T cell is CD4+.

In one aspect, the effector T cell is a tumor infiltrating T cell. In one aspect, the regulatory T cell is a tumor infiltrating T cell.

In one aspect, the effector T cell is a circulating T cell. In one aspect, the regulatory T cell is a circulating T cell.

In one embodiment, methods for increasing sensitivity to an agent directed to ICOS in a human are provided, the methods comprising administering to the human an anti-PD-1 antibody.

In one aspect, the anti-PD-1 antibody is selected from pembrolizumab and nivolumab. In one aspect, the agent directed to ICOS is an ICOS agonist. In one aspect, the agent directed to ICOS is an agonist antibody directed to ICOS. In one aspect, the agonist antibody directed to ICOS comprises one or more of: CDRH1 as set forth in SEQ ID NO: 1; CDRH2 as set forth in SEQ ID NO:2; CDRH3 as set forth in SEQ ID NO:3; CDRL1 as set forth in SEQ ID NO:4; CDRL2 as set forth in SEQ ID NO:5 and/or CDRL3 as set forth in SEQ ID NO:6 or a direct equivalent of each CDR wherein a direct equivalent has no more than two amino acid substitutions in said CDR.

In one embodiment, methods of treating cancer in a human in need thereof comprising administering an anti-PD-1 antibody and an anti-ICOS antibody to the human are provided, wherein the anti-PD-1 antibody increases T cell sensitivity to the ICOS antibody. In one aspect the anti-PD-1 antibody is selected from selected from pembrolizumab and nivolumab. In one aspect, the T cell is CD4+. In one aspect, the T cell is CD8+. In one aspect, the anti-ICOS antibody is an agonist antibody directed to ICOS. In one embodiment, the agonist antibody directed to ICOS comprises one or more of: CDRH1 as set forth in SEQ ID NO:1; CDRH2 as set forth in SEQ ID NO:2; CDRH3 as set forth in SEQ ID NO:3; CDRL1 as set forth in SEQ ID NO:4; CDRL2 as set forth in SEQ ID NO:5 and/or CDRL3 as set forth in SEQ ID NO:6 or a direct equivalent of each CDR wherein a direct equivalent has no more than two amino acid substitutions in said CDR. In one embodiment, the agonist antibody directed to ICOS or antigen binding portion thereof comprises a $V_H$ domain comprising an amino acid sequence at least 90% identical to the amino acid sequence set forth in SEQ ID NO:7; and a $V_L$ domain comprising an amino acid sequence at least 90% identical to the amino acid sequence as set forth in SEQ ID NO:8. In one embodiment, the agonist antibody directed to ICOS or antigen binding portion thereof comprises a $V_H$ domain comprising an amino acid sequence set forth in SEQ ID NO:7; and a $V_L$ domain comprising the amino acid sequence set forth in SEQ ID NO:8. In one embodiment the agonist antibody direct to ICOS or antigen binding portion thereof of comprises a hIgG4PE scaffold.

In one embodiment, in vitro methods are provided for increasing expression of ICOS on an effector T cell, the method comprising contacting the effector T cell with an anti-PD-1 antibody, thereby increasing the expression of said ICOS on said effector T cell. In one aspect, the anti-PD-1 antibody is selected from pembrolizumab and nivolumab. In one aspect, the effector T cell is CD4+ and/or CD8+. In one aspect, the regulatory T cell is CD4+.

In one embodiment, in vitro methods are provided for decreasing expression of ICOS on a regulatory T cell, the method comprising contacting the regulatory T cell with an anti-PD-1 antibody, thereby decreasing expression of said ICOS on said regulatory T cell. In one aspect, the anti-PD-1 antibody is selected from pembrolizumab and nivolumab. In one aspect, the effector T cell is CD4+ and/or CD8+. In one aspect, the regulatory T cell is CD4+.

In one embodiment, an anti-PD-1 antibody is provided for use in treating cancer in a human in need thereof, wherein the anti-PD-1 antibody is administered with an anti-ICOS antibody in said human. In one aspect, administration of the anti-PD-1 antibody increases T cell sensitivity to the ICOS antibody in said human. In one aspect, administration of the anti-PD-1 antibody increases expression of ICOS in said human. In one aspect the anti-PD-1 antibody is selected from selected from pembrolizumab and nivolumab. In one aspect, the anti-ICOS antibody is an agonist antibody directed to ICOS. In one embodiment, the agonist antibody directed to ICOS comprises one or more of: CDRH1 as set forth in SEQ ID NO: 1; CDRH2 as set forth in SEQ ID NO:2; CDRH3 as set forth in SEQ ID NO:3; CDRL1 as set forth in SEQ ID NO:4; CDRL2 as set forth in SEQ ID NO:5 and/or CDRL3 as set forth in SEQ ID NO:6 or a direct equivalent of each CDR wherein a direct equivalent has no more than two amino acid substitutions in said CDR. In one embodiment, the agonist antibody directed to ICOS or antigen binding portion thereof comprises a $V_H$ domain comprising an amino acid sequence at least 90% identical to the amino acid sequence set forth in SEQ ID NO:7; and a $V_L$ domain comprising an amino acid sequence at least 90% identical to the amino acid sequence as set forth in SEQ ID NO:8. In one embodiment, the agonist antibody directed to ICOS or antigen binding portion thereof comprises a $V_H$ domain comprising an amino acid sequence set forth in SEQ ID NO:7; and a $V_L$ domain comprising the amino acid sequence set forth in SEQ ID NO:8. In one embodiment the agonist antibody directed to ICOS or antigen binding portion thereof of comprises a hIgG4PE scaffold.

In one embodiment, an anti-ICOS antibody is provided for use in treating cancer in a human in need thereof, wherein the anti-ICOS antibody is administered with an anti-PD-1 antibody in said human. In one aspect, administration of the anti-PD-1 antibody increases T cell sensitivity to the ICOS antibody in said human. In one aspect, administration of the anti-PD-1 antibody increases expression of ICOS in said human. In one aspect the anti-PD-1 antibody is selected from selected from pembrolizumab and nivolumab. In one aspect, the anti-ICOS antibody is an agonist antibody directed to ICOS. In one embodiment, the agonist antibody directed to ICOS comprises one or more of: CDRH1 as set forth in SEQ ID NO: 1; CDRH2 as set forth in SEQ ID NO:2; CDRH3 as set forth in SEQ ID NO:3; CDRL1 as set forth in SEQ ID NO:4; CDRL2 as set forth in SEQ ID NO:5 and/or CDRL3 as set forth in SEQ ID NO:6 or a direct equivalent of each CDR wherein a direct equivalent has no more than two amino acid substitutions in said CDR. In one embodiment, the agonist antibody directed to ICOS or antigen binding portion thereof comprises a $V_H$ domain comprising an amino acid sequence at least 90% identical to the amino acid sequence set forth in SEQ ID NO:7; and a $V_L$ domain comprising an amino acid sequence at least 90% identical to the amino acid sequence as set forth in SEQ ID NO:8. In one embodiment, the agonist antibody directed to ICOS or antigen binding portion thereof comprises a $V_H$ domain comprising an amino acid sequence set forth in SEQ ID NO:7; and a $V_L$ domain comprising the amino acid sequence set forth in SEQ ID NO:8. In one embodiment the agonist antibody directed to ICOS or antigen binding portion thereof of comprises a hIgG4PE scaffold.

In one embodiment, an anti-PD-1 antibody and an anti-ICOS antibody are provided for use in treating cancer in a human. In one aspect, administration of the anti-PD-1 antibody increases T cell sensitivity to the ICOS antibody in said human. In one aspect, administration of the anti-PD-1 antibody increases expression of ICOS in said human. In one aspect, the anti-PD-1 antibody is administered prior to administration of the anti-ICOS antibody. In one aspect the anti-PD-1 antibody is selected from selected from pembrolizumab and nivolumab. In one aspect, the anti-ICOS antibody is an agonist antibody directed to ICOS. In one embodiment, the agonist antibody directed to ICOS comprises one or more of: CDRH1 as set forth in SEQ ID NO:1; CDRH2 as set forth in SEQ ID NO:2; CDRH3 as set forth in SEQ ID NO:3; CDRL1 as set forth in SEQ ID NO:4; CDRL2 as set forth in SEQ ID NO:5 and/or CDRL3 as set forth in SEQ ID NO:6 or a direct equivalent of each CDR wherein a direct equivalent has no more than two amino acid substitutions in said CDR. In one embodiment, the agonist antibody directed to ICOS or antigen binding portion thereof comprises a $V_H$ domain comprising an amino acid sequence at least 90% identical to the amino acid sequence set forth in SEQ ID NO:7; and a $V_L$ domain comprising an amino acid sequence at least 90% identical to the amino acid sequence as set forth in SEQ ID NO:8. In one embodiment, the agonist antibody directed to ICOS or antigen binding portion thereof comprises a $V_H$ domain comprising an amino acid sequence set forth in SEQ ID NO:7; and a $V_L$ domain comprising the amino acid sequence set forth in SEQ ID NO:8. In one embodiment the agonist antibody directed to ICOS or antigen binding portion thereof of comprises a hIgG4PE scaffold.

In one embodiment, an anti-PD-1 antibody and an anti-ICOS antibody are provided for use in treating sepsis in a human. In one aspect, administration of the anti-PD-1 antibody increases T cell sensitivity to the ICOS antibody in said human. In one aspect, administration of the anti-PD-1 antibody increases expression of ICOS in said human. In one aspect the anti-PD-1 antibody is selected from selected from pembrolizumab and nivolumab. In one aspect, the anti-ICOS antibody is an agonist antibody directed to ICOS. In one embodiment, the agonist antibody directed to ICOS comprises one or more of: CDRH1 as set forth in SEQ ID NO: 1; CDRH2 as set forth in SEQ ID NO:2; CDRH3 as set forth in SEQ ID NO:3; CDRL1 as set forth in SEQ ID NO:4; CDRL2 as set forth in SEQ ID NO:5 and/or CDRL3 as set forth in SEQ ID NO:6 or a direct equivalent of each CDR wherein a direct equivalent has no more than two amino acid substitutions in said CDR. In one embodiment, the agonist antibody directed to ICOS or antigen binding portion thereof comprises a $V_H$ domain comprising an amino acid sequence at least 90% identical to the amino acid sequence set forth in SEQ ID NO:7; and a $V_L$ domain comprising an amino acid sequence at least 90% identical to the amino acid sequence as set forth in SEQ ID NO:8. In one embodiment, the agonist antibody directed to ICOS or antigen binding portion thereof comprises a $V_H$ domain comprising an amino acid sequence set forth in SEQ ID NO:7; and a $V_L$ domain comprising the amino acid sequence set forth in SEQ ID NO:8. In one embodiment the agonist antibody directed to ICOS or antigen binding portion thereof of comprises a hIgG4PE scaffold.

In one embodiment, an anti-PD-1 antibody and an anti-ICOS antibody are provided for use in treating chronic infection in a human. In one aspect, administration of the anti-PD-1 antibody increases T cell sensitivity to the ICOS antibody in said human. In one aspect, administration of the anti-PD-1 antibody increases expression of ICOS in said human. In one aspect the anti-PD-1 antibody is selected from selected from pembrolizumab and nivolumab. In one aspect, the anti-ICOS antibody is an agonist antibody directed to ICOS. In one embodiment, the agonist antibody directed to ICOS comprises one or more of: CDRH1 as set forth in SEQ ID NO:1; CDRH2 as set forth in SEQ ID NO:2; CDRH3 as set forth in SEQ ID NO:3; CDRL1 as set forth in SEQ ID NO:4; CDRL2 as set forth in SEQ ID NO:5 and/or CDRL3 as set forth in SEQ ID NO:6 or a direct equivalent of each CDR wherein a direct equivalent has no more than two amino acid substitutions in said CDR. In one embodiment, the agonist antibody directed to ICOS or antigen binding portion thereof comprises a $V_H$ domain comprising an amino acid sequence at least 90% identical to the amino acid sequence set forth in SEQ ID NO:7; and a $V_L$ domain comprising an amino acid sequence at least 90% identical to the amino acid sequence as set forth in SEQ ID NO:8. In one embodiment, the agonist antibody directed to ICOS or antigen binding portion thereof comprises a $V_H$ domain comprising an amino acid sequence set forth in SEQ ID NO:7; and a $V_L$ domain comprising the amino acid sequence set forth in SEQ ID NO:8. In one embodiment the agonist antibody directed to ICOS or antigen binding portion thereof of comprises a hIgG4PE scaffold.

In another embodiment, the methods of the present invention further comprise administering an anti-CTLA4 antibody to the human. In one aspect, the anti-CTLA4 antibody is ipilimumab.

In one embodiment, the anti-PD-1 antibody and the anti-ICOS antibody are administered to the human simultaneously. In one aspect, the methods comprise administering at least one additional neoplastic agent to the human and/or at least one immunostimulatory agent.

In one aspect the cancer is selected from head and neck cancer, breast cancer, lung cancer, colon cancer, ovarian cancer, prostate cancer, gliomas, glioblastoma, astrocytomas, glioblastoma multiforme, Bannayan-Zonana syndrome, Cowden disease, Lhermitte-Duclos disease, inflammatory breast cancer, Wilm's tumor, Ewing's sarcoma, Rhabdomyosarcoma, ependymoma, medulloblastoma, kidney cancer, liver cancer, melanoma, pancreatic cancer, sarcoma, osteosarcoma, giant cell tumor of bone, thyroid cancer, lymphoblastic T cell leukemia, Chronic myelogenous leukemia, Chronic lymphocytic leukemia, Hairy-cell leukemia, acute lymphoblastic leukemia, acute myelogenous leukemia, AML, Chronic neutrophilic leukemia, Acute lymphoblastic T cell leukemia, plasmacytoma, Immunoblastic large cell leukemia, Mantle cell leukemia, Multiple myeloma Megakaryoblastic leukemia, multiple myeloma, acute megakaryocytic leukemia, promyelocytic leukemia, Erythroleukemia, malignant lymphoma, hodgkins lymphoma, non-hodgkins lymphoma, lymphoblastic T cell lymphoma, Burkitt's lymphoma, follicular lymphoma, neuroblastoma, bladder cancer, urothelial cancer, vulval cancer, cervical cancer, endometrial cancer, renal cancer, mesothelioma, esophageal cancer, salivary gland cancer, hepatocellular cancer, gastric cancer, nasopharangeal cancer, buccal cancer, cancer of the mouth, GIST (gastrointestinal stromal tumor), and testicular cancer.

In one aspect, the methods of the present invention further comprise administering at least one neo-plastic agent and/or at least one immunostimulatory agent to said human.

In one aspect the human has a solid tumor. In one aspect the tumor is selected from head and neck cancer, gastric cancer, melanoma, renal cell carcinoma (RCC), esophageal cancer, non-small cell lung carcinoma, prostate cancer, colorectal cancer, ovarian cancer and pancreatic cancer. In another aspect the human has a liquid tumor such as diffuse large B cell lymphoma (DLBCL), multiple myeloma, chronic lyphomblastic leukemia (CLL), follicular lymphoma, acute myeloid leukemia and chronic myelogenous leukemia.

The present disclosure also relates to a method for treating or lessening the severity of a cancer selected from: brain (gliomas), glioblastomas, Bannayan-Zonana syndrome, Cowden disease, Lhermitte-Duclos disease, breast, inflammatory breast cancer, Wilm's tumor, Ewing's sarcoma, Rhabdomyosarcoma, ependymoma, medulloblastoma, colon, head and neck, kidney, lung, liver, melanoma, ovarian, pancreatic, prostate, sarcoma, osteosarcoma, giant cell tumor of bone, thyroid, lymphoblastic T-cell leukemia, chronic myelogenous leukemia, chronic lymphocytic leukemia, hairy-cell leukemia, acute lymphoblastic leukemia, acute myelogenous leukemia, chronic neutrophilic leukemia, acute lymphoblastic T-cell leukemia, plasmacytoma, immunoblastic large cell leukemia, mantle cell leukemia, multiple myeloma megakaryoblastic leukemia, multiple myeloma, acute megakaryocytic leukemia, promyelocytic leukemia, erythroleukemia, malignant lymphoma, Hodgkins lymphoma, non-hodgkins lymphoma, lymphoblastic T cell lymphoma, Burkitt's lymphoma, follicular lymphoma, neuroblastoma, bladder cancer, urothelial cancer, lung cancer, vulval cancer, cervical cancer, endometrial cancer, renal cancer, mesothelioma, esophageal cancer, salivary gland cancer, hepatocellular cancer, gastric cancer, nasopharangeal cancer, buccal cancer, cancer of the mouth, GIST (gastrointestinal stromal tumor) and testicular cancer.

By the term "treating" and grammatical variations thereof as used herein, is meant therapeutic therapy. In reference to a particular condition, treating means: (1) to ameliorate or prevent the condition of one or more of the biological manifestations of the condition, (2) to interfere with (a) one or more points in the biological cascade that leads to or is responsible for the condition or (b) one or more of the biological manifestations of the condition, (3) to alleviate one or more of the symptoms, effects or side effects associated with the condition or treatment thereof, or (4) to slow the progression of the condition or one or more of the biological manifestations of the condition. Prophylactic therapy is also contemplated thereby. The skilled artisan will appreciate that "prevention" is not an absolute term. In medicine, "prevention" is understood to refer to the prophylactic administration of a drug to substantially diminish the likelihood or severity of a condition or biological manifestation thereof, or to delay the onset of such condition or biological manifestation thereof. Prophylactic therapy is appropriate, for example, when a subject is considered at high risk for developing cancer, such as when a subject has a strong family history of cancer or when a subject has been exposed to a carcinogen.

As used herein, the terms "cancer," "neoplasm," and "tumor" are used interchangeably and, in either the singular or plural form, refer to cells that have undergone a malignant transformation that makes them pathological to the host organism. Primary cancer cells can be readily distinguished from non-cancerous cells by well-established techniques, particularly histological examination. The definition of a cancer cell, as used herein, includes not only a primary cancer cell, but any cell derived from a cancer cell ancestor. This includes metastasized cancer cells, and in vitro cultures and cell lines derived from cancer cells. When referring to a type of cancer that normally manifests as a solid tumor, a "clinically detectable" tumor is one that is detectable on the basis of tumor mass; e.g., by procedures such as computed tomography (CT) scan, magnetic resonance imaging (MRI), X-ray, ultrasound or palpation on physical examination, and/or which is detectable because of the expression of one or more cancer-specific antigens in a sample obtainable from a patient. Tumors may be a hematopoietic (or hematologic or hematological or blood-related) cancer, for example, cancers derived from blood cells or immune cells, which may be referred to as "liquid tumors." Specific examples of clinical conditions based on hematologic tumors include leukemias such as chronic myelocytic leukemia, acute myelocytic leukemia, chronic lymphocytic leukemia and acute lymphocytic leukemia; plasma cell malignancies such as multiple myeloma, MGUS and Waldenstrom's macroglobulinemia; lymphomas such as non-Hodgkin's lymphoma, Hodgkin's lymphoma; and the like.

The cancer may be any cancer in which an abnormal number of blast cells or unwanted cell proliferation is present or that is diagnosed as a hematological cancer, including both lymphoid and myeloid malignancies. Myeloid malignancies include, but are not limited to, acute myeloid (or myelocytic or myelogenous or myeloblastic) leukemia (undifferentiated or differentiated), acute promyeloid (or promyelocytic or promyelogenous or promyeloblastic) leukemia, acute myelomonocytic (or myelomonoblastic) leukemia, acute monocytic (or monoblastic) leukemia, erythroleukemia and megakaryocytic (or megakaryoblastic) leukemia. These leukemias may be referred together as acute myeloid (or myelocytic or myelogenous) leukemia (AML). Myeloid malignancies also include myeloproliferative disorders (MPD) which include, but are not limited to, chronic myelogenous (or myeloid) leukemia (CML), chronic myelomonocytic leukemia (CMML), essential thrombocythemia (or thrombocytosis), and polcythemia vera (PCV). Myeloid malignancies also include myelodysplasia (or myelodysplastic syndrome or MDS), which may be referred to as refractory anemia (RA), refractory anemia with excess blasts (RAEB), and refractory anemia with excess blasts in transformation (RAEBT); as well as myelofibrosis (MFS) with or without agnogenic myeloid metaplasia.

Hematopoietic cancers also include lymphoid malignancies, which may affect the lymph nodes, spleens, bone marrow, peripheral blood, and/or extranodal sites. Lymphoid cancers include B-cell malignancies, which include, but are not limited to, B-cell non-Hodgkin's lymphomas (B-NHLs). B-NHLs may be indolent (or low-grade), intermediate-grade (or aggressive) or high-grade (very aggressive). Indolent Bcell lymphomas include follicular lymphoma (FL); small lymphocytic lymphoma (SLL); marginal zone lymphoma (MZL) including nodal MZL, extranodal MZL, splenic MZL and splenic MZL with villous lymphocytes; lymphoplasmacytic lymphoma (LPL); and mucosa-associated-lymphoid tissue (MALT or extranodal marginal zone) lymphoma.

Intermediate-grade B-NHLs include mantle cell lymphoma (MCL) with or without leukemic involvement, diffuse large cell lymphoma (DLBCL), follicular large cell (or grade 3 or grade 3B) lymphoma, and primary mediastinal lymphoma (PML). High-grade B-NHLs include Burkitt's lymphoma (BL), Burkitt-like lymphoma, small non-cleaved cell lymphoma (SNCCL) and lymphoblastic lymphoma. Other B-NHLs include immunoblastic lymphoma (or immunocytoma), primary effusion lymphoma, HIV associated (or AIDS related) lymphomas, and post-transplant lymphoproliferative disorder (PTLD) or lymphoma. B-cell malignancies also include, but are not limited to, chronic lymphocytic leukemia (CLL), prolymphocytic leukemia (PLL), Waldenstrom's macroglobulinemia (WM), hairy cell leukemia (HCL), large granular lymphocyte (LGL) leukemia, acute lymphoid (or lymphocytic or lymphoblastic) leukemia, and Castleman's disease. NHL may also include T-cell non-Hodgkin's lymphoma s(T-NHLs), which include, but are not limited to T-cell non-Hodgkin's lymphoma not otherwise specified (NOS), peripheral T-cell lymphoma (PTCL), anaplastic large cell lymphoma (ALCL), angioimmunoblastic lymphoid disorder (AILD), nasal natural killer (NK) cell/T-cell lymphoma, gamma/delta lymphoma, cutaneous T cell lymphoma, mycosis fungoides, and Sezary syndrome.

Hematopoietic cancers also include Hodgkin's lymphoma (or disease) including classical Hodgkin's lymphoma, nodular sclerosing Hodgkin's lymphoma, mixed cellularity Hodgkin's lymphoma, lymphocyte predominant (LP) Hodgkin's lymphoma, nodular LP Hodgkin's lymphoma, and lymphocyte depleted Hodgkin's lymphoma. Hematopoietic cancers also include plasma cell diseases or cancers such as multiple myeloma (MM) including smoldering MM, monoclonal gammopathy of undetermined (or unknown or unclear) significance (MGUS), plasmacytoma (bone, extramedullary), lymphoplasmacytic lymphoma (LPL), Waldenström's Macroglobulinemia, plasma cell leukemia, and primary amyloidosis (AL). Hematopoietic cancers may also include other cancers of additional hematopoietic cells, including polymorphonuclear leukocytes (or neutrophils), basophils, eosinophils, dendritic cells, platelets, erythrocytes and natural killer cells. Tissues which include hematopoietic cells referred herein to as "hematopoietic cell tissues" include bone marrow; peripheral blood; thymus; and peripheral lymphoid tissues, such as spleen, lymph nodes, lymphoid tissues associated with mucosa (such as the gut-associated lymphoid tissues), tonsils, Peyer's patches and appendix, and lymphoid tissues associated with other mucosa, for example, the bronchial linings.

Typically, any anti-neoplastic agent that has activity versus a susceptible tumor being treated may be co-administered in the treatment of cancer in the present invention. Examples of such agents can be found in Cancer Principles and Practice of Oncology by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Typical anti-neoplastic agents useful in the present invention include, but are not limited to, anti-microtubule agents such as diterpenoids and vinca alkaloids; platinum coordination complexes; alkylating agents such as nitrogen mustards, oxazaphosphorines, alkylsulfonates, nitrosoureas, and triazenes; antibiotic agents such as anthracyclins, actinomycins and bleomycins; topoisomerase II inhibitors such as epipodophyllotoxins; antimetabolites such as purine and pyrimidine analogues and anti-folate compounds; topoisomerase I inhibitors such as camptothecins; hormones and hormonal analogues; signal transduction pathway inhibitors; non-receptor tyrosine kinase angiogenesis inhibitors; immunotherapeutic agents; proapoptotic agents; and cell cycle signaling inhibitors.

Examples of a further active ingredient or ingredients for use in combination or co-administered with the present methods are anti-neoplastic agents including any chemotherapeutic agents, immuno-modulatory agents or immune-modulators and immunostimulatory adjuvants.

Anti-microtubule or anti-mitotic agents are phase specific agents active against the microtubules of tumor cells during M or the mitosis phase of the cell cycle. Examples of anti-microtubule agents include, but are not limited to, diterpenoids and vinca alkaloids.

Diterpenoids, which are derived from natural sources, are phase specific anti-cancer agents that operate at the G2/M phases of the cell cycle. It is believed that the diterpenoids stabilize the β-tubulin subunit of the microtubules, by binding with this protein. Disassembly of the protein appears then to be inhibited with mitosis being arrested and cell death following.

Examples of diterpenoids include, but are not limited to, paclitaxel and its analog docetaxel.

Paclitaxel, 5β,20-epoxy-1,2α,4,7β,10β,13α-hexa-hydroxytax-11-en-9-one 4,10-diacetate 2-benzoate 13-ester with (2R,3S)—N-benzoyl-3-phenylisoserine; is a natural diterpene product isolated from the Pacific yew tree *Taxus brevifolia* and is commercially available as an injectable solution TAXOL®. It is a member of the taxane family of terpenes. It was first isolated in 1971 by Wani et al. J. Am. Chem, Soc., 93:2325. 1971), who characterized its structure by chemical and X-ray crystallographic methods. One mechanism for its activity relates to paclitaxel's capacity to bind tubulin, thereby inhibiting cancer cell growth. Schiff et al., Proc. Natl, Acad, Sci. USA, 77:1561-1565 (1980); Schiff et al., Nature, 277:665-667 (1979); Kumar, J. Biol, Chem, 256: 10435-10441 (1981). For a review of synthesis and anticancer activity of some paclitaxel derivatives see: D. G. I. Kingston et al., Studies in Organic Chemistry vol. 26, entitled "New trends in Natural Products Chemistry 1986", Attaur-Rahman, P. W. Le Quesne, Eds. (Elsevier, Amsterdam, 1986) pp 219-235.

Paclitaxel has been approved for clinical use in the treatment of refractory ovarian cancer in the United States (Markman et al., Yale Journal of Biology and Medicine, 64:583, 1991; McGuire et al., Ann. Intem, Med., 111:273, 1989) and for the treatment of breast cancer (Holmes et al., J. Nat. Cancer Inst., 83:1797, 1991.) It is a potential candidate for treatment of neoplasms in the skin (Einzig et. al., Proc. Am. Soc. Clin. Oncol., 20:46) and head and neck carcinomas (Forastire et. al., Sem. Oncol., 20:56, 1990). The compound also shows potential for the treatment of polycystic kidney disease (Woo et. al., Nature, 368:750. 1994, lung cancer and malaria. Treatment of patients with paclitaxel results in bone marrow suppression (multiple cell lineages, Ignoff, R. J. et. al, Cancer Chemotherapy Pocket Guide, 1998) related to the duration of dosing above a threshold concentration (50 nM) (Kearns, C. M. et. al., Seminars in Oncology, 3(6) p.16-23, 1995).

Docetaxel, (2R,3S)—N-carboxy-3-phenylisoserine,N-tert-butyl ester, 13-ester with 5β-20-epoxy-1,2α,4,7β,10β, 13α-hexahydroxytax-11-en-9-one 4-acetate 2-benzoate, trihydrate; is commercially available as an injectable solution as TAXOTERE®. Docetaxel is indicated for the treatment of breast cancer. Docetaxel is a semisynthetic derivative of paclitaxel q.v., prepared using a natural precursor, 10-deacetyl-baccatin III, extracted from the needle of the European Yew tree. The dose limiting toxicity of docetaxel is neutropenia.

Vinca alkaloids are phase specific anti-neoplastic agents derived from the periwinkle plant. Vinca alkaloids act at the M phase (mitosis) of the cell cycle by binding specifically to tubulin. Consequently, the bound tubulin molecule is unable to polymerize into microtubules. Mitosis is believed to be arrested in metaphase with cell death following. Examples of vinca alkaloids include, but are not limited to, vinblastine, vincristine, and vinorelbine.

Vinblastine, vincaleukoblastine sulfate, is commercially available as VELBAN® as an injectable solution. Although, it has possible indication as a second line therapy of various solid tumors, it is primarily indicated in the treatment of testicular cancer and various lymphomas including Hodgkin's Disease; and lymphocytic and histiocytic lymphomas. Myelosuppression is the dose limiting side effect of vinblastine.

Vincristine, vincaleukoblastine, 22-oxo-, sulfate, is commercially available as ONCOVIN® as an injectable solution. Vincristine is indicated for the treatment of acute leukemias and has also found use in treatment regimens for Hodgkin's and non-Hodgkin's malignant lymphomas. Alopecia and neurologic effects are the most common side effect of vincristine and to a lesser extent myelosupression and gastrointestinal mucositis effects occur.

Vinorelbine, 3',4'-didehydro-4'-deoxy-C'-norvincaleuko-blastine [R—(R*,R*)-2,3-dihydroxybutanedioate (1:2) (salt)], commercially available as an injectable solution of vinorelbine tartrate (NAVELBINE®), is a semisynthetic vinca alkaloID Vinorelbine is indicated as a single agent or in combination with other chemotherapeutic agents, such as cisplatin, in the treatment of various solid tumors, particularly non-small cell lung, advanced breast, and hormone refractory prostate cancers. Myelosuppression is the most common dose limiting side effect of vinorelbine.

Platinum coordination complexes are non-phase specific anti-cancer agents, which are interactive with DNA. The platinum complexes enter tumor cells, undergo, aquation and form intra- and interstrand crosslinks with DNA causing adverse biological effects to the tumor. Examples of platinum coordination complexes include, but are not limited to, cisplatin and carboplatin.

Cisplatin, cis-diamminedichloroplatinum, is commercially available as PLATINOL® as an injectable solution. Cisplatin is primarily indicated in the treatment of metastatic testicular and ovarian cancer and advanced bladder cancer. The primary dose limiting side effects of cisplatin are nephrotoxicity, which may be controlled by hydration and diuresis, and ototoxicity.

Carboplatin, platinum, diammine [1,1-cyclobutane-dicarboxylate(2-)-O,O'], is commercially available as PARAPLATIN® as an injectable solution. Carboplatin is primarily indicated in the first and second line treatment of advanced ovarian carcinoma. Bone marrow suppression is the dose limiting toxicity of carboplatin.

Alkylating agents are non-phase anti-cancer specific agents and strong electrophiles. Typically, alkylating agents form covalent linkages, by alkylation, to DNA through nucleophilic moieties of the DNA molecule such as phosphate, amino, sulfhydryl, hydroxyl, carboxyl, and imidazole groups. Such alkylation disrupts nucleic acid function leading to cell death. Examples of alkylating agents include, but are not limited to, nitrogen mustards such as cyclophosphamide, melphalan, and chlorambucil; alkyl sulfonates such as busulfan; nitrosoureas such as carmustine; and triazenes such as dacarbazine.

Cyclophosphamide, 2-[bis(2-chloroethyl)amino]tetrahydro-2H-1,3,2-oxazaphosphorine 2-oxide monohydrate, is commercially available as an injectable solution or tablets as CYTOXAN®. Cyclophosphamide is indicated as a single agent or in combination with other chemotherapeutic agents, in the treatment of malignant lymphomas, multiple myeloma, and leukemias. Alopecia, nausea, vomiting and leukopenia are the most common dose limiting side effects of cyclophosphamide.

Melphalan, 4-[bis(2-chloroethyl)amino]-L-phenylalanine, is commercially available as an injectable solution or tablets as ALKERAN®. Melphalan is indicated for the palliative treatment of multiple myeloma and non-resectable epithelial carcinoma of the ovary. Bone marrow suppression is the most common dose limiting side effect of melphalan.

Chlorambucil, 4-[bis(2-chloroethyl)amino]benzenebutanoic acid, is commercially available as LEUKERAN® tablets. Chlorambucil is indicated for the palliative treatment of chronic lymphatic leukemia, and malignant lymphomas such as lymphosarcoma, giant follicular lymphoma, and Hodgkin's disease. Bone marrow suppression is the most common dose limiting side effect of chlorambucil.

Busulfan, 1,4-butanediol dimethanesulfonate, is commercially available as MYLERAN® TABLETS. Busulfan is indicated for the palliative treatment of chronic myelogenous leukemia. Bone marrow suppression is the most common dose limiting side effects of busulfan.

Carmustine, 1,3-[bis(2-chloroethyl)-1-nitrosourea, is commercially available as single vials of lyophilized material as BiCNU®. Carmustine is indicated for the palliative treatment as a single agent or in combination with other agents for brain tumors, multiple myeloma, Hodgkin's disease, and non-Hodgkin's lymphomas. Delayed myelosuppression is the most common dose limiting side effects of carmustine.

Dacarbazine, 5-(3,3-dimethyl-1-triazeno)-imidazole-4-carboxamide, is commercially available as single vials of material as DTIC-Dome®. Dacarbazine is indicated for the treatment of metastatic malignant melanoma and in combination with other agents for the second line treatment of Hodgkin's Disease. Nausea, vomiting, and anorexia are the most common dose limiting side effects of dacarbazine.

Antibiotic anti-neoplastics are non-phase specific agents, which bind or intercalate with DNA. Typically, such action results in stable DNA complexes or strand breakage, which disrupts ordinary function of the nucleic acids leading to cell death. Examples of antibiotic anti-neoplastic agents include, but are not limited to, actinomycins such as dactinomycin, anthrocyclins such as daunorubicin and doxorubicin; and bleomycins.

Dactinomycin, also know as Actinomycin D, is commercially available in injectable form as COSMEGEN®. Dactinomycin is indicated for the treatment of Wilm's tumor and rhabdomyosarcoma. Nausea, vomiting, and anorexia are the most common dose limiting side effects of dactinomycin.

Daunorubicin, (8S-cis-)-8-acetyl-10-[(3-amino-2,3,6-trideoxy-a-L-lyxo-hexopyranosyl)oxy]-7,8,9,10-tetrahydro-6,8,11-trihydroxy-1-methoxy-5,12 naphthacenedione hydrochloride, is commercially available as a liposomal injectable form as DAUNOXOME® or as an injectable as CERUBIDINE®. Daunorubicin is indicated for remission induction in the treatment of acute nonlymphocytic leukemia and advanced HIV associated Kaposi's sarcoma. Myelosuppression is the most common dose limiting side effect of daunorubicin.

Doxorubicin, (8S, 10S)-10-[(3-amino-2,3,6-trideoxy-a-L-lyxo-hexopyranosyl)oxy]-8-glycoloyl, 7,8,9,10-tetrahydro-6,8,11-trihydroxy-1-methoxy-5,12 naphthacenedione hydrochloride, is commercially available as an injectable form as RUBEX® or ADRIAMYCIN RDF®. Doxorubicin is primarily indicated for the treatment of acute lymphoblastic leukemia and acute myeloblastic leukemia, but is also a useful component in the treatment of some solid tumors and lymphomas. Myelosuppression is the most common dose limiting side effect of doxorubicin.

Bleomycin, a mixture of cytotoxic glycopeptide antibiotics isolated from a strain of *Streptomyces verticillus*, is commercially available as BLENOXANE®. Bleomycin is indicated as a palliative treatment, as a single agent or in combination with other agents, of squamous cell carcinoma, lymphomas, and testicular carcinomas. Pulmonary and cutaneous toxicities are the most common dose limiting side effects of bleomycin.

Topoisomerase II inhibitors include, but are not limited to, epipodophyllotoxins.

Epipodophyllotoxins are phase specific anti-neoplastic agents derived from the mandrake plant. Epipodophyllotoxins typically affect cells in the S and $G_2$ phases of the cell cycle by forming a ternary complex with topoisomerase II and DNA causing DNA strand breaks. The strand breaks accumulate and cell death follows. Examples of epipodophyllotoxins include, but are not limited to, etoposide and teniposide.

Etoposide, 4'-demethyl-epipodophyllotoxin 9[4,6-0-(R)-ethylidene-β-D-glucopyranoside], is commercially available as an injectable solution or capsules as VePESID® and is commonly known as VP-16. Etoposide is indicated as a single agent or in combination with other chemotherapy agents in the treatment of testicular and non-small cell lung cancers. Myelosuppression is the most common side effect of etoposide. The incidence of leucopenia tends to be more severe than thrombocytopenia.

Teniposide, 4'-demethyl-epipodophyllotoxin 9[4,6-0-(R)-thenylidene-β-D-glucopyranoside], is commercially available as an injectable solution as VUMON® and is commonly known as VM-26. Teniposide is indicated as a single agent or in combination with other chemotherapy agents in the treatment of acute leukemia in children. Myelosuppression is the most common dose limiting side effect of teniposide. Teniposide can induce both leucopenia and thrombocytopenia.

Antimetabolite neoplastic agents are phase specific antineoplastic agents that act at S phase (DNA synthesis) of the cell cycle by inhibiting DNA synthesis or by inhibiting purine or pyrimidine base synthesis and thereby limiting DNA synthesis. Consequently, S phase does not proceed and cell death follows. Examples of antimetabolite anti-neoplastic agents include, but are not limited to, fluorouracil, methotrexate, cytarabine, mecaptopurine, thioguanine, and gemcitabine. 5-fluorouracil, 5-fluoro-2,4-(1H,3H) pyrimidinedione, is commercially available as fluorouracil. Administration of 5-fluorouracil leads to inhibition of thymidylate synthesis and is also incorporated into both RNA and DNA. The result typically is cell death. 5-fluorouracil is indicated as a single agent or in combination with other chemotherapy agents in the treatment of carcinomas of the breast, colon, rectum, stomach and pancreas. Myelosuppression and mucositis are dose limiting side effects of 5-fluorouracil. Other fluoropyrimidine analogs include 5-fluoro deoxyuridine (floxuridine) and 5-fluorodeoxyuridine monophosphate.

Cytarabine, 4-amino-1-β-D-arabinofuranosyl-2 (1H)-pyrimidinone, is commercially available as CYTOSAR-U® and is commonly known as Ara-C. It is believed that cytarabine exhibits cell phase specificity at S-phase by inhibiting DNA chain elongation by terminal incorporation of cytarabine into the growing DNA chain. Cytarabine is indicated as a single agent or in combination with other chemotherapy agents in the treatment of acute leukemia. Other cytidine analogs include 5-azacytidine and 2',2'-difluorodeoxycytidine (gemcitabine). Cytarabine induces leucopenia, thrombocytopenia, and mucositis.

Mercaptopurine, 1,7-dihydro-6H-purine-6-thione monohydrate, is commercially available as PURINETHOL®. Mercaptopurine exhibits cell phase specificity at S-phase by inhibiting DNA synthesis by an as of yet unspecified mechanism. Mercaptopurine is indicated as a single agent or in combination with other chemotherapy agents in the treatment of acute leukemia. Myelosuppression and gastrointestinal mucositis are expected side effects of mercaptopurine at high doses. A useful mercaptopurine analog is azathioprine.

Thioguanine, 2-amino-1,7-dihydro-6H-purine-6-thione, is commercially available as TABLOID®. Thioguanine exhibits cell phase specificity at S-phase by inhibiting DNA synthesis by an as of yet unspecified mechanism. Thioguanine is indicated as a single agent or in combination with other chemotherapy agents in the treatment of acute leukemia.

Myelosuppression, including leucopenia, thrombocytopenia, and anemia, is the most common dose limiting side effect of thioguanine administration. However, gastrointestinal side effects occur and can be dose limiting. Other purine analogs include pentostatin, erythrohydroxynonyladenine, fludarabine phosphate, and cladribine.

Gemcitabine, 2'-deoxy-2', 2'-difluorocytidine monohydrochloride (β-isomer), is commercially available as GEMZAR®. Gemcitabine exhibits cell phase specificity at S-phase and by blocking progression of cells through the G1/S boundary. Gemcitabine is indicated in combination with cisplatin in the treatment of locally advanced non-small cell lung cancer and alone in the treatment of locally advanced pancreatic cancer. Myelosuppression, including leucopenia, thrombocytopenia, and anemia, is the most common dose limiting side effect of gemcitabine administration.

Methotrexate, N-[4[[(2,4-diamino-6-pteridinyl) methyl] methylamino] benzoyl]-L-glutamic acid, is commercially available as methotrexate sodium. Methotrexate exhibits cell phase effects specifically at S-phase by inhibiting DNA synthesis, repair and/or replication through the inhibition of dyhydrofolic acid reductase which is required for synthesis of purine nucleotides and thymidylate. Methotrexate is indicated as a single agent or in combination with other chemotherapy agents in the treatment of choriocarcinoma, meningeal leukemia, non-Hodgkin's lymphoma, and carcinomas of the breast, head, neck, ovary and bladder. Myelosuppression (leucopenia, thrombocytopenia, and anemia) and mucositis are expected side effect of methotrexate administration.

Camptothecins, including, camptothecin and camptothecin derivatives are available or under development as Topoisomerase I inhibitors. Camptothecins cytotoxic activity is believed to be related to its Topoisomerase I inhibitory activity. Examples of camptothecins include, but are not limited to irinotecan, topotecan, and the various optical forms of 7-(4-methylpiperazino-methylene)-10,11-ethylenedioxy-20-camptothecin described below.

Irinotecan HCl, (4S)-4,11-diethyl-4-hydroxy-9-[(4-piperidinopiperidino) carbonyloxy]-1H-pyrano[3',4',6,7]indolizino[1,2-b]quinoline-3,14(4H,12H)-dione hydrochloride, is commercially available as the injectable solution CAMPTOSAR®.

Irinotecan is a derivative of camptothecin which binds, along with its active metabolite SN-38, to the topoisomerase I-DNA complex. It is believed that cytotoxicity occurs as a result of irreparable double strand breaks caused by interaction of the topoisomerase I:DNA:irintecan or SN-38 ternary complex with replication enzymes. Irinotecan is indicated for treatment of metastatic cancer of the colon or rectum. The dose limiting side effects of irinotecan HCl are myelosuppression, including neutropenia, and GI effects, including diarrhea.

Topotecan HCl, (S)-10-[(dimethylamino)methyl]-4-ethyl-4,9-dihydroxy-1H-pyrano[3',4',6,7]indolizino[1,2-b]quinoline-3,14-(4H,12H)-dione monohydrochloride, is commercially available as the injectable solution HYCAMTIN®. Topotecan is a derivative of camptothecin which binds to the topoisomerase I-DNA complex and prevents religation of singles strand breaks caused by Topoisomerase I in response to torsional strain of the DNA molecule. Topotecan is indicated for second line treatment of metastatic carcinoma of the ovary and small cell lung cancer. The dose limiting side effect of topotecan HCl is myelosuppression, primarily neutropenia.

Rituximab is a chimeric monoclonal antibody which is sold as RITUXAN® and MABTHERA®. Rituximab binds to CD20 on B cells and causes cell apoptosis. Rituximab is administered intravenously and is approved for treatment of rheumatoid arthritis and B-cell non-Hodgkin's lymphoma.

Ofatumumab is a fully human monoclonal antibody which is sold as ARZERRA®. Ofatumumab binds to CD20 on B cells and is used to treat chronic lymphocytic leukemia CLL; a type of cancer of the white blood cells) in adults who are refractory to treatment with fludarabine (Fludara) and alemtuzumab Campath).

Trastuzumab (HEREPTIN®) is a humanized monoclonal antibody that binds to the HER2 receptor. It original indication is HER2 positive breast cancer.

Cetuximab (ERBITUX®) is a chimeric mouse human antibody that inhibits epidermal growth factor receptor (EGFR).

mTOR inhibitors include but are not limited to rapamycin (FK506) and rapalogs, RAD001 or everolimus (Afinitor), CCI-779 or temsirolimus, AP23573, AZD8055, WYE-354, WYE-600, WYE-687 and Pp121.

Bexarotene is sold as Targretin® and is a member of a subclass of retinoids that selectively activate retinoid X receptors (RXRs). These retinoid receptors have biologic activity distinct from that of retinoic acid receptors (RARs). The chemical name is 4-[1-(5,6,7,8-tetrahydro-3,5,5,8,8-pentamethyl-2-naphthalenyl) ethenyl] benzoic acID Bexarotene is used to treat cutaneous T-cell lymphoma CTCL, a type of skin cancer) in people whose disease could not be treated successfully with at least one other medication.

Sorafenib marketed as Nexavar® is in a class of medications called multikinase inhibitors. Its chemical name is 4-[4-[[4-chloro-3-(trifluoromethyl)phenyl]carbamoylamino] phenoxy]-N-methyl-pyridine-2-carboxamide. Sorafenib is used to treat advanced renal cell carcinoma (a type of cancer that begins in the kidneys). Sorafenib is also used to treat unresectable hepatocellular carcinoma (a type of liver cancer that cannot be treated with surgery).

Examples of erbB inhibitors include lapatinib, erlotinib, and gefitinib. Lapatinib, N-(3-chloro-4-{[(3-fluorophenyl)methyl]oxy}phenyl)-6-[5-({[2-(methylsulfonyl)ethyl]aminoImethyl)-2-furanyl]-4-quinazolinamine (represented by formula II, as illustrated), is a potent, oral, small-molecule, dual inhibitor of erbB-1 and erbB-2 (EGFR and HER2) tyrosine kinases that is approved in combination with capecitabine for the treatment of HER2-positive metastatic breast cancer.

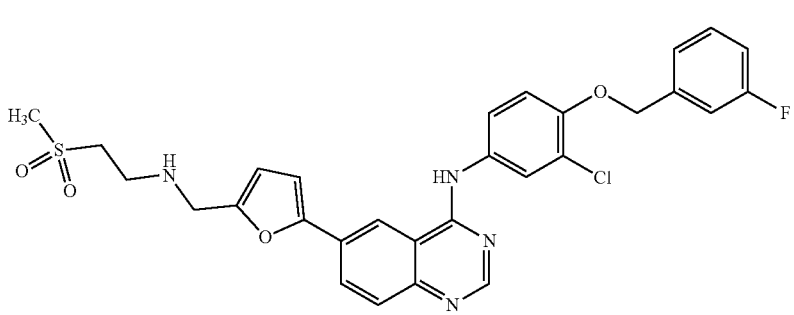

II

The free base, HCl salts, and ditosylate salts of the compound of formula (II) may be prepared according to the procedures disclosed in WO 99/35146, published Jul. 15, 1999; and WO 02/02552 published Jan. 10, 2002.

Erlotinib, N-(3-ethynylphenyl)-6,7-bis{[2-(methyloxy)ethyl]oxy}-4-quinazolinamine Commercially available under the tradename Tarceva) is represented by formula III, as illustrated:

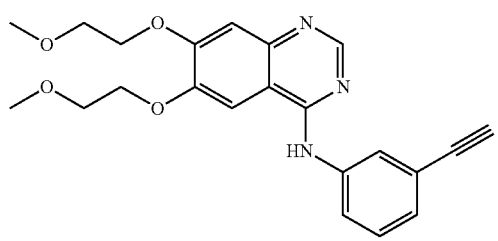

III

The free base and HCl salt of erlotinib may be prepared, for example, according to U.S. Pat. No. 5,747,498, Example 20.

Gefitinib, 4-quinazolinamine,N-(3-chloro-4-fluorophenyl)-7-methoxy-6-[3-4-morpholin)propoxy] is represented by formula IV, as illustrated:

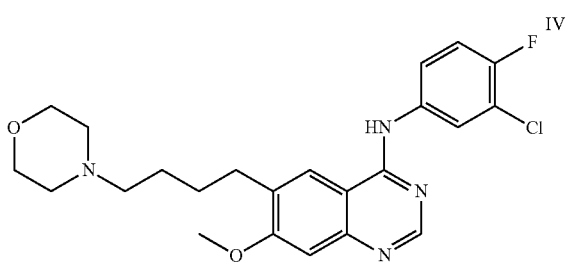 [SMILES: COc1cc2ncnc(Nc3ccc(F)c(Cl)c3)c2cc1CCCCN1CCOCC1]

Gefitinib, which is commercially available under the trade name IRESSA® (Astra-Zenenca) is an erbB-1 inhibitor that is indicated as monotherapy for the treatment of patients with locally advanced or metastatic non-small-cell lung cancer after failure of both platinum-based and docetaxel chemotherapies. The free base, HCl salts, and diHCl salts of gefitinib may be prepared according to the procedures of International Patent Application No. PCT/GB96/00961, filed Apr. 23, 1996, and published as WO 96/33980 on Oct. 31, 1996.

Also of interest, is the camptothecin derivative of formula A following, currently under development, including the racemic mixture (R,S) form as well as the R and S enantiomers:

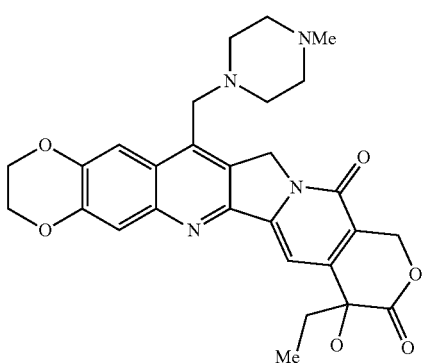

known by the chemical name "7-(4-methylpiperazino-methylene)-10,11-ethylenedioxy-20(R,S)-camptothecin (racemic mixture) or "7-(4-methylpiperazino-methylene)-10,11-ethylenedioxy-20(R)-camptothecin (R enantiomer) or "7-(4-methylpiperazino-methylene)-10,11-ethylenedioxy-20(S)-camptothecin (S enantiomer). Such compound as well as related compounds are described, including methods of making, in U.S. Pat. Nos. 6,063,923; 5,342,947; 5,559,235; 5,491,237 and pending U.S. patent application Ser. No. 08/977,217 filed Nov. 24, 1997.

Hormones and hormonal analogues are useful compounds for treating cancers in which there is a relationship between the hormone(s) and growth and/or lack of growth of the cancer. Examples of hormones and hormonal analogues useful in cancer treatment include, but are not limited to, adrenocorticosteroids such as prednisone and prednisolone which are useful in the treatment of malignant lymphoma and acute leukemia in children; aminoglutethimide and other aromatase inhibitors such as anastrozole, letrazole, vorazole, and exemestane useful in the treatment of adrenocortical carcinoma and hormone dependent breast carcinoma containing estrogen receptors; progestrins such as megestrol acetate useful in the treatment of hormone dependent breast cancer and endometrial carcinoma; estrogens, androgens, and anti-androgens such as flutamide, nilutamide, bicalutamide, cyproterone acetate and 5α-reductases such as finasteride and dutasteride, useful in the treatment of prostatic carcinoma and benign prostatic hypertrophy; anti-estrogens such as tamoxifen, toremifene, raloxifene, droloxifene, iodoxyfene, as well as selective estrogen receptor modulators (SERMS) such those described in U.S. Pat. Nos. 5,681,835, 5,877,219, and 6,207,716, useful in the treatment of hormone dependent breast carcinoma and other susceptible cancers; and gonadotropin-releasing hormone (GnRH) and analogues thereof which stimulate the release of leutinizing hormone (LH) and/or follicle stimulating hormone (FSH) for the treatment prostatic carcinoma, for instance, LHRH agonists and antagagonists such as goserelin acetate and luprolide.

Signal transduction pathway inhibitors are those inhibitors, which block or inhibit a chemical process which evokes an intracellular change. As used herein this change is cell proliferation or differentiation. Signal tranduction inhibitors useful in the present invention include inhibitors of receptor tyrosine kinases, non-receptor tyrosine kinases, SH2/SH3domain blockers, serine/threonine kinases, phosphotidyl inositol-3 kinases, myo-inositol signaling, and Ras oncogenes.

Several protein tyrosine kinases catalyse the phosphorylation of specific tyrosyl residues in various proteins involved in the regulation of cell growth. Such protein tyrosine kinases can be broadly classified as receptor or non-receptor kinases.

Receptor tyrosine kinases are transmembrane proteins having an extracellular ligand binding domain, a transmembrane domain, and a tyrosine kinase domain. Receptor tyrosine kinases are involved in the regulation of cell growth and are generally termed growth factor receptors. Inappropriate or uncontrolled activation of many of these kinases, i.e. aberrant kinase growth factor receptor activity, for example by over-expression or mutation, has been shown to result in uncontrolled cell growth. Accordingly, the aberrant activity of such kinases has been linked to malignant tissue growth. Consequently, inhibitors of such kinases could provide cancer treatment methods. Growth factor receptors include, for example, epidermal growth factor receptor (EGFr), platelet derived growth factor receptor (PDGFr), erbB2, erbB4, vascular endothelial growth factor receptor (VEGFr), tyrosine kinase with immunoglobulin-like and epidermal growth factor homology domains (TIE-2), insulin growth factor-I (IGFI) receptor, macrophage colony stimulating factor Cfms), BTK, ckit, cmet, fibroblast growth factor (FGF) receptors, Trk receptors (TrkA, TrkB, and TrkC), ephrin (eph) receptors, and the RET protooncogene. Several inhibitors of growth receptors are under development and include ligand antagonists, antibodies, tyrosine kinase inhibitors and anti-sense oligonucleotides. Growth factor receptors and agents that inhibit growth factor receptor function are described, for instance, in Kath, John C., Exp. Opin. Ther. Patents (2000) 10(6):803-818; Shawver et al DDT Vol 2, No. 2 Feb. 1997; and Lofts, F. J. et al, "Growth factor receptors as targets", New Molecular Targets for Cancer Chemotherapy, ed. Workman, Paul and Kerr, David, CRC press 1994, London.

Tyrosine kinases, which are not growth factor receptor kinases are termed non-receptor tyrosine kinases. Non-receptor tyrosine kinases useful in the present invention, which are targets or potential targets of anti-cancer drugs, include cSrc, Lck, Fyn, Yes, Jak, cAbl, FAK (Focal adhesion kinase), Brutons tyrosine kinase, and Bcr-Abl. Such non-receptor kinases and agents which inhibit non-receptor tyrosine kinase function are described in Sinh, S. and Corey, S. J., (1999) Journal of Hematotherapy and Stem Cell Research 8 (5): 465-80; and Bolen, J. B., Brugge, J. S., (1997) Annual review of Immunology. 15: 371-404.

SH2/SH3 domain blockers are agents that disrupt SH2 or SH3 domain binding in a variety of enzymes or adaptor proteins including, PI3-K p85 subunit, Src family kinases, adaptor molecules (She, Crk, Nck, Grb2) and Ras-GAP. SH2/SH3 domains as targets for anti-cancer drugs are discussed in Smithgall, T. E. (1995), Journal of Pharmacological and Toxicological Methods. 34(3) 125-32.

Inhibitors of Serine/Threonine Kinases including MAP kinase cascade blockers which include blockers of Raf kinases (rafk), Mitogen or Extracellular Regulated Kinase (MEKs), and Extracellular Regulated Kinases (ERKs); and Protein kinase C family member blockers including blockers of PKCs (alpha, beta, gamma, epsilon, mu, lambda, iota, zeta). IkB kinase family (IKKa, IKKb), PKB family kinases, AKT kinase family members, and TGF beta receptor kinases. Such Serine/Threonine kinases and inhibitors thereof are described in Yamamoto, T., Taya, S., Kaibuchi, K., (1999), Journal of Biochemistry. 126 (5) 799-803; Brodt, P, Samani, A., and Navab, R. (2000), Biochemical Pharmacology, 60. 1101-1107; Massague, J., Weis-Garcia, F. (1996) Cancer Surveys. 27:41-64; Philip, P. A., and Harris, A. L. (1995), Cancer Treatment and Research. 78: 3-27, Lackey, K. et al Bioorganic and Medicinal Chemistry Letters, (10), 2000, 223-226; U.S. Pat. No. 6,268,391; and Martinez-Iacaci, L., et al, Int. J. Cancer (2000), 88(1), 44-52.

Inhibitors of Phosphotidyl inositol-3 Kinase family members including blockers of PI3-kinase, ATM, DNA-PK, and Ku are also useful in the present invention. Such kinases are discussed in Abraham, R. T. (1996), Current Opinion in Immunology. 8 (3) 412-8; Canman, C. E., Lim, D. S. (1998), Oncogene 17 (25) 3301-3308; Jackson, S. P. (1997), International Journal of Biochemistry and Cell Biology. 29 (7):935-8; and Zhong, H. et al, Cancer res, (2000) 60(6), 1541-1545.

Also useful in the present invention are Myo-inositol signaling inhibitors such as phospholipase C blockers and Myoinositol analogues. Such signal inhibitors are described in Powis, G., and Kozikowski A., (1994 New Molecular Targets for Cancer Chemotherapy ed., Paul Workman and David Kerr, CRC press 1994, London.

Another group of signal transduction pathway inhibitors are inhibitors of Ras Oncogene. Such inhibitors include inhibitors of farnesyltransferase, geranyl-geranyl transferase, and CAAX proteases as well as anti-sense oligonucleotides, ribozymes and immunotherapy. Such inhibitors have been shown to block ras activation in cells containing wild type mutant ras, thereby acting as antiproliferation agents. Ras oncogene inhibition is discussed in Scharovsky, O. G., Rozados, V. R., Gervasoni, S. I. Matar, P. (2000), Journal of Biomedical Science. 7(4 292-8; Ashby, M. N. (1998), Current Opinion in Lipidology. 9 (2) 99-102; and Bennett, C. F. and Cowsert, L. M. BioChim. Biophys. Acta, (1999) 1489 (1):19-30.

As mentioned above, antibody antagonists to receptor kinase ligand binding may also serve as signal transduction inhibitors. This group of signal transduction pathway inhibitors includes the use of humanized antibodies to the extracellular ligand binding domain of receptor tyrosine kinases. For example Imclone C225 EGFR specific antibody (see Green, M. C. et al, Monoclonal Antibody Therapy for Solid Tumors, Cancer Treat. Rev., (2000), 26(4, 269-286); Herceptin® erbB2 antibody (see Tyrosine Kinase Signalling in Breast cancer:erbB Family Receptor Tyrosine Kniases, Breast cancer Res., 2000, 2(3), 176-183); and 2CB VEGFR2 specific antibody (see Brekken, R. A. et al, Selective Inhibition of VEGFR2 Activity by a monoclonal Anti-VEGF antibody blocks tumor growth in mice, Cancer Res. (2000) 60, 5117-5124.

Non-receptor kinase angiogenesis inhibitors may also find use in the present invention. Inhibitors of angiogenesis related VEGFR and TIE2 are discussed above in regard to signal transduction inhibitors (both receptors are receptor tyrosine kinases). Angiogenesis in general is linked to erbB2/EGFR signaling since inhibitors of erbB2 and EGFR have been shown to inhibit angiogenesis, primarily VEGF expression. Thus, the combination of an erbB2/EGFR inhibitor with an inhibitor of angiogenesis makes sense. Accordingly, non-receptor tyrosine kinase inhibitors may be used in combination with the EGFR/erbB2 inhibitors of the present invention. For example, anti-VEGF antibodies, which do not recognize VEGFR (the receptor tyrosine kinase), but bind to the ligand; small molecule inhibitors of integrin (alpha$_v$ beta$_3$) that will inhibit angiogenesis; endostatin and angiostatin (non-RTK) may also prove useful in combination with the disclosed erb family inhibitors. (See Bruns C J et al (2000), Cancer Res., 60: 2926-2935; Schreiber A B, Winkler M E, and Derynck R. (1986), Science, 232: 1250-1253; Yen L et al. (2000), Oncogene 19: 3460-3469).

Agents used in immunotherapeutic regimens may also be useful in combination with the compounds of formula (I). There are a number of immunologic strategies to generate an immune response against erbB2 or EGFR. These strategies are generally in the realm of tumor vaccinations. The efficacy of immunologic approaches may be greatly enhanced through combined inhibition of erbB2/EGFR signaling pathways using a small molecule inhibitor. Discussion of the immunologic/tumor vaccine approach against erbB2/EGFR are found in Reilly R T et al. (2000), Cancer Res. 60: 3569-3576; and Chen Y, Hu D, Eling D J, Robbins J, and Kipps T J. (1998), Cancer Res. 58: 1965-1971.

Agents used in proapoptotic regimens (e.g., bcl-2 antisense oligonucleotides) may also be used in the combination of the present invention. Members of the Bcl-2 family of proteins block apoptosis. Upregulation of bcl-2 has therefore been linked to chemoresistance. Studies have shown that the epidermal growth factor (EGF) stimulates anti-apoptotic members of the bcl-2 family (i.e., mcl-1). Therefore, strategies designed to downregulate the expression of bcl-2 in tumors have demonstrated clinical benefit and are now in Phase II/III trials, namely Genta's G3139 bcl-2 antisense oligonucleotide. Such proapoptotic strategies using the antisense oligonucleotide strategy for bcl-2 are discussed in Water J S et al. (2000), J. Clin. Oncol. 18: 1812-1823; and Kitada S et al. (1994, Antisense Res. Dev. 4: 71-79.

Trastuzumab (HEREPTIN®) is a humanized monoclonal antibody that binds to the HER2 receptor. It original indication is HER2 positive breast cancer.

Trastuzumab emtansine (trade name Kadcyla) is an antibody-drug conjugate consisting of the monoclonal antibody trastuzumab (Herceptin) linked to the cytotoxic agent mertansine (DM1). Trastuzumab alone stops growth of cancer cells by binding to the HER2/neu receptor, whereas mertansine enters cells and destroys them by binding to tubulin. Because the monoclonal antibody targets HER2, and HER2 is only over-expressed in cancer cells, the conjugate delivers the toxin specifically to tumor cells. The conjugate is abbreviated T-DM1.

Cetuximab (ERBITUX®) is a chimeric mouse human antibody that inhibits epidermal growth factor receptor (EGFR).

Pertuzumab (also called 2C4, trade name Omnitarg) is a monoclonal antibody. The first of its class in a line of agents called "HER dimerization inhibitors". By binding to HER2, it inhibits the dimerization of HER2 with other HER receptors, which is hypothesized to result in slowed tumor growth. Pertuzumab is described in WO01/00245 published Jan. 4, 2001.

Rituximab is a chimeric monoclonal antibody which is sold as RITUXAN® and MABTHERA®. Rituximab binds to CD20 on B cells and causes cell apoptosis. Rituximab is administered intravenously and is approved for treatment of rheumatoid arthritis and B-cell non-Hodgkin's lymphoma.

Ofatumumab is a fully human monoclonal antibody which is sold as ARZERRA®. Ofatumumab binds to CD20 on B cells and is used to treat chronic lymphocytic leukemia (CLL; a type of cancer of the white blood cells) in adults who are refractory to treatment with fludarabine (Fludara) and alemtuzumab (Campath).

Cell cycle signalling inhibitors inhibit molecules involved in the control of the cell cycle.

A family of protein kinases called cyclin dependent kinases CDKs) and their interaction with a family of proteins termed cyclins controls progression through the eukaryotic cell cycle. The coordinate activation and inactivation of different cyclin/CDK complexes is necessary for normal progression through the cell cycle. Several inhibitors of cell cycle signalling are under development. For instance, examples of cyclin dependent kinases, including CDK2, CDK4, and CDK6 and inhibitors for the same are described in, for instance, Rosania et al, Exp. Opin. Ther. Patents (2000) 10(2):215-230.

As used herein "immunostimulatory agent" refers to any agent that can stimulate the immune system. As used herein immunostimulatory agents include, but are not limited to, vaccine adjuvants.

EXAMPLES

The following examples illustrate various non-limiting aspects of this invention.

Example 1

Cancer immunity is regulated by co-stimulatory mechanisms that when triggered can mount effective anticancer responses. Inducible T cell Co-Stimulator (ICOS) is a T cell restricted co-stimulatory receptor belonging to the CD28/CTLA immunoglobulin super family whose expression is highly induced on CD4+ and CD8+ T cells upon T cell receptor (TCR) engagement. Here we describe the development of a monoclonal antibody with specific, high-affinity binding to human ICOS capable of delivering agonistic activity and stimulating effector CD4+ and cytotoxic CD8+ T cell activation, expansion and function. Antibody-induced ICOS agonism elicited potent T cell activation and antitumor responses alone and in combination with PD-1 blockade. The ICOS agonist antibody described herein offers a promising next-generation immunotherapy agent for the treatment of cancer.

Robust antitumor responses including complete cures have been achieved by modulating patients' immune system. Antibodies targeting the immune checkpoint receptors Cytotoxic T-Lymphocyte-Associated Protein 4 (CTLA-4) and Programmed cell death protein 1 (PD-1)/PD Ligand-1 (PD-L1) have demonstrated impressive activity in select patients, however most cancers remain non-responsive to this class of agents. The first-in-class ICOS agonist antibody described herein is a complementary and synergistic immunomodulatory approach together with immune checkpoint inhibition, which offers the potential to enhance the magnitude and duration of antitumor responses in patients whose tumors are already sensitive to current immunotherapy approaches as well as potentially expanding the population of patients and range of tumor types that respond to immunotherapy.

ICOS is a co-stimulatory receptor with structural and functional relation to the CD28/CTLA-4-Ig superfamily (Hutloff, A., et al. (1999) ICOS is an inducible T-cell co-stimulator structurally and functionally related to CD28. Nature 397(6716), 263-266). Activation of ICOS occurs through binding by ICOS-L (B7RP-1/B7-H2). Neither B7-1 nor B7-2 (ligands for CD28 and CTLA4) bind or activate ICOS. However, ICOS-L has been shown to bind to both CD28 and CTLA-4 (Yao, S., et al. (2011). B7-H2 is a costimulatory ligand for CD28 in human. Immunity 34(5), 729-40). Expression of ICOS is primarily restricted to T cells, varying between different T cell subsets and dependent upon activation status. ICOS expression has been shown on resting $T_H17$, T follicular helper ($T_{FH}$) and regulatory T ($T_{reg}$) cells, however, unlike CD28; it is not highly expressed on naïve $T_H1$ and $T_H2$ effector T cell populations (Paulos, C M., et al. (2010) The inducible costimulator (ICOS) is critical for the development of human Th17 cells. Sci Transl Med. 2(55), 55ra78). ICOS expression is highly induced on CD4+ and CD8+ effector T cells following activation through TCR engagement (Wakamatsu, E., et al. (2013) Convergent and divergent effects of costimulatory molecules in conventional and regulatory CD4+ T cells. Proc Natl Acad Sci USA 110(3), 1023-8). Co-stimulatory signaling through ICOS only occurs in T cells receiving a concurrent TCR activation signal (Hutloff, A., et al. (1999) ICOS is an inducible T-cell co-stimulator structurally and functionally related to CD28. Nature 397(6716), 263-266; Sharpe, A H. and Freeman, G J. (2002) The B7-CD28 Superfamily. Nat. Rev Immunol. 2(2), 116-26). In activated, antigen-specific T cells, ICOS regulates the production of both $T_H1$ and $T_H2$ cytokines including IFN-γ, TNF-α, IL-10, IL-4, IL-13 and others and has been shown to stimulate effector T cell proliferation, albeit to a lesser extent than CD28 (Sharpe, A H. and Freeman, G J. (2002) The B7-CD28 Superfamily. Nat. Rev Immunol. 2(2), 116-26). Additionally, ICOS plays a crucial role in the survival and expansion of effector T cells and T regs, both in the steady state and during antigen stimulated immune responses (Burmeister Y, et al. (2008) ICOS controls the pool size of effector-memory and regulatory T cells. J Immunol. 180(2), 774-82).

Prior reports support the concept that activating ICOS on CD4+ and CD8+ effector T cells has anti-tumor potential. An ICOS-L-Fc fusion protein caused tumor growth delay and complete tumor eradication in mice with SA-1 (sarcoma), Meth A (fibrosarcoma), EMT6 (breast), P815 (mastocytoma) and EL-4 (plasmacytoma) syngeneic tumors (Ara, G., et al (2003). Potent activity of soluble B7RP-1-Fc in therapy of murine tumors in syngeneic hosts. Int. J Cancer. 103(4); 501-7). Potent activity of soluble B7RP-1-Fc in therapy of murine tumors in syngeneic hosts. Int. J Cancer. 103(4); 501-7). The anti-tumor activity of ICOS-L-Fc was dependent upon an intact immune response, as the activity was completely lost in tumors grown in nude mice. Analysis of tumors from ICOS-L-Fc treated mice demonstrated a significant increase in CD4+ and CD8+ T cell infiltration in tumors responsive to treatment, supporting the immunostimulatory effect of ICOS-L-Fc in these models (Ara, G., et al (2003). Potent activity of soluble B7RP-1-Fc in therapy of murine tumors in syngeneic hosts. Int. J Cancer. 103(4); 501-7). Another report using ICOS$^{-/-}$ and ICOS-L$^{-/-}$ mice demonstrated the requirement of ICOS signaling in mediating the anti-tumor activity of an anti-CTLA4 antibody in the B16/B16 syngeneic melanoma tumor model (Fu, T., et al. (2011) The ICOS/ICOSL pathway is required for optimal antitumor responses mediated by anti-CTLA-4 therapy. Cancer Res. 71(16), 5445-54). Mice lacking ICOS or ICOS-L had significantly decreased survival rates as compared to wild-type mice after anti-CTLA4 antibody treatment.

Emerging data from patients treated with anti-CTLA4 antibodies also point to the positive role of ICOS+ effector T cells in mediating an anti-tumor immune response. Patients with metastatic melanoma (Di Giacomo, A M., et al (2013) Long-term survival and immunological parameters in metastatic melanoma patients who respond to ipilimumab 10 mg/kg within an expanded access program. Cancer Immunol Immunother. 62(6); 1021-8), urothelial (Carthon, B C., et al. (2010) Preoperative CTLA-4 blockade: Tolerability and immune monitoring in the setting of a presurgical clinical trial. Clin Cancer Res. 16(10), 2861-71), breast (Vonderheide, R H., et al. (2010) Tremelimumab in combination with exemestane in patients with advanced breast cancer and treatment-associated modulation of inducible costimulator expression on patient T cells. Clin Cancer Res. 16(13), 3485-94) and prostate cancer which have increased absolute numbers of circulating and tumor infiltrating CD4$^+$ICOS+ and CD8$^+$ICOS$^+$ T cells after ipilimumab treatment have significantly better treatment related outcomes than patients where little or no ICOS expression increases are observed. Importantly, it was shown that ipilimumab changes the ICOS$^+$ T$_{effector}$:T$_{reg}$ ratio, reversing an abundance of T$_{regs}$ pre-treatment to a significant abundance of T effectors following treatment (Liakou, C I., et al. (2008) CTLA-4 blockade increases IFN-gamma producing CD4+ICOS$^{hi}$ cells to shift the ratio of effector to regulatory T cells in cancer patients. Proc Natl Acad Sci USA. 105(39), 14987-92; Vonderheide, R H., et al. (2010) Tremelimumab in combination with exemestane in patients with advanced breast cancer and treatment-associated modulation of inducible costimulator expression on patient T cells. Clin Cancer Res. 16(13), 3485-94). Therefore, ICOS+ T effector cells are a positive predictive biomarker of ipilimumab response which points to the potential advantage of activating this population of cells with an agonist ICOS antibody.

ICOS has also recently been shown to be critical for the development and function of unique CD4$^+$ helper T cell subsets including T$_H$17 T cells (Paulos, C M., et al. (2010) The inducible costimulator (ICOS) is critical for the development of human Th17 cells. Sci Transl Med. 2(55), 55ra78) and circulating T follicular helper-like (TFH) cells (Bentebibel, S E., et al (2013) Induction of ICOS+CXCR3+CXCR5+ TH cells correlates with antibody responses to influenza vaccination.

Sci Transl Med 5(176), 176ra32). ICOS was shown to mediate the production of memory B cell and antibody responses following influenza vaccination. Similarly, the co-stimulatory function of ICOS on T$_H$17 cells was shown to be distinct among various co-stimulatory receptors which were tested, including CD28, OX40 and 4-1BB (Guedan, S., et al. (2014) ICOS-based chimeric antigen receptors program bipolar TH17/TH1 cells. Blood 124(7), 1070-80). This population of ICOS$^+$ T$_H$17 cells showed impressive anti-tumor activity in a mesothelioma mouse tumor model when used as the donor cells in an engineered chimeric antigen receptor (CAR) approach (Paulos, C M., Carpenito, C., Plesa, G., Suhoski, M M., Varela-Rohena, A., Golovina, T N., Carroll, R G., Riley, J L., June, C H. (2010) The inducible costimulator (ICOS) is critical for the development of human Th17 cells. Sci Transl Med. 2(55), 55ra78). In addition, T$_H$17-polarized T cells which were transduced with a CAR vector containing a portion of the ICOS intracellular domain showed superior anti-tumor activity as compared to CD28 and 4-1BB domain containing CARs in the same mesothelioma model. Importantly, ICOS T$_H$17 CAR T cells showed significantly increased expansion and prolonged duration in vivo as compared to CD28 and 4-1BB domain containing CARs, indicating that ICOS is critical for the proliferation and survival of this population (Guedan, S., et al. (2014) ICOS-based chimeric antigen receptors program bipolar TH17/TH1 cells. Blood 124(7), 1070-80). Here we have developed and characterized a novel agonist antibody targeted to human ICOS, offering the first potent and selective therapeutic against this important co-stimulatory T cell receptor.

Figures 9A, 9B:
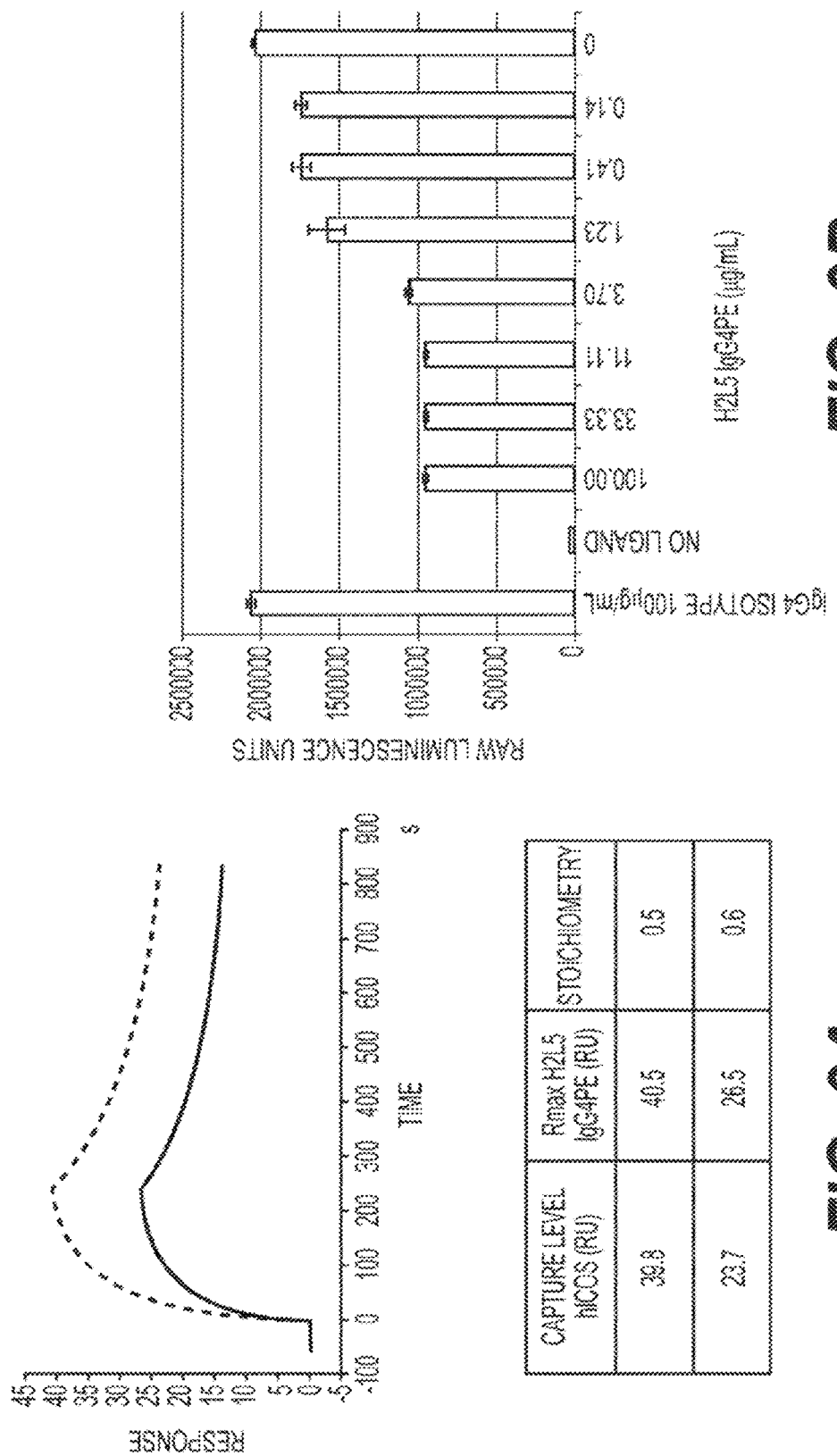
FIG. 9: H2L5 IgG4PE binding stoichiometry and ligand competition (A) H2L5 IgG4PE antibody binds to human ICOS receptor with a 1:2 stoichiometry (B) H2L5 IgG4PE partially competes for binding to ICOS receptor with human ICOS-L

The following are further described herein:
  Comprehensive characterization of a first-in-class agonist antibody against human ICOS
  Antibody isotype and FcγR-mediated crosslinking are critical features required for optimal activity
  Antibody-mediated ICOS activation potentiates effector CD4$^+$ and cytotoxic CD8$^+$ T cell function
  Combining antibody-mediated ICOS agonism and PD-1 blockade results in increased immune responses and synergistic antitumor activity Results Development of a Potent and Selective ICOS Agonistic Monoclonal Antibody The monoclonal antibody (mAb) H2L5 is a humanized, IgG4PE antibody against human ICOS. It binds to human ICOS with an affinity of 1.34 nM (FIG. 1A), which is approximately 17-fold higher than the native ICOS-L/CD275 (FIG. 1B). H2L5 was also found to bind with equivalent affinity to ICOS from cynomolgous macaques (0.95 nM). However, no cross-reactive binding was observed to murine ICOS. Importantly, H2L5 also had no detectable binding to either human CD28 or CTLA-4 protein, the two nearest structurally related proteins (Hutloff, A., et al. (1999) ICOS is an inducible T-cell co-stimulator structurally and functionally related to CD28. Nature 397 (6716), 263-266). This is in contrast to the native human ICOSL which has been shown to bind to both CTLA-4 and CD28 (Yao, S., et al (2011). B7-H2 is a costimulatory ligand for CD28 in human. Immunity 34(5), 729-40). The cross-reactivity of the native ICOSL reduces the therapeutic applicability of a recombinant version of this protein, and underscores the need for a potent and ICOS-selective agonistic mAb. Endogenous human ICOS is expressed as a disulfide-linked homodimer and as such a human Fc-fusion version of the recombinant ICOS protein was used for binding studies to mimic the dimeric native state of the protein (Chattopadhyay, K., et al. (2006) Structural basis of inducible costimulator ligand costimulatory function: determination of the cell surface oligomeric state and functional mapping of the receptor binding site of the protein. J Immunol. 177(6), 3920-9). Using a quantitative BIAcore target capture approach, H2L5 was found to bind with a 1:2 stoichiometry to ICOS (FIG. 9A). H2L5 was shown to partially compete with ICOSL binding to ICOS as shown in an MSD competition assay where a 10-fold excess of H2L5 resulted in approximately 50% inhibition of ICOSL binding, indicating an overlapping but unique binding site for H2L5 as compared to ICOSL (FIG. 9B). H2L5 binding was also evaluated by flow cytometry using naïve or activated CD4+ and CD8+ T cells isolated from healthy human donors. Activated PBMCs from every human donor tested showed significant binding of H2L5 to both $CD4^+$ and $CD8^+$ T cell populations (FIG. 1C).

Figures 10A, 10B:
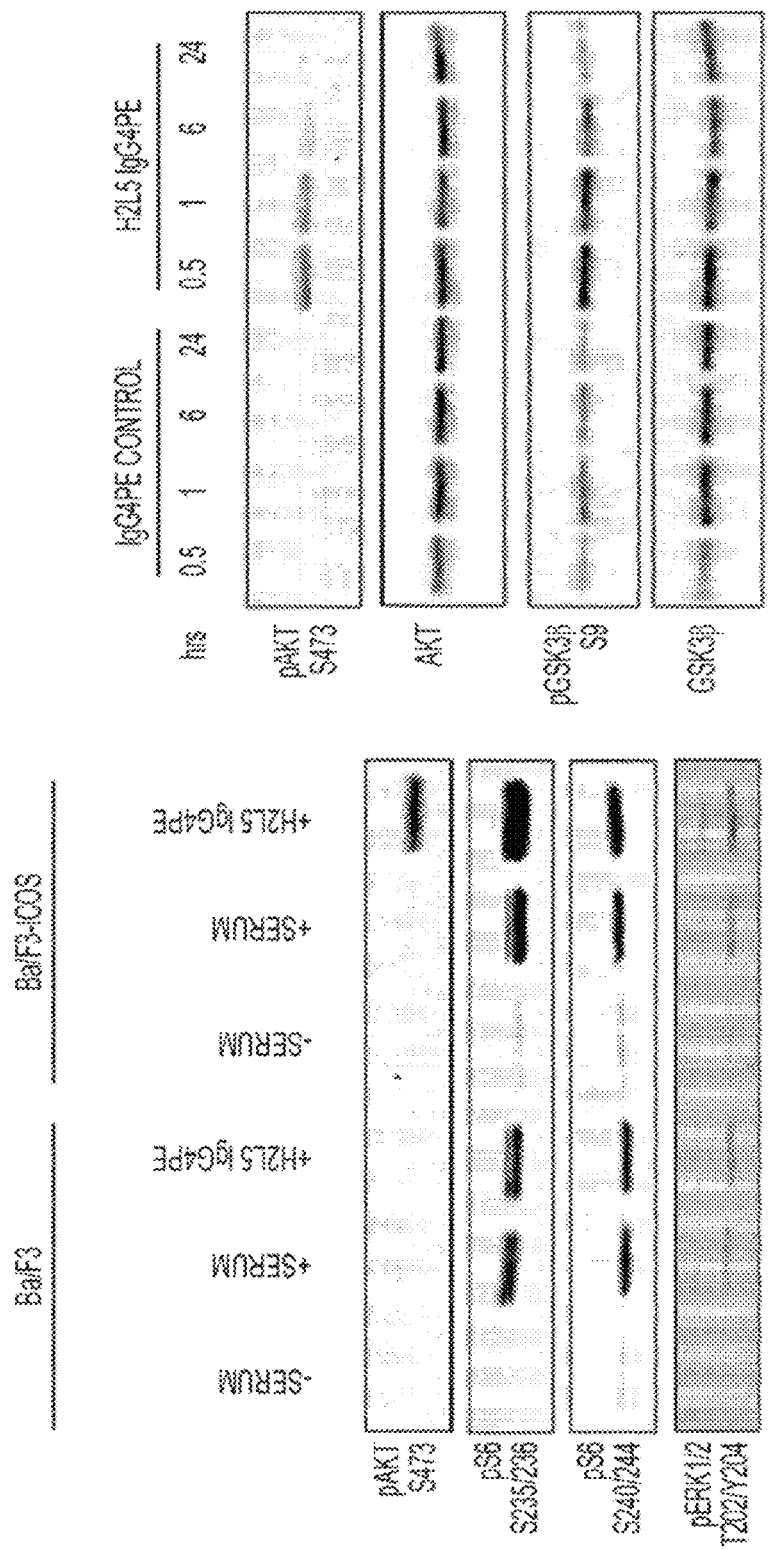
FIG. 10: H2L5 IgG4PE induces phospho-AKT (A) Treatment with H2L5 IgG4PE antibody at (20 ug/mL) for 1 hr in Ba/F3 cells with and without expression of human ICOS receptor (B) Treatment with H2L5 IgG4PE at (10 ug/mL) in primary CD4+ T cells

ICOS has previously been shown to activate AKT in response to ICOSL binding in human T cells (Okamoto, N., et al. (2003) PI3-kinase and MAP-kinase signaling cascades in AILIM/ICOS- and CD28-costimulated T-cells have distinct functions between cell proliferation and IL-10 production. Biochem Biophys Res Commun. 310(3), 691-702). To determine whether binding of H2L5 to ICOS could induce activation of downstream signaling, a stable mouse Ba/F3 cell line was engineered to express high levels of human ICOS. Using this cell line H2L5 showed a concentration-dependent increase in phospho-AKT levels (FIG. 1D). H2L5 also resulted in phosphorylation of other proteins downstream of AKT, such as GSK3α and ribosomal protein S6 in a concentration and time dependent manner in the Ba/F3-ICOS expressing cell line (Table 2). Signaling in this cell line was dependent upon ICOS expression as no AKT activation was observed in the parental Ba/F3 cell line (FIG. 10A). H2L5 was also tested in activated CD3+ T cells isolated from healthy human donors. Pre-activated primary human CD4+ T cells showed a similar increase in phospho-AKT (Ser473) in response to treatment indicating that H2L5 is able to signal through ICOS via activation of the AKT pathway in primary human T cells (FIG. 10B).

Figure 11:
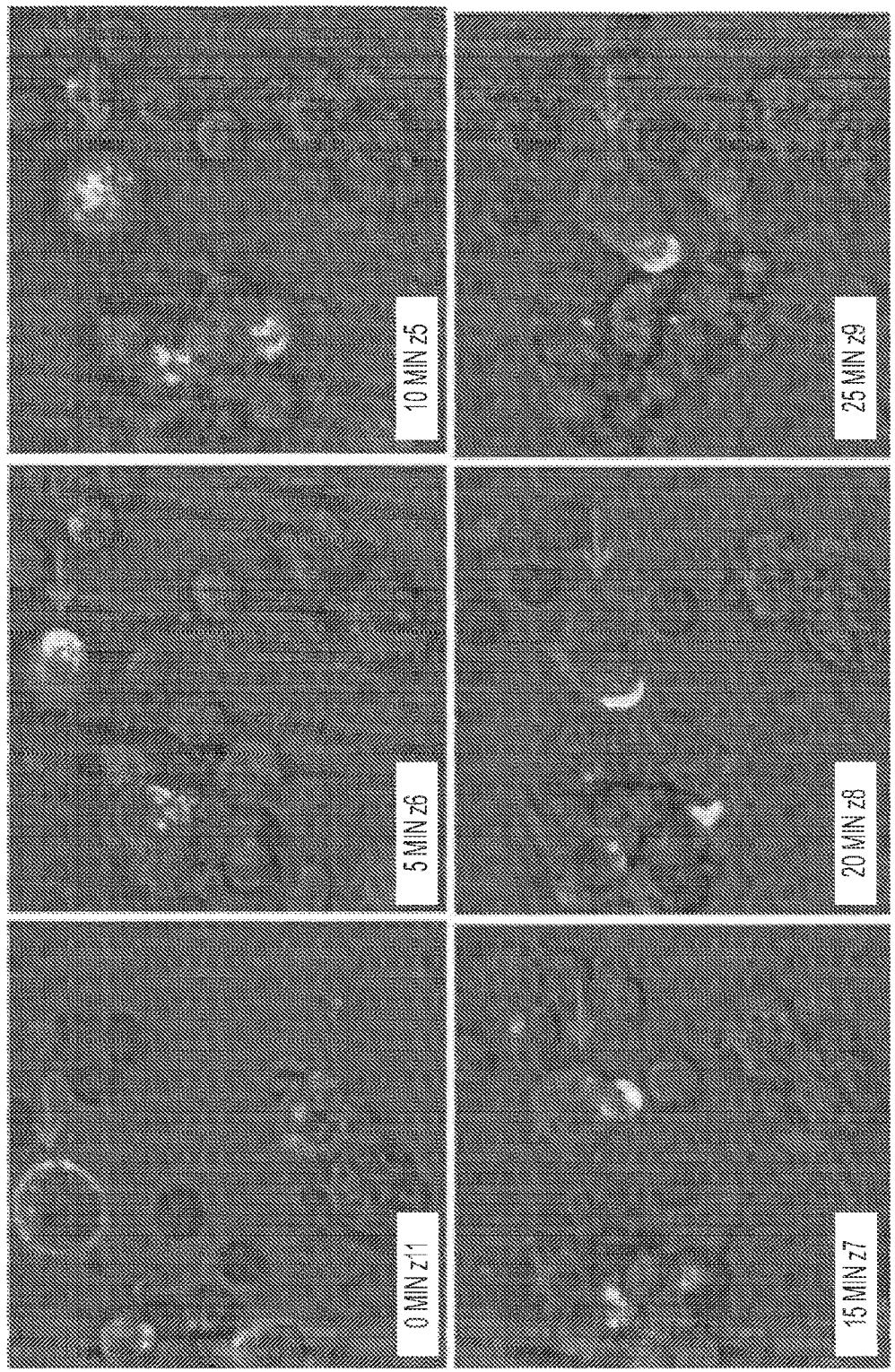
FIG. 11: Membrane trafficking of H2L5 IgG4PE following binding. H2L5 IgG4PE after binding to primary CD4+ T cells in co-culture with monocyte-derived human dendritic cells. Timecourse indicates time following addition of H2L5 IgG4PE to cells.

Additionally, H2L5 binding and the resulting membrane trafficking was evaluated by confocal microscopy on activated primary human $CD3^+$ T cells. H2L5 mAb was labelled with an AlexaFluor488 dye to image the kinetics of H2L5 cell localization in a time-course following binding. Strikingly, it was found that the H2L5 mAb:ICOS receptor complex rapidly polarized following binding. The caps containing H2L5 mAb:ICOS receptor were crescent shaped foci resembling an immune synapse on the surface of T cells. In instances where T cells were in cell:cell contact, H2L5 accumulated at the point of contact (FIG. 1E). Co-staining with an endosome specific marker showed that no H2L5 appeared to be internalized into T cells. In unactivated T cells, staining with labelled H2L5 showed limited binding, as expected due to low ICOS expression. Additional studies using co-cultures of human dendritic and T cells demonstrated that H2L5 mAb:ICOS complexes are rapidly co-localized to the polarized caps of activated T cells as well as the subsequent immune synapses formed upon T cell binding to dendritic cells (FIG. 11). These results indicate that ICOS activation is important for the formation and function of T cell immune synapses and can be induced with H2L5.

Figure 12B:
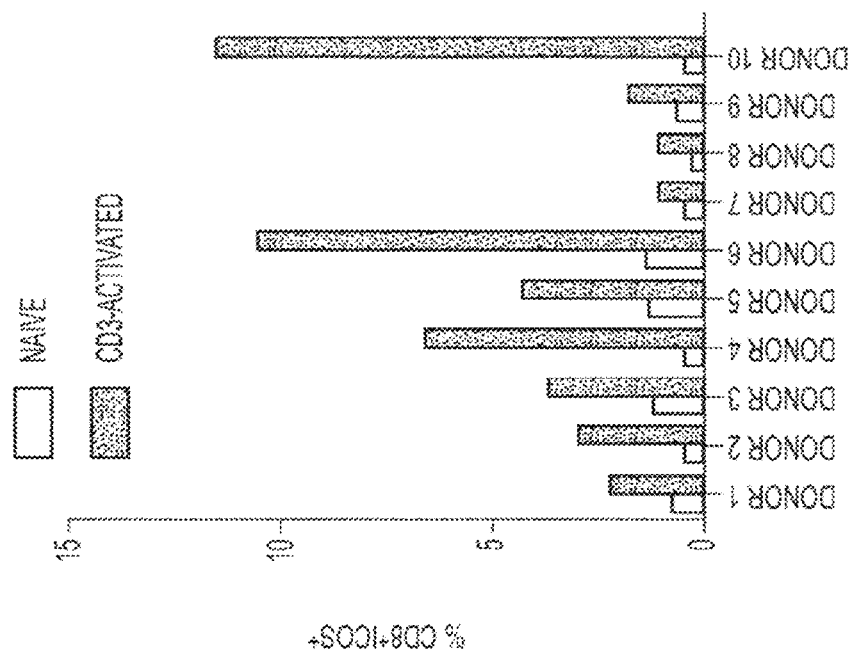
FIG. 12: Overnight activation with anti-CD3 antibody induces ICOS receptor expression (A) Percentage of healthy donor CD4+ and (B) CD8+ cells which are positive for ICOS expression following 24 hour stimulation with anti-CD3 antibody
Figure 12A:
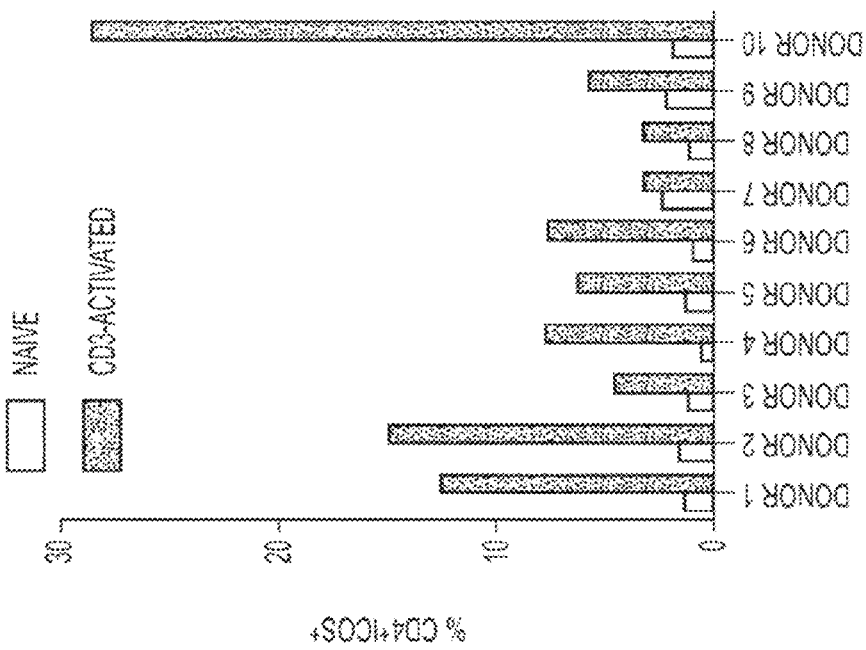

H2L5 Induces Potent T Cell Activation, Proliferation and Function in a TCR-Dependent Manner A key, desired activity of an anti-ICOS agonist mAb is to co-stimulate the proliferation of activated effector $CD4^+$ and cytotoxic $CD8^+$ T cells in the context of simultaneous TCR engagement (i.e., not acting as a super-agonist). The ability of H2L5 to co-stimulate T cells was evaluated in assays wherein H2L5 was administered either alone or in combination with an anti-CD3 antibody in primary human PBMC from 10 healthy donors. Cytokine release (IL-2, IL-10, IL-6, TNF-α and IFNγ) was used as a measure of T cell activation in response to H2L5 binding. Three different incubation conditions were evaluated: 1) overnight culture of PBMC (unactivated) followed by incubation of H2L5 for 24 hours; 2) overnight culture of PBMC in the presence of immobilized anti-CD3 (0.3 µg/mL) to stimulate signaling through the TCR followed by incubation with H2L5 for 24 hours, and; 3) overnight culture of PBMC in the presence of immobilized anti-CD3 (0.3 µg/mL) to stimulate signaling through the TCR followed by incubation with H2L5 and anti-CD3 for 24 hours. As a positive control an agonist CD28 mAb was added to each condition. The initial overnight activation with immobilized anti-CD3 modestly increased ICOS expression to varying extents on CD4+ and CD8+ T cells from all 10 human donors tested (FIG. 12).

In unactivated PBMC cultures (assay system 1), no significant induction of cytokines were observed with H2L5 as compared to the isotype control antibody (FIG. 2A). Similarly, no significant cytokine induction was observed as compared to the isotype control in activated PBMC incubated with H2L5 (assay system 2) (FIG. 2B). In both conditions, the anti-CD28 antibody induced cytokine production. In contrast, significant IFNγ induction observed in 6/10 donors when PBMC were first activated then incubated with both H2L5 and anti-CD3 (assay system 3) (FIG. 2C). Under those conditions, H2L5 induced levels of IL-2, IL-10, TNF-α in 3, 5 and 2 out of 10 donors, respectively, as compared to the isotype control IgG4. However, H2L5 did not significantly increase IL 6 production above control IgG4 levels in any donor tested using this assay format. These results indicate that H2L5 is not a super-agonist and co-stimulation through the TCR is required for productive H2L5 agonist function.

Figure 2D:
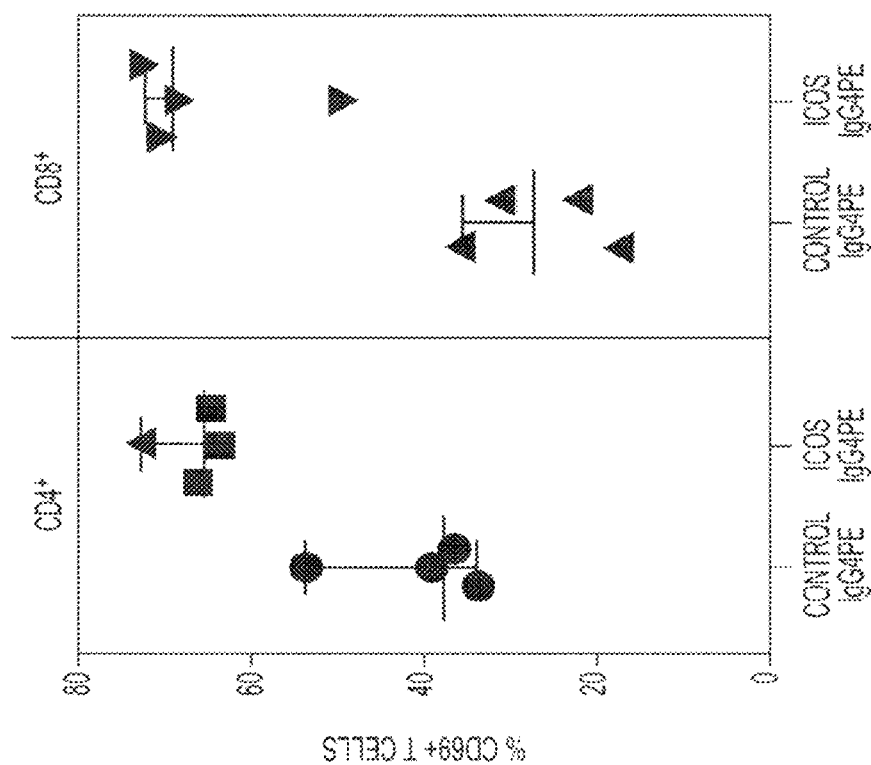
Figure 2G:
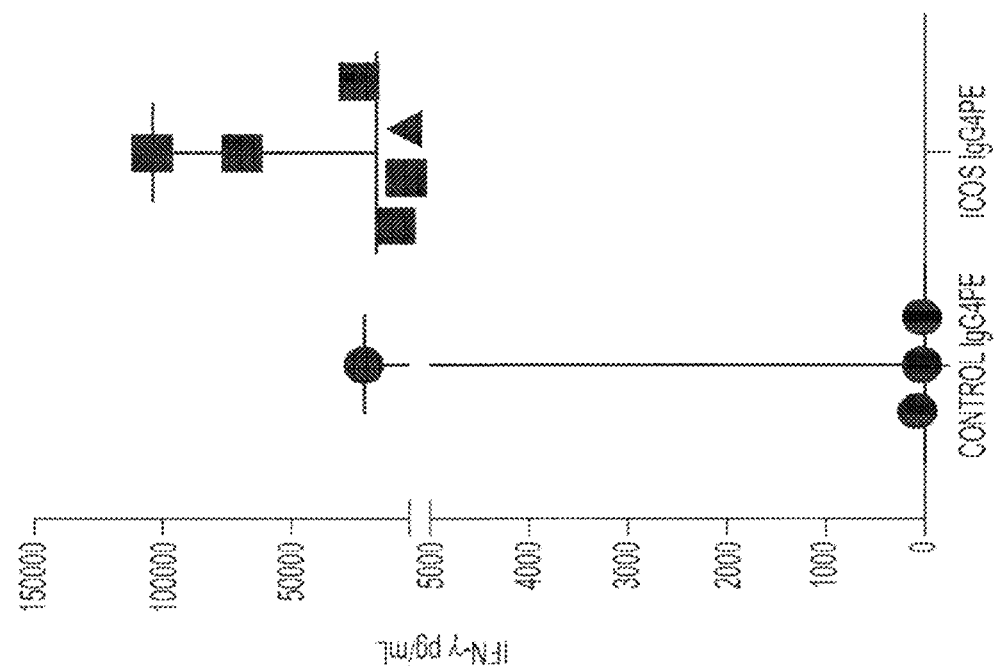
Figure 2F:
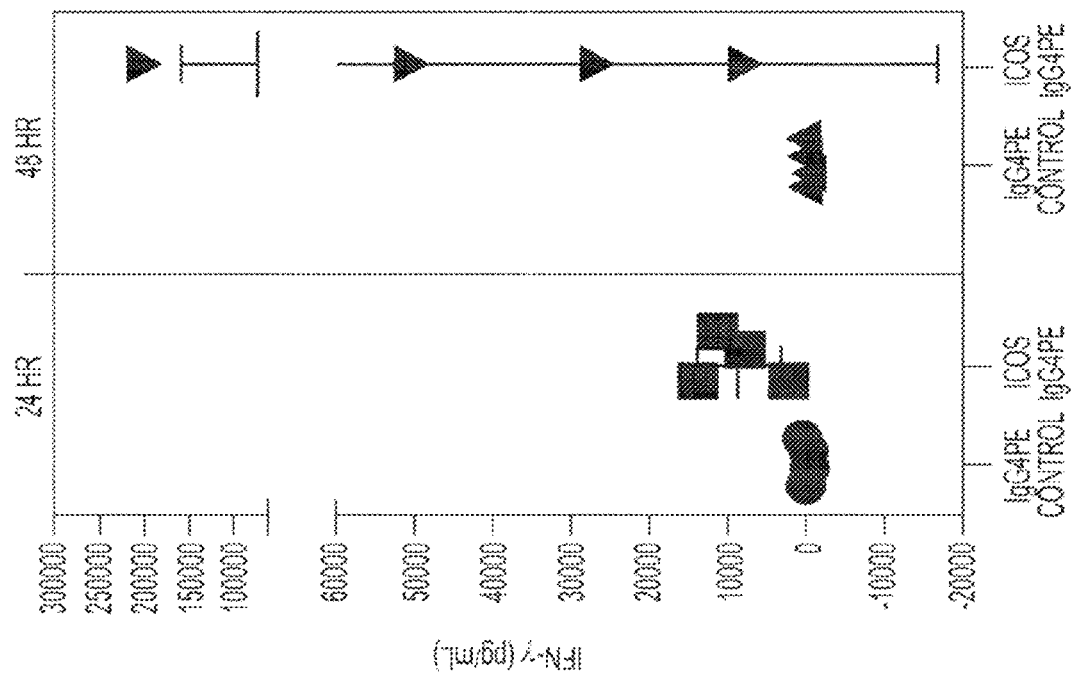

To determine the full effect of the H2L5 agonist function on T cells an additional 4 healthy donor PBMC samples were tested to determine the ability of H2L5 to induce T cell activation, proliferation and cytokine production. The functional effects of H2L5 were evaluated with concurrent TCR engagement via plate-bound anti-human CD3. Under these conditions, H2L5 significantly increased the percentage of CD4+ and CD8+ T cells expression of the T cell activation marker CD69 and OX40 (FIG. 2D). Significant increases in proliferation of CD4+ and CD8+ T cells, ranging from 2 to 8 fold, were also observed as evidenced by increased staining with the nuclear proliferation marker Ki67 (FIG. 2E). Cytokine analysis from the cell culture supernatants of healthy subject PMBC showed that H2L5 antibody induced Th1, Th2 and Th17 cytokines IFNγ, TNF-α, IL-17a, IL-10, IL-6 and to a lesser extent IL-2, IL-5 and IL-13 (FIG. 2F). PBMC were also isolated from patients with cancers including non-small cell lung carcinoma (NSCLC), head and neck and melanoma and treated with H2L5 antibody. H2L5 induced significant IFNγ production in all cancer PBMC samples tested (FIG. 2G).

Requirement for FcγR-Mediated Crosslinking for Optimal H2L5 Agonist Function

The requirement for FcγR-mediated crosslinking has been shown to be critical for the optimal function of agonist antibodies targeting other immune receptors (Dahal, L N., et al. (2015) FcγR requirements leading to successful immunotherapy. Immunol Rev. 268(1), 104-22). We therefore tested whether FcγR-dependent crosslinking was also important for the agonist function of H2L5. H2L5 was first tested against isolated human $CD4^+$ T cells (n=2 donors) in both a plate bound (immobilized antibody) format as well as with H2L5 in solution in order to test the agonist activity in the absence of FcγR expressing cell populations. The activity of H2L5 was then determined by measuring the production of IFNγ. H2L5 in the immobilized format induced significantly greater levels of IFNγ as compared to the soluble antibody (FIG. 3A). EC50 values of IFNγ induction for both donors were 3.8 and 4.5 µg/mL, respectively, for immobilized format and were 6.0 and 4.3 µg/mL, respectively, for the soluble format.

Figure 3D:
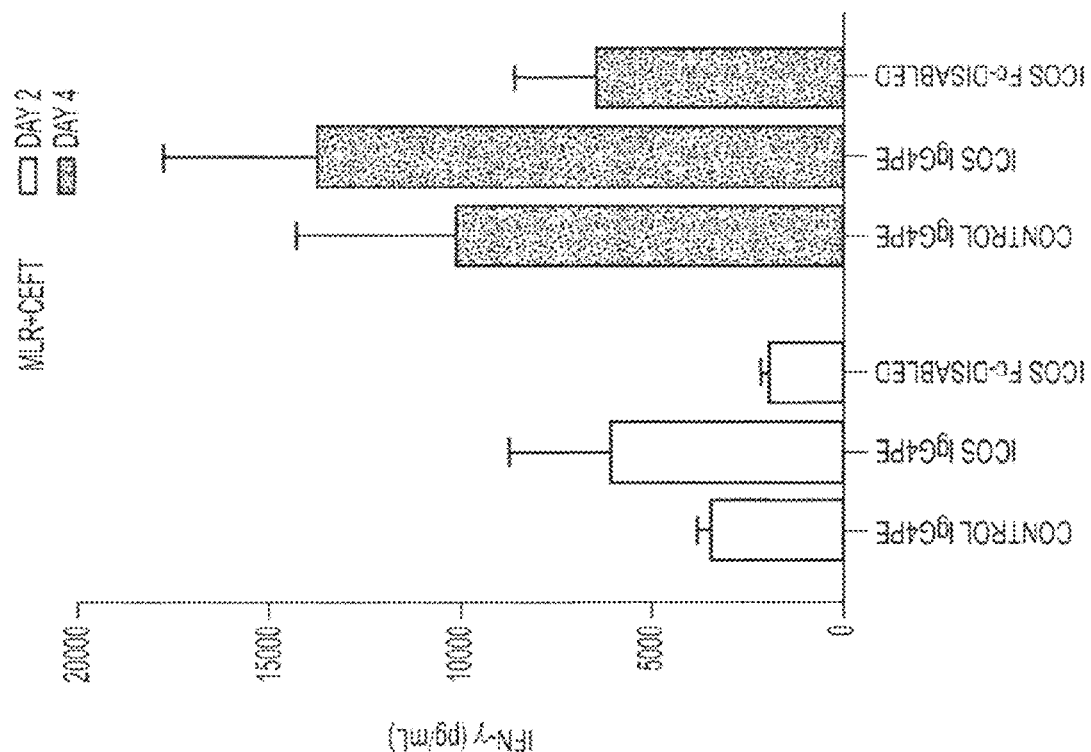
FIG. 3: FcγR-mediated crosslinking is required for optimal H2L5 agonist function (A) Isolated CD4$^+$ T cells from healthy subjects treated with indicated concentrations of H2L5 IgG4PE for 60 hrs (B) PBMCs from a healthy subject treated with soluble H2L5 IgG4PE (ICOS IgG4PE) or H2L5 Fc-disabled at (10 ug/mL) for 3.5 days (C) Modified mixed-lymphocyte reaction (MLR) with anti-CD3 antibody followed by treatment with soluble H2L5 IgG4PE or H2L5 Fc-disabled antibody at (10 ug/mL) (D) Modified mixed-lymphocyte reaction with CEFT peptide followed by treatment with soluble H2L5 IgG4PE (ICOS IgG4PE) or H2L5 Fc-disabled antibody at (11.1 ug/mL) (E) Co-culture of isolated T cells and monocytes from the same donor followed by treatment with soluble H2L5 IgG4PE at (10 ug/mL) for 4 days.
Figure 3C:
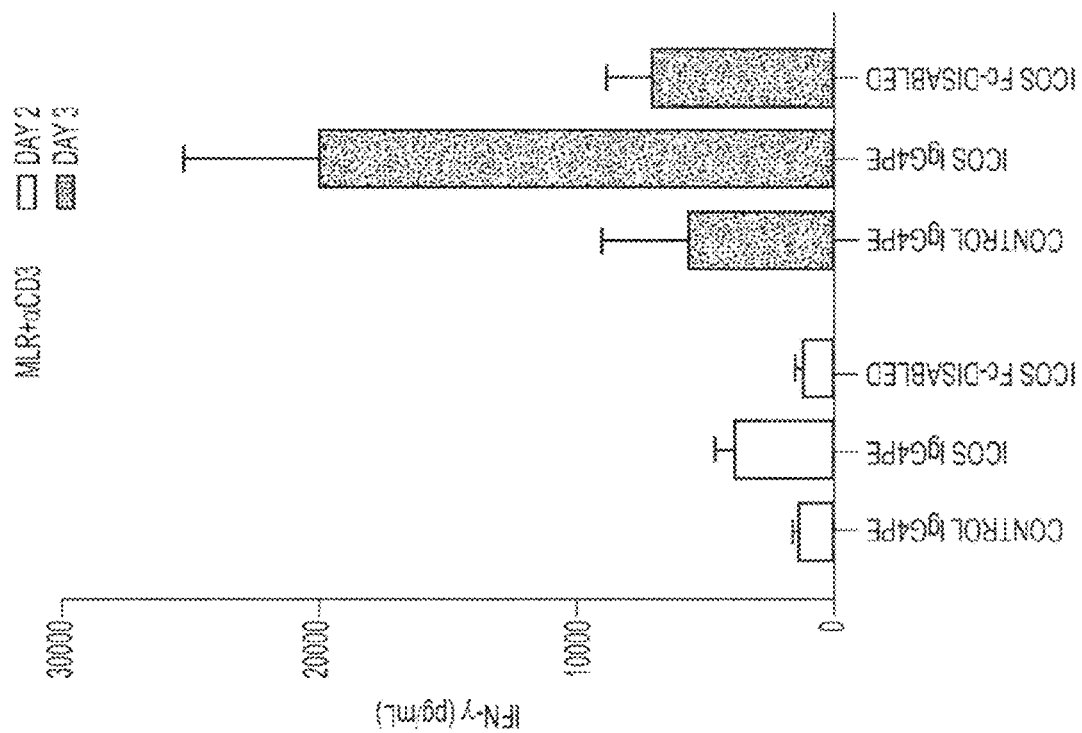
Figure 3E:
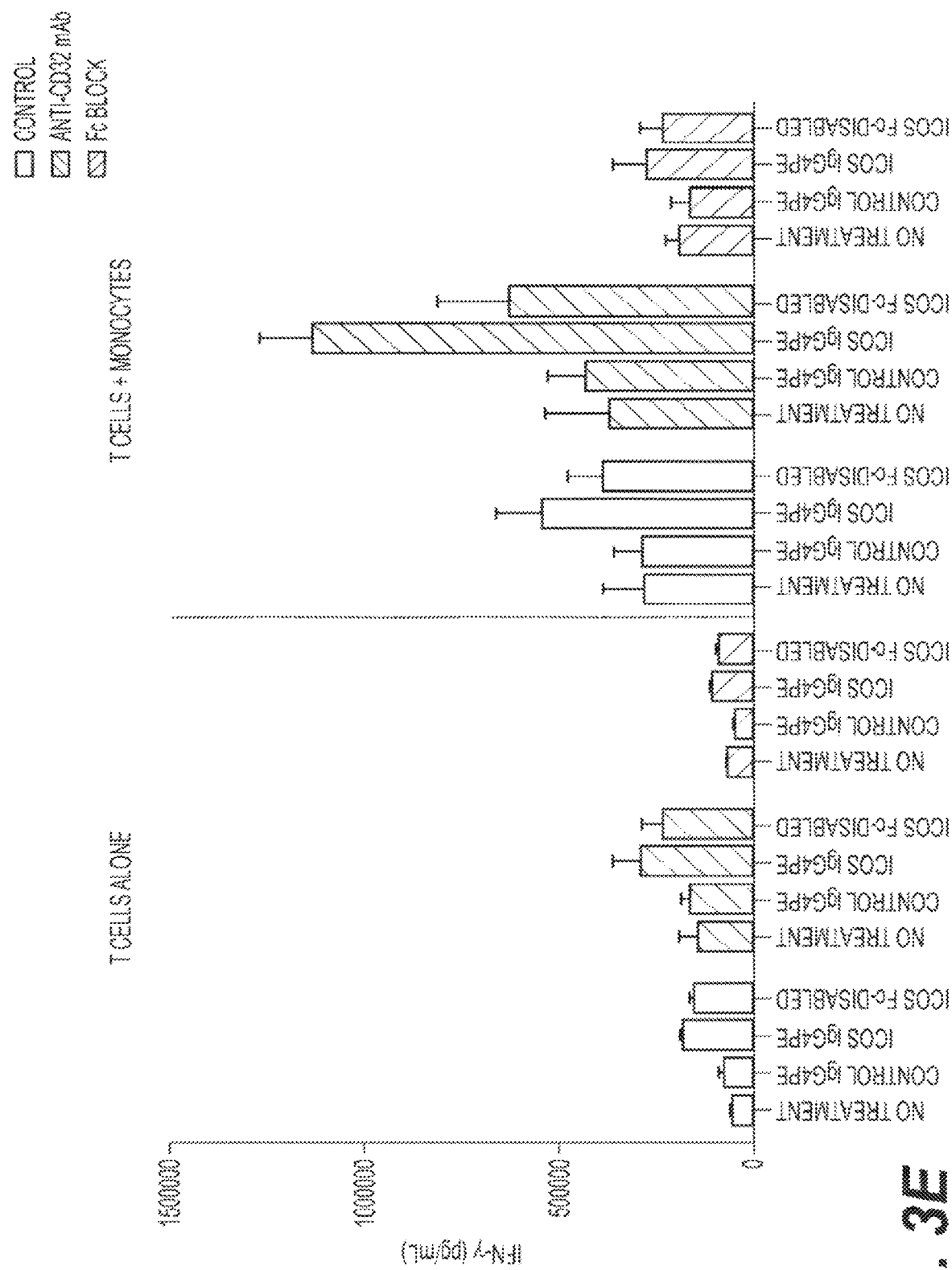

In the soluble assay format, H2L5 was next evaluated in an activated human PBMC assay, in which FcγR-expressing cells (monocytes, B cells, etc.) are present. The CDR binding domains of H2L5 were re-cloned onto an Fc-disabled isotype backbone which cannot efficiently engage FcγR (Bartholomew, M., et al. (1995). Functional analysis of the effects of a fully humanized anti-CD4 antibody on resting and activated human T cells. Immunology 85(1), 41-8) to evaluate the FcγR-dependency of H2L5 for effective T cell agonism. In the activated human PBMC assay, H2L5 IgG4PE resulted in a greater than 2-fold induction of IFNγ whereas the Fc-disabled version of H2L5 had no cytokine induction activity as compared to isotype control (FIG. 3B). The IgG4PE and Fc-disabled versions of H2L5 were also tested in a modified mixed lymphocyte reaction (MLR) where isolated CD3+ T cells from one human donor were co-cultured with the matured dendritic cells from a separate human donor, resulting in an allogenic response. H2L5 was then added to the T cell:dendritic cell co-culture together with the anti-CD3 antibody. Similar to the PBMC results, the H2L5 IgG4PE mAb provided a greater than 2-fold induction of IFNγ whereas the Fc-disabled H2L5 mAb had no activity as compared to isotype control (FIG. 3C). Similarly, in the same MLR assay format a CEFT peptide mixture was added together with H2L5 instead of anti-CD3 to induce a more physiologically relevant TCR activation. Like the PBMC and anti-CD3 MLR assays, the CEFT MLR assay also resulted in induction of IFNγ only when H2L5 was in an IgG4PE format (FIG. 3D). Next a CD4+ T cell/CD14+ monocyte donor-matched co-culture assay was utilized across three separate donors to determine whether FcγR-expressing monocytes increased the agonist potential of soluble H2L5. Similar to the MLR assay format, H2L5 only induced IFNγ when tested as an IgG4PE isotype, as the Fc-disabled showed no significant cytokine induction as compared to isotype control. The addition of monocytes resulted in a significant increase in H2L5 IgG4PE induced cytokine production as compared to T cells alone. The optimal ratio of Tcells:monocytes was found to be 1:2 for achieving H2L5-induced cytokine production and T cell proliferation. Interaction with CD32 has been shown to be critical for the agonistic activity of other immunomodulatory antibodies targeting TNF-α family receptors as well as CD28 (Bartholomaeus, P., et al. (2014) Cell contact-dependent priming and Fc interaction with CD32+ immune cells contribute to the TGN1412-triggered cytokine response. J Immunol. 192(5), 2091-8). To determine whether CD32/FcRII was important for the agonist activity of the H2L5 IgG4PE mAb an anti-CD32 antibody was added to induce crosslinking of the CD32 protein on monocytes. Strikingly, the anti-CD32 mAb resulted in significant induction of cytokine production when added together with H2L5 IgG4PE. This suggests that clustering/oligimerization of CD32 is important for optimal agonist potential of H2L5 antibody. Conversely, the addition of an Fc-blocking antibody completely inhibited the H2L5-induced cytokine induction (FIG. 3E). These results show that FcγR-mediated crosslinking is critical to the optimal agonist potential of the anti-ICOS H2L5 IgG4PE antibody.

Isotype Selection is Critical to Avoid FcγR-Mediated ICOS+ Cell Depletion

We next tested whether an IgG1 isotype format would be suitable for therapeutic design as this isotype allows for maximal FcγR binding and our observation that FcγR binding was shown to be critical for the full agonist potential of the H2L5 mAb. The H2L5 CDRs were cloned as different human IgG isotypes (IgG1, IgG2, IgG4PE, IgG Fc-disabled) and subsequently tested in functional assays using healthy donor PBMCs. Using surface plasmon resonance (SPR) technology, H2L5 binding was determined against human FcγR I, FcγR IIa (H131), FcγR IIa (R131), FcγR IIb, FcγR IIIa (V158) and FcγR IIIa (F158). As expected H2L5 IgG1 bound strongly to all FcγRs tested with modest binding against FcγR IIb (Table 3). H2L5 IgG4PE was shown to retain binding to human FcγRIIb but had very little or no binding to FcγRIIIa and significantly reduced binding affinities for FcγRI and IIa, whereas H2L5 IgG2 and IgG Fc-disabled formats showed little-no binding to any to FcγR (Table 3). The different H2L5 antibody variants were tested in a 6 day proliferation assay with different PBMC donors. The H2L5 IgG1 antibody demonstrated a greater than 1.3-fold decrease in proliferation as compared to the IgG1 isotype control in CD4+ cells from 8/12 donors and CD8+ cells from 6/12 of donors, respectively. In contrast, use of IgG2, IgG4PE or Fc-disabled isotype variants of H2L5 did not result in substantial proliferation inhibition of either CD4+ or CD8+ T cells in any donors (FIG. 4A). The inhibitory effect of H2L5 IgG1 was further demonstrated to be dependent upon NK cells in the PMBC mixture, as removal of NK cells eliminated the proliferation inhibition of H2L5 IgG1 on both CD4+ and CD8+ cells (FIG. 4B). The H2L5 antibodies were also tested in a reporter assay which detects signaling induced by activation of FcγRIIIa, the primary activatory FcγR responsible for Antibody-Dependent Cellular Cytotoxicity (ADCC) in humans. Exposure of an ADCC reporter cell line demonstrated that while H2L5 IgG1 induced a significant increase in luciferase signaling, neither the H2L5 IgG4PE nor Fc-disabled antibodies induced FcγRIIIa-mediated signaling (FIG. 4C). Additionally, T cell death as determined by flow cytometry was evaluated in response to treatment with H2L5 IgG1, IgG4PE and Fc-disabled antibodies. H2L5 IgG1 induced cell death in greater than 15% of total PBMC (predominantly due to a loss of CD4+ cells) while neither H2L5 IgG4PE or Fc-disabled resulted in any significant increase in cell death as compared to isotype control treatment (FIG. 4D). Similar to the PBMC proliferation assay the cell death inhibition induced by H2L5 IgG1 was shown to be dependent upon NK cells in the PBMC pool (FIG. 4D). An anti-CD52 antibody known to induce ADCC-mediated cell killing was included as a positive control for both of these assays and showed strong signaling of FcγRIIIa (FIG. 4C) and death (FIG. 4D) of PBMCs.

Figure 5A:
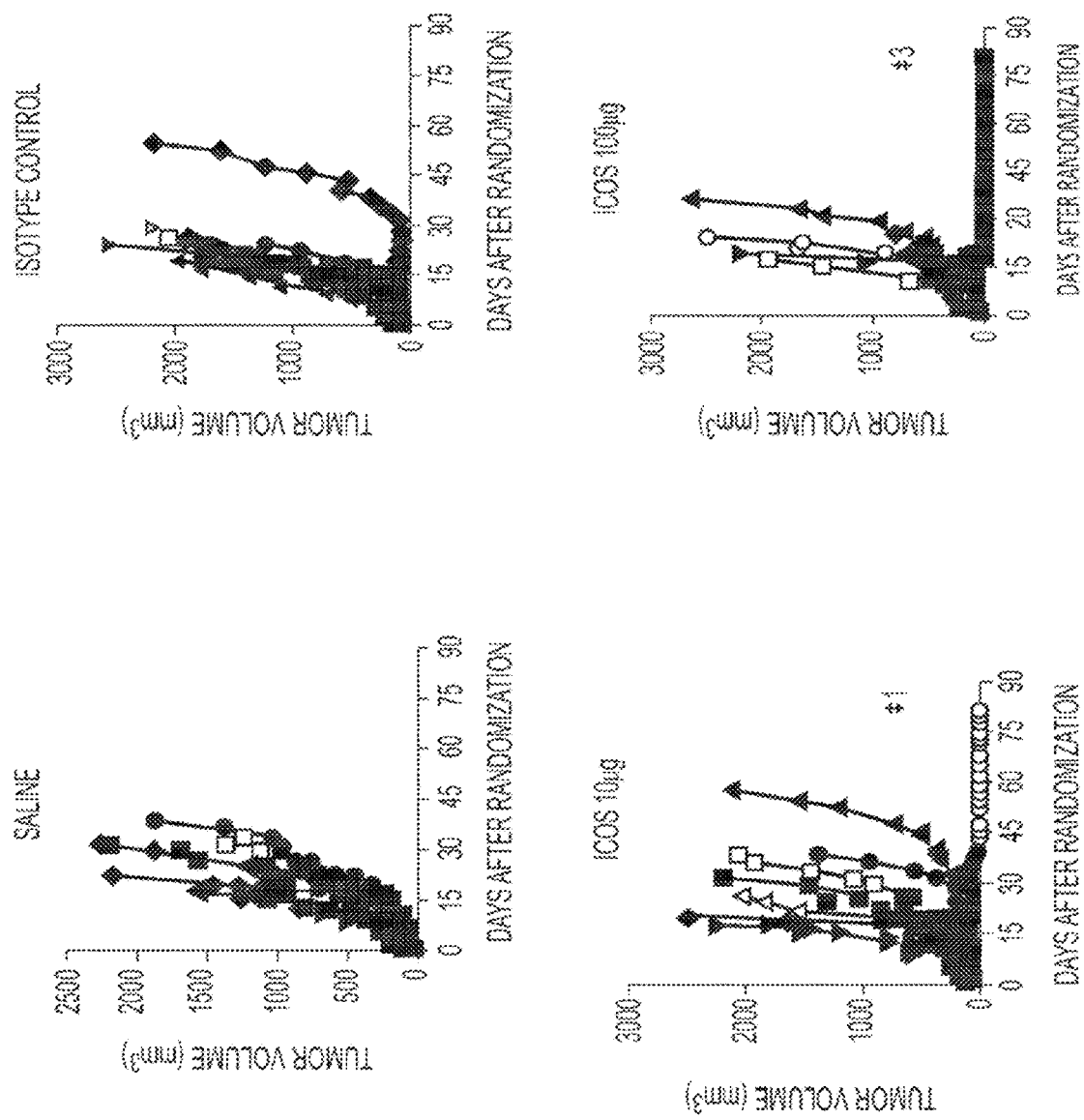
FIG. 5: Anti-mouse ICOS agonist antibody results in anti-tumor responses in syngeneic mouse tumor models (A) Mice with EMT6 murine breast carcinoma tumors treated with indicated doses of 7E.17G9 antibody twice weekly for 3 weeks. Numbers indicate the number of mice with minimally detectable or non-detectable tumors at study endpoint (B) Mice with CT26 tumors treated with 7E.17G9 antibody twice weekly for 3 weeks (C) Percentage of CD4+ CD62L+ CD44+ (Effector Memory) and CD4+ CD62L− CD44+ (Central Memory) T cells in the blood of mice with EMT6 tumors 48 hrs following the third dose of 7E.17G9 antibody (D) The CD8:Treg ratio score as measured by Nanostring analysis from mice with EMT6 tumors 48 hrs following the third dose of 7E.17G9.
Figure 5B:
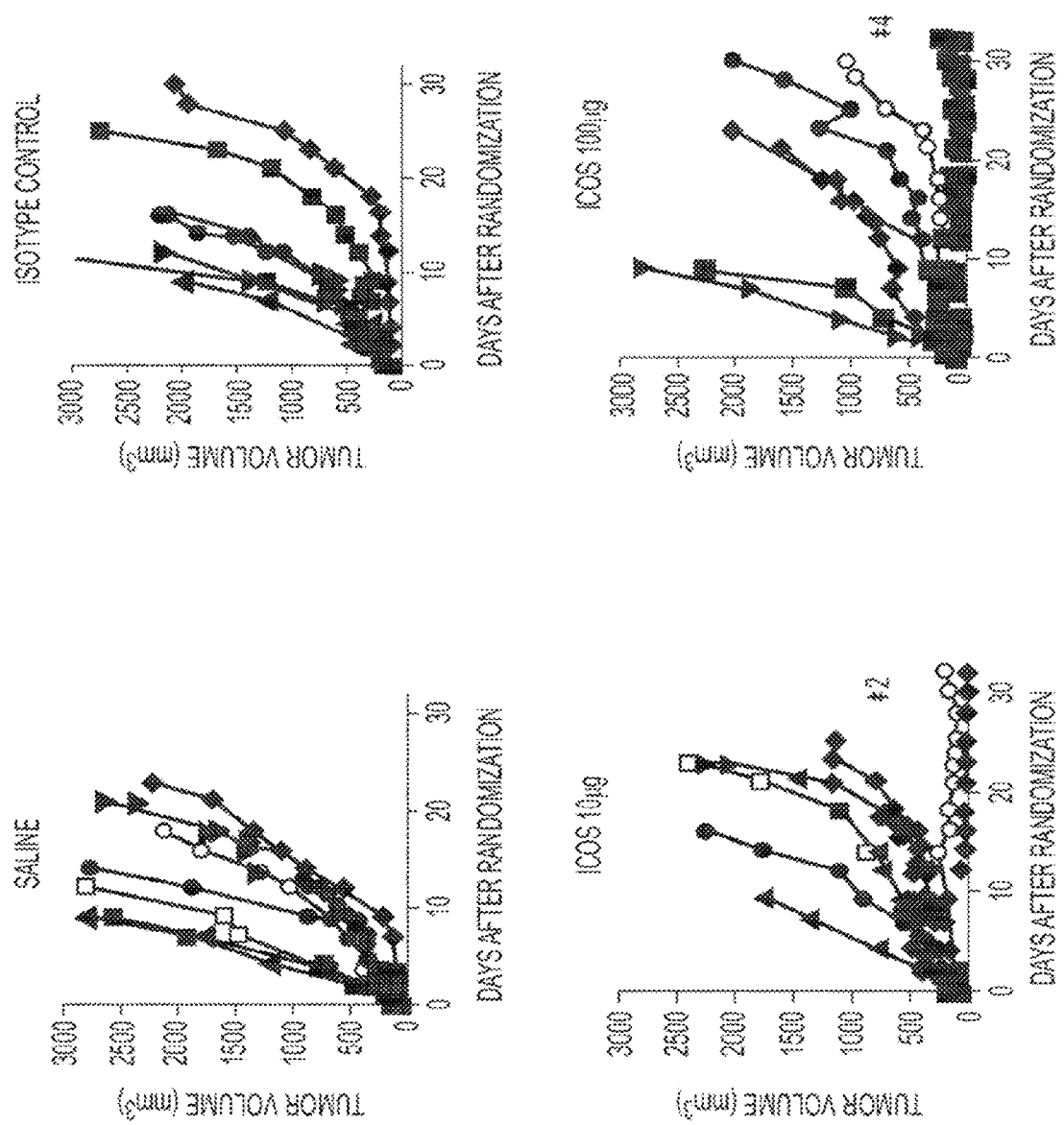
Figure 5D:
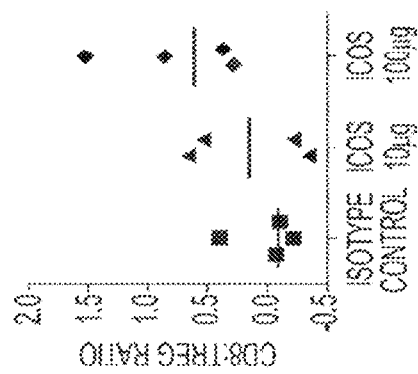
Figure 5C:
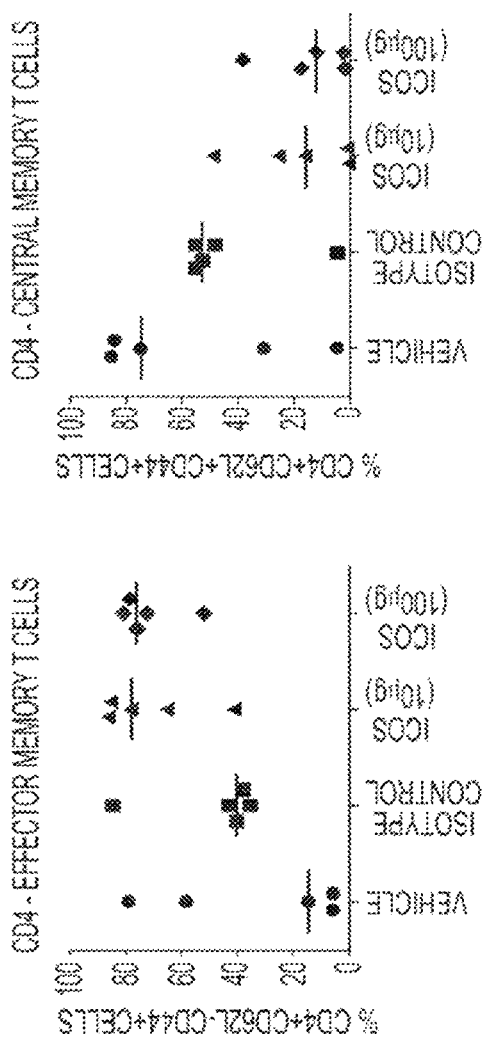
Figure 13C:
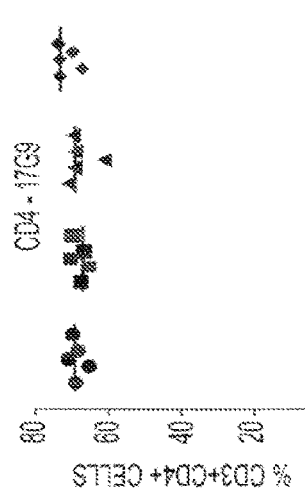
FIG. 13: Characterization of an anti-mouse ICOS agonist antibody. (A) Anti-mouse ICOS agonist antibody (7E.17G9) induces IFNγ production in disseminated mouse splenocytes cultured ex vivo (B) Percentage of apoptotic/necrotic blood CD45+ cells 48 hours after the 3$^{rd}$ dose of 7E.17G9 in mice with EMT-6 tumors (C) No significant change in CD4+ or (D) CD8+ T cell percentage 48 hours after the 3$^{rd}$ dose of 7E.17G9 in mice with EMT-6 tumors
Figure 13D:
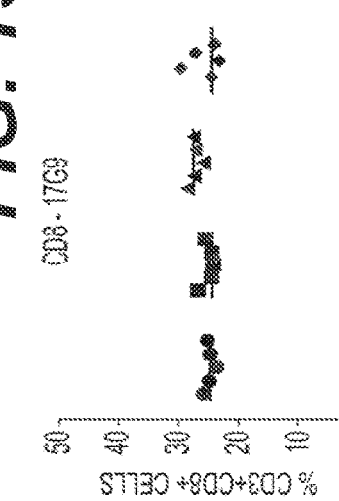
Figure 13A:
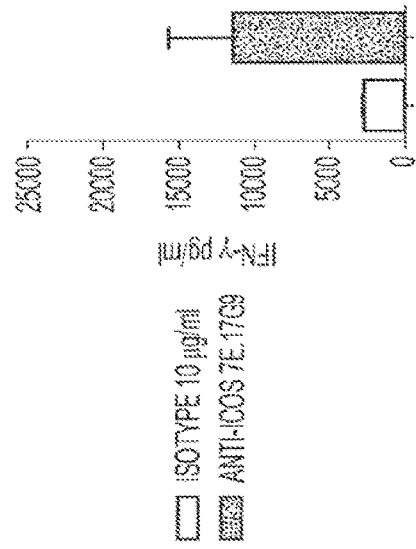
Figure 13B:
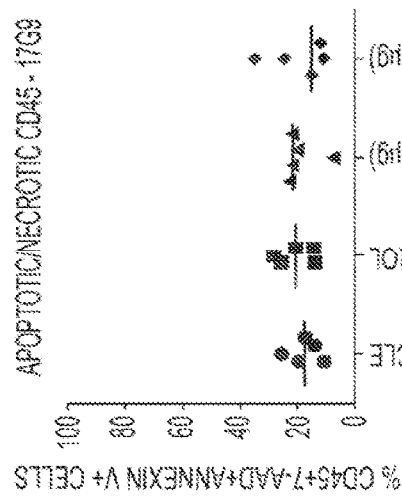

A Mouse Surrogate ICOS Agonist Antibody Induces Anti-Tumor Responses in Syngeneic Mouse Tumor Models H2L5 exhibits no binding cross-reactivity for murine ICOS. For this reason a suitable murine surrogate ICOS agonist antibody was required to perform studies in immune competent mouse tumor models. An anti-mICOS antibody (7E.17G9 mIgG2a) was shown to induce IFNγ in an in vitro splenocyte assay (FIG. 13A). This antibody demonstrated no significant increase in CD45+ cell death or decrease in circulating CD4+ or CD8+ T cell percentage when dosed in EMT6 tumor bearing mice (FIGS. 13B-13D). Conversely, the antibody provided a dose-dependent increase in the proliferation of circulating T cells, as would be expected of an ICOS agonist antibody (FIG. 14). Therefore, 7E.17G9 was determined to be a suitable murine surrogate ICOS agonist antibody for use in mouse tumor models. 7E.17G9 demonstrated sustained anti-tumor responses in 10 and 30% of mice with EMT6 breast carcinoma tumors at 10 µg and 100 µg, respectively, when administered twice weekly for 6 total doses (FIG. 5A) and in 20 and 40% of mice with CT26 colorectal carcinoma tumors at 10 µg and 100 µg, respectively (FIG. 5B). The anti-tumor activity was associated with an increase in circulating effector memory T cells, a corresponding decrease in central memory cells (FIG. 5C) and a significant increase in the CD8/Treg score ratio was also observed in 7E.17G9 treated tumors (FIG. 5D).

Murine ICOS Agonist Induces an IFN-γ Signature and PDL-1 Increase in Tumors.

Figure 6A:
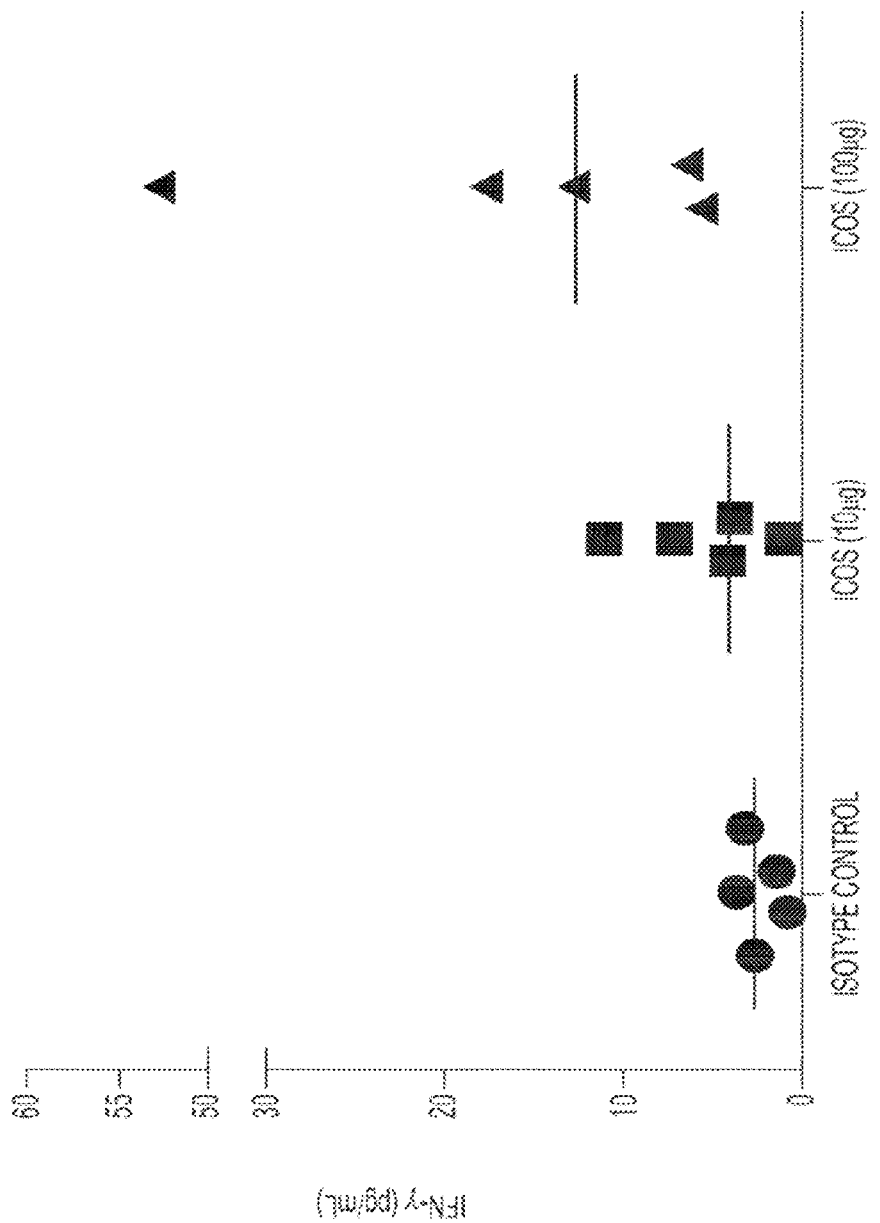
FIG. 6: anti-mouse ICOS agonist antibody induces an IFN-γ signature and PDL-1 increase in tumors. (A) Soluble IFNγ from the blood of mice with EMT6 tumors 48 hrs following the third dose with 7E.17G9 antibody (B) Nanostring gene expression analysis from EMT6 tumors 48 hrs following the third dose of 7E.17G9 antibody (C) Ifng, (D) PDL-1 and (E) PD-1 gene expression from EMT6 tumors following treatment with 7E.17G9 antibody (F) Percentage of PD-1$^+$CD4$^+$ T cells in the blood of mice with EMT6 tumors 48 hrs following the third dose of 7E.17G9 antibody.
Figure 6B:
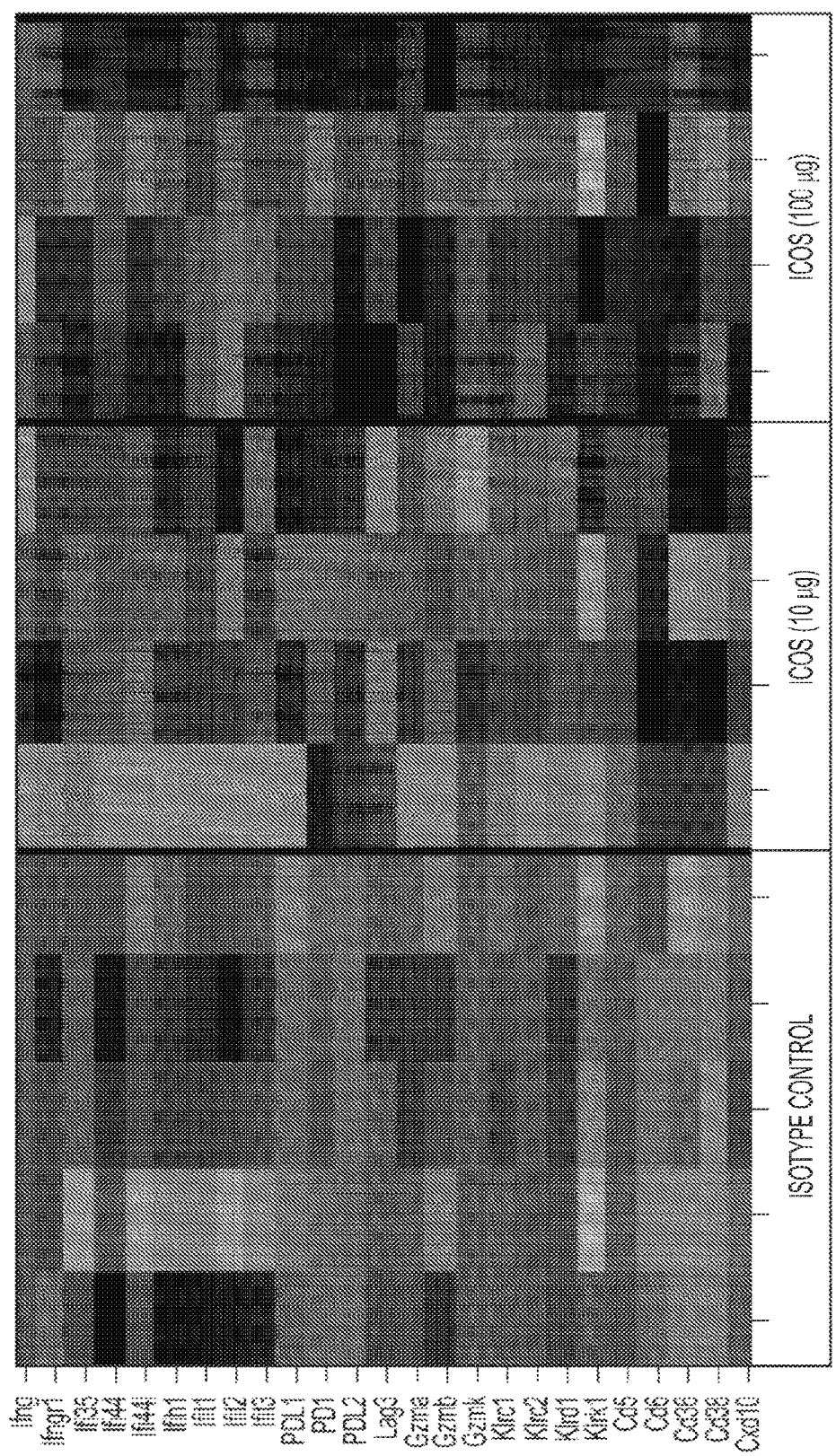
Figures 6C, 6D:
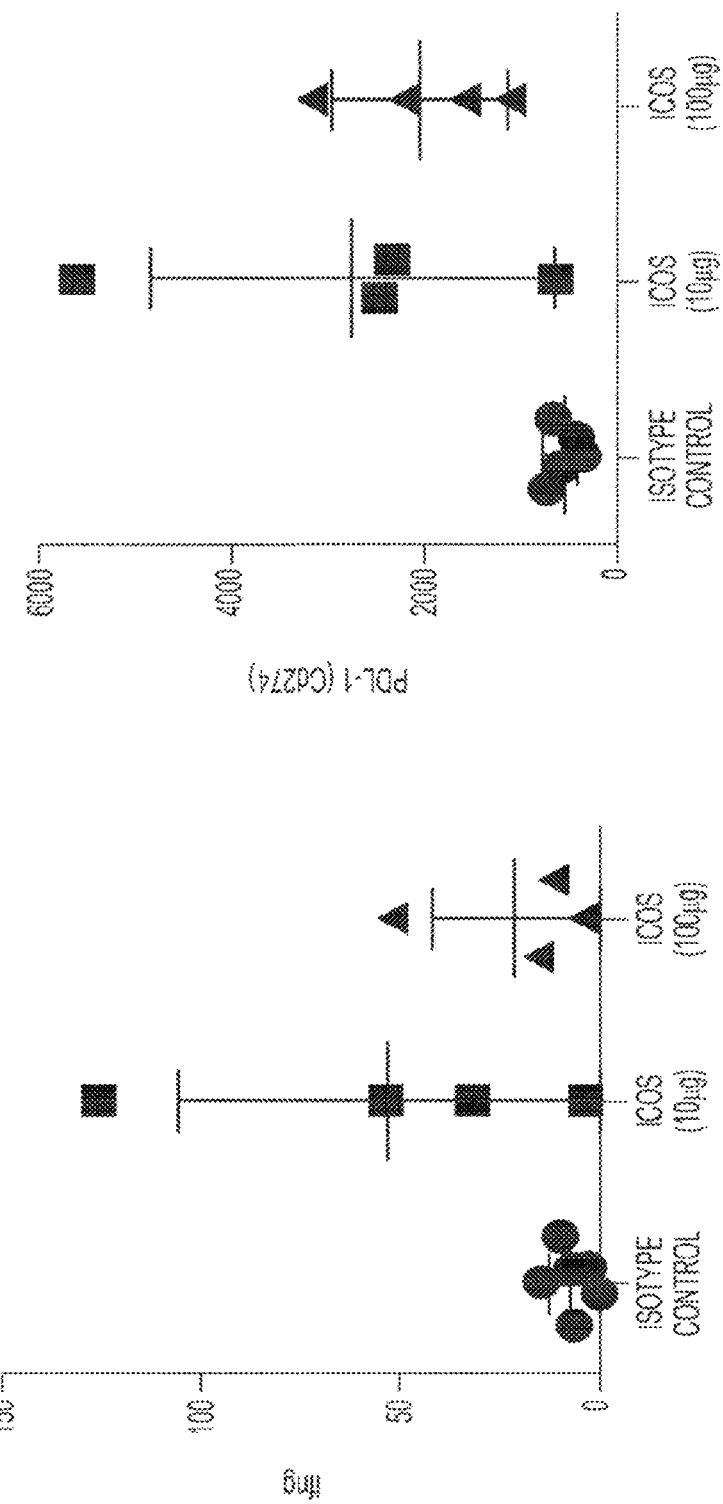
Figure 6F:
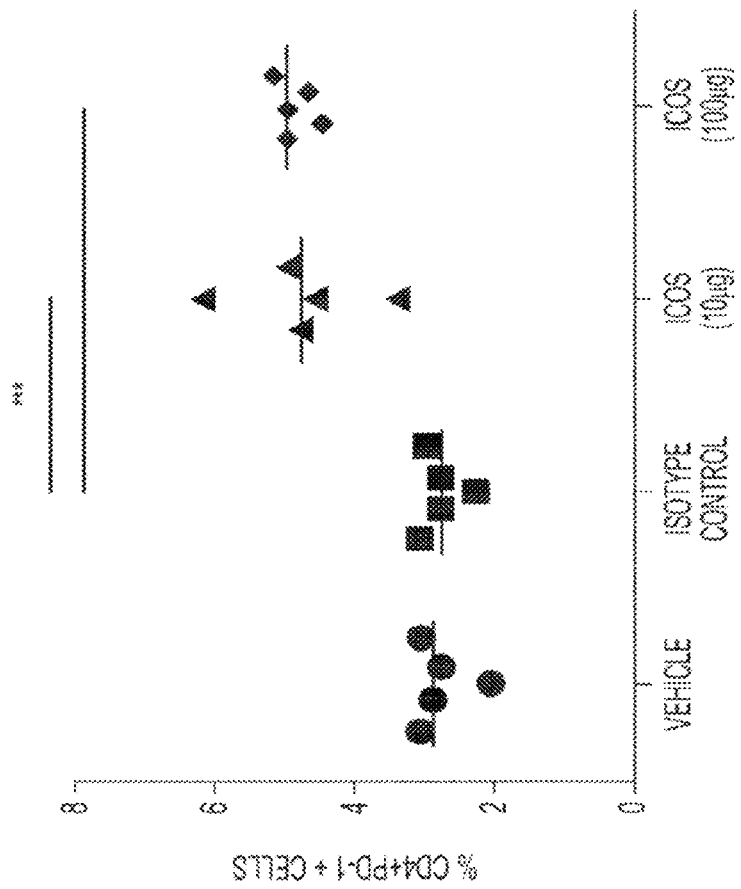
Figure 6E:
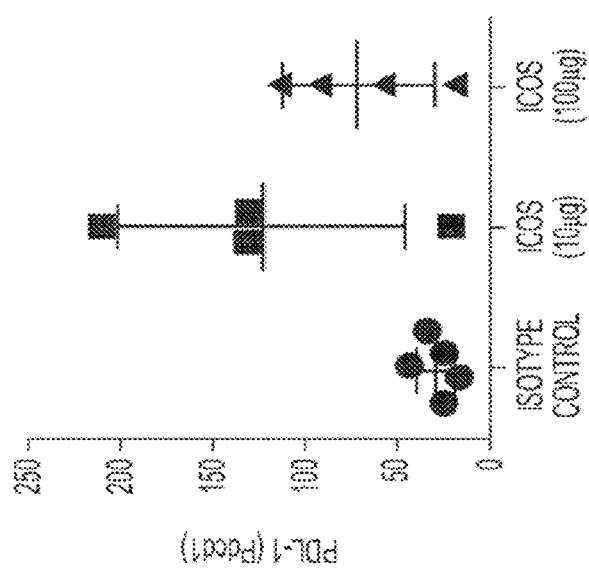
Figures 15A, 15B, 15C:
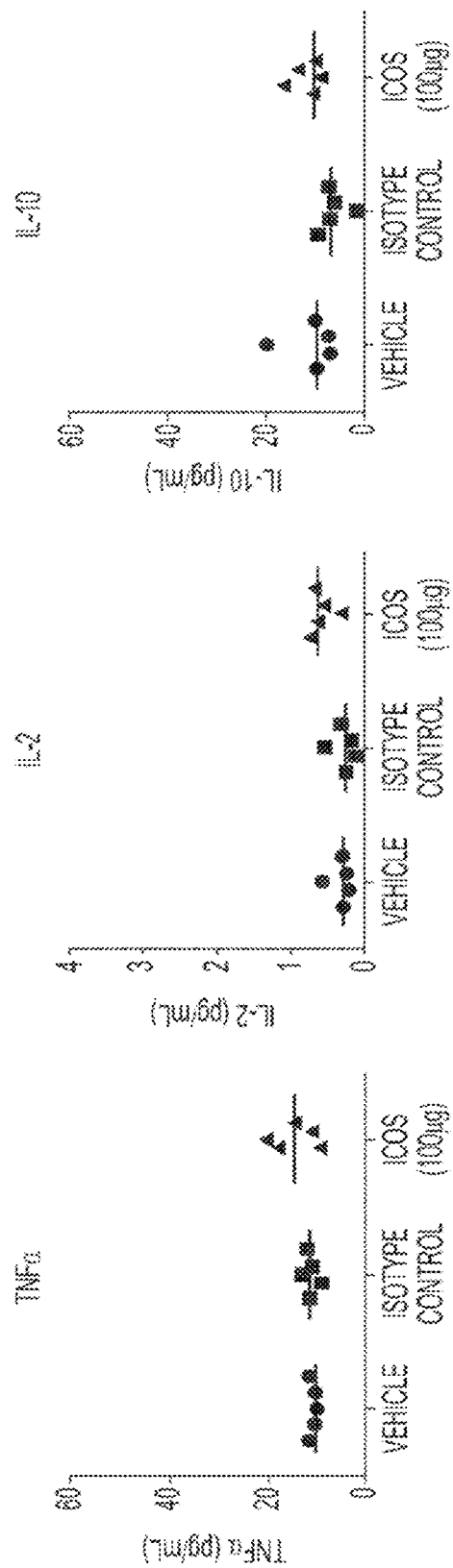
FIG. 15: Anti-mouse ICOS agonist antibody 7E.17G9 does not significantly induce other cytokines in vivo. (A) Levels of TNFα (B) IL-2 and (C) IL-10 in the blood of mice with EMT-6 tumors 48 hours after the 3$^{rd}$ dose of 7E.17G9

Similar to the potent IFN-γ induction activity observed with H2L5 in the human assays, 7E.17G9 resulted in increased in IFNγ levels in the blood of tumor bearing mice (FIG. 6A). No significant increases in other cytokines (IL-2, IL-10, TNF-α) were observed (FIG. 15). The tumors of treated mice were analyzed by Nanostring to determine the gene changes associated with ICOS agonist treatment. One of the most noticeable changes in response to 7E.17G9 was an increase in IFN-γ associated genes (FIGS. 6B-6C). PD-L1, a known IFN-γ responsive gene, was also shown to increase significantly in the tumors of 7E.17G9 treated mice (FIG. 6D). Additionally, PD-1 was induced in the tumors of treated mice (FIG. 6E) as well as on the circulating CD4+ T cells (FIG. 6F).

Figure 7A:
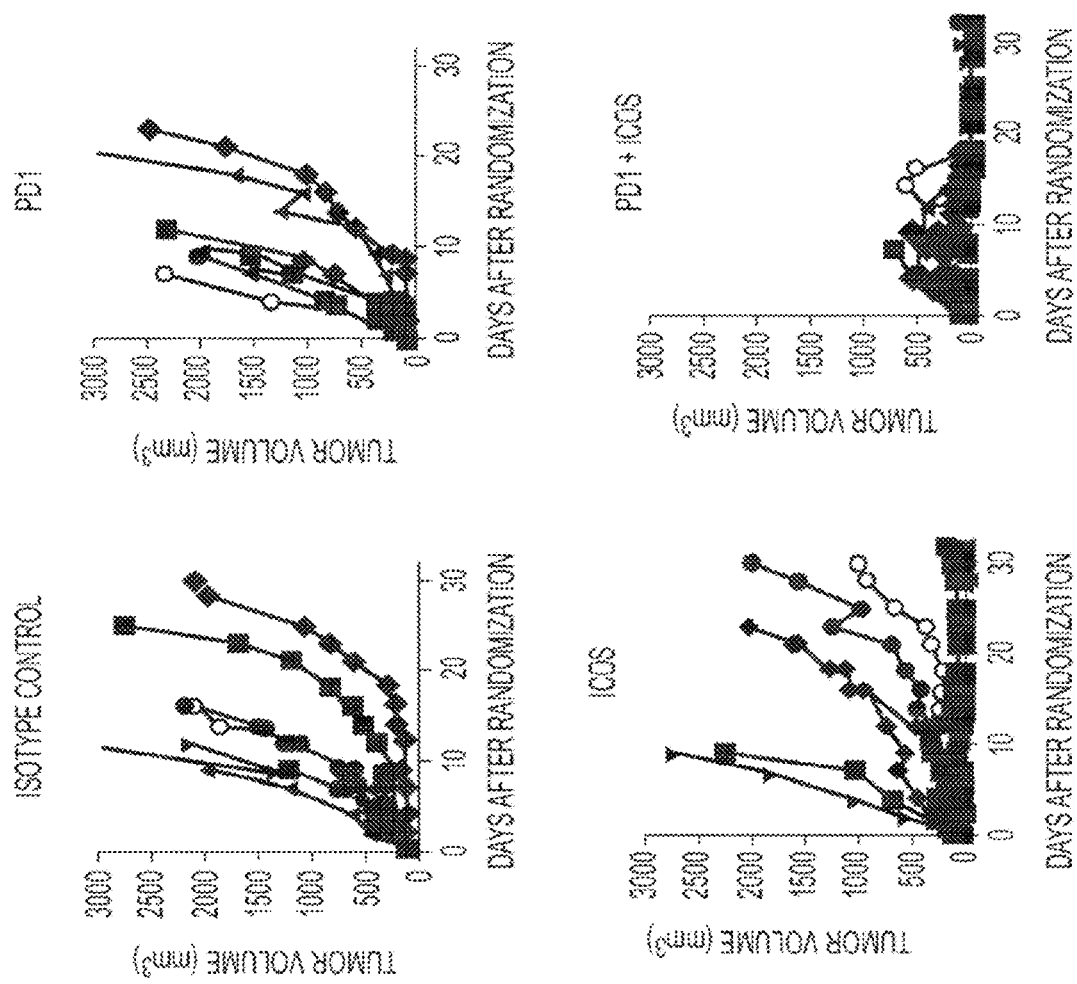
FIG. 7: Synergistic activity of anti-mouse ICOS agonist antibody in combination with anti-PD-1 in mouse tumor models (A) Mice with CT26 tumors treated with 7E.17G9 (100 μg), anti-PD1 (200 μg) or the combination of 7E.17G9 and anti-PD1 dosed concomitantly, twice weekly for 3 weeks (B) Mice with EMT6 tumors treated with 7E.17G9 (10 μg), anti-PD1 (200 μg) or the combination of 7E.17G9 and anti-PD1 dosed concomitantly, twice weekly for 3 weeks (C) CD8$^+$ICOS$^+$ T cells from the blood of CT26 tumor bearing mice 72 hrs after the first, second and third dose of anti-PD1 antibody (200 μg) (D) CD8+ICOS+ T cells from the tumors of CT26 tumor bearing mice 72 hrs after the first, second and third dose of anti-PD1 antibody (E) CD4+ FoxP3+ICOS+ T cells from CT26 tumors 72 hrs following treatment with anti-PD1 antibody (200 μg) (F) ICOS expression on CD8+ T cells (TIL) treated with anti-PD1 antibody (G) ICOS expression on $T_{effector}$ cells (TIL) treated with anti-PD1 antibody (H) ICOS expression on $T_{reg}$ cells (TIL) treated with anti-PD1 antibody.
Figure 7B:
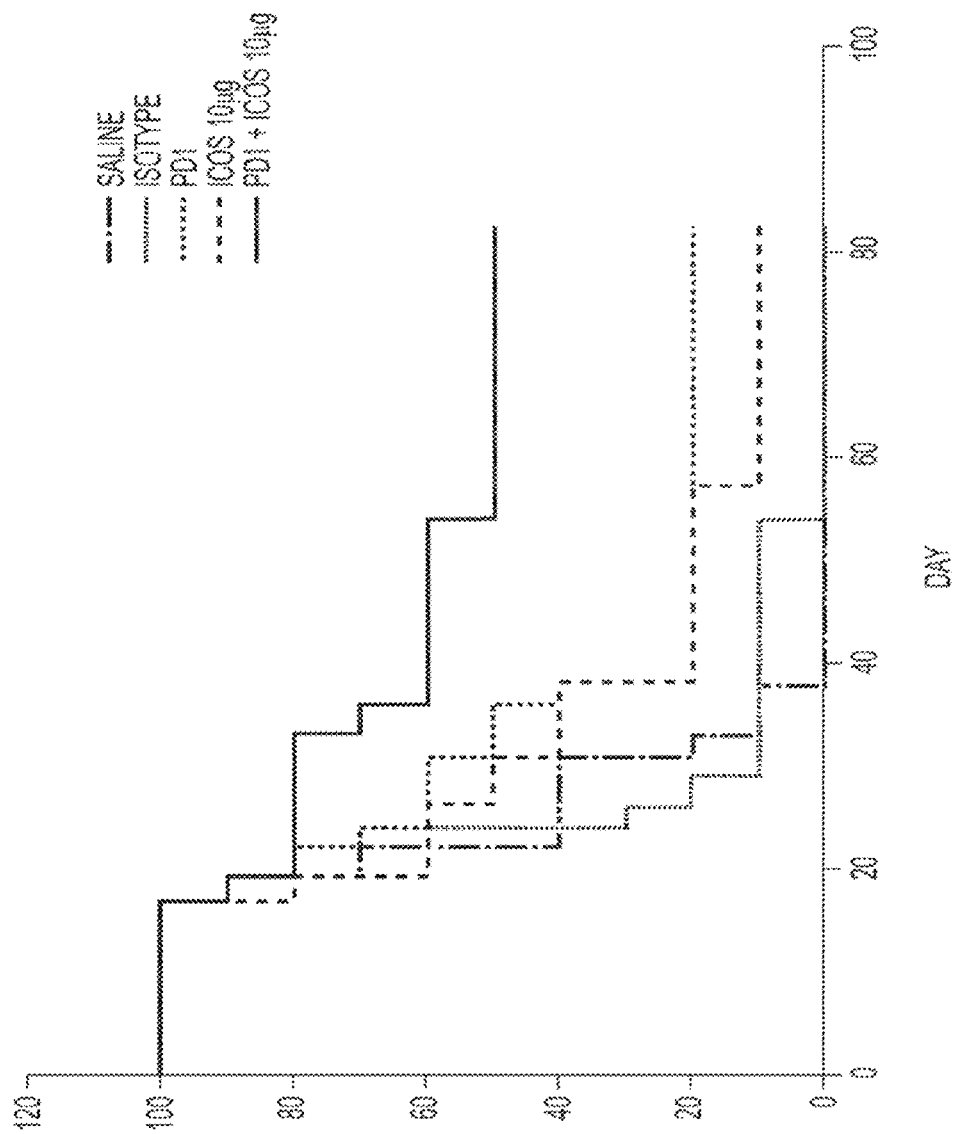
Figure 16B:
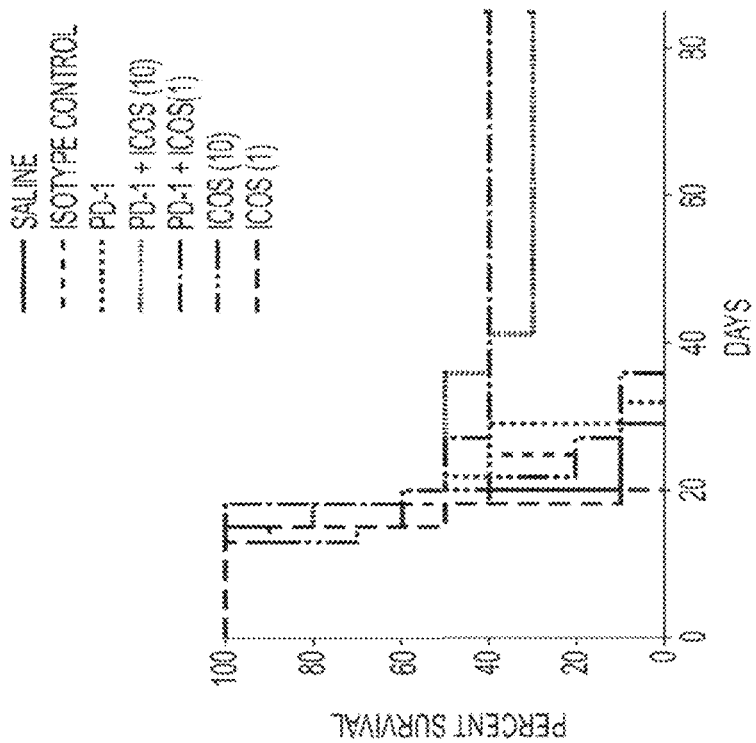
FIG. 16: Another anti-mouse ICOS agonist antibody leads to anti-tumor response and synergy with anti-PD1 blocking antibody in syngeneic mouse tumor models. (A) Treatment with anti-mouse ICOS agonist antibody (C398.4A) results in increased survival of mice with CT-26 and (B) EMT-6 tumors alone and synergistically in combination with anti-PD1 blocking antibody
Figure 16A:
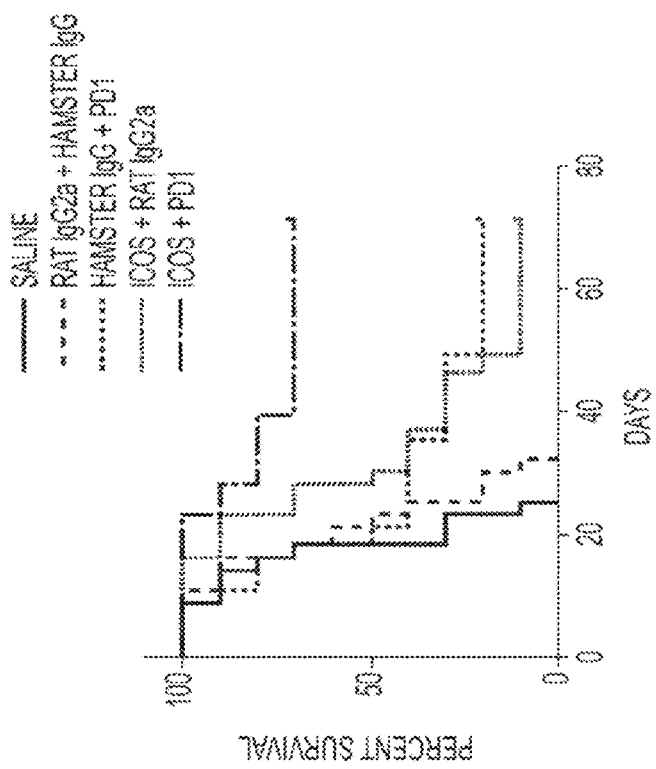

Synergistic Activity of ICOS Agonism in Combination with Anti-PD-1 in Mouse Tumor Models Since treatment with the ICOS agonist antibody resulted in increased PDL-1/PD1 expression in the tumors, we tested whether combination with a PD-1 blocking antibody could augment the activity of the ICOS agonist antibody. The 7E.17G9 antibody was dosed alone or in combination with the anti-PD-1 antibody in both the EMT6 and the CT26 tumor models. In the CT26 model, combination of the ICOS agonist and PD-1 blocking antibody resulted in near complete tumor regression in 10/10 mice, as compared to 4/10 using the ICOS agonist alone and 0/10 with the PD-1 antibody alone (FIG. 7A). In the EMT6 model the combination also resulted in potent antitumor response and long-term survival in 50% of mice (FIG. 7B). Additionally, a second anti-mouse ICOS antibody, clone C398.4A, previously described as an ICOS agonist (Sakthivel, P., et al. (2014) Attenuation of Immune-Mediated Influenza Pneumonia by Targeting the Inducible Co-Stimulator (ICOS) Molecule on T Cells. PLoS One. 9(7)) was tested in these models. Similar to with 7E.17G9, the combination with anti-PD1 resulted in synergistic anti-tumor response as well as 70% and 40% long-term survival in the CT26 and EMT6 tumor models, respectively (FIG. 16). Blood and tumor samples from PD-1 treated CT26 tumor bearing mice were analyzed to better understand the effect of a PD-1 blocking antibody on the ICOS receptor expression of T cells.

Figure 7E:
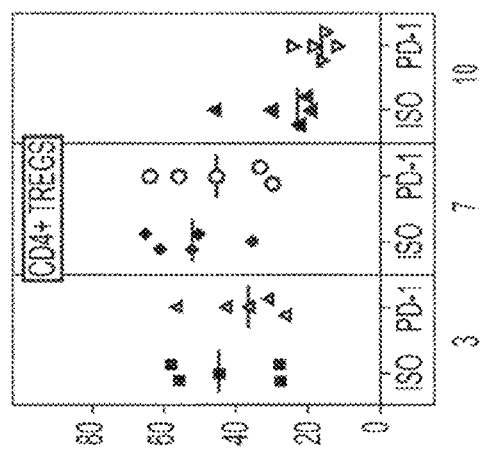
Figure 7D:
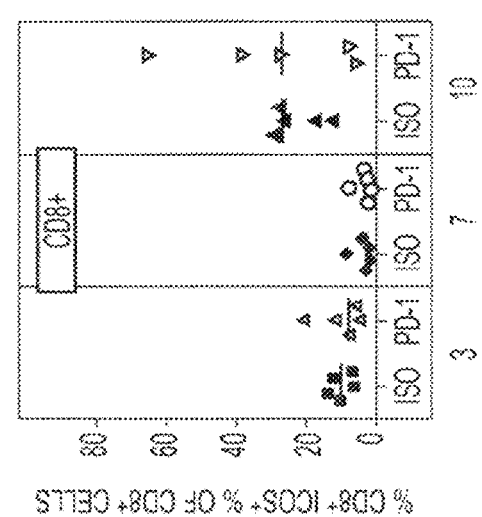
Figure 7C:
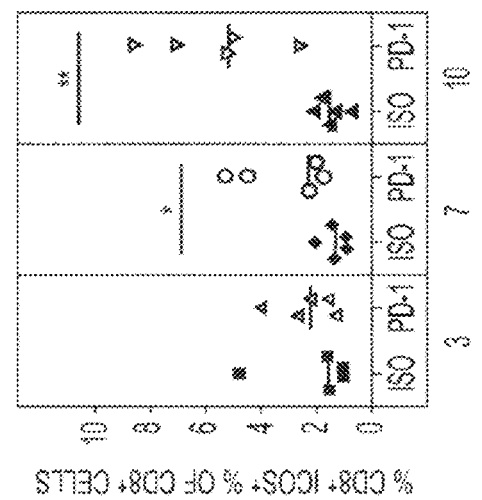
Figures 7F, 7G, 7H:
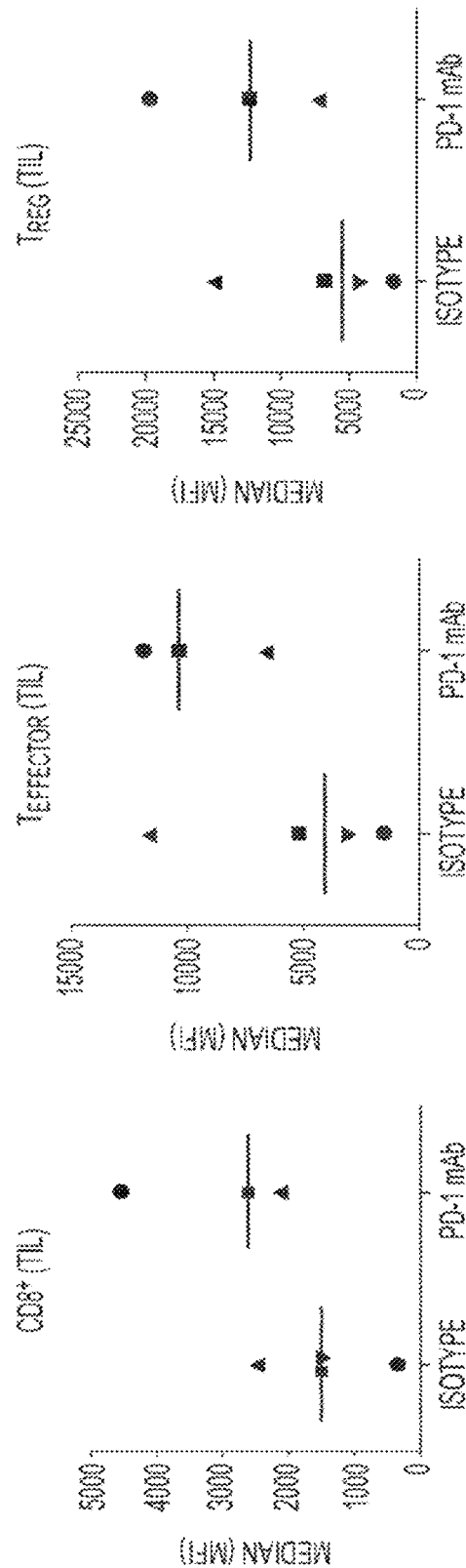

Treatment with the PD-1 antibody resulted in a statistically significant increase in ICOS expression on circulating CD8+ T cells (FIG. 7C). This effect was also observed in the tumors of PD-1 treated mice; albeit to a lesser extent than on circulating T cells (FIG. 7D). Interestingly, while ICOS receptor levels were induced on CD8+ T cells, the expression of ICOS was decreased on CD4+ Tregs (FIG. 7E). FIGS. 7F-7H show ICOS expression on CD8+, $T_{effector}$, and $T_{reg}$ tumor infiltrating lymphocytes (TILs) after PD-1 antibody treatment.

Figure 8A:
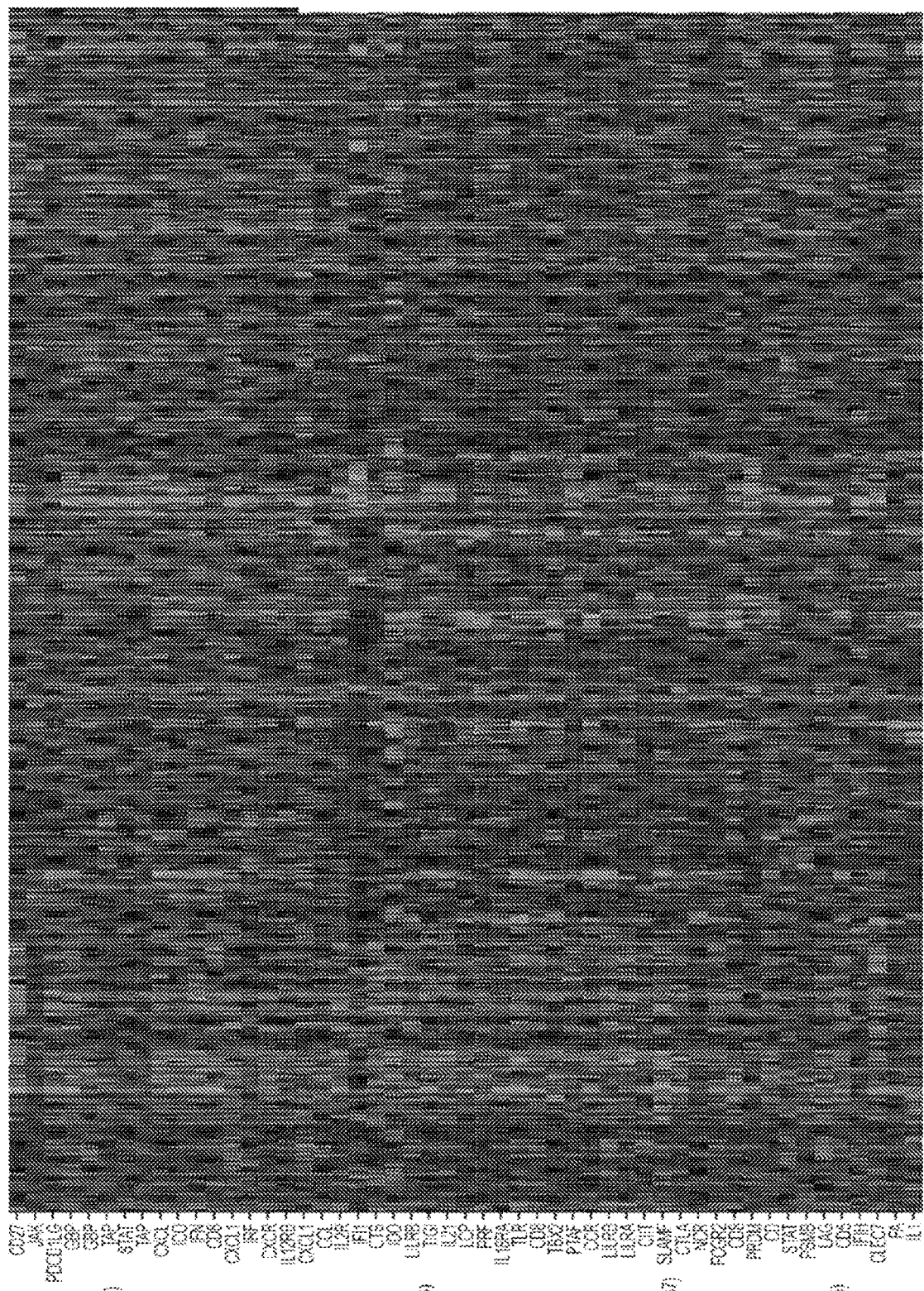
FIG. 8: Expression of ICOS and PDL-1 are closely associated in human tumors and concurrent targeting augments T cell function (A) Unbiased clustering analysis of PD-L1 associated gene expression in tumors from the TCGA database (B) Selected tumor types showing the association of expression of ICOS, ICOS-L and PDL-1 (C) Modified MLR from healthy subject cells treated with soluble H2L5 IgG4PE (11 μg/mL) alone or in combination with Keytruda (11 μg/mL) for 4 days (D) Disseminated tumors from patients with NSCLC treated with anti-CD3 and H2L5 IgG4PE (10 μg/mL) for 24 hrs.
Figure 8B:
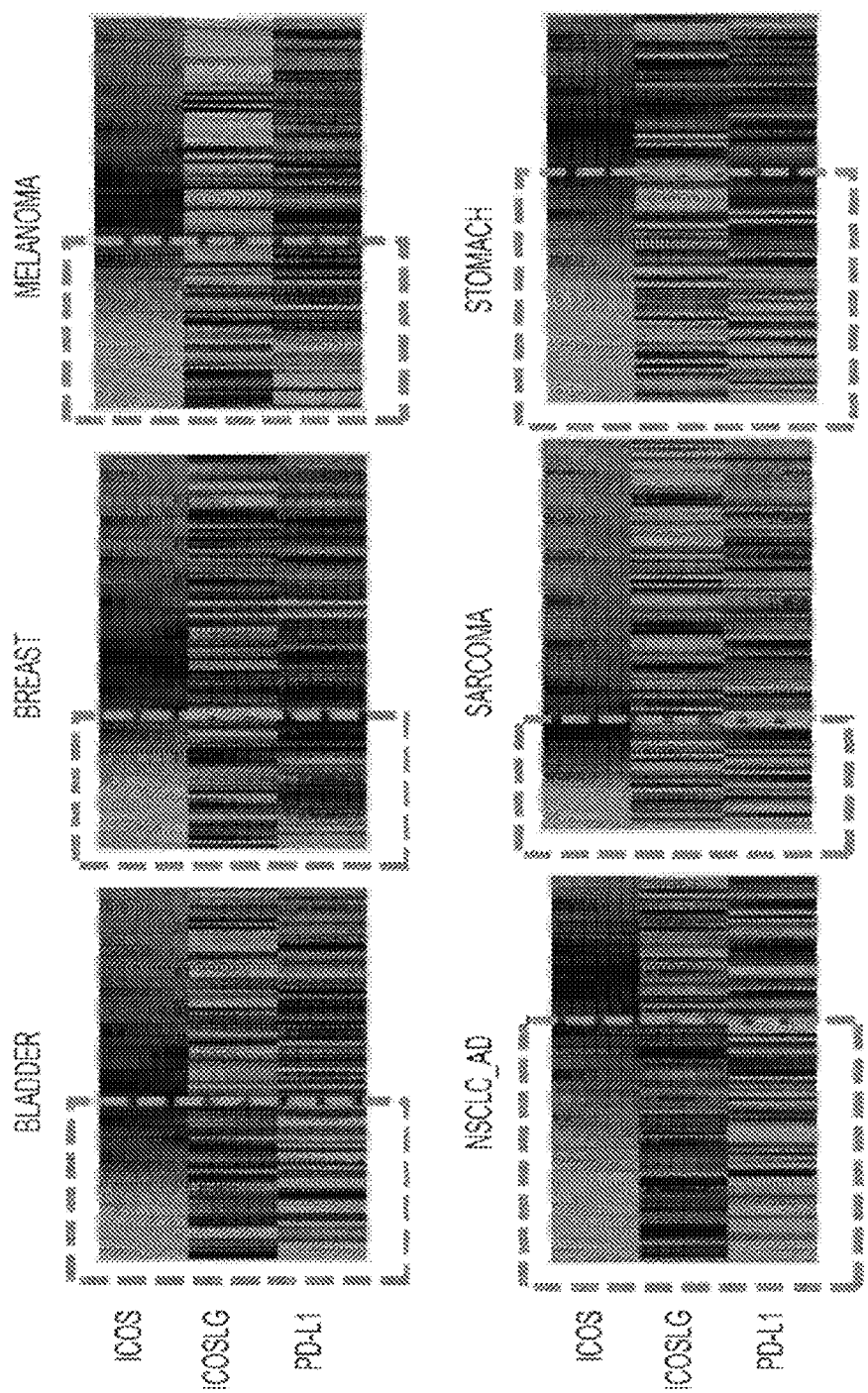

Expression of ICOS and PDL-1 are Closely Associated in Human Tumors and H2L5 Combination with Pembrolizumab Results in Combinatorial Induction of T Cell Function As ICOS agonist treatment in mice was shown to induce significant IFNγ production and PDL-1 expression in the tumors of treated mice, we sought to determine whether there was an association between the expression of ICOS and PDL-1 in human tumors. Analysis of The Cancer Genome Atlas (TCGA) database containing more than 10,000 primary human tumors revealed that, strikingly, ICOS was among the 10 highest associated genes with PDL-1 across all human tumors (FIG. 8A). The association of ICOS expression ranked just above IFNG, a known regulator of PDL-1 expression (Spranger, S., et al. (2013) Up-regulation of PD-L1, IDO, and T(regs) in the melanoma tumor microenvironment is driven by CD8(+) T cells. Sci Trans. Med. 5(200)). This strong association was true across multiple tumor types including bladder, breast and melanoma (FIG. 8B). These results demonstrate that ICOS is commonly co-expressed with PDL-1 in primary human tumors and suggest that induction of ICOS may be linked to expression of PDL-1 in primary human tumors. This associated expression of ICOS and PDL-1 also provides strong rationale for targeting both of these pathways simultaneously.

Figure 8D:
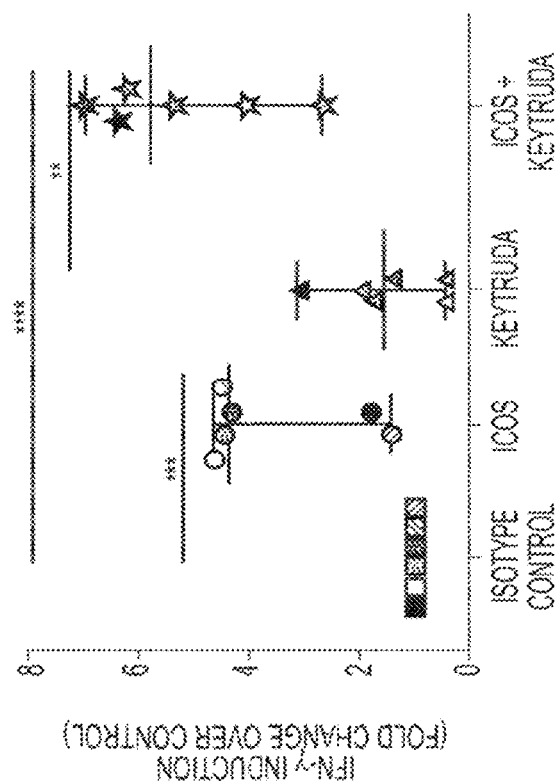
Figure 8C:
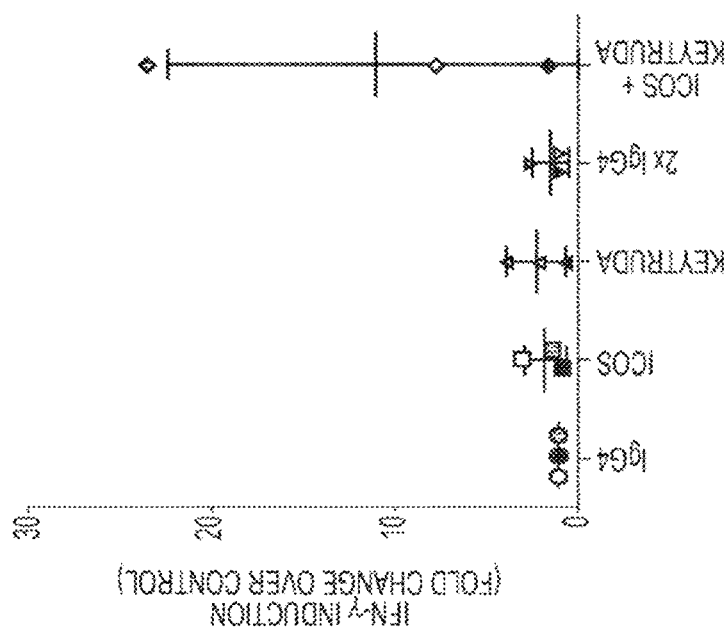

Pembrolizumab (Keytruda®) is an antibody that blocks the interaction between PD-1 and its ligands, PD-L1 and PD-L2 (Garon, E B., et al. (2015) Pembrolizumab for the treatment of Non-Small Cell Lung Cancer. N Engl J Med 372:2018-2028). H2L5 IgG4PE antibody was therefore tested alone or in combination with Keytruda in a modified allogeneic human MLR assay. In the modified MLR assay, combined treatment with H2L5 and pembrolizumab resulted in increased IFNγ levels as compared to either agent alone, in ⅔ of the donor pairs tested (FIG. 8C). Additionally, primary resected tumors from 3 patients with NSCLC were dissociated and expanded in IL-2 supplemented RPMI media. The expanded TIL were then treated with anti-CD3 and H2L5 IgG4PE antibody alone or in combination with Keytruda. While treatment with H2L5 IgG4PE alone resulted in a significant increase in IFNγ in ⅔ of the NSCLC tumor samples tested, the combination of H2L5 and Keytruda resulted in increased IFNγ levels in all 3 (FIG. 8D).

Discussion

Here we have provided the first comprehensive report of an agonist antibody targeting human ICOS. The H2L5 hIgG4PE antibody is a potent and selective ICOS agonist, which effectively induces effector T cell proliferation and cytokine release. There are multiple examples of agonistic antibodies against other co-stimulatory immune receptors including the TNFR super family targets CD27, CD40, OX40 and 4-1BB as well as GITR and CD28. An emerging body of literature supports the idea that FcγR-mediated crosslinking is critical to achieving antibody-induced agonist function against some of these receptors (White et al. 2011; Bartholomaeus, P., et al. (2014) Cell contact-dependent priming and Fc interaction with CD32+ immune cells contribute to the TGN1412-triggered cytokine response. J Immunol. 192(5), 2091-8; Dahan R, et al. (2016) Therapeutic Activity of Agonistic, Human Anti-CD40 Monoclonal Antibodies Requires Selective FcγR Engagement. Cancer Cell. 29(6):820-31; DiLillo, D J., Ravetch, J V. (2015). Fc-Receptor Interactions Regulate Both Cytotoxic and Immunomodulatory Therapeutic Antibody Effector Functions. Cancer Immunol Res. 3(7), 704-13). Therefore, isotype selection becomes a critical feature for these agents. In particular, the ability to balance FcγR-dependent crosslinking and FcγR-mediated ADCC/ADCP effector function on antigen-expressing target cells must be well understood for each antibody and receptor target pairing. Here we show that in the case of ICOS the optimal isotype for achieving agonist function is an engineered form of IgG4. The particular IgG4 used here incorporates the mutations S228P and L235E (EU numbering) relative to the native human IgG4. These specific amino acid changes stabilize the native IgG4 hinge to de-risk heterogeneous exchange with native IgG4 (Aalberse, R C and Schuurman, J. (2002) IgG4 Breaking the Rules. Immunology 105.1, 9-19) and decrease binding to activating FcγR and C1q, and thereby diminish the cytotoxic potential of H2L5 that would result in depletion of ICOS-positive T cells through antibody-dependent or complement-dependent mechanisms, respectively. Moreover, the IgG4PE isoform retains functional binding to the inhibitory FcγR, FcγRIIb, important for modulating agonist activity against several stimulatory immune receptors (White et al., 2011 for CD40; Bartholomaeus, P., et al. (2014) Cell contact-dependent priming and Fc interaction with CD32+ immune cells contribute to the TGN1412-triggered cytokine response. J Immunol. 192(5), 2091-8; Hussain et al. Blood 2015 for CD28, OX40, 41BB; reviewed in Dahal et al. (2015) FcγR requirements leading to successful immunotherapy. Immunol Rev. 268(1), 104-22), which may also be essential for optimal ICOS agonist activity and associated antitumor effects in humans. We have shown that the H2L5 IgG4PE is able to effectively crosslink FcγR and induce agonist function through ICOS while avoiding significant FcγR-mediated cell killing as was observed with the IgG1 version of the H2L5 antibody (FIG. 4).

ICOS expression on regulatory T cells is a factor which must be considered when developing an ICOS agonist antibody for the treatment of cancer, since it would be undesirable to stimulate the proliferation and/or function of this T cell population. This risk may be mitigated by either targeting tumor types where $T_{regs}$ are rare in the tumor microenvironment or by combining H2L5 with other agents that are known to have a Treg inhibitory function (i.e. anti-CTLA-4 or OX-40 antibodies, etc.). (Romano, E., et al. (2015) Ipilimumab-dependent cell-mediated cytotoxicity of regulatory T cells ex vivo by nonclassical monocytes in melanoma patients. Proc Natl Acad Sci USA. 112(19), 6140-5; Vu, M D., et al. (2007) OX40 costimulation turns off Foxp3+ Tregs. Blood. 110(7):2501-10) Interestingly, we observed that monotherapy administration of the murine ICOS agonist antibody in mice with CT26 tumors resulted in a significant increase in the gene signature ratio of CD8:Treg in the tumor microenvironment (FIG. 5D). This tumor type which is known to have a high abundance of Tregs at baseline (Selby, M J., Engelhardt, J J., Quigley, M., Henning, K A., Chen, T., Srinivasan, M., Korman, A J. (2013) Anti-CTLA-4 antibodies of IgG2a isotype enhance antitumor activity through reduction of intratumoral regulatory T cells. Cancer Immunol Res. 1(1), 32-42) responds to monotherapy ICOS agonist treatment, suggesting that the risk of Treg induction by ICOS agonist function may be limited in the tumor microenvironment.

Additionally, we show that in mice treated with anti-PD1 antibody, the percentage of ICOS$^+$ regulatory T cells decreases in the tumor microenvironment (FIG. 7E). This suggests that co-administration or prior administration of a PD-1 blocking antibody together with H2L5 IgG4PE antibody may limit the potential for activation of Tregs by the ICOS agonist. The ability of an anti-PD1 antibody to induce ICOS expression on CD8$^+$ and CD4$^+$ effector populations makes patients who have previously received PD-1 therapy an attractive population for treatment with an ICOS agonist antibody. It is not clear how durable the expression of ICOS is on T cells following PD-1 treatment however, studies with ipilimumab suggest that ICOS expression can persist for months following administration of drug on circulating memory T cell populations (Di Giacomo, A M. et al. (2013) Long-term survival and immunological parameters in metastatic melanoma patients who respond to ipilimumab 10 mg/kg within an expanded access program. Cancer Immunol Immunother. 62(6); 1021-8). This suggests that patients who have previously received and failed to respond to PD-1 treatment may be particularly sensitive to treatment with an ICOS agonist antibody such as H2L5 IgG4PE.

In summary, the novel ICOS agonist antibody described here offers a promising next generation cancer immunotherapy both alone in combination with other agents. Due to the immune boosting mechanism of the ICOS agonist it is possible that this antibody may have activity across a broad range of tumor types and clinical settings, including current areas of high unmet need such as 1) tumors with low baseline levels of immune infiltrate "cold tumors" not responsive to CTLA4 and PD-1/PDL-1 immune checkpoint antibodies alone, where an ICOS agonist may boost the quantity and/or function of the infiltrate 2) in tumors refractory to treatment with tumor targeted modalities such as chemotherapy, radiation or targeted therapy known to be immunogenic and thus may induce ICOS expression (Zitvogel, L., et al. (2013) Mechanism of action of conventional and targeted anticancer therapies: reinstating immunosurveillance. Immunity. 39(1), 74-88) and 3) in patients refractory to other immunotherapy agents including immune checkpoint antibodies, cancer vaccines or cellular therapies. Interestingly, our analysis of ICOS expression in the TCGA bank of human tumors found that the highest levels of ICOS expression are observed in tumors which co-express PDL-1 (FIG. 8). Many of the samples in this dataset are from tumor tissue collected at diagnosis and thus may not necessarily reflect the effect of prior therapy on ICOS expression. Therefore, the dataset may be an underrepresentation of ICOS expression in tumors which have received multiple lines of prior therapy. Therefore, strong rationale exists for an ICOS/PD-1 combination, both in tumors which already express PDL-1 as well as in tumors which are negative for PDL-1 but may be induced in response to ICOS activation. However, the applicability of an ICOS agonist is not limited to combination with a PD-1 antibody.

Therefore, an ICOS agonist antibody offers a unique opportunity to provide therapeutic benefit specifically in patients with the greatest need.

TABLE 2

Summary of phospho-proteins (n = 24) investigated in Ba/F3-ICOS cells treated with H2L5 IgG4PE antibody at 20 ug/mL

| phospho protein | western blot | antibody array | Observations upon H2L5 IgG4PE treatment |
|---|---|---|---|
| AKT (T308) | Y | Y | increase up to 48 hours (WB only) |
| ART (S473) | Y | Y | increase from 1-6 hour |
| ERK1/2 (T202/Y204) | Y | Y | no effect |
| p70 S6K (T389) | N | Y | no effect |
| S6 (S235/236) | Y | Y | increase at 1 hour only |
| S6 (S240/244) | Y | N | no effect |
| GSR3α (S21) | Y | N | modest increase from 1-6 hour |
| GSK3β (S9) | Y | Y | no effect |
| PRAS40 (T246) | Y | Y | no effect |
| 4EBP1 (T37/46) | Y | N | no effect |
| FOXO1/FOXO3a (T24/T32) | Y | N | no effect |

TABLE 2-continued

Summary of phospho-proteins (n = 24) investigated in
Ba/F3-ICOS cells treated with H2L5 IgG4PE antibody at 20 ug/mL

| phospho protein | western blot | antibody array | Observations upon H2L5 IgG4PE treatment |
|---|---|---|---|
| mTOR (S2448) | N | Y | no effect |
| NDRG1 (T346) | Y | N | no effect |
| RSK1/2 (S221/227) | Y | N | no effect |
| Stat1 (Y701) | N | Y | no effect |
| Stat3 (Y705) | N | Y | no effect |
| AMPKα (T172) | N | Y | no effect |
| HSP27 (S78) | N | Y | no effect |
| Bad (S112) | N | Y | no effect |
| p53 (S15) | N | Y | no effect |
| p38 (T180/Y182) | N | Y | no effect |
| SAPK/JNK (T183/Y185) | N | Y | modest increase at 48 hour only |
| PARP (D214) | N | Y | no effect |
| Caspase-3 (D175) | N | Y | no effect |

TABLE 3

Binding affinities of H2L5 Isotype variants (KD nM)
to human Fcγ Receptors as measured by BIAcore

| Antibodies | FcγR I KD (nM) | FcγR IIa H131 KD (nM) | FcγR IIa R131 KD (nM) | FcγR IIb KD (nM) | FcγR IIIa V158 KD (nM) | FcγR IIIa F158 KD (nM) |
|---|---|---|---|---|---|---|
| ICOS IgG1 WT | 60.8 | 405 | 662 | 1340 | 281 | 862 |
| ICOS IgG4PE | 645 | NB | 2500 | 1470 | NB | NB |
| ICOS Fc-disabled | NB | NB | NB | NB | NB | NB |
| Fix Fc+ (wildtype control) | 31.9 | 473 | 593 | 1450 | 203 | 718 |
| Fix Fc − (Fc disabled control) | NB | NB | NB | NB | NB | NB |

* NB (no binding)

Experimental Procedures
Humanized H12L5 Antibody
H2L5 is a humanized variant of the murine monoclonal antibody clone 422.2 obtained from the lab of Daniel Olive, Institut Paoli-Calmettes, INSERM (Marseille, France). The 422.2 murine monoclonal antibody was generated using standard hybridoma technology by immunizing 2 balb/c mice 4 times (intraperitoneally) biweekly, with recombinant human ICOS-Fc. The recombinant protein used human IgG1 as the Fc tag and was produced at the Olive lab using COS7 cells.
Cell Lines and Primary Cell Cultures
Ba/F3-ICOS cells were obtained from the lab of Daniel Olive, Institut Paoli-Calmettes, INSERM (Marseille, France) and cultured in murine IL-3 (R&D Systems, Minneapolis, Minn.), Geneticin (ThermoFisher, Waltham, Mass.) and 10% FBS supplemented Dulbecco's Modified Eagle's Medium (DMEM). All patient material was obtained with the appropriate informed written consent for each donor and in accordance with the GSK human biological sample management (HBSM) policy and SOP. Whole blood in sodium heparin tubes (BD Biosciences) and surgically resected tumor tissues from cancer patients were obtained from Avaden Biosciences (Seattle) shipped overnight by post.
Primary T cells or PBMC from healthy human donors were purified from whole blood collected in sodium heparin tubes at the GSK on-site blood donation units with appropriate consent and in accordance with the GSK HBSM policy. PBMC were isolated by density gradient centrifugation through Histopaque. Further isolation of T-cells was performed by negative isolation using Dynabeads™ Untouched™ Human T cell kit (Life Technologies) or RosetteSep human CD4 or CD8 T cell enrichment kits (StemCell) for binding and functional assays where indicated. Isolated T-cells were pre-activated with plate-bound anti-CD3 (clone OKT3, eBioscience) and anti-CD28 (clone CD28.2, eBioscience) for 48-96 hrs to upregulate ICOS expression.
Mice, Tumor Challenge and Treatment
6-8 week old female BALB/c mice (Harlan/Envigo) were utilized for in-vivo studies in compliance with the USDA Laboratory Animal Welfare Act, in a fully accredited AAALAC facility and in accordance with procedures in IACUC protocol #AUP0606. $5.0 \times 10^4$ cells/mouse CT26 mouse colon carcinoma or $1 \times 10^5$ EMT6 mouse mammary carcinoma (ATCC) tumor cells were inoculated sub-cutaneously into the right flank. Palpable tumors were measured using a digital caliper with tumor volume calculated as $0.52 \times Length \times Width^2$. Mice (n=10/treatment group) were randomized when the tumors reached 100 mm³ and received the mouse anti-ICOS (clone 7E.17G9) and/or mouse anti-PD1 (clone RMP1-14) antibodies or saline via intraperitoneal injection twice weekly starting on randomization day for a total of 6 doses. Similar experiments were also performed with mouse anti-ICOS clone C398.4a, an armenian hamster IgG1 and it's isotype control. Tumor measurement of greater than 2,000 mm3 for an individual mouse and/or development of open ulcerations resulted in mice being removed from study. In order to evaluate the expression of ICOS following treatment with anti-PD-1 monoclonal antibodies, mice bearing CT26 tumors (100 mm³),were dosed twice a week with isotype control (IgG2a 200 μg) or anti-PD-1 (RMP1-14, 200 μg) and harvested on day 3, 7 and 10 following the first dose. Mice collected on day 3, 7 and 10 received 1, 2 and 3 doses respectively.
Binding Studies
The binding affinity and kinetics of H2L5 IgG4PE binding to rabbit Fc-tagged recombinant human or Cynomolgus ICOS (generated in-house) was determined using a Biacore™ T200 (GE Healthcare™). The ICOS binding data was fitted to a 1:1 kinetics model using the T200 data analysis software. Cell surface binding of H2L5IgG4PE to both freshly isolated unactivated and CD3/CD28 activated CD4 and CD8 T cells was determined via detection of anti-human IgG, kappa light chain FITC (Sigma) binding to H2L5 IgG4PE by flow cytometry.

Antibodies

The following anti-human antibodies were used for flow cytometry analysis, CD4 (RPA-T4, BD Biosciences), CD8 (RPA-T8, Biolegend); CD69 (FN50, Biolegend), OX40 (ACT-35, eBioscience); Ki67 (B56, BD Biosciences); ICOS (ISA3, eBioscience); pAKT (S473, #4060 and T308, #13038), total Akt (#9272), pGSK3P (#5558), total GSK3P (#12456), pS6 (S235/236, #2211 and S240/244, #5364), total S6 (#2317), and pERK (#9101) (all from Cell Signaling Technology) for western. Following anti-mouse antibodies were used, CD3 (145-2C11, BD Biosciences); CD4 (RM4-5,BD Biosciences); CD8 (53-6.7, BD Biosciences); CD25 (PC61, BD Biosciences); CD44 (IM7, Biolegend); CD62L (MEL14, BD Biosciences); Foxp3 (Fjk-16s, eBioscience); ICOS (C398.4a, Biolegend); Ki67 (16A8, Biolegend). Apoptotis was measured using Annexin V kit with 7-AAD (Biolegend).

ADCC Assays

Whole PBMC or NK depleted PBMC were activated with plate-bound anti-CD3 and anti-CD28 antibodies. Cells were incubated with anti-ICOS antibodies (H2L5 IgG1, H2L5 IgG4PE and H2L5 Fc-disabled) or control antibodies at 10 µg/mL final concentration for 24 hours. Cells were stained with anti-CD8 and CD4 antibodies followed by incubation with NIR Live/Dead dye. Stained cells were analyzed by flow cytometry (FACSCanto, BD Biosciences) to determine the level of T-cell killing based on NIR Live/Dead cell dye staining.

In the FcγRIIIa engagement reporter bioassay (Promega, Madison Wis.), anti-CD3/CD28 pre-activated CD4 T cells were incubated with the anti-ICOS and control antibodies for 45 minutes prior to the addition of Jurkat-FcγRIIIA-NFAT-luciferase effector cells at an E:T cell ratio of 6:1. ONE-GLO luciferase reagent was added to each well after 6 hrs of treatment and luminescence intensity measured to determine engagement between the target CD4+ T-cells and the Promega FcγRIIIa expressing effector cells on an Envision plate reader (Perkin Elmer, Waltham Mass.).

Functional Assays

H2L5 IgG4PE was tested in human PBMC assays either in a plate-bound format with concurrent CD3 stimulation using freshly isolated PBMC or in a soluble format in CD3/CD28 pre-stimulated PBMC as described earlier. For PBMC from cancer patients, an overnight rest step was included before treatment with plate bound anti-CD3 and ICOS agonist antibodies or its isotype controls. 10 µg/mL soluble Pembrolizumab was used in in-vitro assays to study effects of combination. Cytokine concentrations in supernatants from these assays were measured using human special order multiplex meso-scale detection kits (MSD, Rockville, Md.). Human monocytes were isolated from whole blood of healthy human donors, using CD14 MicroBeads (Miltenyi Biotec, San Diego, Calif.) for the T cell-monocyte mixed culture assays. T cell and monocytes were donor matched. CD3/CD28 pre-stimulated T cells and monocytes were mixed at 2:1 ratio in AIM-V serum-free media and cultured together with anti-CD3 dynabeads, 100 IU of recombinant human IL-2 and 100 ng/ml of M-CSF (Peprotech) prior to incubating with soluble H2L5 IgG4PE or other control antibodies at 37° C. for 4 days. 20 µg/mL human Fc block (B564220) (BD biosciences) or anti-CD32 mAb (MCA1075EL, Clone AT10) (AbD serotec) were used to test the role of FcγR cross linking.

For the mixed lymphocyte reaction (MLR) assays, monocytes (Lonza, Switzerland) were grown in GM-CSF and IL-4 (Pepro Tech) supplemented LGM-3 media (Lonza) for 9 days for differentiating into mDCs and TNFα (R&D Systems) for an additional day before use in the MLR assay. The mDC-T cell (1:10 ratio) mix was treated with 10 µg/mL soluble H2L5 IgG4PE Fc-disabled or the isotype control antibodies either in the presence of anti-CD3 beads at a 1:10 bead to cell ratio (Life Technologies) or CEFT peptide mix (0.02 µg/mL) (JPT Peptide Technologies) for 4 days before collecting the supernatants for cytokine analysis by MSD. Primary patient tumors were dissociated using GentleMACS (Miltenyi Biotec) tissue dissociator. TIL were expanded in IL-2 supplemented RPMI media (Baldan, V., et al. (2015) Efficient and reproducible generation of tumour-infiltrating lymphocytes for renal cell carcinoma. 112, 1510-1518) before treating with anti-CD3 plus anti-ICOS agonist antibody.

In the cytokine release assay, overnight rested PBMCs were incubated with immobilized H2L5 IgG4PE (10 µg/mL) in the absence of anti-CD3 costimulation for 24 hrs. In other assay conditions, PBMCs were pre-stimulated overnight with immobilized anti-CD3 (0.3 µg/mL) and then incubated in a secondary stimulation for 24 hrs with immobilized H2L5 IgG4PE (up to 10 µg/mL) in the presence or absence of immobilized anti-CD3 (0.6 µg/mL). Cytokine concentrations in supernatants were measured by multiplex bead-based assays.

For PBMC assays testing different H2L5 isotypes, anonymized leukocyte cones from healthy donors were obtained from the National Blood Service at Southampton General Hospital, UK and used within 4 hours. Use of human samples was approved by local ethical committees in accordance with the Declaration of Helsinki. PBMCs were isolated by density gradient centrifugation (Lymphoprep) and cultured in RPMI medium 1640 (Life Technologies) supplemented with glutamine (2 mM), sodium pyruvate (1 mM), penicillin, and streptomycin (100 IU/mL) at 37° C. in 5% $CO_2$.

Proliferation assays were performed as detailed previously (Hussain et al Blood 2014/5). Briefly, fresh PBMCs were labelled with 1 µM carboxyfluorescein succinimidyl ester (CFSE) and cultured at high density ($1 \times 10^7$/mL) for 48 hours prior to antibody stimulations. For the PBMC stimulation, cells were transferred into round-bottomed 96-well plates at $1 \times 10^5$ per well and stimulated with 1 ug/ml OKT3 (plate-bound) and 5ug/ml (soluble) H2L5 mAbs. On day 6, cells were labelled with anti-CD8-e450 (SK-1, ebioscience) and anti-CD4-APC (RPA-T4, insight biotechnology), and proliferation assessed by CFSE dilution on a FACSCantoII flow cytometer (BD Biosciences). NK depletion was performed using CD56 micro beads (Miltenyi Biotec) according to the manufacturer's instructions post 48 hours high density culture.

Immunofluorescence Studies

Un-stimulated and CD3/CD28 stimulated T cells were Fc blocked and then treated with 6 µg/mL cold labeled antibody (anti-ICOS or IgG4PE isotype control) on ice for 1 hr. Cells were washed in cold buffer and transferred to 37° C. for various times (0, 5, 15, 30 minutes and 1 hr) to allow protein trafficking before fixing with freshly prepared 4% paraformaldehyde (Sigma). Samples post 1 hr and 2 hrs of the initial pulse at 37° C. were re-pulsed with Alexa Fluor 647 labeled anti-ICOS for 30 minutes at 37° C., washed and fixed in paraformaldehyde. The cells were transferred to Poly-L-lysine coated coverslips for 15 minutes and then mounted on slides in ProLong Gold with DAPI (Invitrogen). Analysis of the samples was performed using a ZEISS LSM510 Meta Confocal microscope with a 63× oil immersion lens.

Western Blotting

Ba/F3-ICOS cells were treated with H2L5 IgG4PE or an isotype control for up to 48 hrs. CD4+ T cells were pre-stimulated with CD3/CD28 Dynabeads® (ThermoFisher) at a cell-to-bead ratio of 1:20 for 48 hours, allowed to rest in the absence of stimulation for 24 hours, and then treated with isotype control antibody or H2L5 IgG4PE (10 μg/mL) in the presence of plate-bound anti-CD3 antibody. Cells were lysed with cell lysis buffer (Cell Signaling Technologies) containing protease and phosphatase inhibitors (Roche). 25-30 μg of protein was run on 4-12% Bis-Tris gels (Invitrogen) and transferred onto nitrocellulose membranes (Invitrogen). Membranes were blocked using LI-COR Odyssey Blocking Buffer and subsequently immunoblotted using the primary and secondary antibodies and scanned on a LI-COR Odyssey imaging system.

FACS Analysis

Non-specific binding on activated T-cells were blocked by incubation with human or mouse Fc block (Miltenyi Biotec) as appropriate prior to the incubation with detection antibodies to cell surface markers conjugated to different fluorophores on ice for 30 minutes. For intracellular staining, the cells were fixed and permeabilized using the Transcription Factor Buffer set (BD biosciences). After compensation, data was acquired on FACS Canto II or Fortessa (BD biosciences) and analyzed with FACSDiva (BD) or Flowjo (Treestar) software.

Statistical Analysis

One way ANOVA with Sidak or Tukey correction was used. Data were analyzed with GraphPad Prism software (GraphPad) and p values of <0.05 were considered to be statistically significant. (* p value <0.05;  p value <0.01; * p value <0.005).

Binding Stoichiometry

Calculation of target capture level and receptor binding stoichiometry was calculated using the formula below:

$$\text{Target capture level } (RU) = \\ Rmax \times Mwt \text{ ligand}/\text{stoichiometry} \times Mwt \text{ analyte}$$

Therefore Stoichiometry = $Rmax \times Mwt$ ligand/Capture × $Mwt$ analyte =

$40.5 \times 81000 / 39.8 / 150000$ and $= 26.5 \times 81000 / 23.7 / 150000$

Confocal Microscopy

CD3 stimulated T cells were treated with 3 μg/mL cold labeled antibody (H2L5 IgG4PE) on ice for 1 hr. Cells were then washed in cold buffer and held on ice. 200ul of Dendritic cells (at 1×10e6/ml) were plated in 8 well chamber coverslips and allowed to attach at RT for 1 hour. Coverslips were then placed on ice, the media removed and the H2L5 IgG4PE treated T-cells (200ul at 1×10e6) added and allowed to settle on ice for 15 minutes. Coverslips were then moved to the heated (37 deg C.) incubation chamber and imaged every 5 minutes with a 20× lens on a ZEISS LSM 780 Confocal to create the time lapse images following antibody labeled ICOS receptor movement over time.

ICOS-L Competition Assay

MSD plates were incubated overnight at 4° C. with 10 μg/mL recombinant ICOS protein (R&D Systems) diluted in PBS. Plates were washed and blocked before adding isotype control or H2L5 IgG4PE in a 7-point dose curve. After overnight incubation and washes, the plates were incubated with 1 μg/mL human ICOS ligand (B7-H2) (R&D Systems) followed by incubation with 10 μg/mL biotinylated anti-human ICOS ligand (B7-H2) (R&D Systems) antibody. Sulfo-tagged streptavidin at 10 μg/mL in Diluent 100 was used for detection of the biotinylated ligand. All incubations were at room temperature for one hour on a plate shaker unless otherwise noted. The plates were read immediately following MSD Read buffer addition on a MSD MESO Quick Plex SQ 120 and data analyzed on MSD workbench software (Meso-Scale, Rockville, Md.).

Fc Gamma Receptor Binding Method

The human Fc gamma receptor binding was assessed using the ProteOn™ XPR36 (BioRad™) biosensor instrument. A murine anti-poly-histidine IgG was immobilised on a GLM biosensor chip by primary amine coupling. This surface was used as a capture surface for the poly-histidine tagged human Fc gamma receptors. Antibodies to be tested were used as the analyte and passed over at 1024 nM, 256 nM, 64 nM, 16 nM and 4 nM with an injection of 0 nM (i.e. buffer alone) used to double reference the binding curves. The murine anti-poly-histidine IgG surface was regenerated with 100 mM phosphoric acid between interactions. The run was carried out at 25° C. using HBS-EP as running buffer. Data were analysed for each receptor separately, setting a global R-max and using the equilibrium model inherent to the ProteOn analysis software.

Example 2: Functional Effects of Soluble H2L5 hIgG4PE Alone and in Combination with Anti-PD1 and Anti-CTLA-4 Antibody in Human PBMC Assay Experimental Preparation(s)

Isolation of Primary Human PBMC

Fresh blood was obtained from GSK Health Center blood donors and was diluted 1:1 with phenol red free-10% RPMI1640 media. Diluted blood was layered on top of the density medium in a Uni-Sep Max 50m conical tube and centrifuge at 400×g for 20 minutes at room temperature with BREAK OFF. The resulted white mononuclear layer (buffy coat) was carefully extracted into a new 50 mL conical tube through a 100 uM cell strainer. An equal volume of Phenol red free-10% RPMI1640 media was added to the buffy coat and centrifuged at 300×g for 10 minutes at room temperature. The cell pellet was resuspended in 10m of red blood cell lysis solution (Sigma Aldrich) and incubated for 5 minutes at room temperature. Cells were washed once with media and centrifuged as previously described. Volume was brought to 40 ml with Phenol red free-10% RPMI1640 media and cells were counted using Vicell cell counter and viability analyzer (Beckman Coulter).

Induction of Monocyte-Derived Immature Dendritic Cells (iDC)

Human monocytes were isolated using the plastic adherence method. Briefly, 20 million freshly isolated PBMC were cultured in a T-75 tissue culture flask in AIM-V media (Thermo Fisher) for 3 hours. Cells that do not bind to plastic were washed off. The adherent monocytes were cultured in a 37° C. 5% $CO_2$ incubator in AIM-V media supplemented with 1000U/ml of human GM-CSF (Calt #300-03, PeproTech) and 500 U/ml of human IL-4 (cat #200-04). After 7-10 days, the iDC cells were collected for co-culturing with T cells from a different donor in the allogeneic Mixed Lymphocyte Reaction assays.

Isolation of Primary Human T Cells Directly from Blood

Human T cells were isolated directly from fresh human blood using a human T cell enrichment cocktail (Stem Cell Technologies). The RosetteSep Human T Cell Enrichment Cocktail (50 μL/mL) was added to whole blood and mixed well. After 20 minutes of incubation at room temperature, an equal volume of PBS+2% FBS was added with gentle mixing. The diluted sample was layered on top of the density medium and centrifuged for 20 minutes at 1200×g at room temperature with the brake off. The enriched cells from the density medium: plasma interface were carefully poured into a new conical tube. Next, the red blood cells were lysed with Red Blood Cell Lying Buffer (Sigma Aldrich) and the enriched cells were washed with PBS+2% FBS twice. The T cells were then resuspended in 40 ml of PBS+2% FBS and counted with a Vi-Cell cell counter.

Experimental Protocols
Human PBMC Pre-Stimulation Assay

Freshly isolated human PBMCs were pre-stimulated with CD3/CD28 T cell expander DynaBeads at a bead to cell ratio of 1:20 in a T-75 tissue culture flask in AIM-V medium supplemented with 100 ng/ml of MCSF and 100IU/ml of IL-2 (PeproTech) at 37° C. After 48 hours, the pre-stimulation beads were magnetically removed and cells were washed, counted and re-stimulated with anti-CD3 Dyna-Beads and therapeutic antibodies in AIM-V medium supplemented with 100 IU/ml of IL-2 (PeproTech) in 96-well non-tissue culture treated round bottom plate. The seeding density was 100 k cells per 100 ul of medium per well. After incubating at 37° C. for 3.5 days, cell culture supernatants were collected for multiplex cytokine measurement by MSD.

Human MLR Activation Assay

Monocyte-derived iDCs from a healthy human volunteer were mixed at a 1:10 ratio (iDC:T) with freshly isolated human T cells from a different donor and pre-incubated at 37° C. in AIM-V media in the presence of 0.02 μg/ml of a CEFT peptide mixture for 24 hours. Different groups of treatment antibodies were added directly to the wells, mixed and further incubated for an additional 4 days. Cell culture supernatants were collected for multiplex cytokine measurement by MSD analysis.

MSD Cytokine Analysis

IFN-γ, IL-10, IL-2 and TNF-α cytokine levels in the tissue culture supernatant were determined using MSD human V-Plex customized kits. Samples were first diluted 1:200 in Diluent 2. Calibrators were also prepared in Diluent 2 following the manufacturer's recommendations. Diluted samples and calibrators were added to black MSD plates which were subsequently sealed with an adhesive plate seal and incubated at room temperature with shaking for 2 hours. After adding 25 μL of the detection antibody solution, which was freshly prepared in Diluent 2 to each well, the plate was re-sealed and incubated at room temperature with shaking for another 2 hours. The plates were washed 3 times with 150 μL/well of PBS plus 0.05% Tween-20 before adding 150 μl/well of freshly diluted 2×read buffer and immediately read on a MESO QuickPlex reader. Data were analyzed using MSD Workbench software.

Data Analysis
MSD Data Analysis

MSD data was analyzed with Discovery Workbench software (MSD, version 4.0.9). Calibrators in the manufacturer's kit were included on each MSD plate to generate plate specific standard curves with $R^2$ value over 0.99 in all cases. The amounts of cytokine detected were back calculated based on the standard curve and the mean and standard deviation from three biological replicates were used to generate the graphs.

Statistical Analysis

One-way ANOVA was performed on log-transformed, fold-change data over each treatment antibody's own isotype control. Dunnett's Multiple Comparison Test was performed to compare both mono-therapies vs. combination across different donors. $P<0.05$ was considered as statistical significant.

Results

PBMC pre-stimulation assay development and test for combinatorial activity of H2L5 hIgG4PE with ipilimumab and pembrolizumab.

Figure 17:
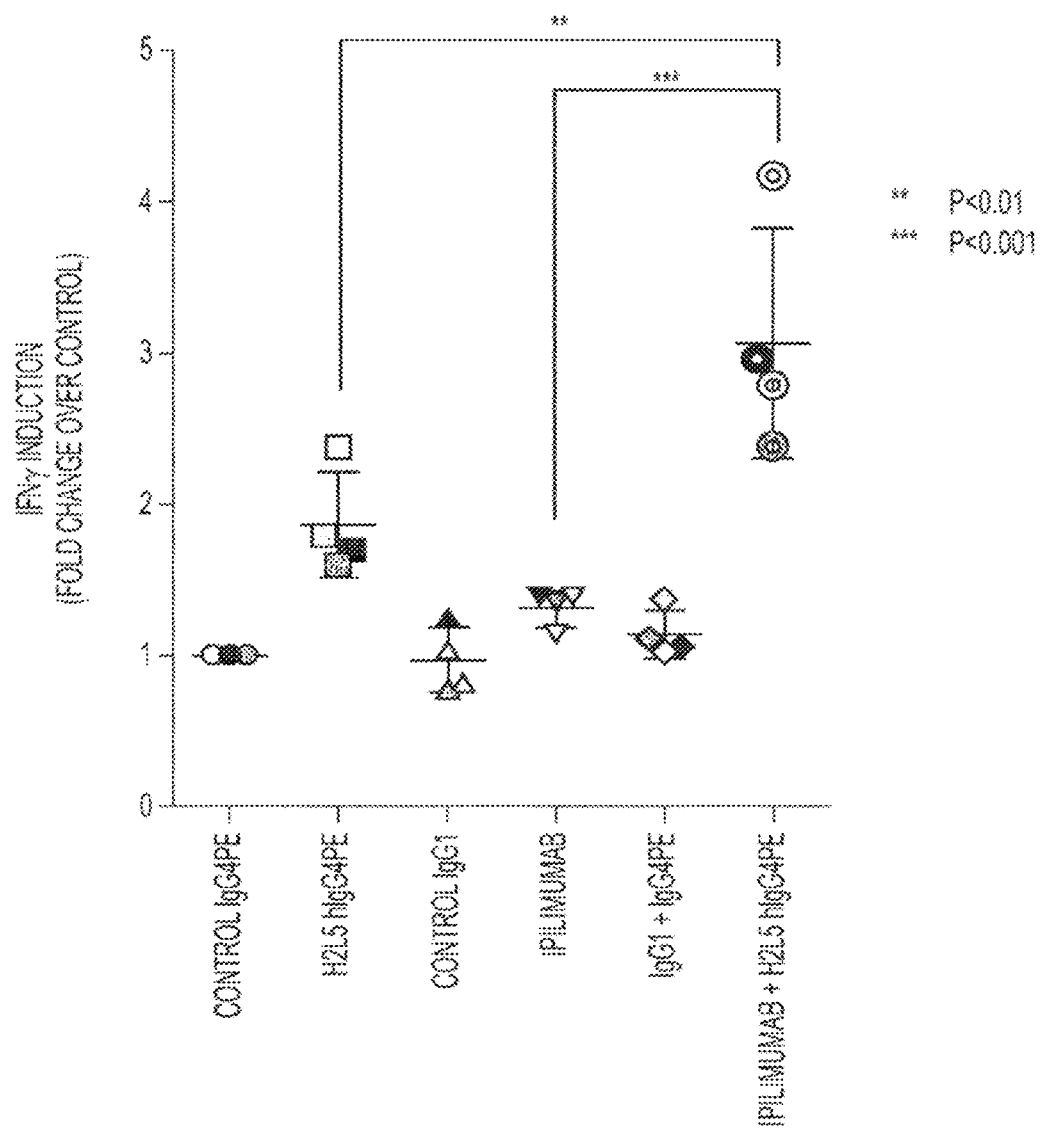
FIG. 17: H2L5 hIgG4PE in combination with ipilimumab results increased proinflammatory cytokine production as compared to single antibody treatment in PBMC pre-stimulation assay.
Figure 18:
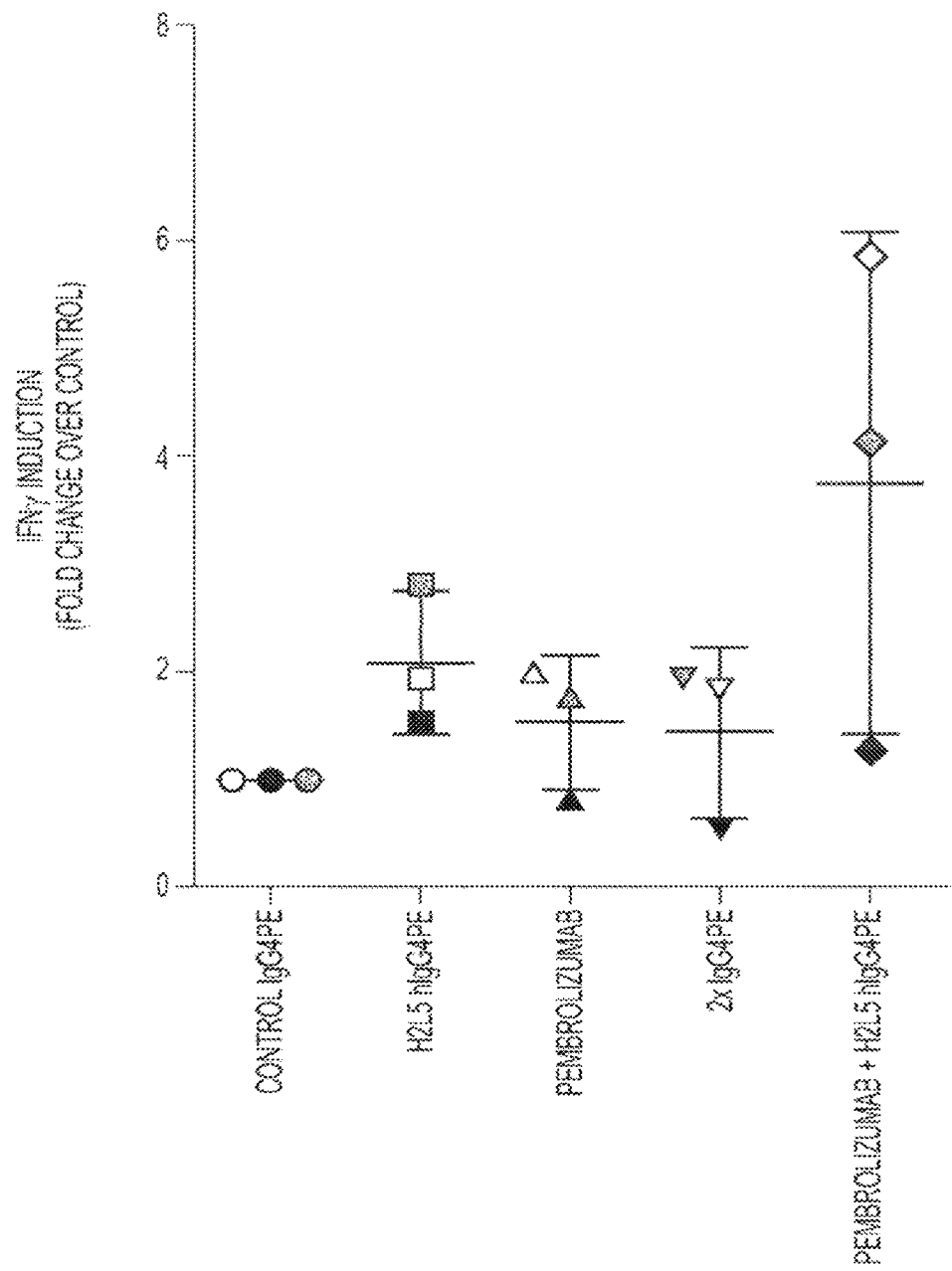
FIG. 18: H2L5 hIgG4PE in combination with pembrolizumab results increased proinflammatory cytokine production as compared to single antibody treatment in PBMC pre-stimulation assay.

In order to determine the optimal conditions for pre-stimulation, human anti-CD3 Dynabeads and anti-CD3/CD28 Dynabeads (Thermo Fisher) were tested at different bead to cell ratios. After 48 hour pre-stimulation, cells were harvested and beads were magnetically removed prior to stimulation with anti-CD3 Dynabeads (bead to cell ratio=1:1) together with anti-ICOS antibody alone or in combination with anti-CTLA-4 or anti-PD1. H2L5 hIgG4PE single agent treatment resulted in induction of IFN-γ as compared to isotype control in all pre-stimulation conditions tested. The magnitude of IFN-γ induced by H2L5 hIgG4PE was inversely correlated with the strength of the pre-stimulation. The combination of H2L5 hIgG4PE together with ipilimumab demonstrated enhanced cytokine production as compared to either H2L5 HIGG4PE or ipilimumab alone in PBMCs that were weakly pre-stimulated. The combination effect was lost under plate-bound anti-CD3/anti-CD28 pre-stimulation conditions, which is considered a stronger pre-stimulation condition. Based upon these results, the pre-stimulation condition using anti-CD3/anti-CD28 beads at a bead to cell ratio of 1:20 was chosen for all future PBMC assays. Results from four individual donors are summarized for anti-CTLA-4 combination in FIG. 17 and combination with anti-PD-1 in FIG. 18.

H2L5 hIgG4PE Results in Dose-Dependent Cytokine Induction in a PBMC Pre-Stimulation Assay The dose-dependent activity of H2L5 hIgG4PE was evaluated in human PBMCs pre-stimulated with anti-CD3/anti-CD28 beads at a pre-determined bead to cell ratio of 1:20. The anti-RSV IgG4PE and anti-ICOS 422.2 IgG1 Fc Disabled were included as controls. Eight concentrations of H2L5 HIGG4PE were tested (100, 30, 10, 3, 1, 0.3, 0.1, and 0.03 μg/ml). IFN-γ, IL-10 and TNF-α were evaluated by MSD in the tissue culture supernatants of PBMC samples. H2L5 hIgG4PE, but not isotype control IgG4 or Fc-Disabled 422.2, induced IFN-γ, IL-10 and TNF-α production in a dose-dependent manner. These results were used to determine the concentration of H2L5 hIgG4PE to be used in combination studies.

Human MLR Assay Development

In an effort to optimize a human MLR assay, in addition to co-culture of human T cells and monocyte-derived immature DCs from a different donor, anti-CD3 beads were also added into the wells to provide a basal TCR stimuli to help prime the cells. Results demonstrated that anti-CD3 beads greatly increased the range of IFN-γ induction. Although ipilimumab alone can induce IFN-γ production in the absence of anti-CD3 beads, H2L5 hIgG4PE alone or the H2L5 HIGG4PE/ipilimumab combination only showed enhanced IFN-γ production over corresponding controls in the presence of anti-CD3 beads.

Combinatorial Activity of H2L5 HIGG4PE and Ipilimumab in a Human MLR Assay

Figure 19:
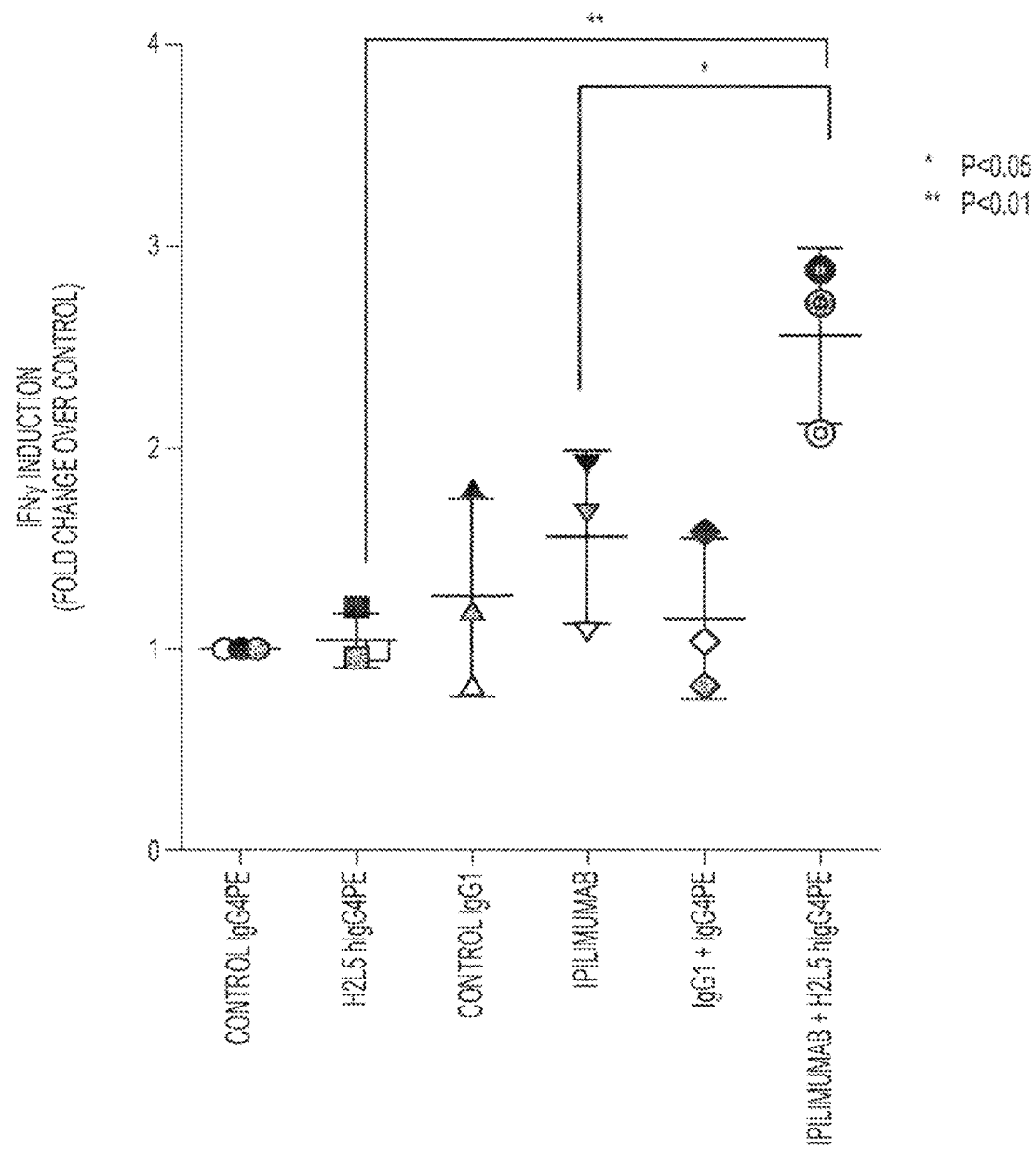
FIG. 19: H2L5 hIgG4PE plus ipilimumab combination induces increased proinflamatory cytokine production in a modified MLR assay with CEFT peptide and pre-incubation.

The immunostimulatory activity of H2L5 hIgG4PE alone or in combination with ipilimumab was tested in an allogeneic human MLR assay in which T cells that were pre-incubated with monocyte-derived immature DCs from an unmatched donor in the presence of 0.02 µg/ml CEFT peptides for 1 day. The H2L5 hIgG4PE/ipilimumab combination resulted in a significant enhancement in IFN-γ production as compared to either agent alone. Results were consistent across three donor pairs tested; however, modest variability was observed between donors (FIG. 19).

Combinatorial Activity of H2L5 hIgG4PE and Pembrolizumab in a Human MLR Assay

Figure 20:
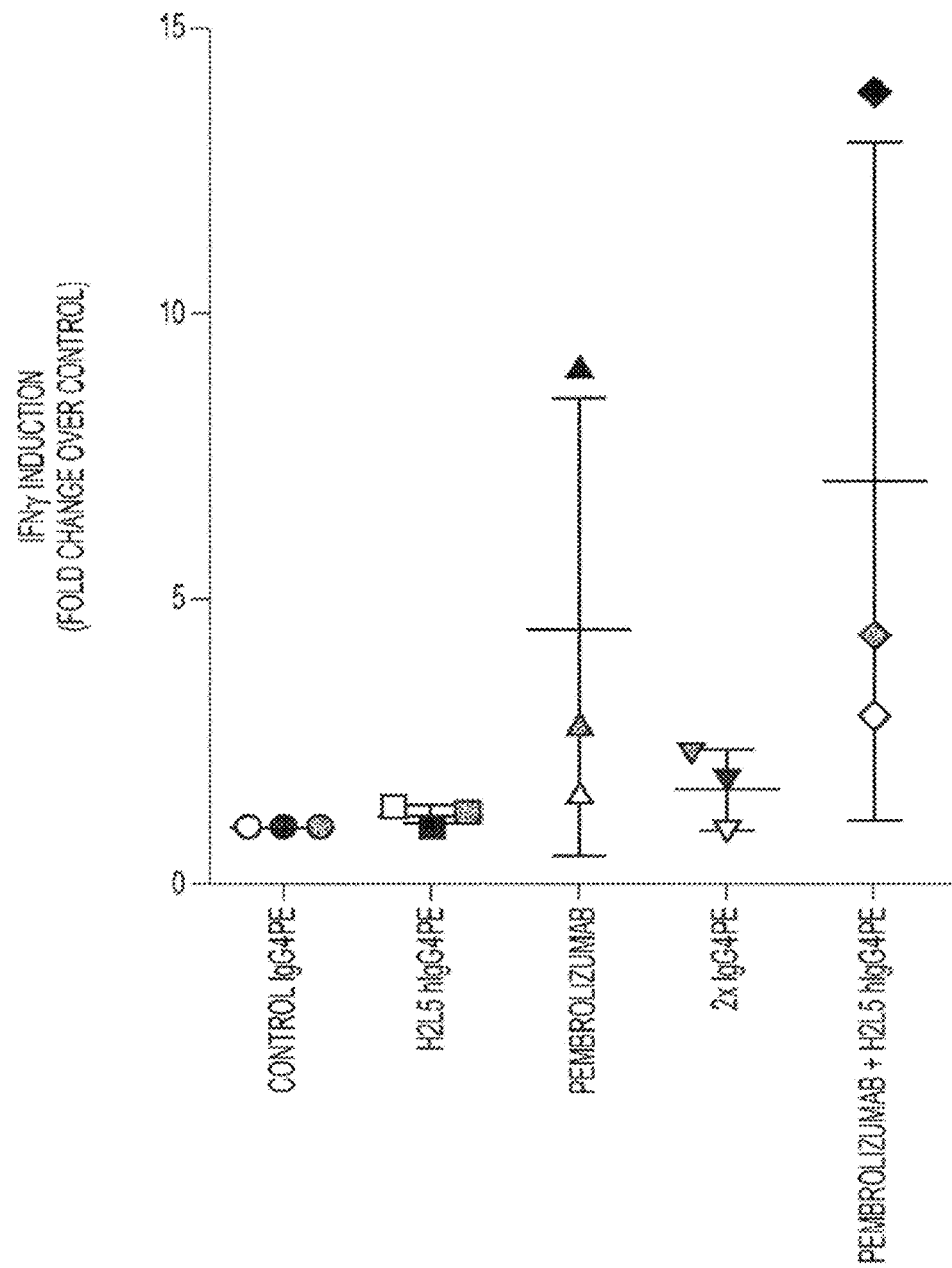
FIG. 20: H2L5 hIgG4PE plus pembrolizumab combination induces increased proinflamatory cytokine production in a modified MLR assay with CEFT peptide and pre-incubation.

The combination of H2L5 hIgG4PE and pembrolizumab was also tested in the human allogeneic MLR assay described above. H2L5 hIg G4PE was tested alone and in combination with pembrolizumab at 10 µg/ml. The combination of H2L5 hIg G4PE and pembrolizumab resulted in increased IFN-γ as compared to either agent alone. However, statistical significance was not reached due to high donor variability and significant activity of single agent anti-PD-1 treatment in some donors (FIG. 20).

Discussion

ICOS is a costimulatory receptor that is weakly expressed on naïve T cells and quickly upregulated in activated CD4+ and CD8+ T cells. The ligand for ICOS is ICOS-L (B7h, B7RP-1, CD275), which is expressed by professional APCs and by peripheral epithelial and endothelial cells following TNF-α stimulation. The ICOS:ICOS-L pathway provides a key costimulatory signal for T-cell proliferation and function. Due to its role in sustaining T-cell activation and effector functions, targeting ICOS by agonist antibodies could be a plausible approach to enhance anti-tumor immunity.

Studies have shown an increase the frequency of $ICOS^{hi}$ CD4+ effector T cells after CTLA-4 blockade by ipilimumab in several cancer models. In addition, upon CTLA-4 blockade, this cell population produced greater levels of INF-γ than $ICOS^{lo}$ CD4+ T cells. In fact, the increase in the frequency of ICOS+ CD4 T cells has been identified as a pharmacodynamic biomarker of ipilimumab treatment in cancer patients. Studies, in wild-type C57BL/6 mice, demonstrated 80 to 90% tumor rejection follow CTLA-4 blockade therapy; however, in ICOS or ICOSL knockout mice the efficacy was decreased to less than 50%. The important role played by ICOS in the effectiveness of CLTA-4 blockade suggests that stimulating the ICOS pathway during anti-CTLA-4 therapy might increase therapeutic efficacy. Therefore, we set out to evaluate the combination activity of H2L5 hIgG4PE and ipilimumab.

Programmed cell death-1 (PD-1) was reported in 2000 to be another immune checkpoint molecule. The expression of PD-L1 (B7-H1), which is one of the ligands of PD-1, can be found on many cell types including T cells, epithelial cells, endothelial cells, and tumor cells. Antibodies targeting the PD-1/PD-L1 axis have also shown clinical responses in multiple tumor types. The FDA recently approved pembrolizumab and nivolumab as second generation of the immune checkpoint blockers for the treatment of cancer. Merck's pembrolizumab was shown to lead to response rates of ~37 to 38% in patients with advanced melanoma, with a subsequent study reporting an overall response rate of 26% in patients who had progressive disease after prior ipilimumab treatment. Nivolumab, the anti-PD-1 antibody from BMS, also showed clinical benefit in patients with metastatic melanoma with a response rate of 40% and an overall survival rate of 72.9% at 1 year. In addition, nivolumab was also FDA-approved for advanced or metastatic non-small cell lung cancer. As the PD-1 checkpoint blockade antibodies become the dominant cancer immune therapy in the clinic, it will be important to evaluate H2L5 hIgG4PE in combination with an anti-PD-1 antibody for their combined anti-tumor activity.

Previously, a PBMC activation assay was developed and used to evaluate the T cell stimulation activity of a panel of anti-ICOS agonist antibodies. The data generated from those studies supported the candidate selection of clone 422.2 with an IgG4PE isotype as H2L5 hIgG4PE. In the previous assay, PBMC cells were pre-stimulated with plate bound anti-CD3 antibody at 1 µg/ml and anti-CD28 antibody at 3 µg/ml for 48 hours before they were harvested and re-stimulated with anti-CD3 and soluble ICOS antibodies that were being investigated. H2L5 hIgG4PE was shown to induce IFN-γ production in a dose-dependent manner. In order to determine the optimal conditions for pre-stimulation, human anti-CD3 Dynabeads and anti-CD3/CD28 Dynabeads (Thermo Fisher) were tested at different bead to cell ratios. Stimulation by beads is considered to be more physiological and the strength of the stimulation can be controlled more easily by constructing different bead to cell ratios. After 48 hours of pre-stimulation, cells were harvested and beads were magnetically removed prior to stimulation with anti-CD3 Dynabeads (bead to cell ratio=1:1) together with anti-ICOS antibody alone or in combination with anti-CTLA-4. The results showed that H2L5 hIgG4PE single agent treatment resulted in IFN-γ induction relative to isotype control in all pre-stimulation conditions tested. The magnitude of IFN-γ induced by H2L5 hIgG4PE was inversely correlated with the strength of the pre-stimulation. The combination of H2L5 hIgG4PE together with ipilimumab demonstrated enhanced cytokine production as compared to either H2L5 hIgG4PE or ipilimumab alone in PBMCs that were weakly pre-stimulated. The combination effect was lost under plate-bound anti-CD3/anti-CD28 pre-stimulation conditions, which is considered a stronger pre-stimulation condition. Based upon these results, the pre-stimulation condition using anti-CD3/anti-CD28 at a bead to cell ratio of 1:20 was chosen for all the future PBMC assays. H2L5 hIgG4PE and ipilimumab combination demonstrated a statistically significant increase in IFN-γ production as compared to either antibody treatment alone.

In the assay optimization effort, with an anti-CD3/anti-CD28 stimulation bead to cell ratio fixed at 1:20, the anti-CD3 beads used during the re-stimulation step were titrated down from bead to cell ratios of 1:1 to 1:3 and 1:10. The results showed that the lower the re-stimulation strength yielded lower the IFN-γ induction by H2L5 hIgG4PE. The combination effect by H2L5 hIgG4PE and ipilimumab was totally lost under re-stimulation at a bead to cell ratio of 1:3 and 1:10. Therefore, the re-stimulation anti-CD3 bead to cell ratio of 1:1 was kept for all future experiments.

With the pre-stimulation and re-stimulation conditions optimized, this assay was used to evaluate the dose response of H2L5 hIgG4PE. A total of 8 antibody concentrations were tested, which were 100, 30, 10, 3, 1, 0.3, 0.1 and 0.03 µg/ml. The anti-RSV IgG4PE and anti-ICOS 422.2 IgG1 Fc Disabled, the Fc Disabled version of H2L5 hIgG4PE, were used as controls. Results showed that H2L5 hIgG4PE, but not isotype control IgG4 or Fc-Disabled 422.2, induced IFN-γ, IL-10 and TNF-α production in a dose-dependent manner. It is interesting that the Fc Disabled version of H2L5 hIg G4PE exhibited a limited cytokine induction response, indicting the Fc receptor engagement is crucial for the T cell agonizing function of H2L5 hIg G4PE. These results were also used to determine the dose of H2L5 hIg G4PE for combination studies.

A mixed lymphocytes reaction (MLR) assay was also developed to evaluate the combination effect of H2L5 hIg G4PE and checkpoint blocking antibodies. MLR assay is an ex vivo cellular immune assay in which primary monocyte-derived immature dendritic cells (iDCs) were mixed with T cells isolated from a different donor. The mismatch of major histocompatibility complex (MHC) molecules on the surface of iDC cells can initiate T cell stimulation in an allogeneic setting. In the clinic, the MLR assay is well-known for identifying the compatibility of tissue transplants between donors and recipients.

In order to develop the MLR assay, fresh human monocytes were cultured in medium supplemented with human recombinant GM-CSF and IL-4 for a week to induce an immature DC phenotype. Then fresh human T cells from a different donor were isolated and mixed with the iDC cells at a 10:1 ratio (T:iDC). H2L5 hIg G4PE and ipilimumab mono-therapy or combinational treatments were added to the T cell/iDC co-culture in the presence or absence of anti-CD3 beads. The purpose of the anti-CD3 beads was to provide a basal TCR stimulus to help prime the T cells. Results showed anti-CD3 beads greatly increased the range of IFN-γ induction in the assay. Although ipilimumab alone can induce IFN-γ production in the absence of anti-CD3 beads, H2L5 hIgG4PE alone or the H2L5 hIgG4PE/ipilimumab combination showed enhanced IFN-γ production over corresponding controls in the presence of anti-CD3 beads. This result suggests that, in this assay, the TCR stimulus by DC cells alone may not be sufficient to induce ICOS expression on the surface of resting T cells that were freshly isolated from PBMCs. In order to improve the situation, a 24 hour iDC and T cells pre-incubation step was added before the addition of therapeutic antibodies. The CEFT peptide mix was also added into the assay procedure to better prime the T cells and to elicit an antigen-specific response. The CEFT peptide pool consists of 27 peptides selected from defined HLA class I and II-restricted T-cell epitopes from human Cytomegalovirus (HHV-5; CMV), Epstein-Barr virus (HHV-4; EBV), Influenza A and *Clostridium tetani*. Considering the high vaccination frequency against Influenza and *Clostridium tetani* and the high prevalence of CMV and EBV in the general population, recall antigen responses were expected for a majority of the human samples. The results showed that increased IFN-γ production was observed when T cells were pre-incubated with iDC cells for 24 hours, and the IFN-γ production further increased when CEFT peptides were added to the co-culture system. The immunostimulatory activity of H2L5 hIgG4PE alone or in combination with ipilimumab was tested in the allogeneic human MLR assay in which T cells that were pre-incubated with monocyte-derived immature DCs from an unmatched donor in the presence of 0.02 μg/ml CEFT peptides for 1 day. The H2L5 hIgG4PE/ipilimumab combination resulted in a significant enhancement in IFN-γ production as compared to either agent alone. The results were consistent across three donor pairs tested; however, modest variability was observed between donors.

Similarly, the combination of H2L5 hIgG4PE and pembrolizumab was also tested in the human allogeneic MLR assay described above. H2L5 hIgG4PE was tested alone and in combination with pembrolizumab at 10 μg/ml. The combination of H2L5 hIgG4PE and pembrolizumab resulted in increased IFN-γ as compared to either agent alone. However, statistical significance was not reached due to high donor variability and significant activity of single agent anti-PD-1 treatment in some donors.

In summary, these studies demonstrated the superior combination activity of H2L5 hIgG4PE with two FDA-approved check point inhibitors, ipilimumab and pembrolizumab, when compared to mono-therapies in two human immune cell based assays. In the studies reported here, H2L5 hIgG4PE was shown to promote T cell activation and $T_H1$ skewing (e.g. IFN-γ production) that is characteristic of productive anti-tumor immune responses.

Example 3: Functional Activity of H2L5 hIgG4PE Alone and in Combination with Anti-PD1 and Anti-CTLA-4 Antibodies In Vivo Human PBMC Mouse Tumor Model
Methods
Experimental Preparations
All procedures on animals were reviewed and approved by the GSK Institutional Animal Care and Use Committee prior to initiation of the studies protocol.
Preparation of cell lines:
A2058 were propagated according to ATCC protocol.
Materials:
    A2058 human melanoma cell line: ATCC, Cat #CRL-11147, lot #59349362
    DPBS: ATCC, Cat #30-2200, Lot #63357436
    Dulbecco's Modified Eagle's Medium: ATCC, Cat #30-2002, Lot #62596471 Expiration: October-2015
    Fetal Bovine Serum: Sigma-Aldrich, Cat #12176c-1000 ml, lot #13G180R0H1, Expiration: July-2018
    0.25% (w/v) Trypsin-0.53 mM EDTA: ATCC, Cat #30-2102, Lot #62420300
    Antibiotic-Antimycotic (100×): Life Technologies, Cat #15240-062
    T175 cell culture flask: Greiner bio-one, Cat #661175
    T75 cell culture flask: Greiner bio-one, Cat #658175
Medium:
    A2058 complete growth medium: Dulbecco's Modified Eagle's Medium+10% FBS. Culture conditions: Atmosphere: Air, 95%; 5% carbon dioxide (CO2); Temperature: 37° C.
Upon receipt of the cells:
Pre-warm complete medium at 37° C.
Thaw the cells quickly in 37° C. water bath. Wipe the tube with 70% ethanol and transfer cells to 15 ml tube filled with prewarmed complete medium.
Centrifuge at 1200 rpm for 5 minutes to collect the cell pellet.
Add the cells back to T75 flask filled with prewarmed complete medium and incubate at 37° C.
Subculture of the Cells:
    Volumes are given for a 75 cm² flask (For T175 cm² flask, adjust the amount of dissociation and culture medium needed proportionally).
    Remove and discard culture medium.
    Briefly rinse the cell layer with DPBS to remove all traces of serum that contains trypsin inhibitor.
    Add 2.0 to 3.0 mL of Trypsin-EDTA solution to flask and observe cells under an inverted microscope until cell layer is dispersed (2-3 minutes).
    Note: To avoid clumping do not agitate the cells by hitting or shaking the flask while waiting for the cells to detach. Cells that are difficult to detach may be placed at 37° C. to facilitate dispersal.
    Add 10 mL of complete growth medium and aspirate cells by gently pipetting.
    Centrifuge at 1200 rpm for 5 minutes to collect the cell pellet, add 10 ml of complete growth medium Add appropriate aliquots of the cell suspension to new culture vessels. Incubate cultures at 37° C.

Medium Renewal: Every 2 to 3 days

Preparation of Tumor Cells for Mice Inoculation:

Wash cells with 1×DPBS, add 3m 1× Trypsin for 2-3 minutes.

Add complete growth media and collect the cell suspension in sterile conical centrifuge tube in the tissue culture hood.

Centrifuge the cells at 1200 rpm for 5 minutes to obtain cell pellet.

Wash cells with 1×DPBS solution, Centrifuge at 1200 rpm for 5 minutes to obtain cell pellet. Repeat the washing 2 times.

Count the cells by hemocytometer for cell number and viability.

Resuspend the cells in ice-cold PBS at concentrations for In Vivo inoculation (A2058, 2.5e7/ml, 2.5e6/100 μl/mouse).

Tumor Cell Line Inoculation to NSG Mice

Materials:

Mouse: NOD.Cg-Prkdcscid Il2rgtm1Wjl/SzJ. The Jackson Laboratory Stock: 005557 Female Age: 6 weeks 1 mL Tuberculin Syringes with Attached Needle 25 G ⅝: Becton Dickinson, Cat #305554

PDI™ Alcohol Prep Pads: Professional Disposables, Cat #B339

PDI™ Povidone-Iodine Prep Pad: Professional Disposables,

Cat #B40600

Preparation of mice

Mice should be 6 weeks old.

Allow 3-5 days acclimatization period after mice have arrived.

Shave the mice on right hind flank

Preparation of the Injection

Clean and sterilize the inoculation area of the mice with iodine followed by ethanol pad Use 1-cc syringe and a 25-gauge needle Pull out the plunger, mix cells and add 100ul of cells to the back of syringe, carefully insert the plunger.

Inject cells subcutaneously (s.c.) into the right hind flank of the mouse.

Tumor Growth Assessment

To measure a tumor, wet fur with 70% ethanol to make it easier to find tumor margins. Measure tumor size and body weight every 2-3 days.

Tumor size is measured with a digital caliper, and the volume is determined as follow: Tumor volume (mm3) =(length)×(width)$^2$/2

Human PBMC Intravenous Administration

Human PBMC administration can start 1 week after when the tumors have reached an average volume of approximately 100 mm3.

Materials:

Fresh Human PBMC: Allcells, cat #C-PB102-3B2

1 mL Tuberculin Syringes with Attached Needle 25 G ⅝: Becton Dickinson, Cat #305554

PDI™ Alcohol Prep Pads: Professional Disposables, Cat #B339

PDI™ Povidone-Iodine Prep Pad: Professional Disposables, Cat #B40600

Gauze sponges: Covidien, cat #441211

Mouse Tail Illuminator Restrainer: Braintree scientific, cat #MTI STD

PBMC preparation

Fresh human PBMC are purchased from Allcells by overnight shipment.

Centrifuge the cells at 1400 rpm for 5 minutes to obtain cell pellet.

Wash cells with 1×DPBS solution, Centrifuge at 1400 rpm for 5 minutes to obtain cell pellet.

Resuspend the cells in ice-cold PBS at concentrations for In Vivo injection (20e7/ml).

Use 1-cc syringe and a 25-gauge needle.

Pull out the plunger, mix cells and add 100ul of cells to the back of syringe, carefully insert the plunger.

Keep the cells on ice.

Tail Vein injection

Warm the mice with an incandescent lamp for 5 minutes

Restrain the mice with tail illuminator restrainer.

Rotate the tail slightly to visualize vein.

Clean and sterilize injection site with iodine followed by ethanol pad

Insert needle into the vein at a slight angle and inject the cells.

Remove the needle and apply gentle compression with Gauze sponges until bleeding has stopped.

Return animals to their cage and observe for 5-10 minutes to make sure that bleeding has not resumed.

Therapeutic Antibody Administration 1-3 days post human PBMC injection, mice are administrated with antibodies by Intraperitoneal injection.

Materials:

Fully human IgG1 isotype control: Eureka therapeutics, cat #ET-901(preclinical grade) Lot #15-726 Expiration: February 2017

Ipilimumab (Yervoy): Bristol-Myers Squibb NDC 0003-2327-11, lot #921873 Expiration: April 2015; lot #4H69490, Expiration: May 2016

Fully human IgG4 isotype control: Eureka therapeutics, cat #ET-904(preclinical grade) Lot #15-726 Expiration: February 2017

Anti human ICOS H2L5 hIgG4PE

Pembrolizumab (Keytruda): Merck, NDC 0006-3026-02, lot #L010592, Expiration: Apr. 26 2016

Intraperitoneal injection:

Draw up, into the syringe and needle, 100 μl of to be administered.

Line the bevel of the needle with the numbers on the syringe.

Sufficiently restrain the animal with your non-dominant hand.

Entry point for the needle: Draw an imaginary line across the abdomen just above the knees, the needle will be inserted along this line on the animal's right side and close to the midline. As this is a female, you can see that the point of entry is cranial to and slightly medial of the last nipple.

Tilt the mouse with its head slightly toward the ground so that its head is lower than its hind end.

Insert the needle into the abdomen at about a 30-degree angle.

The shaft of the needle should enter to a depth of about half a centimeter.

After injection, withdraw the needle and return the mouse to its cage.

Blood and tumor sampling

Materials:

Microvette CB300 (Serum): Braintree Scientific, Cat #MV-CB300 16440

Microvette CB300 (Hematology/Potassium EDTA): Braintree Scientific, Cat #MV-CB300 16444

Blood:

Mice were tail vein bled once a week.

30 µl of blood was collected in Microvette CB300 (Hematology/Potassium EDTA) for flow cytometry analysis.

Another 30 µl of blood was collected in serum Microvette CB300 and incubated for 2 hours at room temperature to allow clotting, followed by centrifugation at 2000×g in order to collect serum. Serum was stored at −20 until further analysis.

Tumor:

Mice were euthanized when tumor size reached 2000 mm$^3$. Tumors were collected and processed in the following procedure.

Experimental Design

All studies were prepared according to procedures listed above.

H2L5 hIgG4PE Dose Response

This study was designed to determine dose-dependent activity of H2L5 hIgG4PE in human PBMC engrafted NSG mice implanted with A2058 melanoma tumors. Nine groups with 10 mice per group and 1 control group (Tumor only no PBMC) with 7 mice were assigned into each study. A summary of the treatment regimen for dose response using human PBMC from donor #7129 is present in Table 4. H2L5 hIgG4PE was dosed at 0.04, 0.4, 1.2 and 4 mg/kg. Ipilimumab was dosed at 3 mg/kg and an Fc-Disabled variant of the anti-ICOS agonist was tested at 1 mg/kg. Test groups were evaluated relative to the vehicle and matched isotype control groups. Survivability analysis concluded on day 49 at termination of the study.

TABLE 4

Summary of Treatment Regimen for H2L5 hIgG4PE Dose Response in Mice

| Groups | Treatment 1 | Treatment 2 | # mice/group | Dosing |
|---|---|---|---|---|
| 1 | Tumor + huPBMC (donor #7129) | Vehicle | 10 | Twice weekly for 3 weeks |
| 2 | Tumor + huPBMC (donor #7129) | human IgG1 Isotype (3 mg/kg) | 10 | Twice weekly for 3 weeks |
| 3 | Tumor + huPBMC (donor #7129) | Ipilimumab (3 mg/kg) | 10 | Twice weekly for 3 weeks |
| 4 | Tumor + huPBMC (donor #7129) | human IgG4 (4 mg/kg) | 10 | Twice weekly for 3 weeks |
| 5 | Tumor + huPBMC (donor #7129) | H2L5 hIgG4PE (0.04 mg/kg) | 10 | Twice weekly for 3 weeks |
| 6 | Tumor + huPBMC (donor #7129) | H2L5 hIgG4PE (0.4 mg/kg) | 10 | Twice weekly for 3 weeks |
| 7 | Tumor + huPBMC (donor #7129) | H2L5 hIgG4PE (1.2 mg/kg) | 10 | Twice weekly for 3 weeks |
| 8 | Tumor + huPBMC (donor #7129) | H2L5 hIgG4PE (4 mg/kg) | 10 | Twice weekly for 3 weeks |
| 9 | Tumor + huPBMC (donor #7129) | ICOS-Fc-disabled (1 mg/kg) | 10 | Twice weekly for 3 weeks |
| 10 | Tumor (no PBMC) (donor #7129) | Untreated | 7 | Twice weekly for 3 weeks |

Efficacy and Pharmacodynamic (PD) Activity Study with H2L5 hIgG4PE in Combination with Ipilimumab and Pembrolizumab Study Objectives:

To evaluate the anti-tumor activity of H2L5 hIgG4PE monotherapy dosed at 0.04 mg/kg and 0.4 mg/kg.

To evaluate the anti-tumor activity of H2L5 hIgG4PE dosed in combination with ipilimumab or pembrolizumab with matched isotype controls.

Collection of tissue for future pharmacodynamic activity study of H2L5 hIgG4PE. A total of 22 treatment groups with 10 mice per group were assigned to this study. Groups 1-16 were the efficacy cohorts and 17-22 were pharmacodynamic activity cohorts.

For combination treatments, H2L5 hIgG4PE (0.04 or 0.4 mg/kg) and ipilimumab or IgG1 (3 mg/kg) or H2L5 hIgG4PE (0.04 or 0.4 mg/kg) and pembrolizumab or IgG4 (5 mg/kg) were dosed. H2L5 hIgG4PE and ipilimumab as well as the matched isotype controls were dosed twice weekly for 6 doses, pembrolizumab and isotype control were dosed every 5 days until end of the H2L5 hIgG4PE dose. For the pharmacodynamic tissue collection cohorts, H2L5 hIgG4PE was dosed at 0.004, 0.04, 0.4 and 1.2 mg/kg. Treatment groups were evaluated relative to the vehicle and isotype control groups. Treatment groups for vehicle, isotypes and H2L5 hIgG4PE alone and in combination with ipilimumab and pembrolizumab using human PBMC from donor number #6711 are shown in Table 5. Analysis concluded on day 59 at termination of the study.

TABLE 5

Treatment groups of mice in A2058 melanoma tumor model

| Group | Treatment 1 | Treatment 2 | # mice/group | Dosing |
|---|---|---|---|---|
| 1 | Tumor + huPBMC (donor #6711) | Vehicle | 10 | Twice a week for 6 doses |
| 2 | Tumor + huPBMC (donor #6711) | Isotype control (IgG1 3 mg/kg + IgG4 5 mg/kg) | 10 | IgG1 Twice a week for 6 doses IgG4 every 5 days until the end of ICOS dose |
| 3 | Tumor + huPBMC (donor #6711) | Ipilimumab 3 mg/kg + IgG4 5 mg/kg | 10 | Twice a week for 6 doses IgG4 every 5 days until the end of ICOS dose |
| 4 | Tumor + huPBMC (donor #6711) | Pembrolizumab 5 mg/kg + IgG1 3 mg/kg | 10 | IgG1 Twice a week for 6 doses Pembrolizumab every 5 days until the end of ICOS dose |
| 5 | Tumor + huPBMC (donor #6711) | H2L5 hIgG4PE 0.04 mg/kg + IgG1 3 mg/kg | 10 | IgG1 and ICOS Twice a week for 6 doses |

TABLE 5-continued

Treatment groups of mice in A2058 melanoma tumor model

| Group | Treatment 1 | Treatment 2 | # mice/group | Dosing |
|---|---|---|---|---|
| 6 | Tumor + huPBMC (donor #6711) | H2L5 hIgG4PE 0.4 mg/kg + IgG1 3 mg/kg | 10 | IgG1 and ICOS Twice a week for 6 doses |
| 7 | Tumor + huPBMC (donor #6711) | Ipilimumab 3 mg/kg + Pembrolizumab 5 mg/kg | 10 | Ipilimumab Twice a week for 6 doses Pembrolizumab every 5 days until the end of ICOS dose |
| 8 | Tumor + huPBMC (donor #6711) | H2L5 hIgG4PE 0.04 mg/kg + Ipilimumab 3 mg/kg | 10 | Ipilimumab and ICOS Twice a week for 6 doses |
| 9 | Tumor + huPBMC (donor #6711) | H2L5 hIgG4PE 0.4 mg/kg + Ipilimumab 3 mg/kg | 10 | Ipilimumab and ICOS Twice a week for 6 doses |
| 10 | Tumor + huPBMC (donor #6711) | H2L5 hIgG4PE 0.04 mg/kg + Pembrolizumab 5 mg/kg | 10 | ICOS Twice a week for 6 doses Pembrolizumab every 5 days until the end of ICOS dose |
| 11 | Tumor + huPBMC (donor #6711) | H2L5 hIgG4PE 0.4 mg/kg + Pembrolizumab 5 mg/kg | 10 | ICOS Twice a week for 6 doses Pembrolizumab every 5 days until the end of ICOS dose |
| 12 | Tumor + huPBMC (donor #6711) | IgG4 5 mg/kg | 10 | Twice a week for 6 doses |
| 13 | Tumor + huPBMC (donor #6711) | Pembrolizumab 2.5 mg/kg | 10 | Pembrolizumab every 5 days until the end of ICOS dose |
| 14 | Tumor + huPBMC (donor #6711) | Pembrolizumab 5 mg/kg | 10 | Pembrolizumab every 5 days until the end of ICOS dose |
| 15 | Tumor + huPBMC (donor #6711) | H2L5 hIgG4PE 0.4 mg/kg | 10 | ICOS Twice a week for 6 doses |
| 16 | Tumor + huPBMC (donor #6711) | H2L5 hIgG4PE 0.4 mg/kg + Pembrolizumab 5 mg/kg + Ipi | 10 | ICOS Twice a week for 6 doses Pembrolizumab every 5 days until the end of ICOS dose |
| 17 | Tumor + huPBMC (donor #6711) | Vehicle | 10 | Twice a week for pharmacodynamic activity, 5 mice harvested 24 hr post 2nd dose and 5 mice harvested 24 hr post 4nd dose |
| 18 | Tumor + huPBMC (donor #6711) | Isotype Control (IgG4) 1.2 mg/kg | 10 | Twice a week for pharmacodynamic activity, 5 mice harvested 24 hr post 2nd dose and 5 mice harvested 24 hr post 4nd dose |
| 19 | Tumor + huPBMC (donor #6711) | H2L5 hIgG4PE 0.004 mg/kg | 10 | Twice a week for pharmacodynamic activity, 5 mice harvested 24 hr post 2nd dose and 5 mice harvested 24 hr post 4nd dose |
| 20 | Tumor + huPBMC (donor #6711) | H2L5 hIgG4PE 0.04 mg/kg | 10 | Twice a week for pharmacodynamic activity, 5 mice harvested 24 hr post 2nd dose and 5 mice harvested 24 hr post 4nd dose |
| 21 | Tumor + huPBMC (donor #6711) | H2L5 hIgG4PE 0.4 mg/kg | 10 | Twice a week for pharmacodynamic activity, 5 mice harvested 24 hr post 2nd dose and 5 mice harvested 24 hr post 4nd dose |
| 22 | Tumor + huPBMC (donor #6711) | H2L5 hIgG4PE 1.2 mg/kg | 10 | Twice a week for pharmacodynamic activity, 5 mice harvested 24 hr post 2nd dose and 5 mice harvested 24 hr post 4nd dose |

Efficacy Study Evaluating H2L5 hIgG4PE Dosed in Combination with Ipilimumab or Pembrolizumab This study was designed to evaluate the anti-tumor efficacy of H2L5 hIgG4PE (dosed at 0.01 and 0.04 mg/kg) in combination with ipilimumab or pembrolizumab with matched isotype controls in the human PBMC engrafted NSG mouse using A2058 melanoma tumor model. A total of 13 groups with 10 mice per group were assigned into the study. Group 2 was the combined isotype control of humanized IgG1 and IgG4. H2L5 hIgG4PE was dosed at 0.01 mg/kg (Group12) and 0.04 mg/kg (Group13) as single agent. For combination treatments, H2L5 hIgG4PE (0.01 and 0.04 mg/kg) and ipilimumab or IgG1 (3 mg/kg) or H2L5 hIgG4PE (0.01 and 0.04 mg/kg) and pembrolizumab or IgG4 (5 mg/kg) was dosed. H2L5 hIgG4PE and ipilimumab as well as the matched isotype controls were dosed twice weekly for 6 doses, pembrolizumab and isotype control was dosed every 5 days until end of the H2L5 hIgG4PE dose. A summary of treatment groups, using human PBMC from donor #4568, is presented in Table 6. Treatment groups were evaluated relative to the vehicle and isotype control groups. Survivability analysis was concluded on day 33 at termination of the study.

TABLE 6

Treatment groups of mice in A2058 melanoma tumor model

| Group | Treatment1 | Treatment2 | # mice/group | Dosing |
|---|---|---|---|---|
| 1 | Tumor + huPBMC (donor #4568) | Vehicle | 10 | Twice a week for 6 doses |
| 2 | Tumor + huPBMC (donor #4568) | Isotype control (IgG1 3 mg/kg + IgG4 5 mg/kg) | 10 | IgG1 Twice a week for 6 doses IgG4 every 5 days until the end of ICOS dose |
| 3 | Tumor + huPBMC (donor #4568) | Ipilimumab 3 mg/kg + IgG4 5 mg/kg | 10 | Twice a week for 6 doses IgG4 every 5 days until the end of ICOS dose |
| 4 | Tumor + huPBMC (donor #4568) | Pembrolizumab 5 mg/kg + IgG1 3 mg/kg | 10 | IgG1 Twice a week for 6 doses Pembrolizumab every 5 days until the end of ICOS dose |
| 5 | Tumor + huPBMC (donor #4568) | H2L5 hIgG4PE 0.01 mg/kg + IgG1 3 mg/kg | 10 | IgG1 and ICOS Twice a week for 6 doses |
| 6 | Tumor + huPBMC (donor #4568) | H2L5 hIgG4PE 0.04 mg/kg + IgG1 3 mg/kg | 10 | IgG1 and ICOS Twice a week for 6 doses |
| 7 | Tumor + huPBMC (donor #4568) | Ipilimumab 3 mg/kg + Pembrolizumab 5 mg/kg | 10 | Ipilimumab Twice a week for 6 doses Pembrolizumab every 5 days until the end of ICOS dose |
| 8 | Tumor + huPBMC (donor #4568) | H2L5 hIgG4PE 0.01 mg/kg + Ipilimumab 3 mg/kg | 10 | Ipilimumab and ICOS Twice a week for 6 doses |
| 9 | Tumor + huPBMC (donor #4568) | H2L5 hIgG4PE 0.04 mg/kg + Ipilimumab 3 mg/kg | 10 | Ipilimumab and ICOS Twice a week for 6 doses |
| 10 | Tumor + huPBMC (donor #4568) | H2L5 hIgG4PE 0.01 mg/kg + Pembrolizumab 5 mg/kg | 10 | ICOS Twice a week for 6 doses Pembrolizumab every 5 days until the end of ICOS dose |
| 11 | Tumor + huPBMC (donor #4568) | H2L5 hIgG4PE 0.04 mg/kg + Pembrolizumab 5 mg/kg | 10 | ICOS Twice a week for 6 doses Pembrolizumab every 5 days until the end of ICOS dose |
| 12 | Tumor + huPBMC (donor #4568) | H2L5 hIgG4PE 0.01 mg/kg | 10 | Twice a week for 6 doses |
| 13 | Tumor + huPBMC (donor #4568) | H2L5 hIgG4PE 0.04 mg/kg | 10 | Twice a week for 6 doses |

Statistical Analysis

The event for survival analysis was tumor volume >2000 mm$^3$, tumor ulceration, mouse body weight loss>20%, moribund or found dead, whichever came first. The exact time to cut-off volume was estimated by fitting a linear line between log tumor volume and day of two observations, the first observation that exceed the cut-off volume and the one observation that immediately preceded the cut-off volume. Kaplan-Meier (KM) method was carried out to estimate the survival probability of different treatment groups at a given time. The median time to endpoint and its corresponding 95% confidence interval was reported. Whether or not KM survival curves are statistically different between any two groups was then tested by log-rank test.

Tumor volume data from the last day in which there were 10 animals per group (i.e. before any animals were euthanized) was utilized to make tumor volume comparisons between the different treatment groups. Prior to the analysis, the tumor volume was natural log transformed due to the inequality of variance in the different treatment groups. ANOVA followed by pair-wise comparison were then carried out on the log transformed data.

Graphpad Prism software was used to plot the tumor growth and body weight data.

Results

Figure 21A:
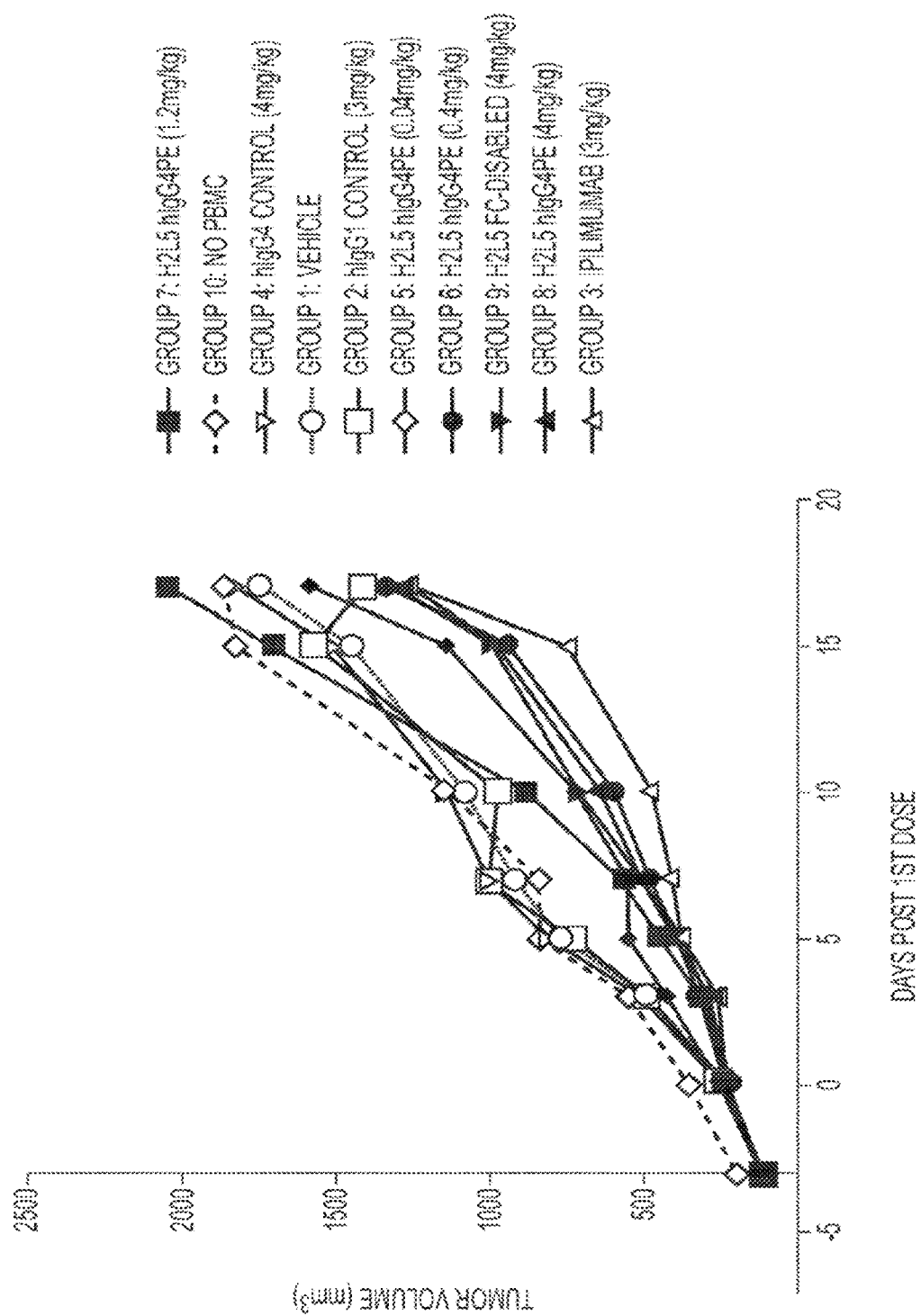
FIG. 21: H2L5 hIgG4PE anti-ICOS agonist mAb alone and in combination with pembrolizumab results in tumor growth inhibition in a human PBMC A2058 Melanoma mouse tumor model.

H2L5 hIgG4PE dose response (FIG. 21A)

Tumor Growth Inhibition:

Control group: Human PBMC (donor 7129) showed no effect on A2058 tumor growth in NSG mice. A2058 tumor bearing mice with or without human PBMC, A2058 tumor bearing mice with human PBMC treated with vehicle and isotype control antibodies developed tumors that progressed as expected (Group #1 vs. Group #10, Group #1 vs. Group #2, Group #1 vs. Group #4, p=1).

Ipilimumab treatment at 3 mg/kg (Group #3) demonstrated significant tumor growth inhibition (p<0.03) as compared to vehicle control Group #1, however the statistical significance was lost (p<0.22) when compared to the isotype control Group #2. This indicated the isotype antibody may affect tumor growth.

H2L5 hIgG4PE treatment at 0.4 mg/kg demonstrated a trend of tumor growth inhibition and increased survivability of mice compared to other doses, although the affects were not statistically significant when compared to either vehicle or isotype control.

Figure 21C:
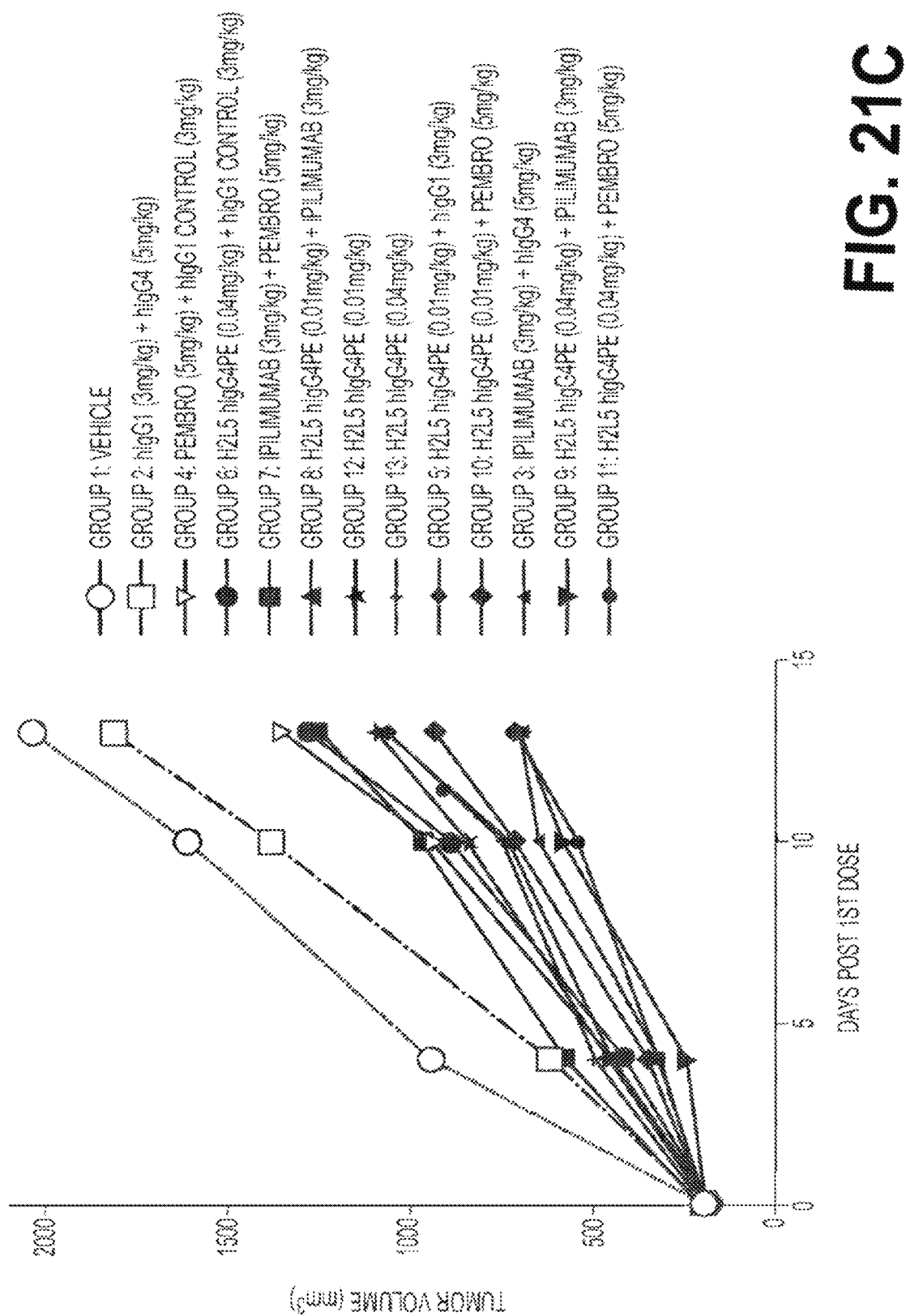

Clinical Observations:

Loss of body weight in mice was observed during the study which was approximately 20% at the end of study. It has been reported that both GvHD and tumor burden can result in a drop in mice body weight, though in this study the body weight loss seemed to be more related to A2058 tumor since tumor bearing mice without PBMC engraftment (group #10) showed the same trend. Tumor ulceration was observed in multiple tumors during the study, including the isotype control group.
Mouse Fates:
Most mice were removed upon tumors reaching volumes >2000 mm$^3$. Three mice were euthanized due to tumor ulceration, and three mice were euthanized due to body weight loss of >20%. Nine mice were found dead randomly across the groups, including two in the vehicle, and three total in the isotype control groups. These deaths were attributed to the susceptibility of the model for a Graft-versus-Host Disease state, and not treatment related since no pattern was observed with treatment groups compared to vehicle or isotype control groups.
Efficacy study with H2L5 hIgG4PE in combination with ipilimumab and Pembrolizumab (FIG. 21B)
Tumor Growth Inhibition:
Control group: A2058 tumor bearing mice with human PBMC treated with vehicle or isotype control antibodies developed tumors which grew as expected.
Monotherapy:
Ipilimumab treatment at 3 mg/kg combined with IgG4 (Group #3) resulted in significant tumor growth inhibition (p<0.04) as compared to vehicle control Group #1. However, when compared to isotype control Group #2, the statistical significance was lost (p<0.23).
Pembrolizumab treatment alone at 2.5 or 5 mg/kg (Group #13, 14) showed observable tumor growth inhibition without statistical significance when compared to vehicle or isotype control group #12. Pembrolizumab combined with IgG1(Group #4), showed observable tumor growth inhibition without statistical significance, however a significant increase in survival was observed (p<0.04) as compared to vehicle control Group #1. Statistical significance was lost (p<0.4) when compared with isotype control Group #2.
H2L5 hIgG4PE treatment alone at 0.4 mg/kg (Group #15) showed observable tumor growth inhibition without statistical significance as compared to vehicle or isotype control group #12. H2L5 hIgG4PE at 0.04 or 0.4 mg/kg combined with IgG1(Group #5 and 6) showed observable delay in tumor progression and mice survival but didn't reach statistical significance.
Combination Treatment:
Combination of H2L5 hIgG4PE (0.04 or 0.4 mg/kg) with ipilimumab (3 mg/kg). Groups #8 and #9 showed no additional tumor growth inhibition as compared to Ipilimumab alone (Group #3). Combination of H2L5 hIgG4PE (0.04 or 0.4 mg/kg) with pembrolizumab (5 mg/kg) Groups #10 and #11 demonstrated modest but insignificant tumor growth inhibition and mice survival compared to pembrolizumab monotherapy, Group #4, or H2L5 hIgG4PE monotherapy Groups #5 and #6.
Clinical Observations:
Mice body weight loss observed during the study was approximately 20%. Tumor ulceration was apparent in multiple tumors during the study across the majority of group.
Mouse Fates:
A total of 100 out of 160 mice were euthanized when tumor volumes reached >2000 mm$^3$. 29 mice were euthanized due to tumor ulceration, 18 mice were found dead, 12 mice were euthanized due to body weight loss >20%, and one mouse was euthanized as moribund. Mice were found dead across the groups including the isotype control group #2. These deaths were attributed to the susceptibility of the model for a Graft-versus-Host Disease state, and not treatment related since no pattern was observed with treatment groups compared to the isotype control group.
Efficacy study evaluating H2L5 hIgG4PE dosed in combination with ipilimumab or pembrolizumab (FIG. 21C)
Tumor Growth Delay:
Control group: A2058 tumor bearing mice with human PBMC treated with vehicle or isotype control antibodies developed tumors which grew as expected.
Monotherapy:
Ipilimumab treatment at 3 mg/kg combined with IgG4 (Group #3) demonstrated significant tumor growth inhibition (p<0.02) and significant increase in survival (p<0.01) as compared to vehicle control Group #1. Compared to isotype control Group #2 however, the tumor growth inhibition did not reach significance (p<0.13) while significant increase in mice survival remained (p<0.04).
Pembrolizumab treatment at 5 mg/kg combined with IgG1 (Group #4) showed tumor growth inhibition without statistical significance as compared to vehicle or isotype control Group #2.
H2L5 hIgG4PE treatment alone at 0.01 mg/kg or 0.04 mg/kg (Group #12 and #13) demonstrated significant tumor growth inhibition (p<0.03) compared to vehicle control group #1 H2L5 hIgG4PE dosed at 0.04 mg/kg also showed a significant increase in mice survival (p<0.048) as compared to vehicle control group #1. However, as compared to isotype control group #2, tumor growth inhibition and survival did not reach statistical significance for groups #12 and #13.
H2L5 hIgG4PE at 0.01 mg/kg combined with IgG1(Group #5) showed significant tumor growth inhibition (p<0.03) and mice survival (p<0.03) as compared to vehicle control group #1. However, as compared to isotype control group #2, tumor growth delay and survival did not reach statistical significance. H2L5 hIgG4PE at 0.04 mg/kg combined with IgG1(Group #6) showed observable tumor growth inhibition and mice survival, but did not reach statistical significance.
Combination Treatment:
The combination of H2L5 hIgG4PE with ipilimumab (0.01 mg/kg plus ipilimumab 3 mg/kg; Group #8) showed observable tumor growth inhibition and mice survival but failed to reach statistical significance. H2L5 hIgG4PE combination with ipilimumab (0.04 mg/kg plus ipilimumab 3 mg/kg; Group #9) demonstrated significant tumor growth inhibition (p<0.00) and a significant increase in mice survival (p<0.04) as compared to vehicle control group #1 or isotype control group #2 (p<0.02). However, as compared to isotype control survival failed to reach statistical significance. Combination activity did not reach significance as compared to monotherapy ipilimumab group #3 or H2L5 hIgG4PE monotherapy groups.
H2L5 hIgG4PE (0.01 mg/kg or 0.04 mg/kg) combination with pembrolizumab (5 mg/kg), Groups #10 and #11, showed significant tumor growth inhibition. (p<0.03) and significant increase of mice survival observed (p<0.03) when comparing to vehicle control group #1. When comparing to isotype control group #2, the tumor growth inhibition significance remained in the 0.04 mg/kg H2L5 hIgG4PE combination with pembrolizumab (p<0.03). The survival benefit failed to reach statistical significance however. The combination failed to reach significance as compared to either monotherapy treatment group pembrolizumab group #3 or H2L5 hIgG4PE group #5 or #6. Thus, H2L5 hIgG4PE combined with pembrolizumab (0.01 or 0.04 mg/kg plus pembrolizumab 5 mg/kg) demonstrated an increase in tumor growth inhibition and mice survival but failed to reach statistical significance versus isotype control or monotherapies.

Clinical Observations:

Mice body weight loss observed during the study was approximately 20%. Tumor ulceration was observed across the majority of groups during the study.

Mouse Fates:

A total of 91 mice were euthanized due to tumor size >2000 mm$^3$, 34 mice were euthanized due to tumor ulcerations, and 5 mice were found dead. These deaths were attributed to the susceptibility of the model for a Graft-versus-Host Disease state.

Discussion

Efficacy of H2L5 hIgG4PE as a monotherapy and in combination with pembrolizumab as well as ipilimumab was evaluated in the human PBMC engrafted NSG mouse model with A2058 melanoma tumors. This model where human PBMC are intravenously injected into adult immunodeficient NSG (NOD/SCID/IL-2Rγnull) mice is known as the Hu-PBMC NSG model. It induces a Graft-versus-Host Disease (GvHD) and has been used to study effector and memory T cell activity. The Hu-PBMC NSG model was implanted with human cancer cell line A2058 subcutaneously to investigate the effect of human immunotherapeutic antibodies on tumor growth. The limitations of this model include onset of GvHD symptoms, loss of body weight, and frequent tumor ulcerations which prevent survival monitoring for longer period of time as is possible with syngeneic mouse tumor models.

Initial studies evaluating H2L5 hIgG4PE at doses ranging from 0.04 mg/kg to 4 mg/kg showed that doses in the lower range demonstrated modest tumor growth inhibition. Delay in tumor progression and increased survival of mice was observed in dose groups ranging from 0.04 to 0.4 mg/kg though not statistically significant when compared to the isotype control groups. Based on these studies, H2L5 hIgG4PE doses of 0.04 to 0.4 mg/kg were selected for further evaluation alone and in combination with pembrolizumab and ipilimumab in two studies with PBMC grafts from two different donors (donor numbers 4568 and 6711). Modest responses for H2L5 hIgG4PE monotherapy and combination with pembrolizumab were observed in one of the two combination studies performed. The combination study using PBMC donor 4568 (Table 6, FIG. 21C) demonstrated anti-tumor activity of the monotherapy and combination while the study using PBMC donor 6711 (Table 5, FIG. 21B) did not show significant anti-tumor effect, which likely was a result of donor PBMC differences between studies, which reflect the patient response variability that may be observed in the clinic. In this second combination study with PBMC donor 4568, enhanced tumor growth inhibition and increased survivability of mice was observed in the combination group when compared to either agent alone, although this difference was not statistically significant. Combination synergy was observed however, since the H2L5 hIgG4PE 0.04 mg/kg dose in combination with pembrolizumab 5 mg/kg resulted in a statistically significant decrease in tumor volume ten days post first dose and increased survivability versus the isotype control group (p<0.05), while the monotherapies did not. In fact, 50% of the mice in the H2L5 hIgG4PE and pembrolizumab combination group remained on study by day 33, but were removed due to tumor ulcerations. Only four mice were removed from study due to tumor volume from this combination group, while 8 to 9 mice were removed from study in the pembrolizumab and isotype groups.

Anti-PD1 therapy did not demonstrate statistically significant activity in this model as seen with the limited change in tumor growth and survival seen with pembrolizumab treated cohort compared to isotope treated cohort. Ipilimumab monotherapy showed a trend of tumor growth inhibition modestly better than pembrolizumab in both studies, and it showed statistically significant increase in survival versus isotype in the second combination study with the responsive PBMC donor 4568 (p<0.04). The H2L5 hIgG4PE 0.01 mg/kg dose in combination with ipilimumab 3 mg/kg showed a significant increase in survival versus ipilimumab (p<0.02), but not versus H2L5 hIgG4PE monotherapy. There were no additional significant effects on tumor volume observed with the combination of H2L5 hIgG4PE and ipilimumab in this model compared to either agent alone. Mice from across all treatment groups including vehicle and isotype control groups were found dead as reported in the Fate Tables. These deaths were attributed to the susceptibility of the model for a Graft-versus-Host Disease state, and not treatment related.

Example 4: Functional Activity of Anti-Murine ICOS Agonist Antibody Alone and in Combination with Anti-PD1 and Anti-CTLA-4 Antibodies In Vivo CT26 and EMT6 Syngeneic Mouse Tumor Models
CT26 murine colon carcinoma mouse tumor model
Methods This study was conducted under a protocol which was approved by the GSK Institutional Animal Care and Use Committee prior to commencement of the study.

Animals

In this study 164 female BALB/c mice from Harlan Sprague Dawley. Mice were 6-8 weeks old at the beginning of the study when they were inoculated.

Cell Culture and Inoculation

One vial of CT-26 cells (ATCC: CRL-2638) (3×10$^6$ cells; P-11) was thawed from −140° C. and plated in RPMI with 10% FBS. Cells were subcultured 3 times over 10 days. Trypsin/EDTA was used to facilitate cell detachment from culture flask during subculturing. Cells were collected, washed twice, and re-suspended in RPMI without FBS at 5×10$^5$ cells/ml. Mice were inoculated subcutaneously with 0.1 ml cells (5×10$^4$ cells/mouse) on the right hind flank. On the day of cell collection and inoculation, cell counts were done on Beckman Coulter Vi-cell XR and checked by hemacytometer. Cells were detached from flask with trypsin/EDTA and washed twice, first with RPMI+10% FBS and second with RPMI only and resuspended in 10 ml RPMI. 178×10$^6$ cells were collected in 20 ml RPMI with 98.8% viability. 1.685 ml cell suspension (15×10$^6$ cells total) was added to 28.315 ml RPMI.

15×10$^6$ cells/30 ml media=5×10$^5$ cells/ml. This equates to 5×10$^4$ cells/100ul.

Antibody Formulation and Preparation

Antibodies were diluted from stock source vials to desired concentrations in sterile 0.9% saline on the day of dosing. Anti-ICOS agonist clone C398.4 was tested at 0.05 mg/kg and 0.5 mg/kg. Each dose was also tested with both anti-PD1 10 mg/kg and anti-CTLA-4 1 mg/kg.

Experimental Protocol(s)
Tumor Monitoring and Dosing

Mice were inoculated on day 0. On day 11 body weight and tumor volume were measured. Mice were randomized into the 12 study groups shown in Table 7 with 10 mice/group based on tumor size. Randomization was done using Studylog Study Director software. Mice were dosed based on the study design chart twice weekly starting on randomization day and continuing for 6 total doses. Dosing was interperitoneal (IP) in 100ul volume of 0.9% saline vehicle. Tumor volume and body weight were measured 3 times per week throughout the study.

Endpoints

Mice were removed from the study for tumor burden when tumor volume was greater than 2000 mm$^3$. Tumor volume was calculated by applying length and width caliper measurements to the following formula: $TV=0.52*L*W^2$.

Additionally mice were removed from study when tumors developed open ulcerations. Ulcerations were observed throughout the experiment, however scabbed over ulcerations alone were not an endpoint unless they formed open holes.

Although it did not apply to any mice in this study a third endpoint established at the beginning of the study was a decrease of 20% body weight.

Drugs and Materials

| Antibody | Vendor | Catalog # | Lot | Clone |
|---|---|---|---|---|
| ICOS | Biolegend | 93108 | B205973 | C398.4 |
| PD1 | BioXcell | BE0146 | 5792-10/0815B | RMP1-14 |
| CTLA-4 | BioXcell | BE0164 | 5632-4/0715 | 9D9 |
| Mouse IgG2b | BioXcell | BE0086 | 4700/1014 | MCP-11 |
| Rat IgG2a | BioXcell | BE0089 | 5679-6/0815 | 2A3 |
| Hamster IgG | Biolegend | 92257 | B205974 | HTK888 |

All antibodies were diluted to desired concentrations in 0.9% saline and saline was used as a vehicle control.

Data Analysis

The event for survival analysis is tumor volume of 2000 mm$^3$ or tumor ulceration, whichever came first. The exact time to cut-off volume was estimated by fitting a linear line between log tumor volume and day of two observations, the first observation that exceed the cut-off volume and the one observation that immediately preceded the cut-off volume. The Kaplan-Meier (KM) method was carried out to estimate the survival probability of different treatment groups at a given time. The median time to endpoint and its corresponding 95% confidence interval was reported. Whether or not KM survival curves are statistically different between any two groups was then tested by the log-rank test.

Tumor volumes at 17 days after initial dosing between the different treatment groups were compared. Prior to the analysis, the tumor volume was natural log transformed due to the inequality of variance in the different treatment groups. ANOVA followed by pair-wise comparison were then carried out on the log transformed data.

TABLE 7

Study Groups

| Group No. | Treatment |
|---|---|
| 1 | Saline |
| 2 | Mouse IgG2b 20 ug + Hamster IgG 10 ug |
| 3 | Rat IgG2a 200 ug + Hamster IgG 10 ug |
| 4 | Hamster IgG 10 ug |
| 5 | ICOS 1 ug |
| 6 | ICOS 10 ug |
| 7 | CTLA-4 20 ug |
| 8 | PD1 200 ug |

TABLE 7-continued

Study Groups

| Group No. | Treatment |
|---|---|
| 9 | ICOS 1 ug + CTLA-4 20 ug |
| 10 | ICOS 10 ug + CTLA-4 20 ug |
| 11 | ICOS 1 ug + PD1 200 ug |
| 12 | ICOS 10 ug + PD1 200 ug |

The raw p-value, as well as the false discovery rate (FDR) adjusted p-values, from the comparisons of days to events by survival analysis and the comparisons of log transformed tumor volume at day 10 between treatment groups are shown in the above table. Comparisons, using FDR adjusted p-values ≤0.05, are declared to be statistically significant.

Results

Mouse fate tracking showed that the number of mice removed from study for tumor burden and tumor ulceration. All remaining mice are tumor free at study day 61 except 1 mouse in G7 which has a tumor volume of 579.16 mm$^3$.

Figure 22:
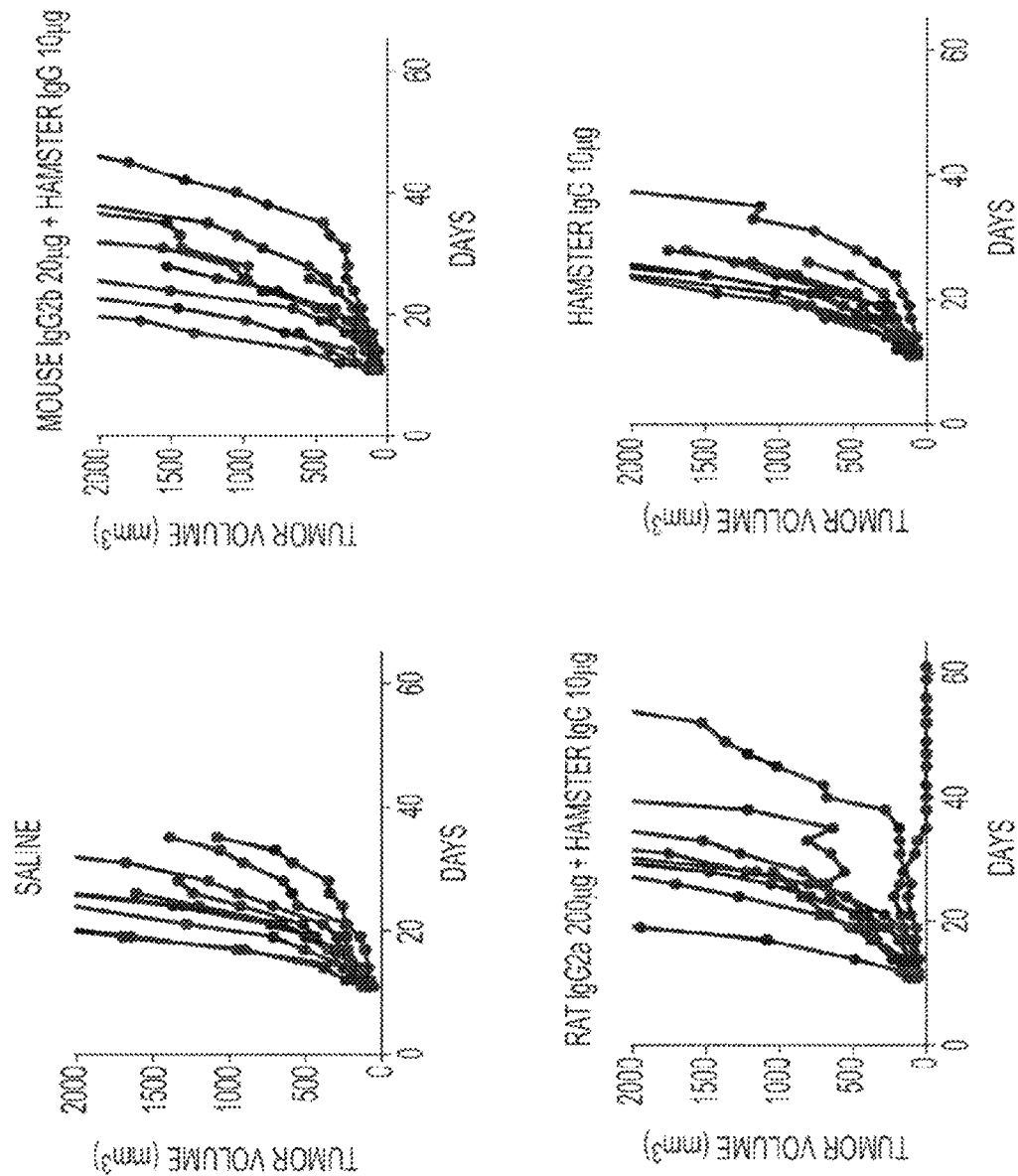
FIG. 22: Anti-ICOS murine surrogate mAb results in significant tumor growth inhibition and increased survival in combination with an anti-PD1 murine surrogate mAb in the CT26 mouse tumor model.
Figure 22:
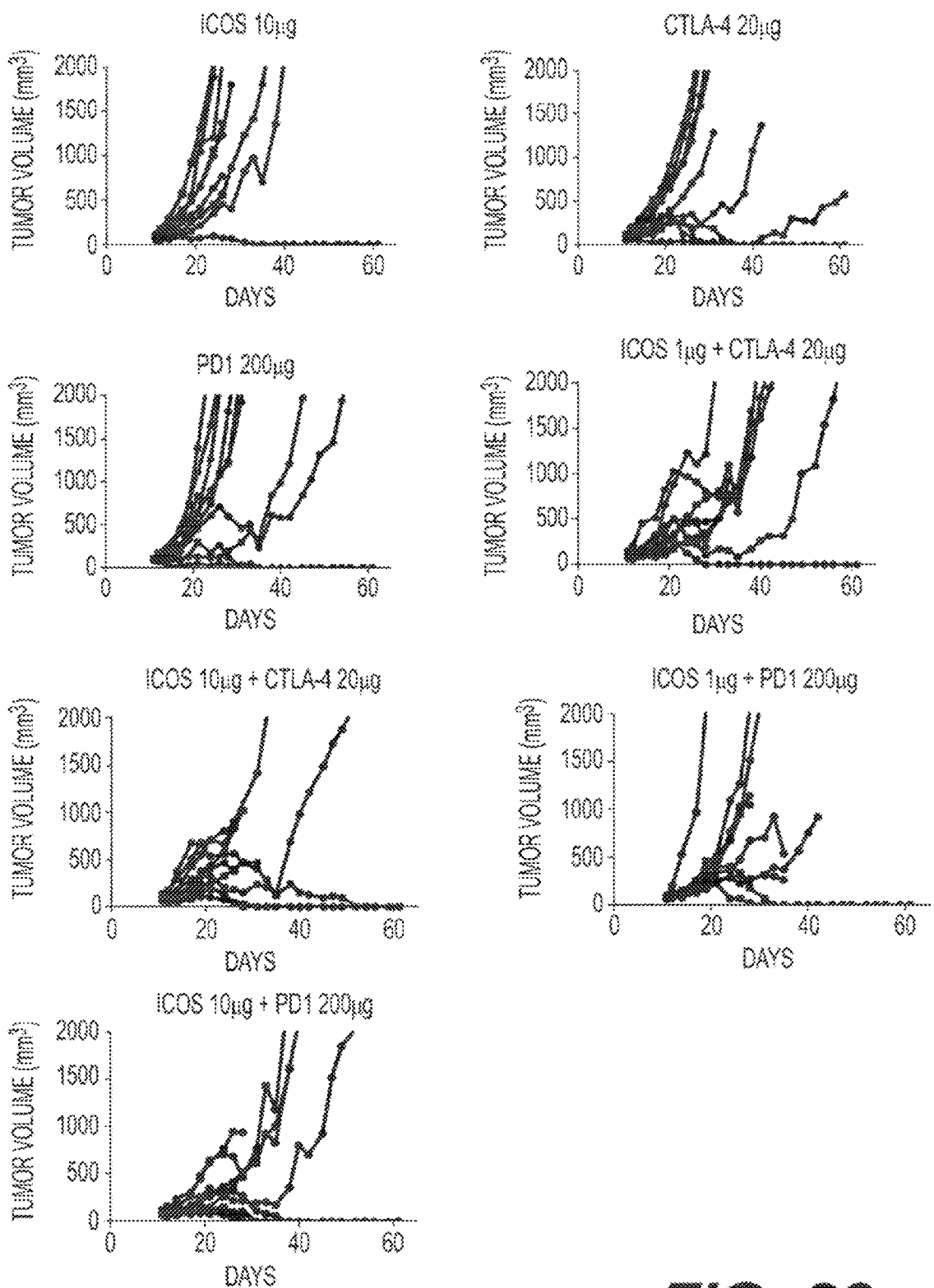

For survival (time to endpoints) groups 9 and 12 showed significant increase in survival compared to the vehicle control group (p=0.008 and p=0.001 respectively). Group 12 showed statistically significant extended survival compared to groups 2, 4, and 5 (p=0.006, 0.001, 0.02). However, no combination group showed statistically significant (p<0.05) increased survival over either monotherapy. (FIG. 22)

Discussion

The combination therapy groups, particularly the high dose anti-ICOS and anti-PD1 combination (Group 12), demonstrated tumor growth inhibition and increased survival over monotherapy and isotype control groups, although statistical significance was not reached at Day 61. The isotype control for group 12 was the Rat IgG2a+ Hamster IgG group 3. The monotherapy groups for comparison are; ICOS 10 ug (group 6) and PD1 200ug (group 8). A total of 5 mice remained as tumor free in group 12 compared to 1 in group 3, 1 in group 6 and 1 in group 8. The survival benefit was quantified by taking the day each mouse reached any of the pre-determined study endpoints. A number of mice were removed from study for open tumor ulcerations and not due to tumor burden.

In the high dose ICOS+CTLA-4 combination group (group 10) an increased number of mice were removed due to tumor ulceration by day 31 which likely masked the survival and anti-tumor benefit that this combination provided. In this group, 5 mice were removed for tumor ulcerations and only 2 for tumor burden reaching 2000 mm$^3$. All tumors removed due to tumor ulceration where still at modest size when taken off study, and it is expected that tumor ulceration may have been the result of a therapy-induced anti-tumor immune response in these mice. Three mice remained tumor free in this group out to day 61. The 2 mice removed for tumor burden were the lowest number of mice removed for tumor burden of all groups.

EMT6 Mammary Carcinoma Mouse Tumor Model

Experimental Protocol(s)

All procedures and euthanization criteria described in this document are in accordance with IACUC protocol AUP0606. Animals are weighed and inoculated on the right hind quarter with 100 ul of 1×10$^5$ EMT6 tumor cells per mouse. The number of mice inoculated is equal to at least 130% of what was needed for the study. Assuming 30% failure rate (either too big or too small at time of start of study), the goal was to have n=10 for each group. After tumor cell inoculation, tumor growth and total body weight were measured 3 times a week with a Fowler "ProMax" digital caliper for 4 weeks or longer. Antibodies were acquired from a commercial vendor and diluted to desired concentration in 0.9% saline. Dosing (i.p.) occurred biweekly, for a total of 6 doses and initiated on the day of randomization, designated as Day 0, when average tumor volume approximated 100 mm$^3$, approximately 7 to 8 days after inoculation. Randomization was performed using the Studylog Study Director Suite software. Length and width of tumors was measured in order to determine tumor volume using the formula (tumor volume=L*W$^2$*0.52). Tumor measurement of greater than 2,000 mm$^3$ for an individual animal resulted in removal from study. Mice may also be removed from the study due to weight loss (>20%), tumor ulceration, or any other obvious inhibition of normal mouse activity due to morbidity.

In this study, a total of 191 animals were inoculated with EMT6 cells in order to generate enough mice with tumors in the desired size range for 13 groups of 10 mice each as shown in Table 8. Saline vehicle injected mice and isotype control groups served as controls for ICOS, PD1 and CTLA-4 mAb treated mice. The isotype control for ICOS (Hamster IgG) was dosed at 10 ug alone and in combination with the isotype for CTLA-4 (mouse IgG2b) or PD-1 (rat IgG2a). Monotherapy treatment groups for anti-CTLA-4 (9D9) and anti-PD-1 (RMP1-14) were dosed at 20 and 200 ug per mouse, respectively, and evaluated in combination with the ICOS isotype control. The C398.4 clone of ICOS agonist was dosed at 10 and 1 ug per mouse. Efficacy of the ICOS agonist was also evaluated at 10 and 1 ug per mouse dosed in combination with anti-CTLA-4 or anti-PD-1. An additional group of PD-1 and CTLA-4 at predescribed concentrations was included as a positive control comparator group. Statistical analysis of tumor volume was performed on day 13 post randomization. Survivability analysis included mice on study through day 60.

TABLE 8

Study Groups

| Dosing | treatment 1 | treatment 2 | n= |
|---|---|---|---|
| Group 1: 1 × 10$^5$ cells per | saline | | 10 |
| Group 2: 1 × 10$^5$ cells per | Hamster IgG 10 µg | mIgG2b 20 µg | 10 |
| Group 3: 1 × 10$^5$ cells per | Hamster IgG 10 µg | rIgG2a 200 µg | 10 |
| Group 4: 1 × 10$^5$ cells per | Hamster IgG 10 µg | | 10 |
| Group 5: 1 × 10$^5$ cells per | ICOS 10 µg | | 10 |
| Group 6: 1 × 10$^5$ cells per | ICOS 1 µg | | 10 |

TABLE 8-continued

Study Groups

| Dosing | treatment 1 | treatment 2 | n= |
|---|---|---|---|
| Group 7: 1 × 10$^5$ cells per | CTLA4 20 µg | Hamster IgG 10 µg | 10 |
| Group 8: 1 × 10$^5$ cells per | PD-1 200 µg | Hamster IgG 10 µg | 10 |
| Group 9: 1 × 10$^5$ cells per | ICOS 10 µg | CTLA4 20 µg | 10 |
| Group 10: 1 × 10$^5$ cells per | ICOS 1 µg | CTLA4 20 µg | 10 |
| Group 11: 1 × 10$^5$ cells per | ICOS 10 µg | PD-1 200 µg | 10 |
| Group 12: 1 × 10$^5$ cells per | ICOS 1 µg | PD-1 200 µg | 10 |
| Group 13: 1 × 10$^5$ cells per | CTLA4 20 µg | PD-1 200 µg | 10 |

Drugs and Materials
Animals
Female Balb/c mice from 6 to 8 weeks of age were received from Harlan Sprague Dawley and housed in accordance with IACUC standards.
EMT6 Cells
EMT6 cells were thawed and cultured in cell culture flasks for eight days prior to inoculation. Cells were passed 3 times in this time. On the day of inoculation, the cells are harvested from the flask in complete medium. Cells are centrifuged and resuspended in Weymouth's (with 15% FBS). This step is repeated 3 times in Weymouth's media without FBS. Cell density and viability are checked via trypan blue exclusion. Cells are then diluted to desired density (1×10$^6$ cells per mL).
Immunotherapeutics
All therapeutics were diluted to desired concentrations in 0.9% sodium chloride on the day of dosing and injected i.p. using a 30G needle. Therapeutic and control dilutions are presented below in Table 9.

TABLE 9

Therapeutic dilutions

| Rx | starting conc. mg/mL | desired conc. mg/mL | dilution 1: | dose/ mouse mg | number of mice | volume needed mL | add stock mL | Total diluent mL | total volume mL |
|---|---|---|---|---|---|---|---|---|---|
| mouse IgG2b | 4.46 | 0.1 | 44.6 | 0.02 | 10 | 2 | 0.10 | 4.36 | 4.46 |
| rat IgG2a | 6.92 | 1 | 6.92 | 0.2 | 10 | 2 | 0.40 | 2.37 | 2.77 |
| Hamster IgG | 1.47 | 0.05 | 29.4 | 0.01 | 50 | 10 | 0.40 | 11.36 | 11.76 |
| CTLA4 | 6.1 | 0.1 | 61 | 0.02 | 40 | 8 | 0.15 | 9 | 9.15 |
| PD-1 | 7.44 | 1 | 7.44 | 0.2 | 40 | 8 | 1.30 | 8.372 | 9.672 |
| ICOS | 5 | 0.05 | 100 | 0.01 | 30 | 6 | 0.10 | 9.9 | 10 |
| ICOS | 0.05 | 0.005 | 10 | 0.001 | 30 | 6 | 1.00 | 9 | 10 |

Data Analysis
Statistical Analysis

The event for survival analysis was tumor volume of 2000 mm$^3$ or tumor ulceration, whichever came first. The exact time to cut-off volume was estimated by fitting a linear line between log tumor volume and day of two observations, the first observation that exceed the cut-off volume and the one observation that immediately preceded the cut-off volume. The Kaplan-Meier (KM) method was carried out to estimate the survival probability of different treatment groups at a given time. The median time to endpoint and its corresponding 95% confidence interval was reported. Whether or not KM survival curves were statistically different between any two groups was then tested by the log-rank test.

Tumor volumes at 13 days after initial dosing between the different treatment groups were compared. Prior to the analysis, the tumor volume was natural log transformed due to the inequality of variance in the different treatment groups. ANOVA followed by pair-wise comparison were then carried out on the log transformed data. SAS 9.3 and R 3.0.2 Analysis Software was utilized.

Results

Balb/c mice were inoculated and randomized into groups of ten based on treatment regimen 8 days later. Administration of therapeutics or controls began on randomization day (Day 0) and continued twice a week for 3 weeks.

The saline treated group grew tumors at the expected rate relative to previous EMT-6 studies. All mice in the saline vehicle group were euthanized due to tumor size or ulceration by day 30. Treatment with hamster IgG alone or in combination with rat IgG2a or mouse IgG2b, resulted in no statistically significant change in average tumor growth or survival when compared to the saline vehicle group.

Figure 23:
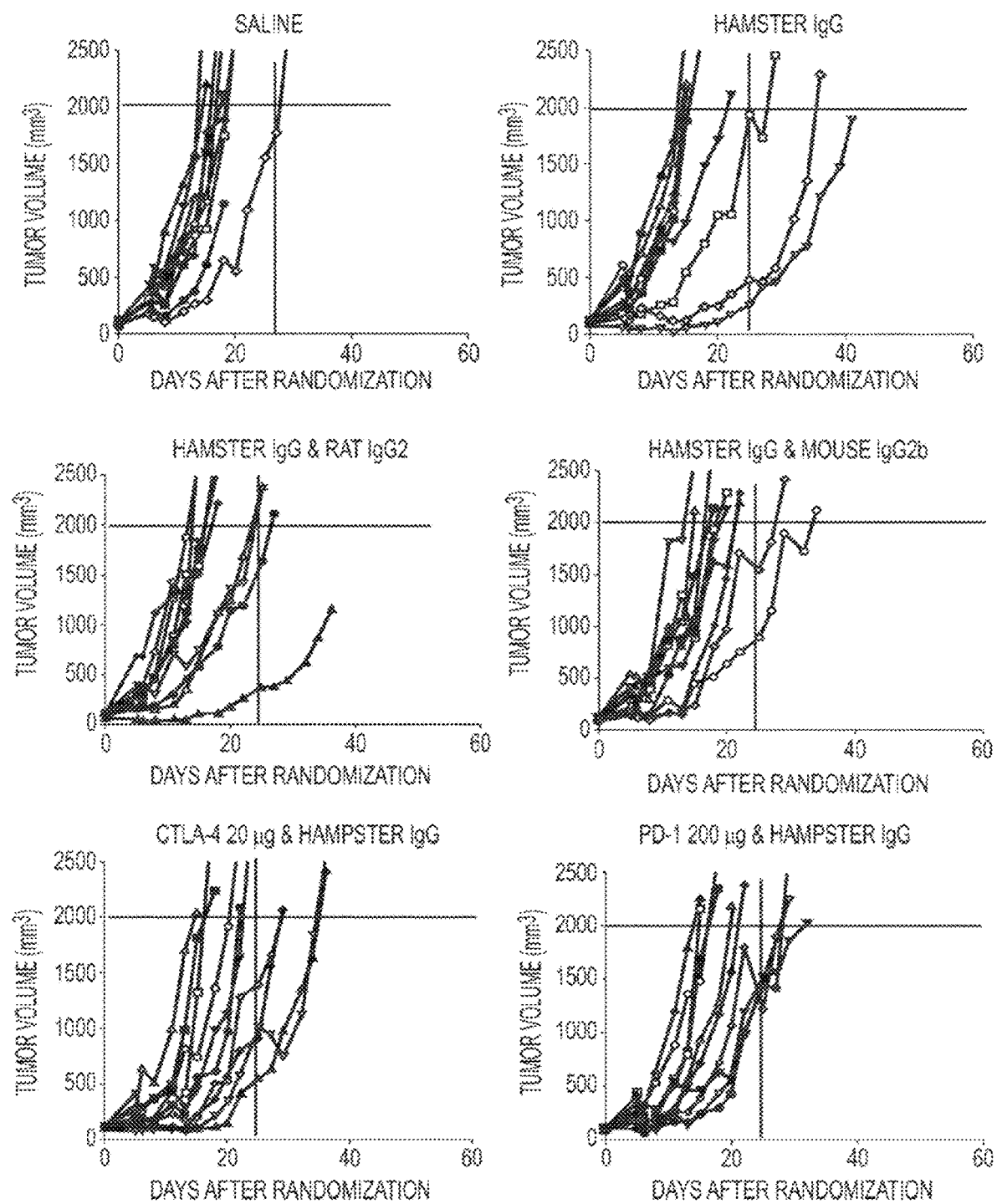
FIG. 23: Anti-ICOS murine surrogate mAb results in significant tumor growth inhibition and increased survival in combination with an anti-PD1 murine surrogate mAb in the EMT6 mouse tumor model.
Figure 23:
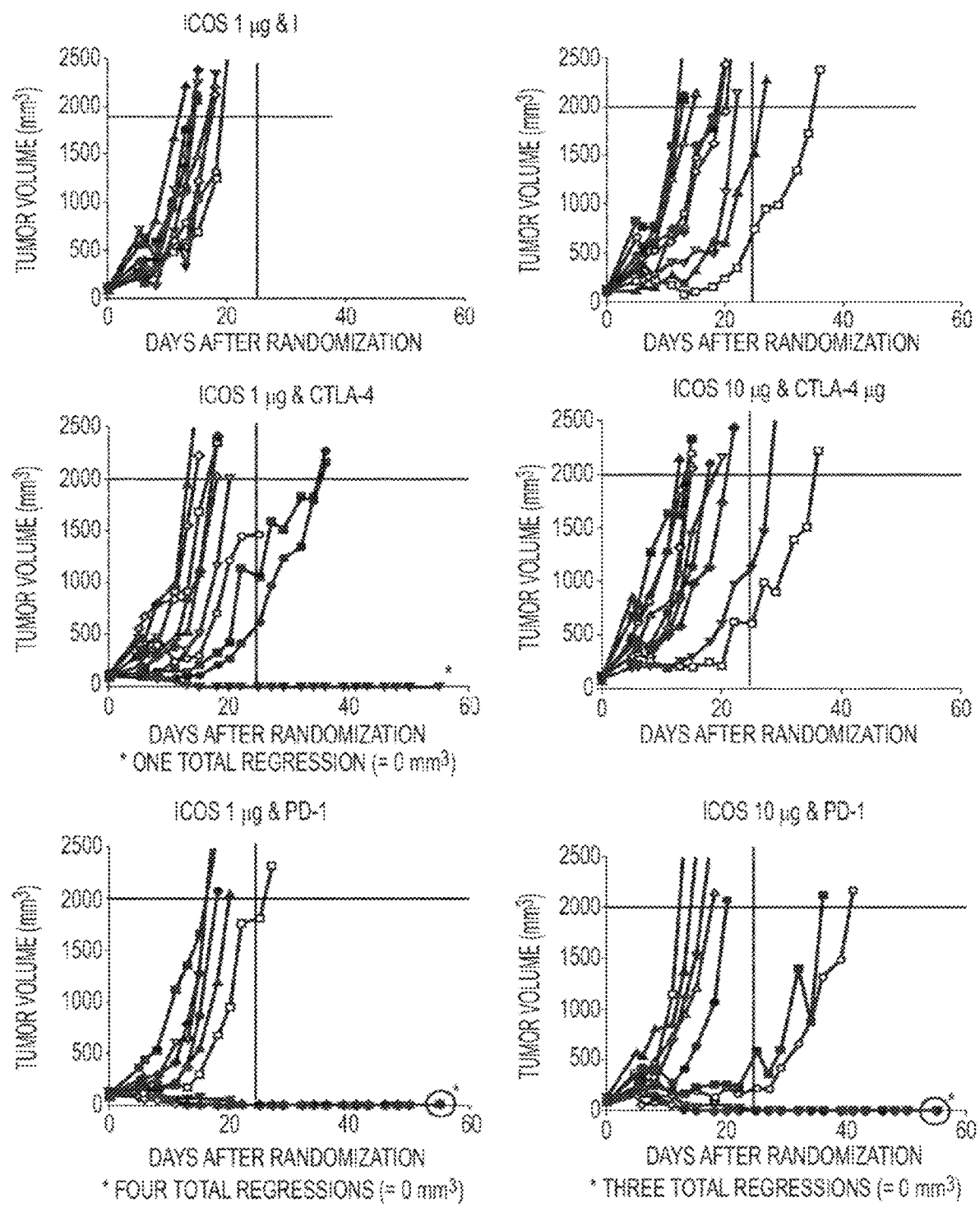
Figure 23:
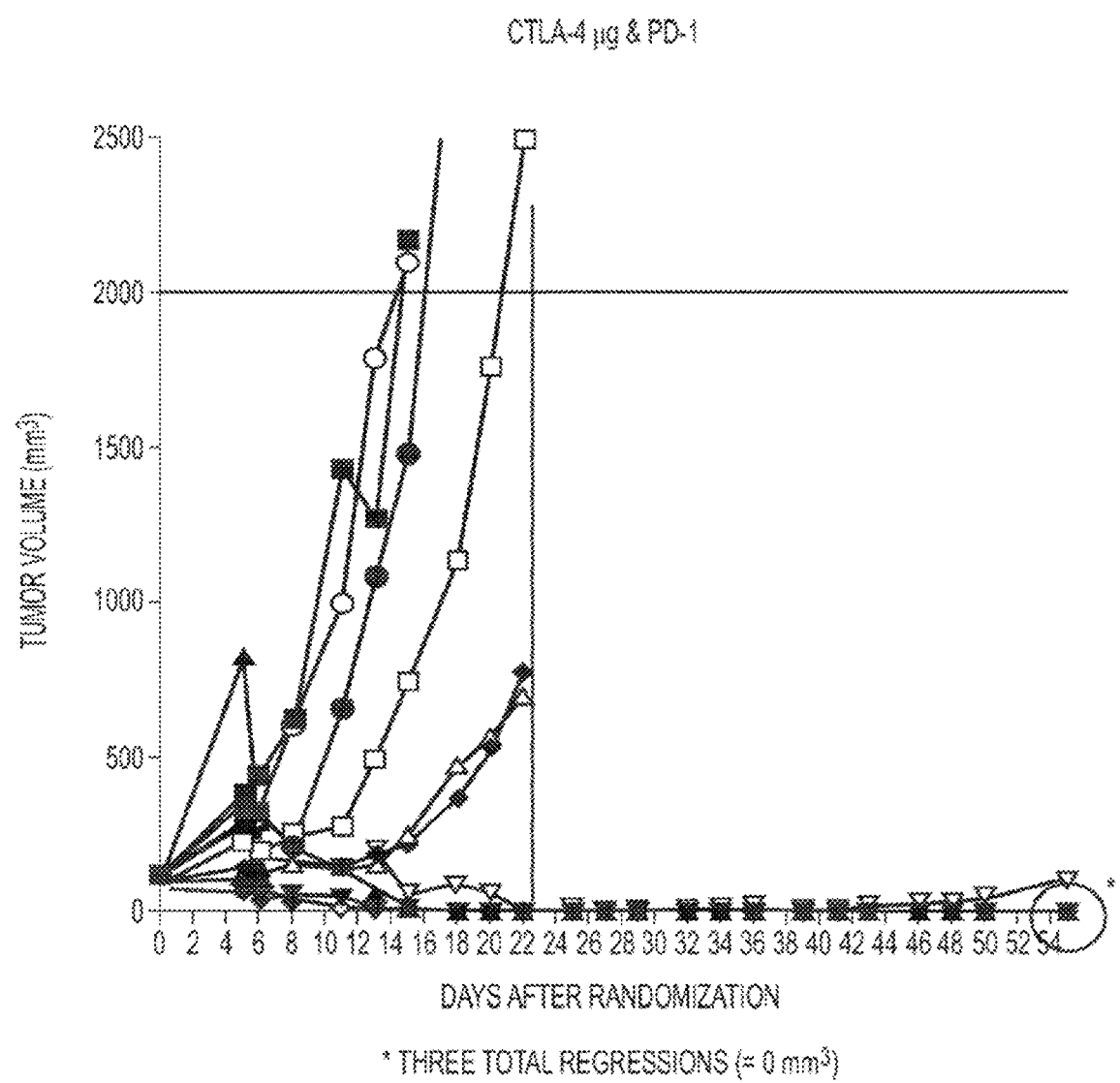

At 13 days post randomization, the ICOS monotherapy groups demonstrated little observable change in average tumor growth as compared to isotype controls. However, the high dose ICOS treatment group (10ug) demonstrated an apparent trend towards more tumor growth inhibition than the low dose group. An effect that was comparable to the CTLA-4 monotherapy activity was observed. Monotherapy treatment with PD-1 mAb also resulted in some observable, but statistically insignificant reduction in average tumor volume at day 13. However, as with ICOS and CTLA-4 monotherapy, this did not result in increased survival when compared to that of the appropriate isotype groups. Treatment with the combination of anti-PD-1 and anti-ICOS antibody clone C398.4 at the 10 ug dose resulted in considerable tumor growth inhibition as compared to control and monotherapy treatment groups (FIG. 23). Three mice in this combination group achieved complete tumor regression, a considerable improvement over control or monotherapy treatment groups. However, due to the statistical criteria used, statistically significant improvement in survival was not reached. The combination of anti-PD-1 with 1 ug of ICOS agonist antibody clone C398.4 did result in a statistically significant decrease in average tumor growth at day 13 as compared to saline vehicle control (p<0.05) and ICOS monotherapy (p<0.05) groups of 1 and 10 ug. Four mice from this treatment regimen achieved complete tumor regression resulting in significant trend towards increased survival that failed to reach statistical significance.

The ICOS antibody at both doses in combination with anti-CTLA-4 demonstrated little observable benefit in tumor growth inhibition or survival as compared to monotherapy treatment with either antibody.

Discussion

While isotype controls resulted in no obvious change in average tumor volume or overall survival when compared to the saline vehicle group, there were individual animals in the hamster IgG group (group 4) and the hamster IgG and rat IgG2a (group 3) that demonstrated delayed tumor growth. In the hamster IgG & rat IgG2a isotype group, one mouse survived beyond the last saline vehicle mouse, being sacrificed on day 36 due to ulceration with a tumor that measured 1156.56 mm$^3$ in volume. Two mice in the hamster IgG group survived longer than the saline group. One animal was euthanized due to tumor size on day 36, and the second one on day 41 due to ulceration with a measurement of 1899.28 mm$^3$.

The dosing regimen of anti-PD-1 with 10 ug of anti-ICOS agonist led to an observable inhibition of tumor growth resulting in a decrease in tumor volume at day 13 when compared to isotype controls, although this difference was less obvious when compared to anti-PD-1 monotherapy. However, the combination did result in a total of five animals surviving beyond any in the anti-PD-1 monotherapy group, with three mice experiencing complete tumor regression as compared to none in the anti-PD-1 monotherapy group.

Pairing anti-PD-1 with a 1 ug dose of ICOS agonist antibody led to an observable decrease in average tumor size at day 13 when compared to isotype controls and respective monotherapy groups. This decrease was statistically significant when compared to saline vehicle control (p<0.05) and the 1 ug ICOS monotherapy group (p<0.05). Four mice experienced complete tumor regression and survived beyond any in the PD-1 monotherapy group The survival benefit observed with the ICOS+PD1 combination group was not found to reach statistical significance relative to controls by day 60. However, the tumor growth inhibition and survival benefit of the ICOS+PD1 combination treatment groups was comparable to the activity observed with the PD1+CTLA-4 combination group, which was considered a positive control for anti-tumor activity in this study. This suggests that a combination of ICOS and PD1 antibodies may have benefit similar to CTLA-4 and PD1 combinations, which have demonstrated significant clinical activity in some tumor types.

Of the 130 mice enrolled in this study, 12 remained alive at day 60 with 11 having achieved complete tumor regression. Of the 118 mice that met endpoints for study removal, 111 were removed due to reaching a tumor size of 2000 mm$^3$. The remaining seven mice were euthanized due to ulceration on the tumor. Occurances of ulceration were spread out among the groups. Groups 1 (Saline), 3 (hamster IgG & rat IgG2a), 4 (hamster IgG), 6 (1 ug ICOS), and 10 (CTLA-4 with 1 ug ICOS) all had one animal removed due to ulceration. Group 13 (CTLA-4+PD-1) showed two animals sacrificed due to ulceration. The remaining groups had no animals removed due to ulceration.

Example 5: ICOS Agonism Induces Effector Memory T Cell Function and Antitumor Activity Antibodies targeting the immune checkpoint receptors CTLA-4 and PD-1/PD-L1 have demonstrated impressive activity in select patients; however most cancers remain non-responsive to this class of agents. New immune targeted therapies are needed to improve the treatment of all cancers. Inducible T cell Co-Stimulator (ICOS) is a T cell-restricted co-stimulatory receptor whose expression is induced on activated and memory T cells upon T cell receptor (TCR) engagement. Here we show that antibody-induced ICOS activation elicits potent memory T cell activation, mobilization of T cells to the tumor site and antitumor responses alone and in synergy with PD-1 blockade. To translate these findings to humans we have developed a humanized agonist monoclonal antibody to human ICOS capable of stimulating effector T cell activation, expansion and function. The first-in-class humanized ICOS agonist antibody described here offers the potential to expand the population of patients and range of tumor types that respond to cancer immunotherapy.

Introduction

Inducible T Cell Co-stimulator (ICOS) is a co-stimulatory receptor with structural and functional relation to the CD28/CTLA-4-Ig superfamily[1]. Expression of ICOS is primarily restricted to T cells, varying between different T cell subsets and their activation status. ICOS expression has been shown on resting $T_H17$, T follicular helper (TFH) and regulatory T ($T_{reg}$) cells. However, unlike CD28, it is not highly expressed on naïve T cell populations[2,3]. In activated, antigen-specific T cells, ICOS can regulate the production of both $T_H1$ and $T_H2$ cytokines and has been shown to stimulate effector T cell proliferation, albeit to a lesser extent than CD28[4]. Additionally, ICOS plays a crucial role in the survival and expansion of effector T cells and $T_{Reg}$, both in steady state and during antigen-stimulated immune responses[5]. ICOS has also recently been shown to be critical for the development and function of unique CD4+ helper T cell subsets including $T_H17$ cells[3,6] and circulating $T_{FH}$-like cells[7].

Prior reports support the concept that activating ICOS on CD4+ and CD8+ effector T cells using recombinant ICOS ligand in mice has antitumor potential[8]. ICOS has also been shown to be critical for anti-CTLA-4 antitumor activity in mice[9,10]. Emerging data from patients treated with anti-CTLA4 antibodies point to the positive role of ICOS-expressing memory T cells in mediating antitumor immune responses and long-term survival[11-14]. Here we have characterized the immunologic activity of antibody-mediated ICOS agonism in mouse tumor models, demonstrating potent effector memory T cell ($T_{EM}$) clonal expansion, tumor homing and infiltration which lead to antitumor responses, both alone and in combination with checkpoint blockade through PD-1. To translate these findings to cancer patients, we have developed and characterized a novel agonist antibody targeted to human ICOS which recapitulates the $T_{EM}$-inducing properties identified with the murine ICOS monoclonal antibody (mAb). The humanized ICOS agonist mAb described here offers the first potent and selective therapeutic designed to activate this important co-stimulatory T cell receptor.

Results

Figure 24D:
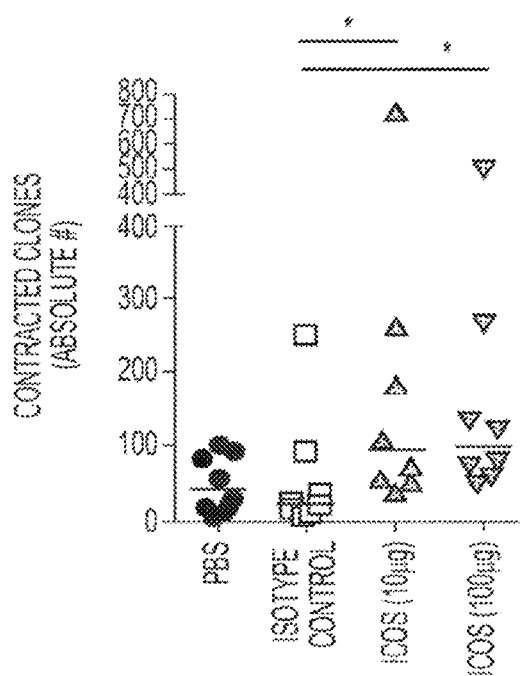
FIG. 24: ICOS agonist mAb treatment induces clonal expansion of $T_{EM}$ cells and redistribution to the periphery (a) quantification of effector memory $T_{EM}$ (CD62L$^-$CD44$^+$) CD8$^+$ and CD4$^+$ T cells in the blood of mice with EMT6 tumors CD8$^+$ (10 μg*P=0.0258 and 100 μg*P=0.0174; F=4.705 df=12) CD4$^+$ (10 μg P=0.0613 and 100 μg P=0.0526; F=2.964 df=12) (b) quantification of central memory $T_{CM}$ (CD62L+CD44$^+$) CD8$^+$ and CD4$^+$ T cells in the blood of mice with EMT6 tumors CD8$^+$ (10 μg*P=0.0296 and 100 μg*P=0.0394; F=3.816 df=12) CD4$^+$ (10 μg group P=0.0625 and 100 μg*P=0.0356; F=3.306 df=12) (c) quantification of naïve (CD62L+CD44) CD8$^+$ and CD4$^+$ T cells in the blood of mice with EMT6 tumors. CD8$^+$ (10 μg group P=0.0659 and 100 μg P=0.1122; F=2.376 df=12) CD4$^+$ (10 μg P=0.1942 and 100 μg P=0.1078; F=1.681 df=12) (d) absolute number of TCR clones contracted in post-treatment blood relative to pre-treatment blood (10 μg*P=0.0327 and 100 μg *P=0.0497; F=3.033 df=28) (e) absolute number of TCR clones expanded in post-treatment blood relative to pre-treatment blood (10 μg P=0.0975 and 100 μg P=0.1915; F=1.958 df=28) (f) productive clonality in post-treatment blood (10 μg P=0.5322 and 100 μg P=0.1915; F=0.6020 df=28) (g) absolute number of clones expanded in post-treatment blood that were also found in tumor (10 μg*P=0.0173 and 100 μg*P=0.0483; F=3.269 df=28) (d-g) prior to one-way ANOVA data was square root transformed to stabilize variances (h) quantification of IFN-γ levels in blood of mice (100 μg*P=0.0392; F=3.027 df=12) (i) percentage of CD8$^+$ GZMB$^+$ relative to total CD8$^+$ (100 μg*P=0.0564; F=3.296 df=12) (j) quantification of Cxcl9 RNA expression the spleen of mice (10 μg*P=0.0134 and 100 μg P=0.1595; F=4.195 df=12) (k) percentage of proliferative (Ki67$^+$) in the spleens of treated mice CD4$^+$ (100 μg*P=0.0114; F=7.152 df=12) and (1) CD8$^+$ (100 μg **P=0.0014; F=13.95 df=12) Each symbol represents an individual mouse. Horizontal lines represent median values, error bars represent interquartile range. All statistical tests were one-way ANOVA, followed by specific treatment comparators.
Figure 24E:
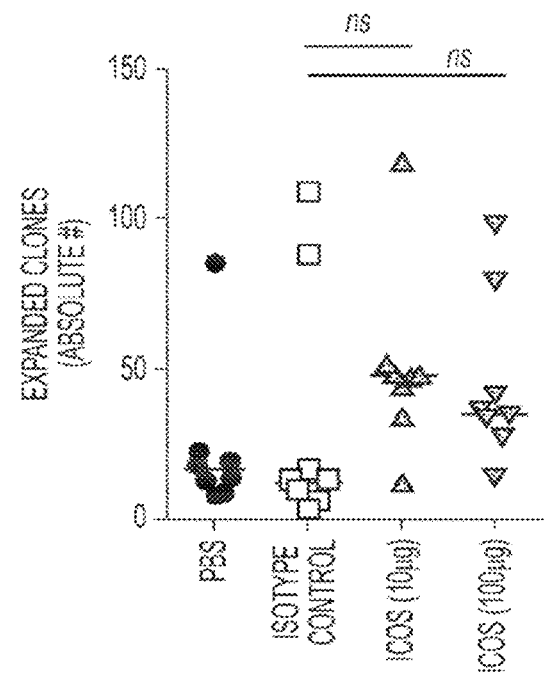
Figure 24F:
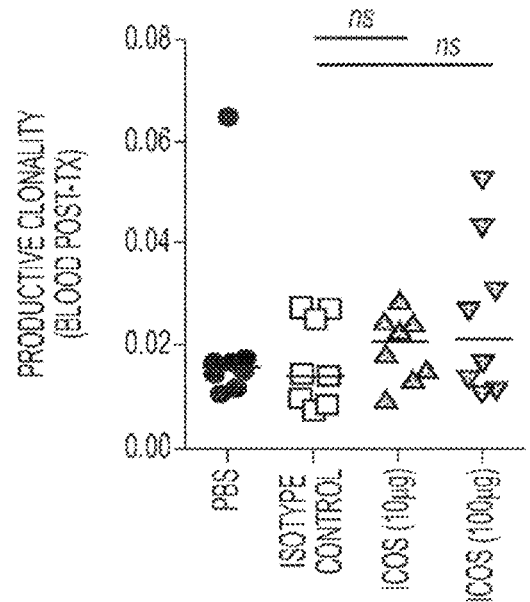
Figure 24G:
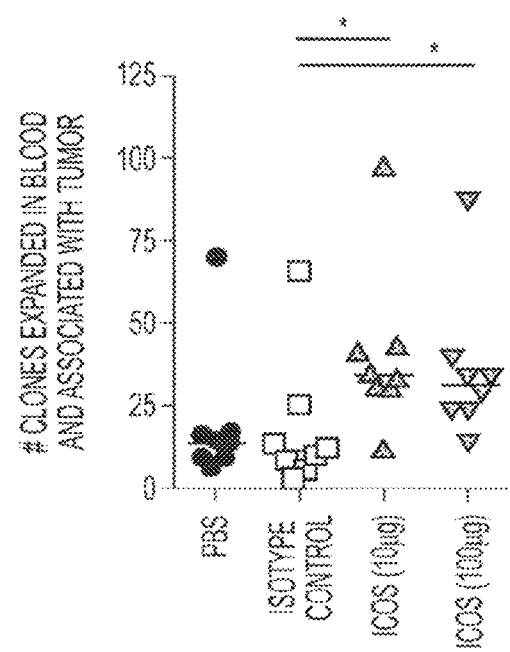
Figures 24H, 24I, 24J:
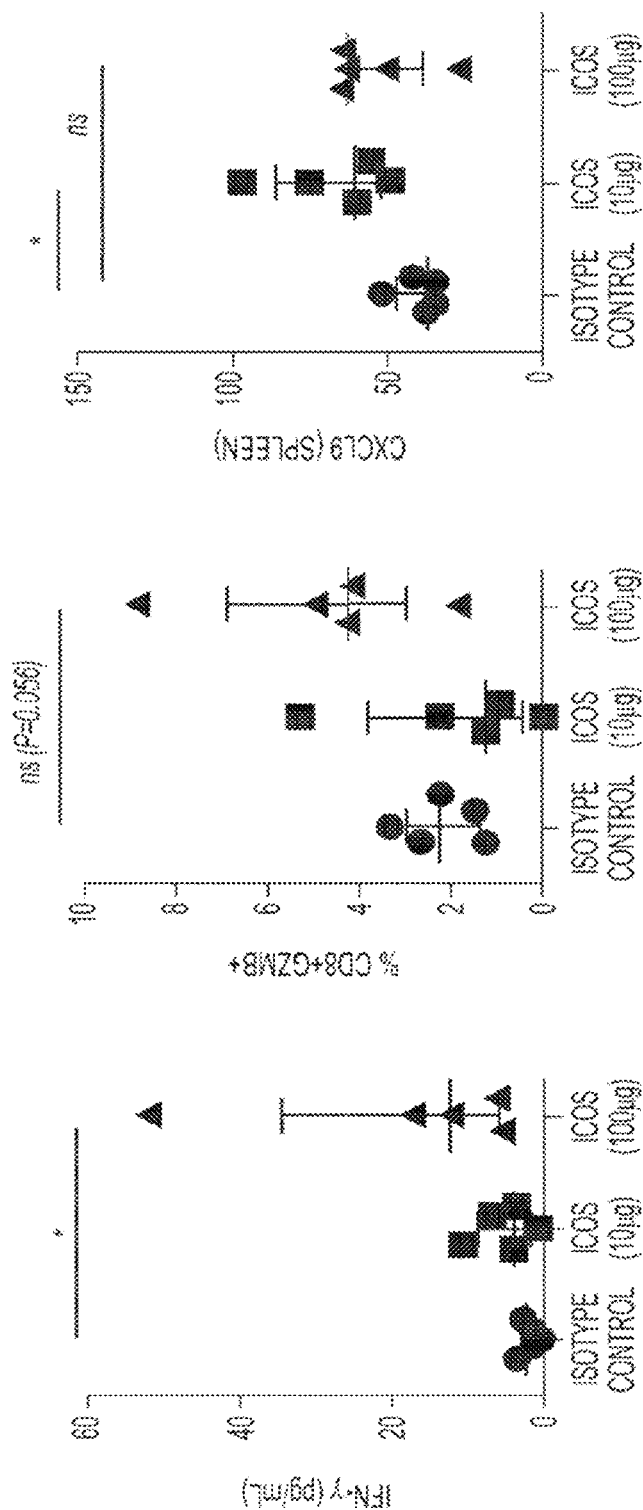
Figures 31A, 31B, 31C:
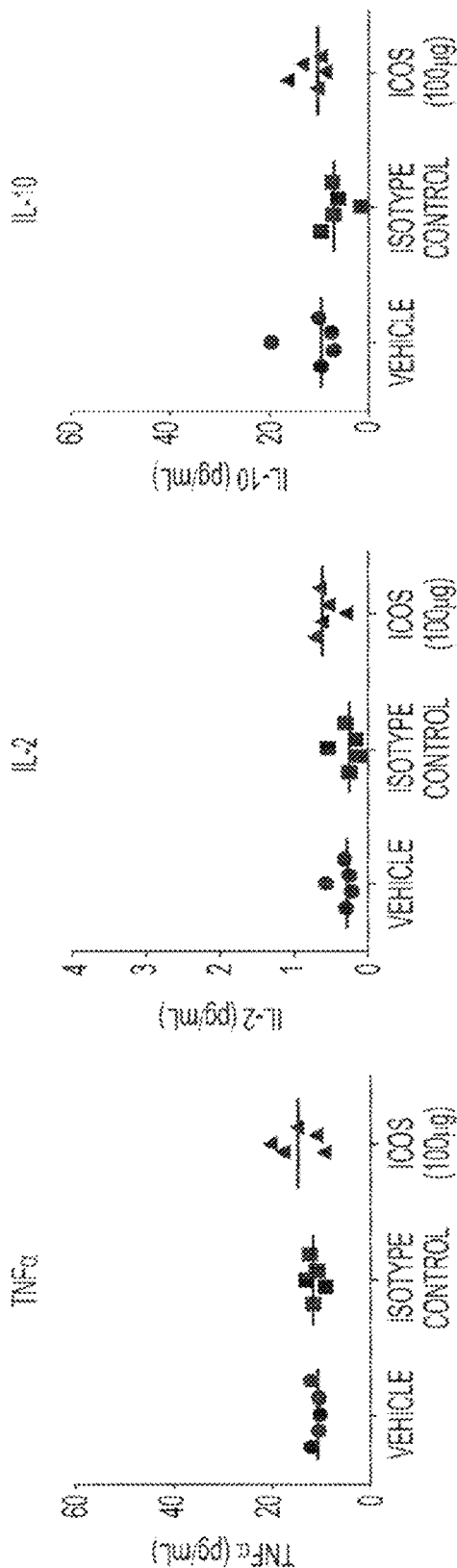

An ICOS Agonist Antibody Induces Clonal Expansion of Effector Memory T Cells and Redistribution to the Periphery Mice bearing EMT6 breast tumors were treated with the anti-murine ICOS mAb (7E.17G9 mIgG2b), an agent which demonstrated agonist potential (FIG. 30). In response to ICOS mAb treatment, significant changes were observed in the relative population of circulating memory T cells. The percentage of CD4+ and CD8+ naïve (FIG. 24A) and central memory ($T_{CM}$) (FIG. 24B) T cells decreased in relation to isotype control treated mice whereas a corresponding increase in $T_{EM}$ cells was observed (FIG. 24C). This was associated with significant changes in the number of unique circulating TCR clones and a corresponding increase in TCR clonality in the blood of ICOS mAb treated mice (FIG. 24D, E). Interestingly, the majority of clones which expanded in the mouse blood in response to ICOS mAb treatment were also found in tumors (FIG. 24F). The relative abundance of the major TCR clone in the blood of ICOS antibody treated mice increased 2.3 and 4.6 fold with 10 μg or 100 μg of ICOS antibody, respectively as compared to a 1.8 fold increase with the isotype control antibody (FIG. 38). These findings indicate that a small pool of tumor-reactive $T_{EM}$ clones expand in response to ICOS mAb treatment. Additionally, we observed a dose-dependent increase in IFN-γ in the blood of ICOS mAb treated mice (FIG. 24G) while no significant increases in IL-2, TNF-α or IL-10 were observed (FIG. 31A-C). Treatment also resulted in a dose-dependent increase in the percentage of Granzyme B positive CD8+ cells (FIG. 24I). In the spleens of ICOS mAb treated mice, we observed an increase in the IFN-γ inducible chemokine CXCL9 (FIG. 24H) which acts to recruit CD4+ effector and cytotoxic CD8+ T cell populations[15]. A corresponding increase in the proliferation of both CD4+ and CD8+ T cells was observed in the spleens of these mice (FIG. 24J-K).

These results indicate that treatment with an ICOS agonist mAb results in $T_{EM}$ cell activation, clonal expansion and migration from the blood to peripheral tissues including the spleen.

Figure 25B:
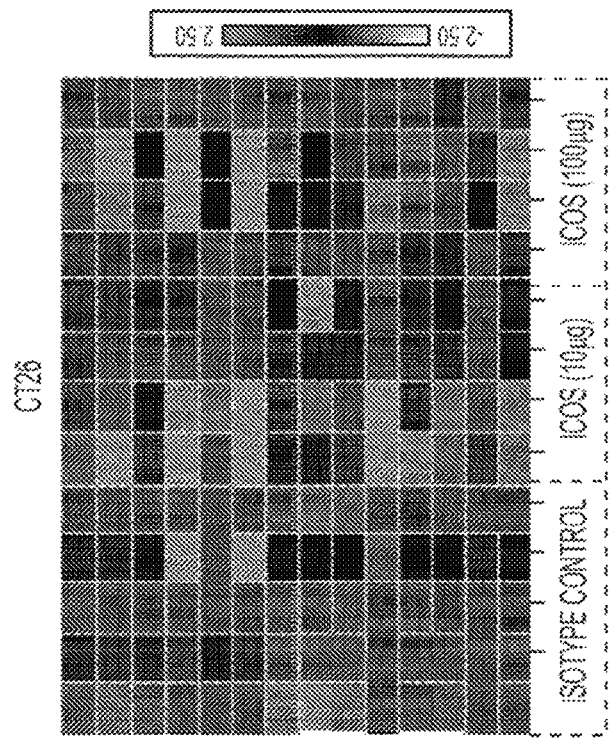
FIG. 25: ICOS agonist mAb increases T cell function, infiltration to tumors and antitumor response (a) Heatmap of RNA expression as measured by Nanostring for indicated immune genes from EMT6 tumors harvested 48 hours post 2$^{nd}$ dose of respective treatment. (b) Heatmap of RNA expression as measured by Nanostring for indicated immune genes from CT26 tumors harvested 48 hours post 2$^{nd}$ dose of respective treatment (a-b) In instances where <5 tumors are represented there was not sufficient tumor material and/or RNA quality available to perform Nanostring analysis. (c) quantification of RNA expression of the chemokine Cxcl9 (10 μg **P=0.0093 and 100 μg P=0.2170; F=5.159 df=10) and (d) Cxcl10 (10 μg*P=0.0183 and 100 μg P=0.1312; F=4.059 df=10) in EMT6 tumors following indicated treatments. (e) Ratio of CD8:Treg Signature as measured by RNA Nanostring analysis (100 μg*P=0.0243; F=3.697 df=10) (c-e) Each symbol represents an individual mouse tumor; in instances where <5 tumors are represented there was not sufficient tumor material and/or RNA quality available to perform Nanostring analysis. Horizontal lines represent median values, error bars represent interquartile range. All statistical tests were one-way ANOVA. (f) Productive TCR clonality (x-axis) (isotype vs. 10 μg*P=0.0145 and 100 μg*P=0.052; F=2.842 df=28 in relation to the T cell fraction (y-axis) in EMT6 tumors (isotype vs. 10 μg P=0.0076 and 100 μg **P=<0.0001; F=11.07 df=28) (g) mice with EMT6 murine breast carcinoma tumors treated with indicated doses of 7E.17G9 antibody twice weekly for 3 weeks. *(numbers) indicate the number of mice with minimally detectable or non-detectable tumors at study endpoint (h) Mice with CT26 tumors treated with 7E.17G9 antibody twice weekly for 3 weeks n=10 mice per group.
Figure 25A:
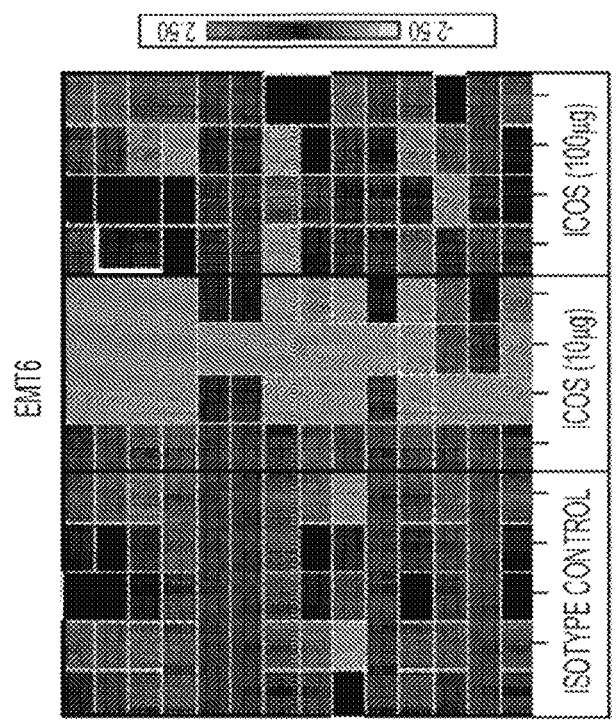
Figures 25C, 25D, 25E:
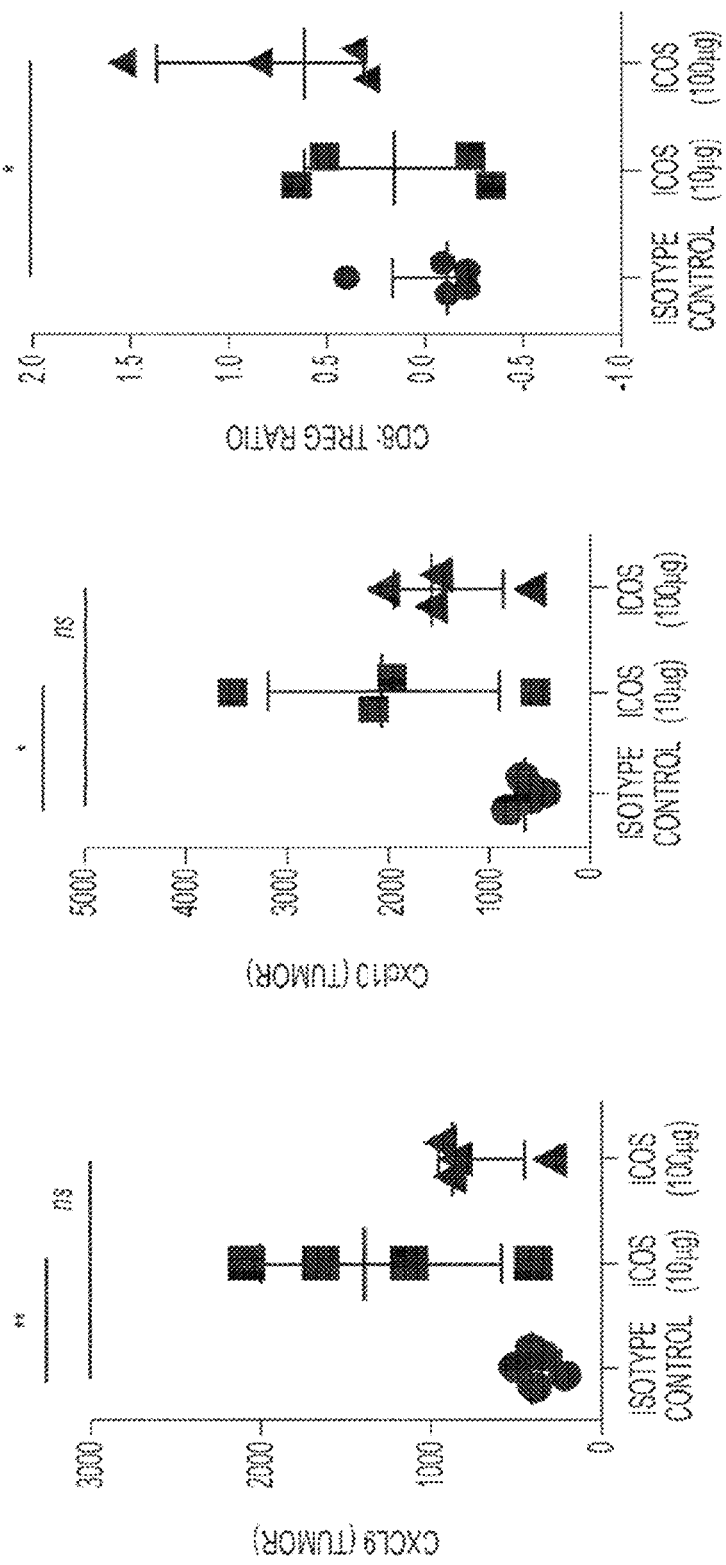
Figure 25F:
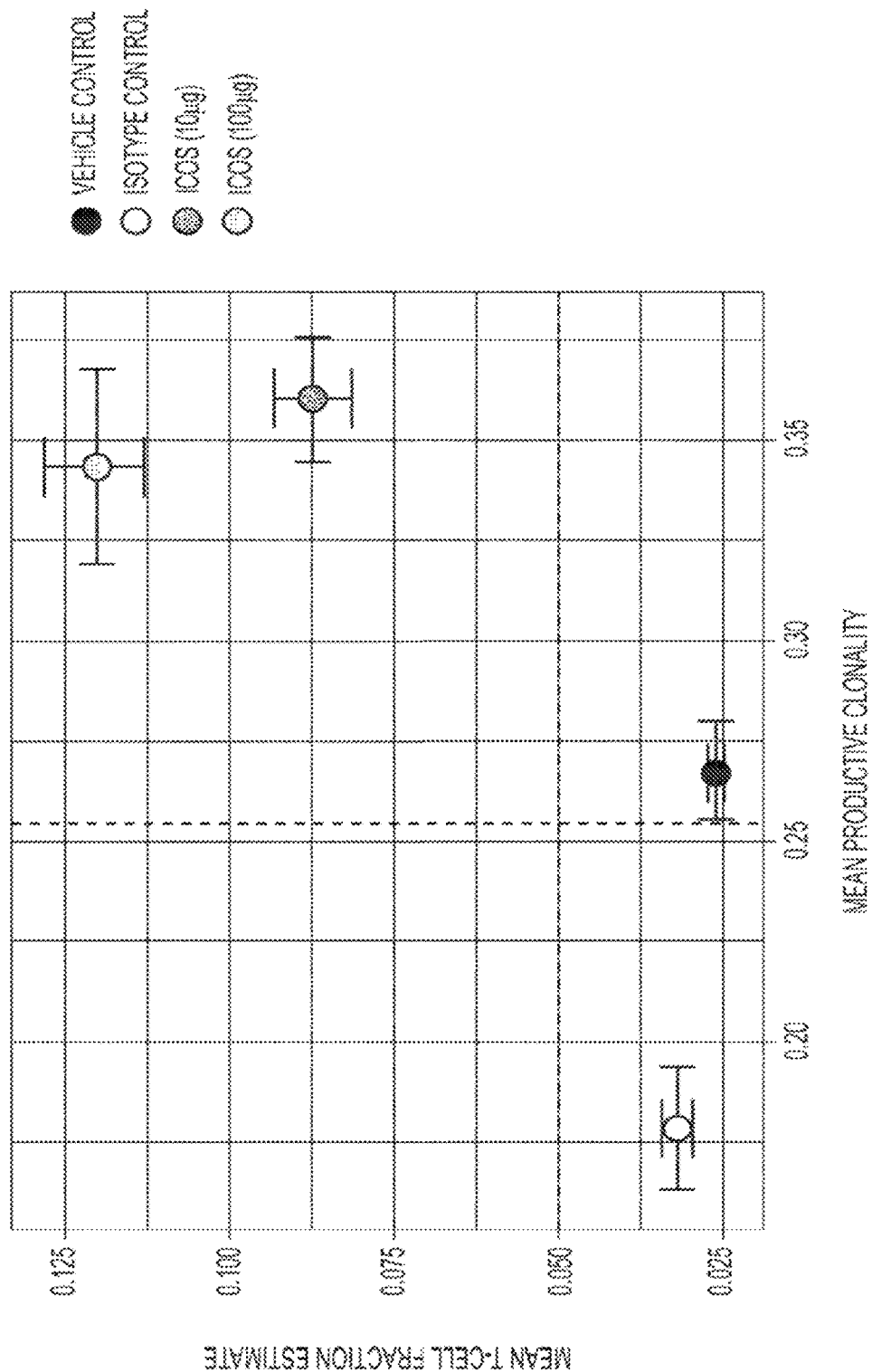
Figure 25G:
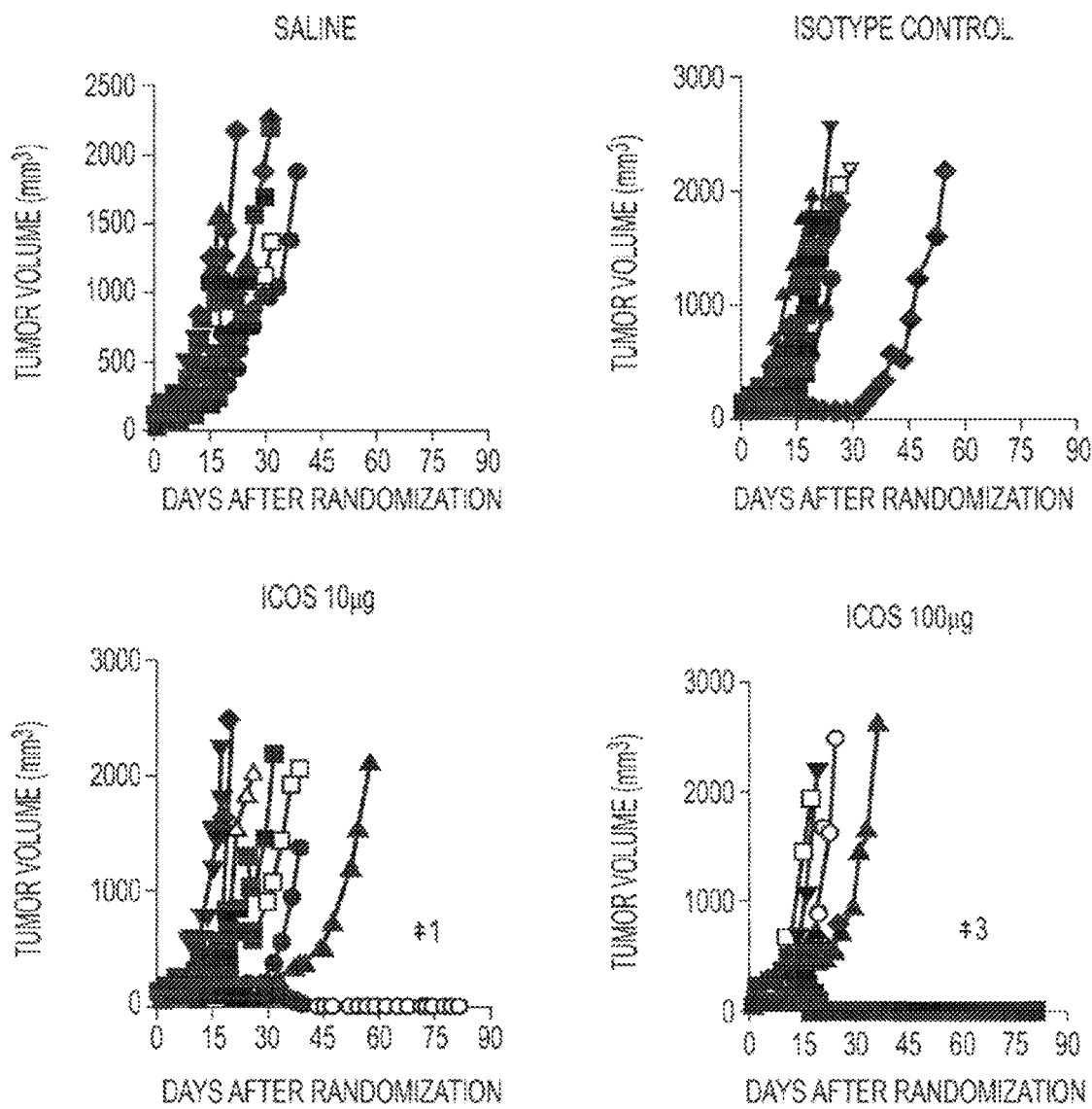
Figure 25H:
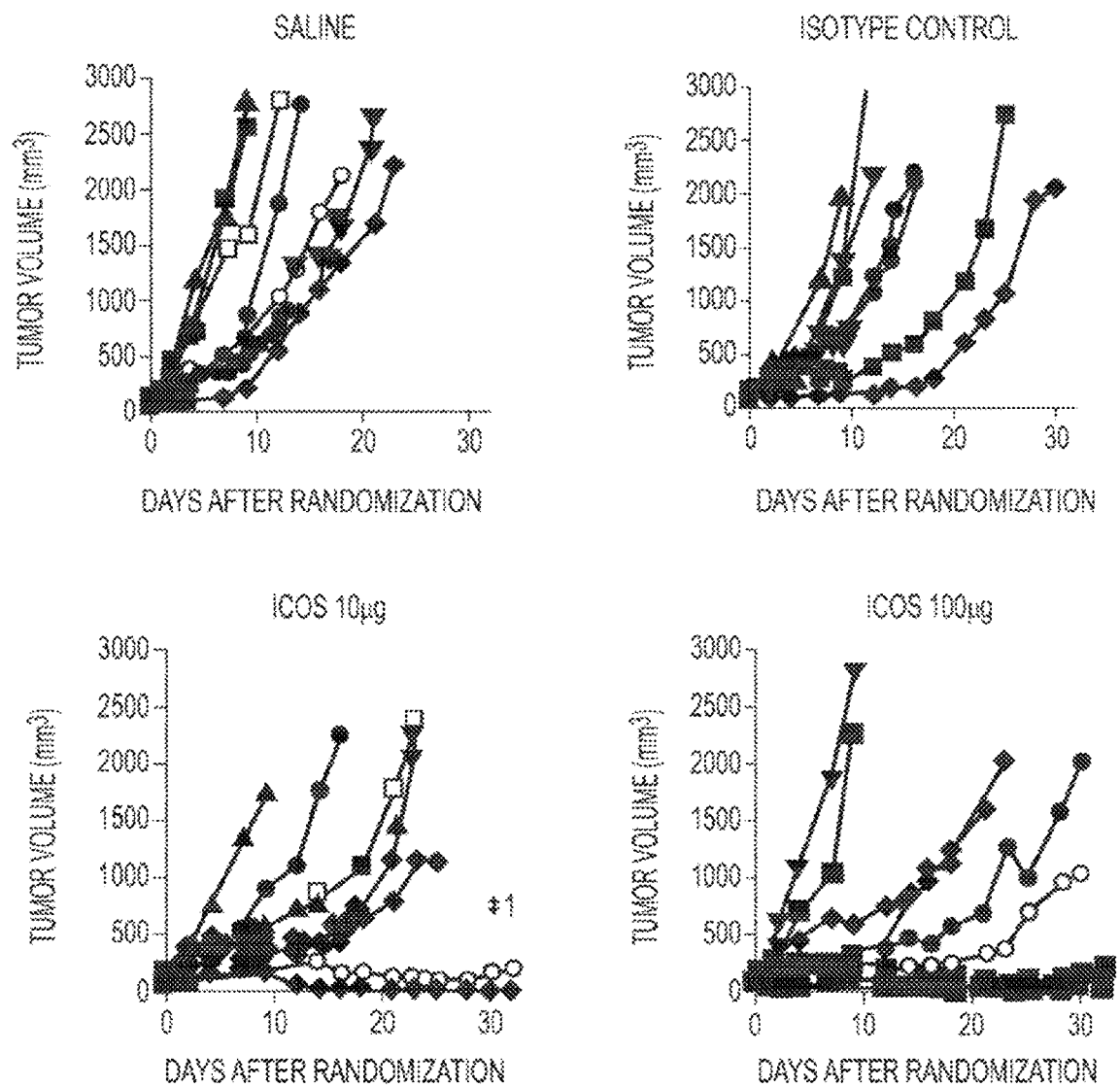

ICOS Agonist Treatment Induces Increased T Cell Homing, Tumor Infiltration and Antitumor Response We harvested EMT6 breast or CT26 colorectal carcinoma tumors in mice following three doses of ICOS antibody to determine whether ICOS agonist mAb treatment also led to increased T cell homing to the tumor microenvironment. The gene signature for CD3+, CD8+ and CD4+ T cells increased in both EMT6 and CT26 tumors, consistent with the expected pattern for increased tumor infiltrating lymphocytes (TIL) (FIG. 25A,B). Increased CD4+ and CD8+ T cell infiltration following ICOS antibody treatment was further confirmed in EMT6 tumors by flow cytometry (FIG. 32A-B). Additionally, expression of the cytotoxicity genes (Prf1, Gzma, Gzmb and Gzmk) as well as Ifng and Icos all were increased in the tumors of ICOS mAb treated mice as compared to isotype control treatment (FIG. 25A,B). Significant increases in the gene expression of inflammatory chemokine ligands Cxcl9 and Cxcl10 were also evident in treated tumors (FIG. 25C,D). Corresponding increases in the chemokine receptors Ccr5, Cxcr3 and Cxcr6, accompanied by a significant decrease in Cx3cr1 (FIG. 32C-F) were also observed. ICOS antibody treatment also resulted in an increased CD8/Treg gene signature ratio (FIG. 25E). TCR sequencing of EMT6 tumors confirmed a significant increase in the abundance of TILs (y-axis) as well as T cell clonality (x-axis) as compared to isotype control treatment (FIG. 25F). This mirrors the increased clonality observed in the blood of ICOS antibody treated mice and suggests that effector T cell clonal populations have expanded at the tumor site and/or increasingly homed to the tumor site. We also observed sustained tumor growth delay and complete antitumor responses in 10 and 30% of mice with EMT6 breast carcinoma tumors at 10 μg and 100 μg, respectively (FIG. 25G) and in 20 and 40% of mice with CT26 colorectal carcinoma tumors at 10 μg and 100 μg, respectively which is consistent with the significant immunomodulatory activity observed with ICOS mAb treatment (FIG. 25H).

ICOS Agonist Treatment Induces PD1I/PDL-1 in Tumors and Demonstrates Synergistic Activity in Combination with Anti-PD-1

Figure 26A:
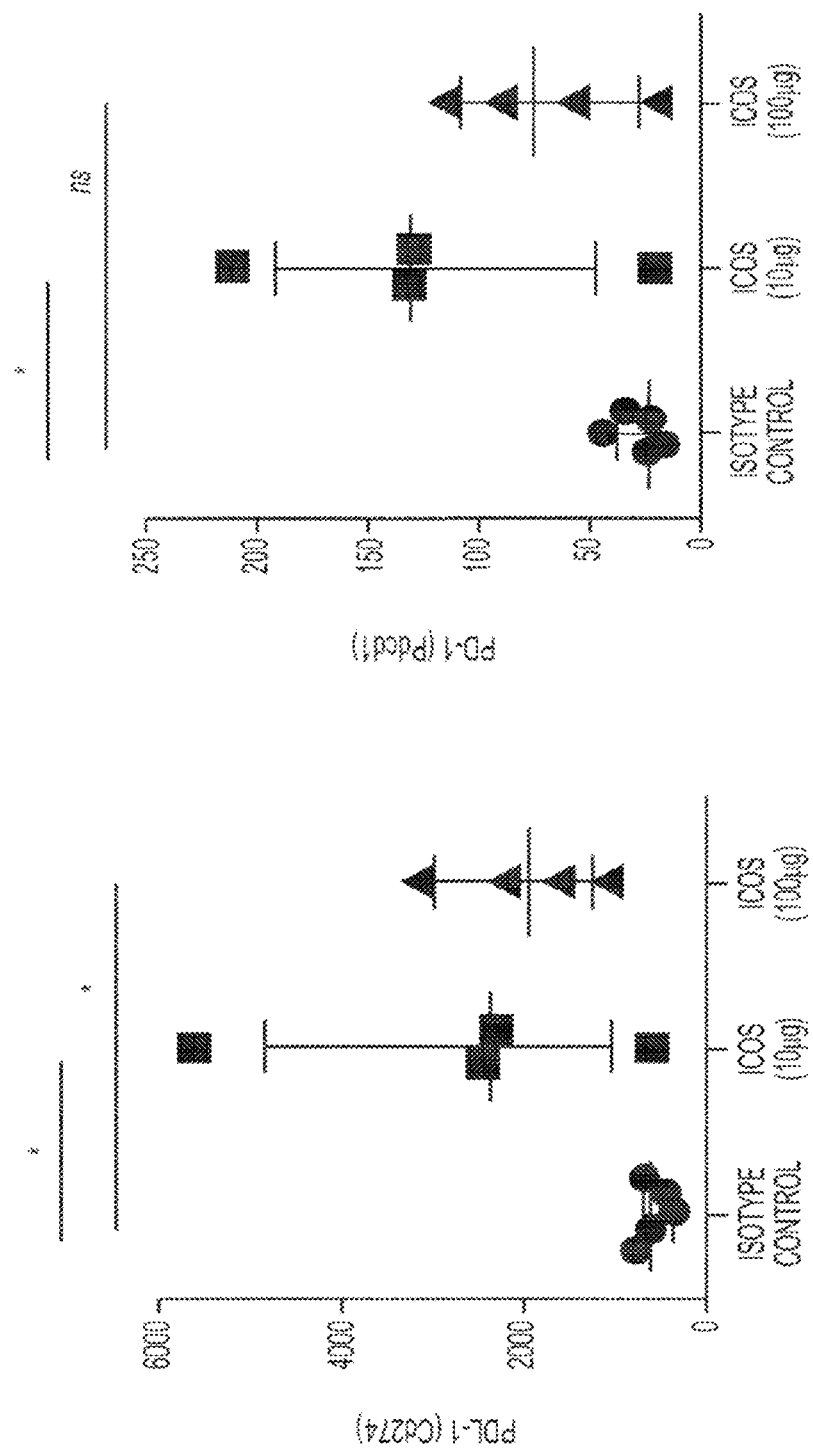
FIG. 26: ICOS agonist mAb induces PD1/PDL-1 expression and synergized with anti-PD1 (a) quantification of RNA expression of PDL-1 (cd274) (10 μg*P=0.0137 and 100 μg *P=0.0374; F=5.175 df=10) and PD1 (Pdcd1) (10 μg*P=0.0194 and 100 μg P=0.1626; F=3.911 df=10) in EMT6 and (b) CT26 tumors PDL-1 (cd274) (10 μg **P=0.0027 and 100 μg*P=0.0144; F=8.729 df=10) and PD1 (Pdcd1) (10 μg*P=0.0476 and 100 μg P=0.1126; F=2.885 df=10) following indicated treatments. (c) mice with EMT6 tumors treated with 7E.17G9 (10 μg), anti-PD1 (200 μg) or the combination of 7E.17G9 and anti-PD1 dosed concomitantly, twice weekly for 3 weeks (d) mice with CT26 tumors treated with 7E.17G9 (100 μg), anti-PD1 (200 μg) or the combination of 7E.17G9 and anti-PD1 dosed concomitantly, twice weekly for 3 weeks. N=10 mice per treatment group. Each line indicates an individual mouse and *(numbers) indicate the number of mice with minimally detectable or non-detectable tumors at study endpoint (e) quantification of the percentage of CD8$^+$GZMB$^+$ T cells from the blood of CT26 tumor bearing mice (ICOS 10 μg vs. PD1+ICOS 10 μg*P=0.0287 and ICOS 100 μg vs. PD1+ICOS 100 μg **P=0.0013 and PD1 vs. PD1+ICOS 100 μg*P=0408; F=4.255 df=24) (f) quantification of soluble IFN-γ levels (ICOS 10 μg vs. PD1+ICOS 10 μg ***P=0.0001, ICOS 100 μg vs. PD1+ICOS 100 μg*P=0.0133, PD1 vs. PD1+ICOS 10 μg **P=<0.0001 and PD1 vs. PD1+ICOS 100 μg P=0.0069; F=8.535 df=24) from the blood of mice with CT26 tumors (g) Heatmap of RNA expression as measured by Nanostring for indicated immune genes from CT26 tumors harvested 24 hours post third dose of respective treatment. In instances where <5 tumors are represented there was not sufficient tumor material and/or RNA quality available to perform Nanostring analysis. (a,b,e,f) Each symbol represents an individual mouse tumor; in instances where <5 tumors are represented there was not sufficient tumor material and/or RNA quality available to perform Nanostring analysis. Horizontal lines represent median values, error bars represent interquartile range. All statistical tests were one-way ANOVA with square root transformed data to stabilize variances.
Figure 26B:
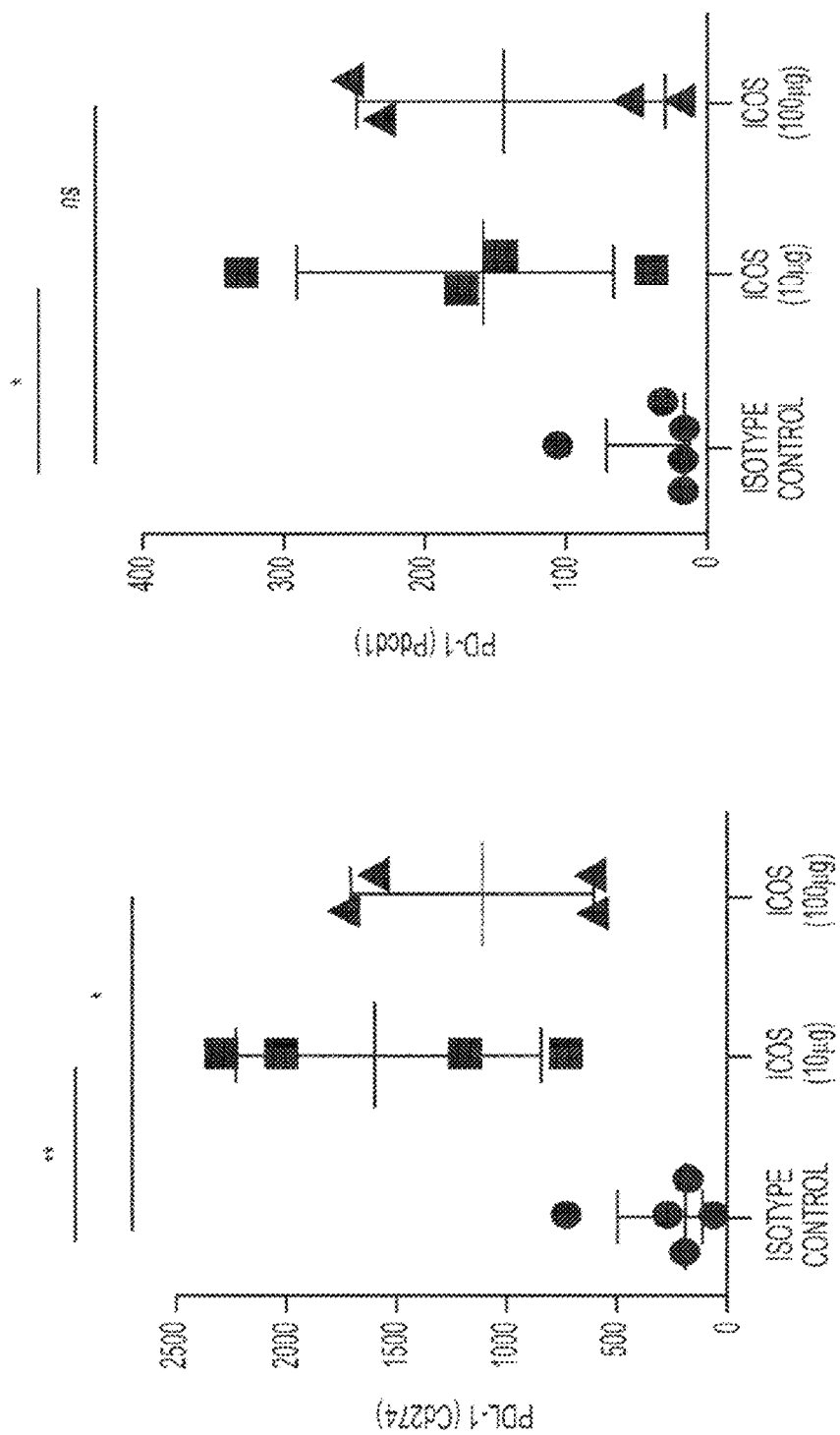
Figure 26C:
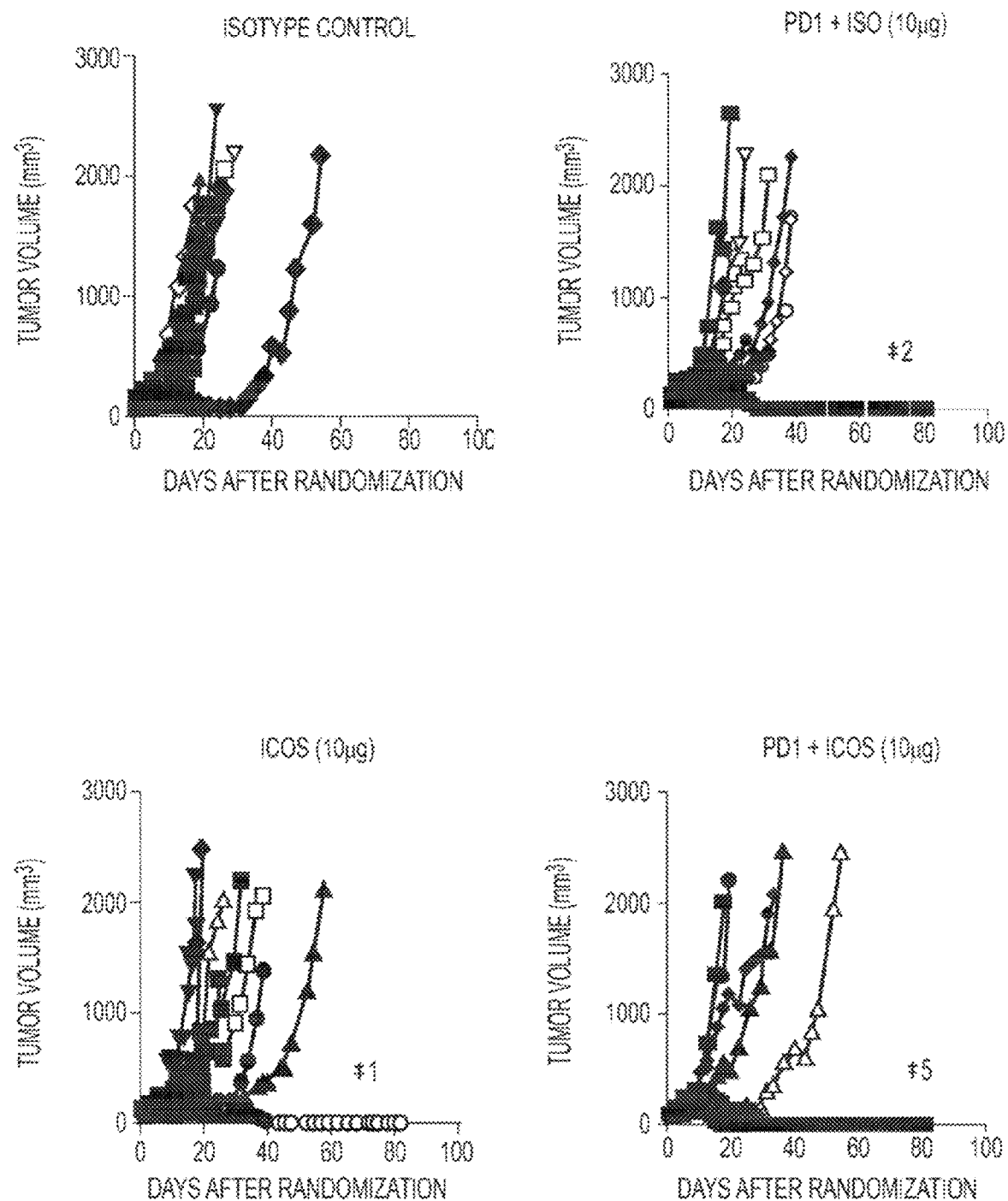
Figure 26D:
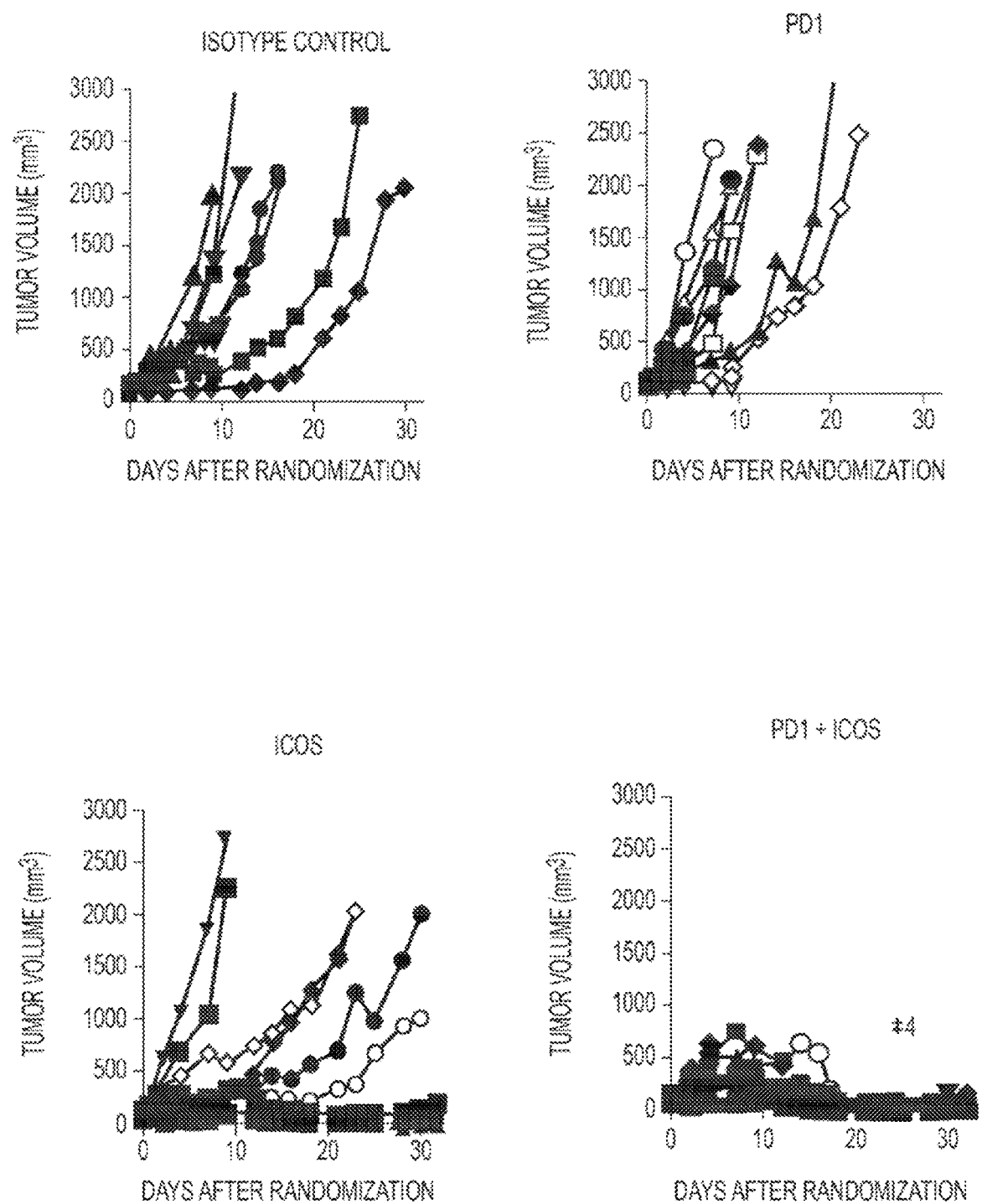
Figure 26F:
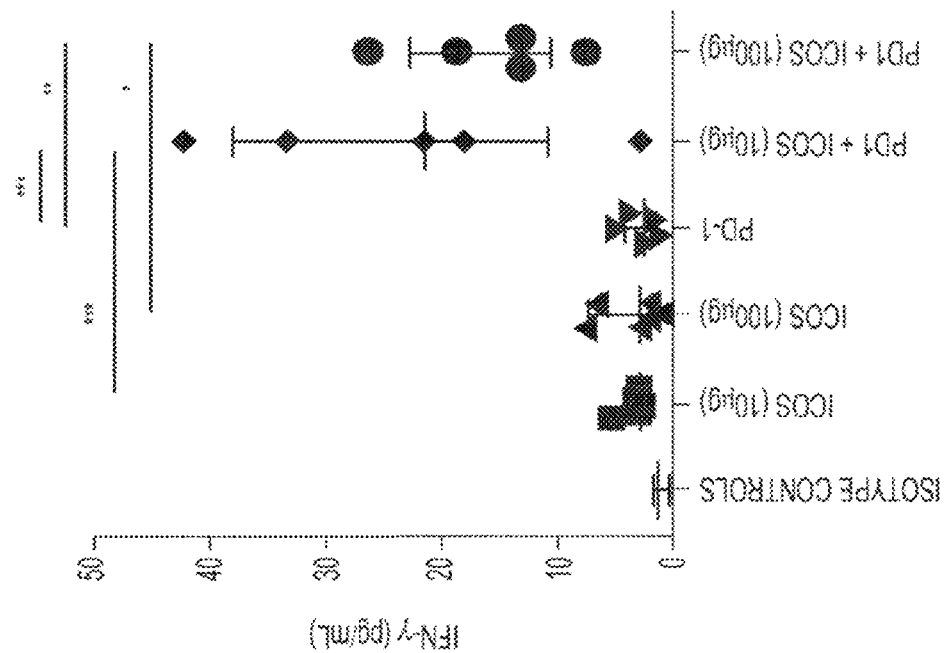
Figure 26E:
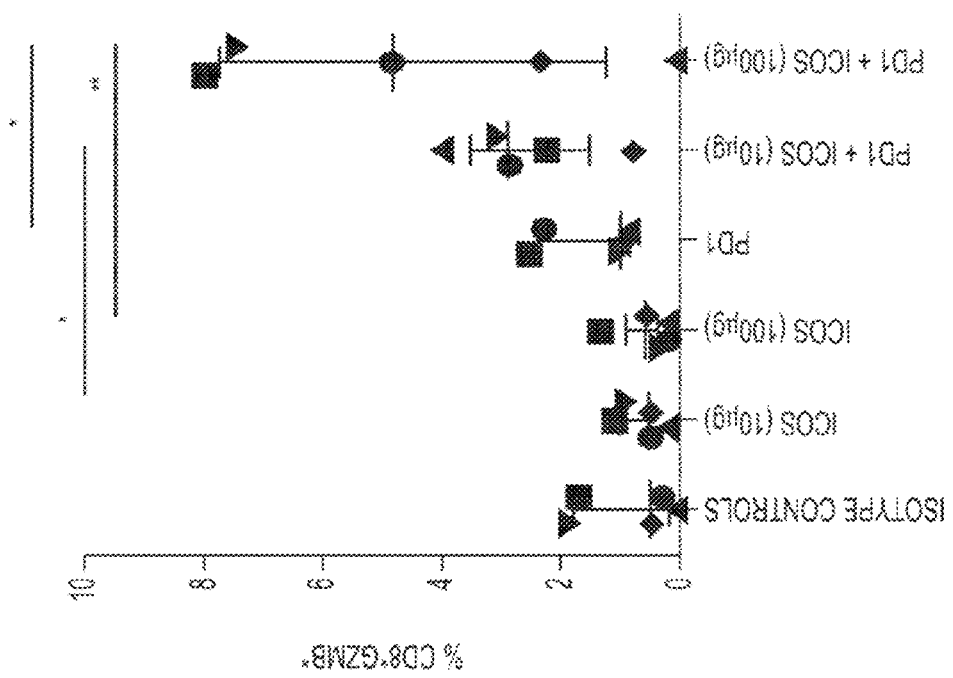
Figure 26G:
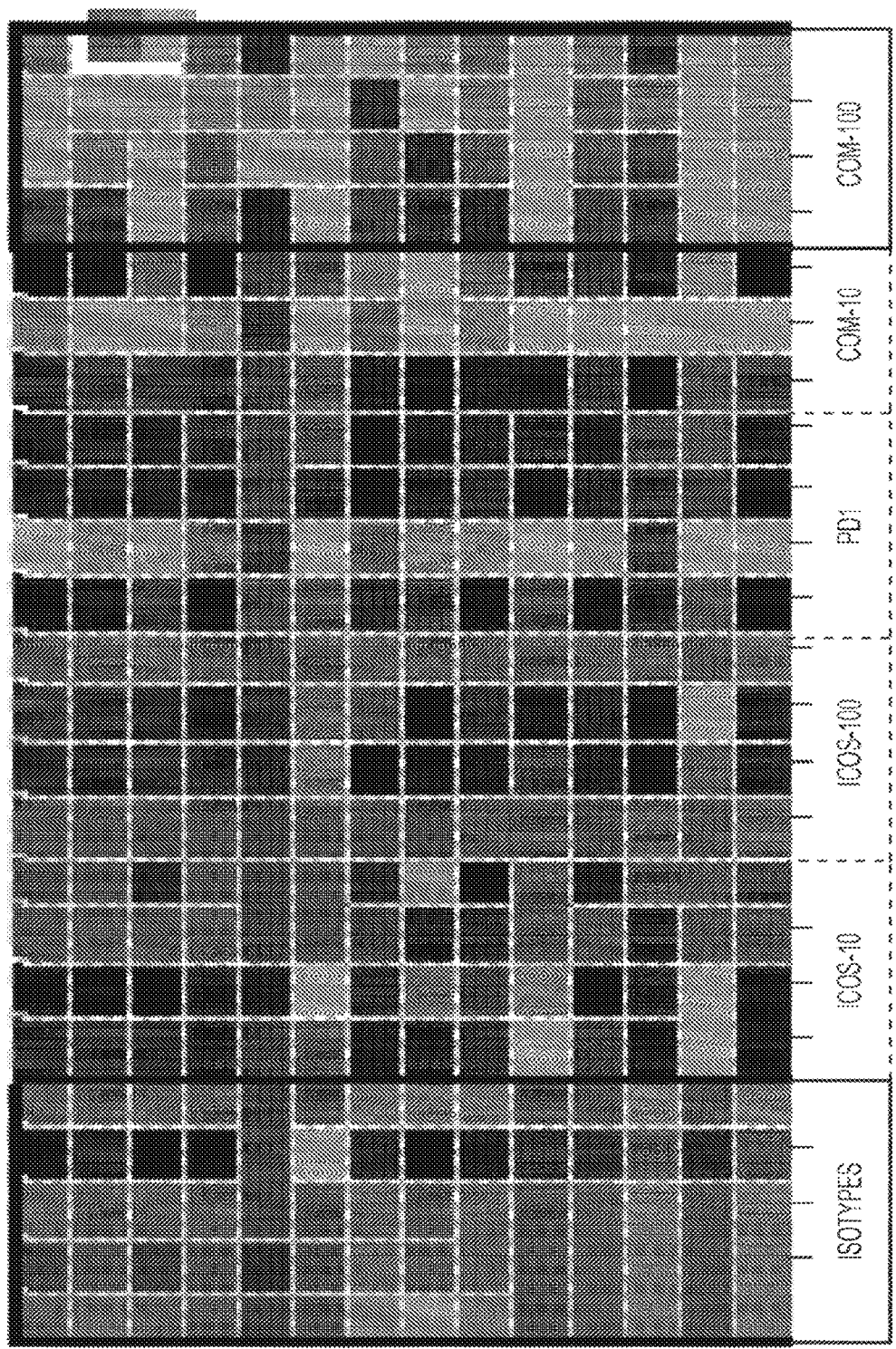

PD-L1, a known IFN-γ responsive gene, as well as PD-1 increased significantly in the tumors of ICOS mAb treated mice (FIG. 26A, B). Therefore, we tested whether combination with a PD-1 blocking antibody could augment the antitumor activity of the ICOS agonist mAb and overcome this potential resistance mechanism. The ICOS agonist mAb was dosed alone or in combination with anti-PD-1 antibody in both the EMT6 and the CT26 tumor models. In the EMT6 model the combination resulted in potent antitumor response and long-term survival in 50% of mice as compared with monotherapy treatment with ICOS or PD-1 antibodies alone which resulted in complete response in only 10% and 20% of mice, respectively (FIG. 26C). In the CT26 model, combination of the ICOS agonist and PD-1 blocking antibody resulted in complete or near complete tumor regression in 70% of mice, with the remaining 30% of mice having to come off study early due to tumor ulceration. The ICOS plus PD-1 combination activity was markedly better outcome than treatment with either ICOS or PD-1 antibody monotherapy in this model, with no complete responses observed in either monotherapy group (FIG. 26D). In the blood of mice with CT26 tumors treated with the combination of ICOS plus PD-1 antibodies there was an increased abundance of Granzyme B positive CD8+ T cells (FIG. 26E) as well as a significant increase in soluble IFN-γ as compared to either single agent (FIG. 26F). In CT26 tumors, the ICOS plus PD-1 antibody combination also showed a marked increase in the TIL gene signature (Cd3e, Cd3g, Cd3d, Cd8a, Cd4, Cd6, Icos) as well as cytotoxicity (Prf1, Gzma, Gzmb and Gzmk) as compared to either monotherapy treatment (FIG. 26G). These data indicate that the addition of an ICOS agonist antibody significantly improved the antitumor activity induced by a PD-1 antibody and moreover a PD-1 blockade is able to circumvent a possible resistance mechanism of ICOS agonist treatment, through inhibition of the ICOS-induced PD-L1/PD-1 expression in tumors.

Figure 27B:
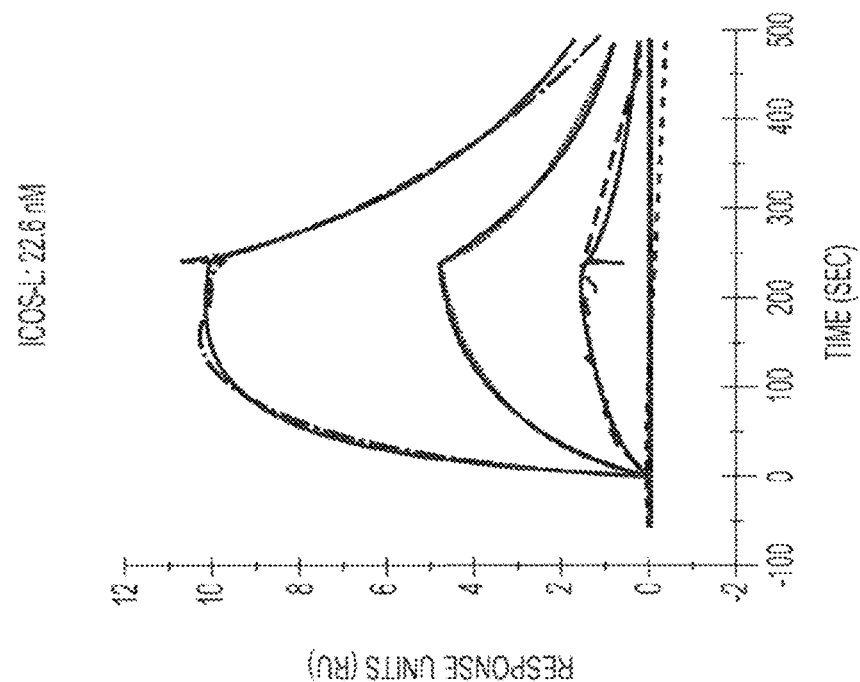
FIG. 27: Development of an anti-human ICOS agonist monoclonal antibody (a) H2L5 IgG4PE binding to dimeric human ICOS (b) human ICOS-L binding to dimeric human ICOS (c) Binding of H2L5 IgG4PE (20 ug/mL) to CD4$^+$ (P=0.0011, t=4.183, df=13) and CD8$^+$ (P=0.0078, t=3.686, df=7) T cells from healthy donor PMBC. Each symbol represents a separate human donor, horizontal lines indicate median, and bars are interquartile range (d) Representative Western Blot demonstrating induction of AKT signaling in Ba/F3-ICOS expressing cell line after treatment with H2L5 IgG4PE (e) Isolated CD4$^+$ T cells from healthy subjects treated with indicated concentrations of H2L5 IgG4PE for 60 hrs (bound isotype vs. bound H2L5 *P=0.0006, t=9.777 df=4, soluble isotype vs. soluble H2L5 *P=0.0003, t=11.50 df=4 and (#) bound H2L5 vs. soluble H2L5 P=0.0017, t=7.530 df=4) (f) PBMC from a healthy subject treated with soluble H2L5 IgG4PE (ICOS IgG4PE) or H2L5 Fc-disabled at (10 ug/mL) for 3.5 days (isotype control vs. H2L5 IgG4PE P=0.0056, t=5.426 df=4), (H2L5 IgG4PE vs. H2L5 Fc-disabled **P=0.0012, t=8.297 df=4) (g) Modified mixed-lymphocyte reaction (MLR) with anti-CD3 antibody followed by treatment with soluble H2L5 IgG4PE or H2L5 Fc-disabled antibody at (10 ug/mL) (isotype control vs. H2L5 IgG4PE *P=0.0166, t=3.966 df=4), (H2L5 IgG4PE vs. H2L5 Fc-disabled *P=0.0158, t=4.022 df=4) (h) Isolated T cells cultured with and without monocytes from the same donor followed by treatment with soluble H2L5 IgG4PE or H2L5 Fc-disabled at (10 ug/mL)+/−anti-CD32 or Fc-blocking antibody for 4 days. (#) *P=0.0009, t=8.734 df=4, ($) P=0.0031, t=6.405 df=4, (&) *P=0.0389, t=3.026 df=4, (@) isotype control vs. H2L5 IgG4PE **P=0.0027, t=6.612 df=4, H2L5 IgG4PE vs. H2L5 Fc-disabled *P=0.0239, t=3.544 df=4, H2L5 IgG4PE (control) vs. H2L5 IgG4PE (anti-CD32) P=0.0066, t=5.184 df=4, H2L5 IgG4PE (anti-CD32) vs. H2L5 IgG4PE (Fc block) P=0.0013, t=8.047 df=4 and H2L5 IgG4PE (control) vs. H2L5 IgG4PE (Fc block) *P=0.0446, t=2.889 df=4. (c, e-h) All statistical comparisons were using two tailed, unpaired t-test. (e-h) Bars represent mean and error bars represent standard deviation of triplicate measurements.
Figure 27A:
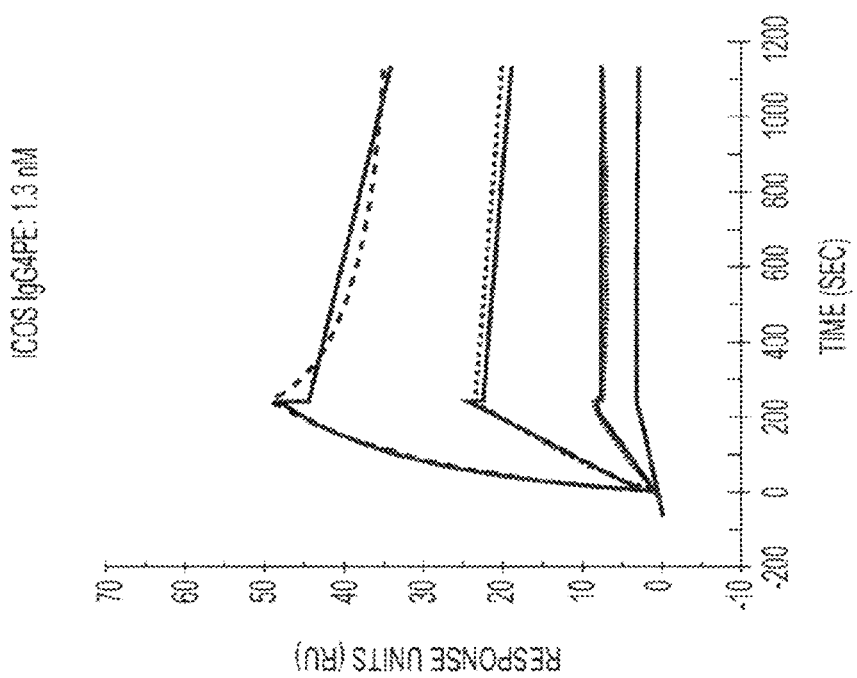
Figure 27C:
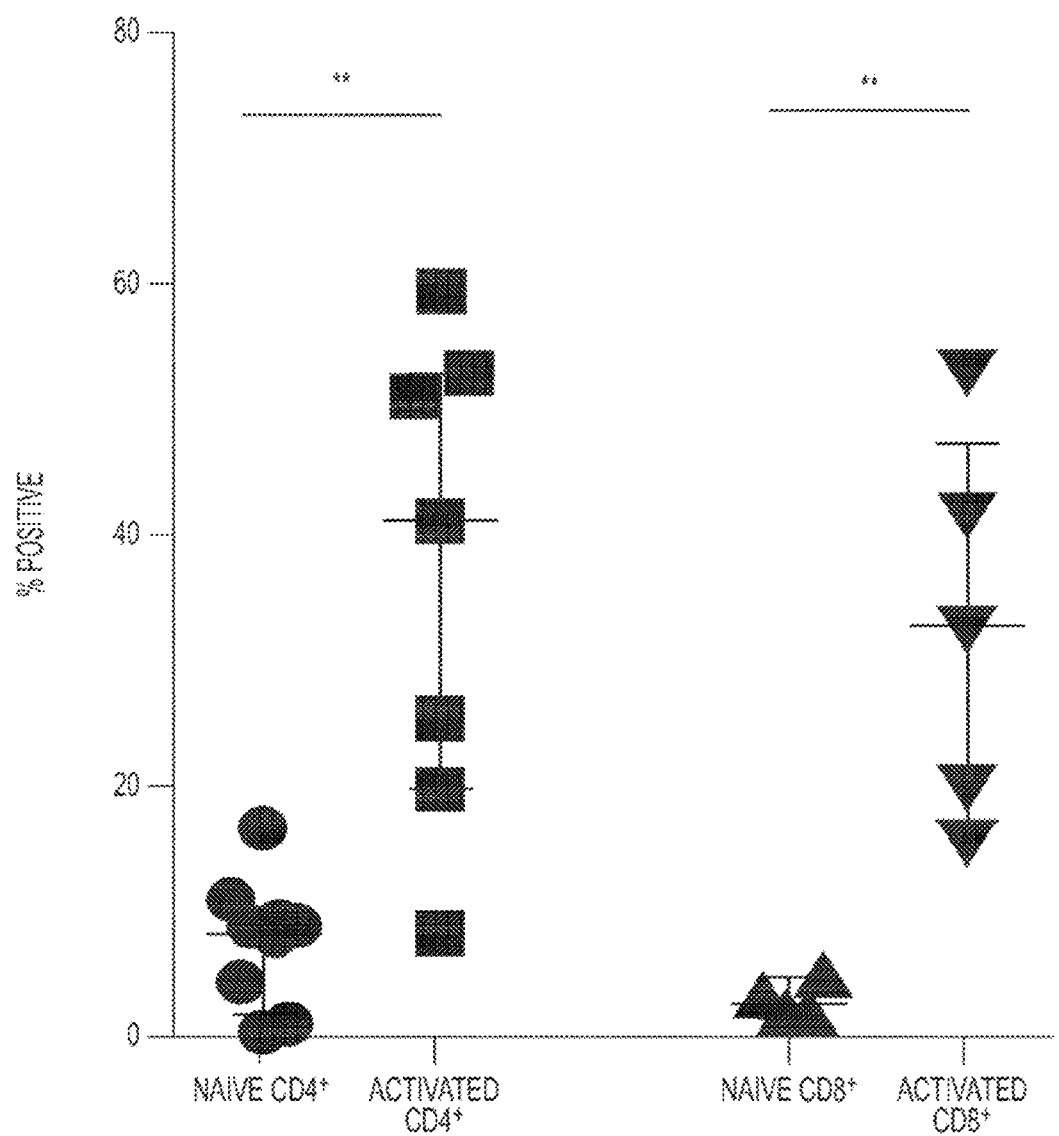
Figure 27D:
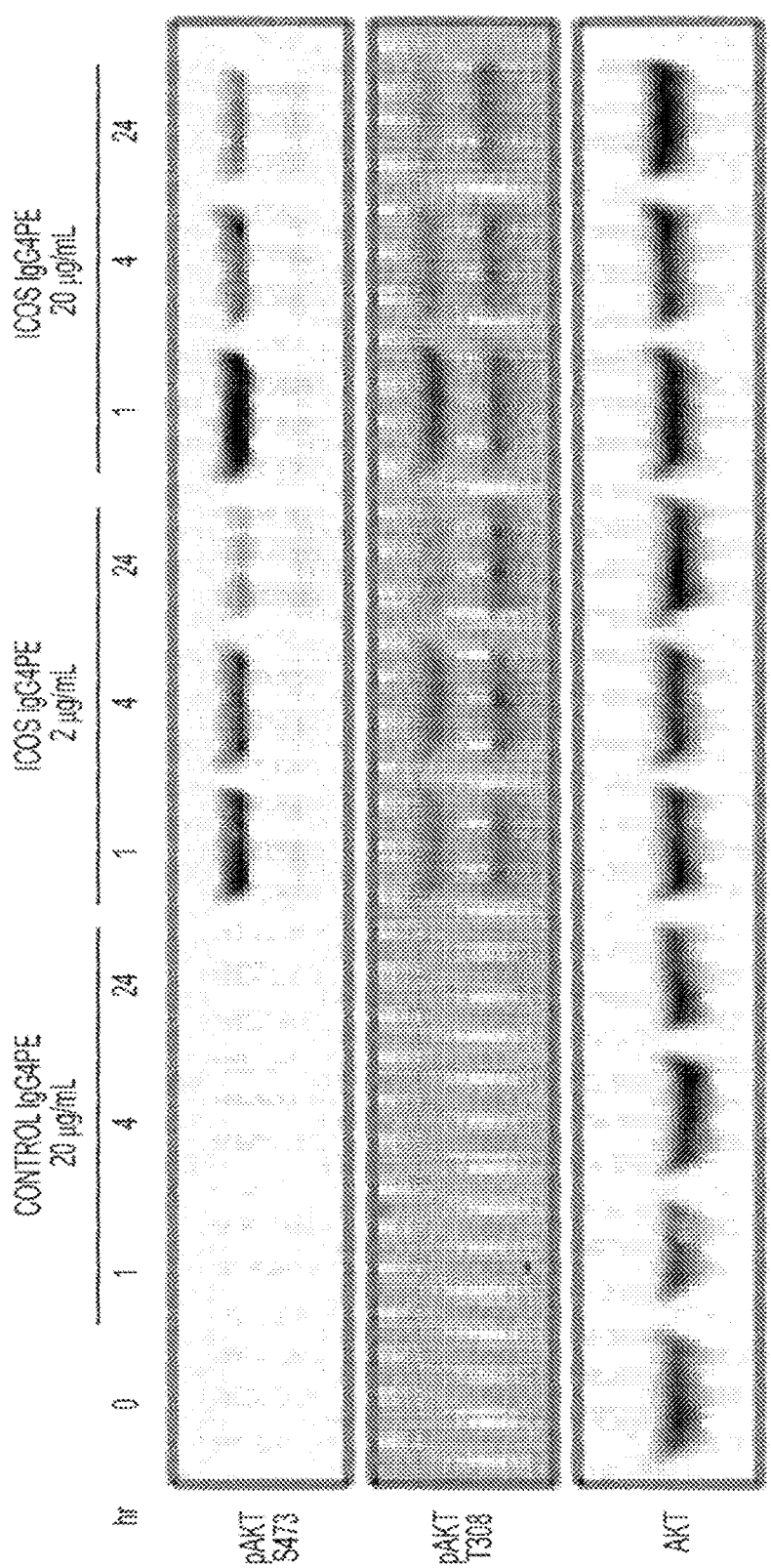
Figure 27G:
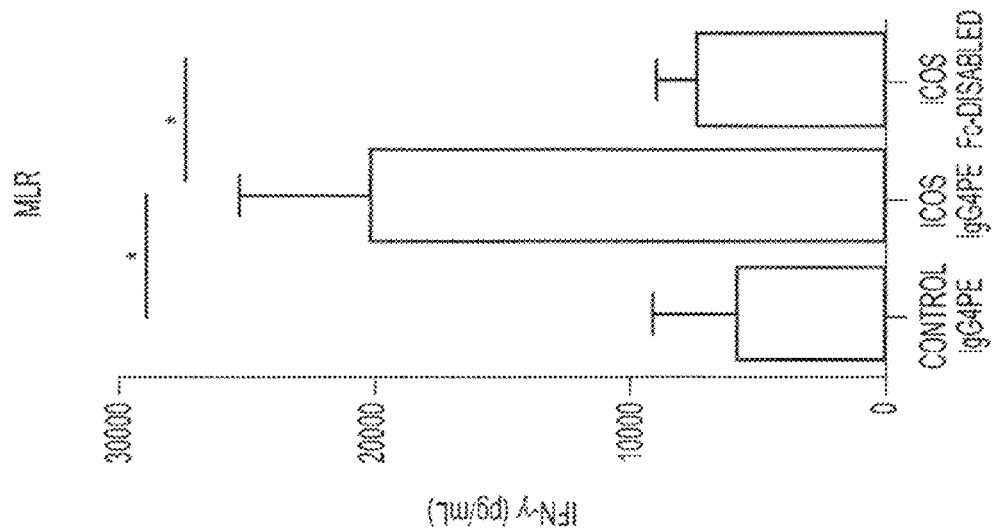
Figure 27F:
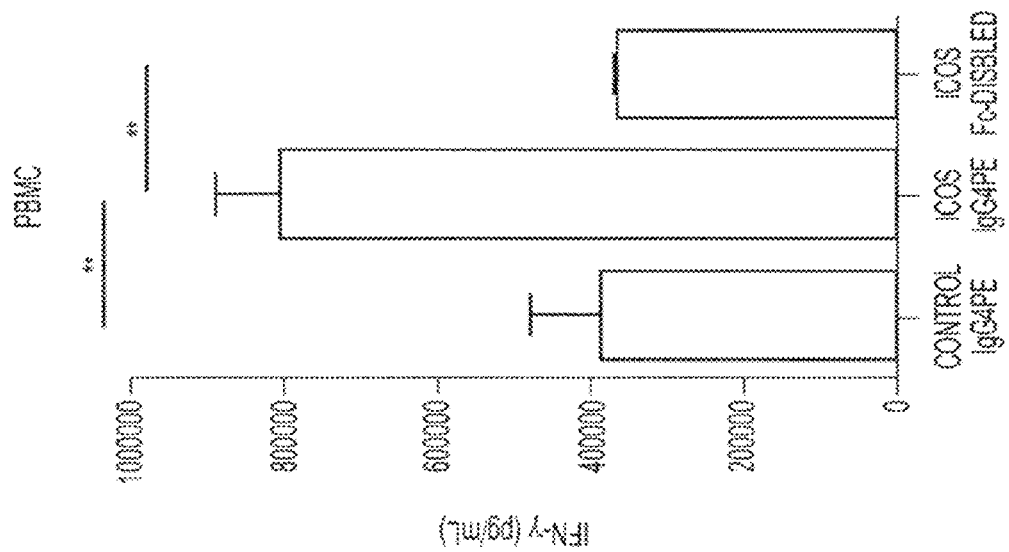
Figure 27H:
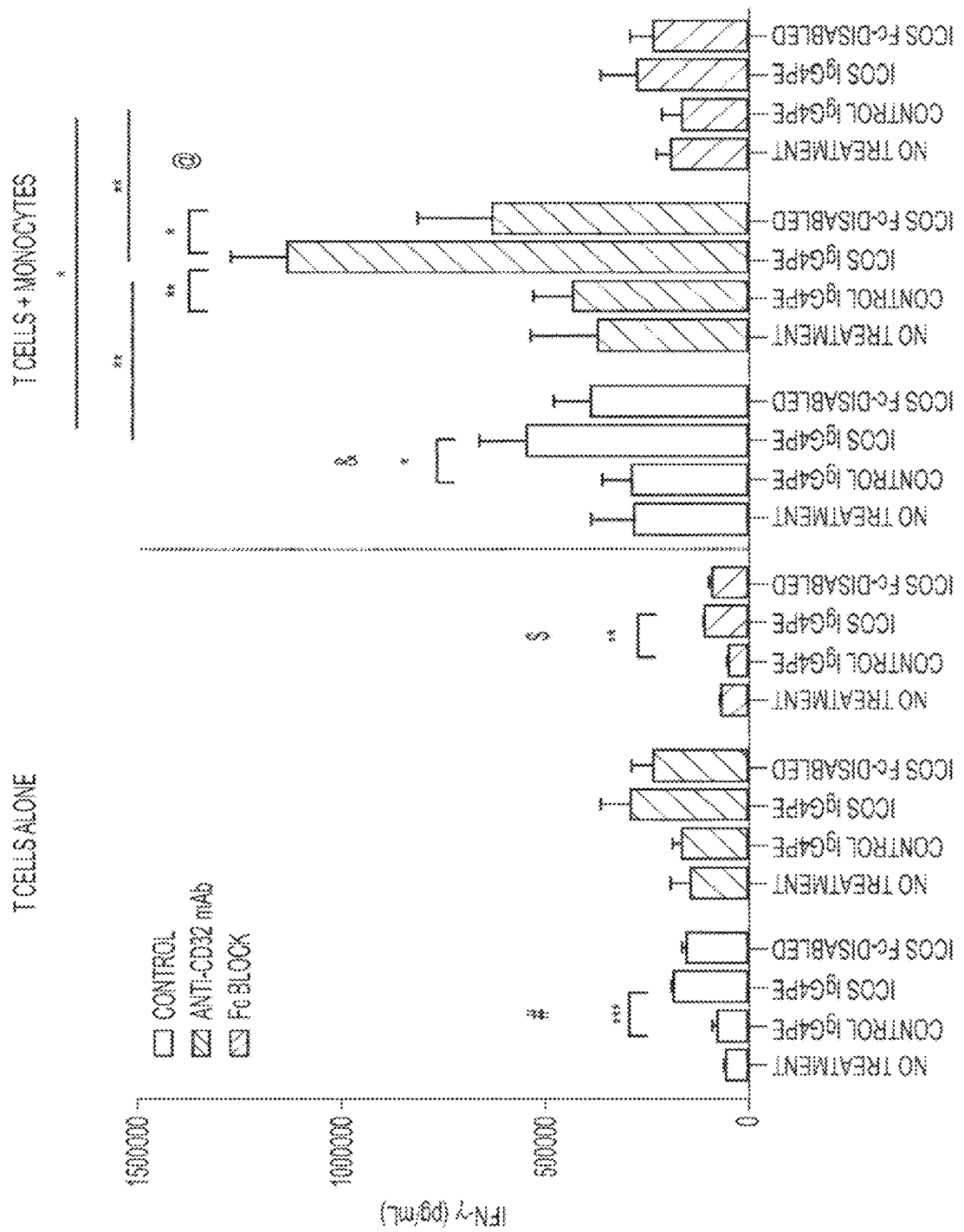
Figures 34A, 34B:
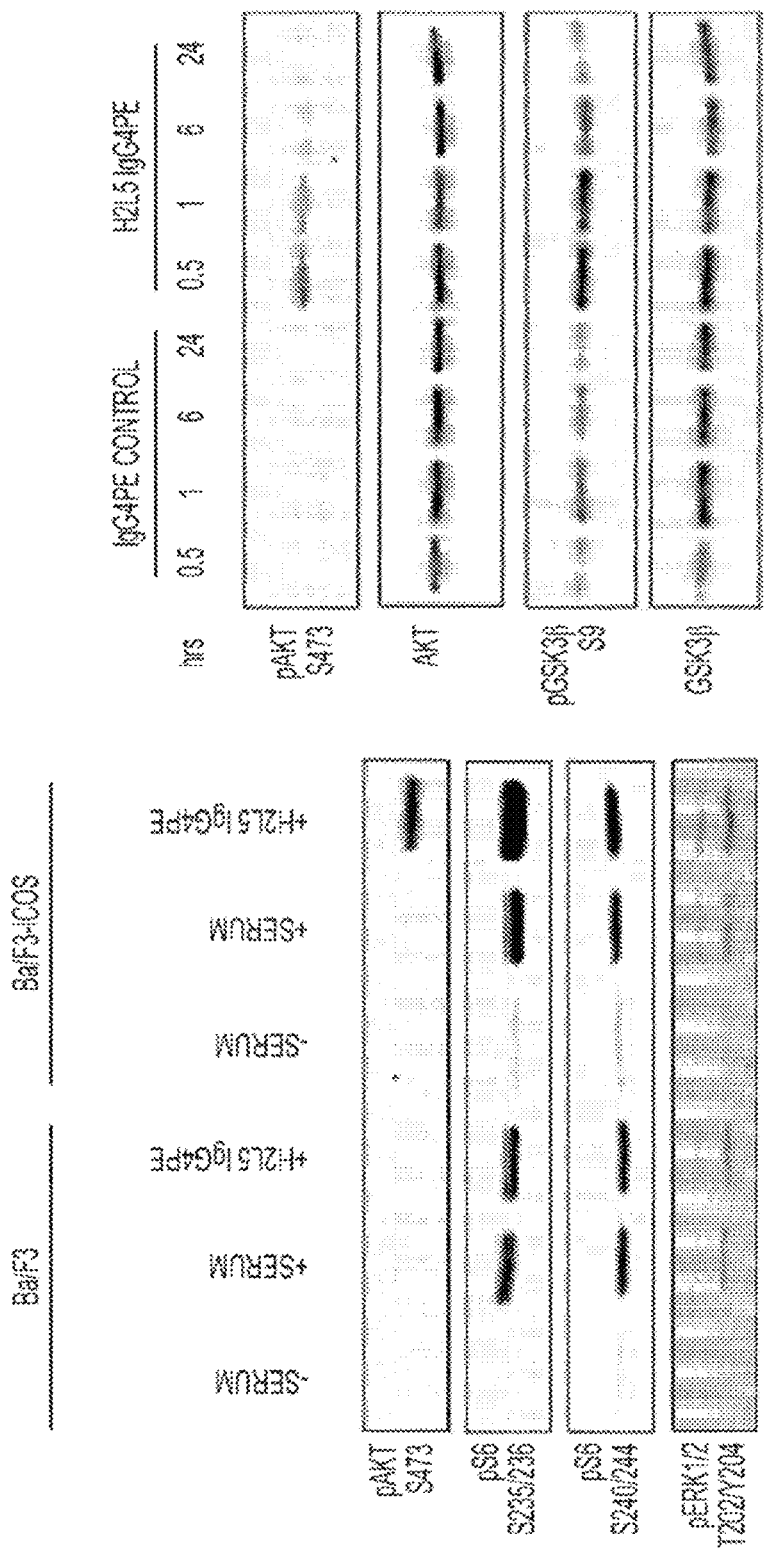
Figures 35A, 35B:
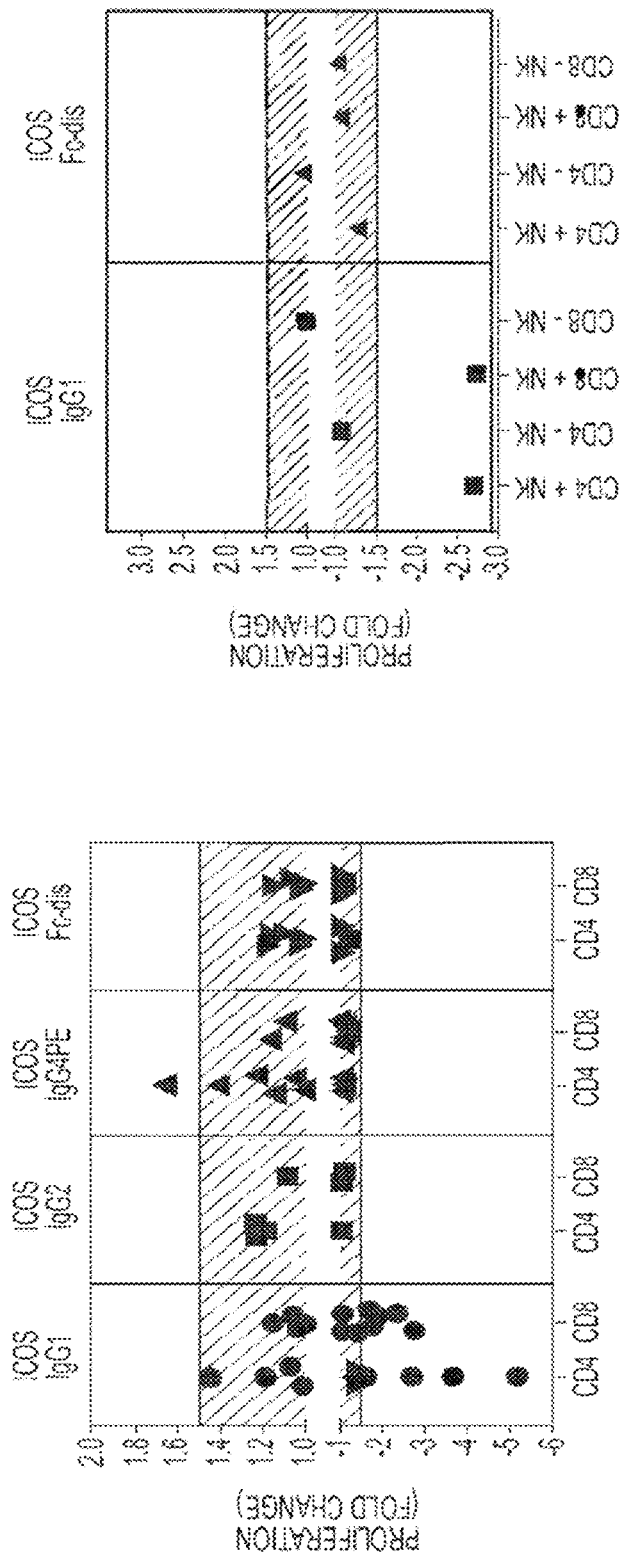
Figures 35C, 35D:
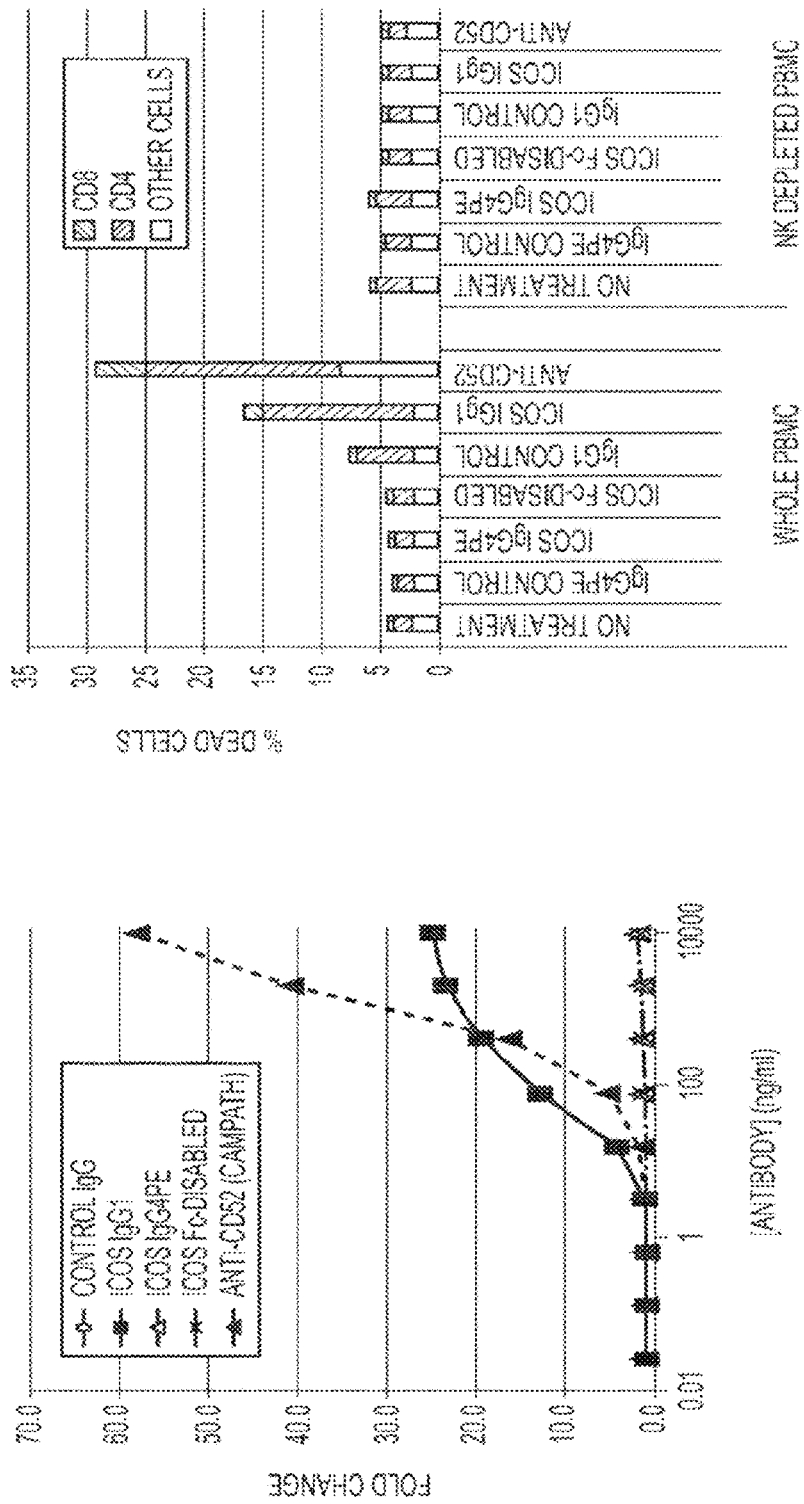

Development of a Potent and Selective Anti-Human ICOS Agonist Monoclonal Antibody To translate the findings of the ICOS agonist in mice to humans, we undertook the generation of an anti-human ICOS agonist monoclonal antibody. We developed H2L5, a humanized, IgG4PE antibody against human ICOS. H2L5 bound to human ICOS with an affinity of 1.34 nM (FIG. 27A), which is approximately 17-fold higher than the native ICOS-L/CD275 interaction (FIG. 27B). H2L5 was also found to bind with equivalent affinity to ICOS from cynomolgus macaques (0.95 nM) (FIG. 39). However, no binding was observed to murine ICOS. Importantly, H2L5 also had no detectable binding to either human CD28 or CTLA-4, the two nearest structurally related proteins[1]. This is in contrast to the native human ICOS-L which has been shown to bind to both CTLA-4 and CD28[16]. The cross-reactivity of the native ICOS-L reduces the therapeutic applicability of a recombinant version of this protein and underscores the need for a potent and ICOS-selective agonistic mAb. Endogenous human ICOS is expressed as a disulfide-linked homodimer, and as such, a human Fc-fusion version of the recombinant ICOS protein was used for binding studies to mimic the dimeric native state of the protein[17]. H2L5 was found to partially compete with ICOS-L for binding to ICOS (FIG. 33). Activated PMBC from healthy human donors showed significant binding of H2L5 to both CD4+ and CD8+ T cell populations (FIG. 27C). ICOS has previously been shown to activate AKT in response to ICOS-L binding in human T cells[18]. Using a stable mouse Ba/F3 cell line engineered to express high levels of human ICOS, H2L5 induced phosphorylation of AKT at S473 and T308 sites (FIG. 27D) as well as other proteins downstream of AKT, such as GSK3α and ribosomal protein S6 (FIG. 40). Signaling in this cell line was dependent upon ICOS expression as no AKT activation was observed in the parental Ba/F3 cell line upon treatment with H2L5 (FIG. 34A). Pre-activated primary human CD4+ T cells showed a similar increase in phospho-AKT in response to treatment with H2L5 (FIG. 34B). The requirement for FcγR-mediated crosslinking has been shown to be critical for the optimal function of agonist antibodies targeting other immune receptors[19]. We therefore tested whether FcγR-dependent crosslinking was also important for the agonist function of H2L5. H2L5 was first tested against isolated human CD4+ T cells in both a plate bound (immobilized antibody) format as well as in solution. H2L5 in the immobilized format induced significantly greater levels of IFN-γ as compared to the soluble antibody (FIG. 27E). H2L5 was next evaluated in an activated human PBMC assay, in which FcγR-expressing cells (monocytes, B cells, etc.) are present. As a control, the CDR binding domains of H2L5 were re-cloned onto an Fc-disabled isotype backbone which cannot efficiently engage FcγR[20] to evaluate the FcγR-dependency of H2L5 for effective T cell agonism. In the activated human PBMC assay, H2L5 IgG4PE resulted in a greater than 2-fold induction of IFN-γ whereas the Fc-disabled version of H2L5 had no cytokine induction activity as compared to isotype control (FIG. 27F). The IgG4PE and Fc-disabled versions of H2L5 were also tested in a modified mixed lymphocyte reaction (MLR). Similar to the PBMC results, the H2L5 IgG4PE mAb provided a greater than 2-fold induction of IFN-γ whereas the Fc-disabled H2L5 mAb had no activity as compared to isotype control (FIG. 27G). Next a CD4+ T cell/CD14+ monocyte donor-matched co-culture assay was utilized to determine whether FcγR-expressing monocytes increased the agonist potential of soluble H2L5. Similar to the MLR assay format, H2L5 only induced IFN-γ when tested as an IgG4PE isotype, as the Fc-disabled antibody showed no significant cytokine induction as compared to isotype control. The addition of monocytes resulted in a significant increase in H2L5 IgG4PE-induced cytokine production as compared to T cells alone. Interaction with CD32 has been shown to be critical for the agonistic activity of other immunomodulatory antibodies targeting TNF-α family receptors as well as CD28[21]. To determine whether CD32/FcRγII was important for the agonist activity of the H2L5 IgG4PE mAb, an anti-CD32 antibody was added to induce crosslinking of the CD32 protein on monocytes. The anti-CD32 mAb resulted in significant induction of cytokine production when added together with H2L5 IgG4PE. Conversely, the addition of an Fc-blocking antibody completely inhibited the H2L5-induced cytokine induction (FIG. 4H). These results show that FcγR-mediated crosslinking is critical to the optimal agonist potential of the anti-ICOS H2L5 IgG4PE antibody. As FcγR binding to be critical for the full agonist potential of the H2L5 mAb, we also tested whether an IgG1 isotype format would be suitable for therapeutic design as this isotype allows for maximal FcγR binding. The H2L5 CDRs were cloned as different human IgG isotypes (IgG1, IgG2, IgG4PE, IgG Fc-disabled) and subsequently tested in functional assays using healthy donor PMBC. The H2L5 IgG1 antibody demonstrated decreased T cell proliferation in greater than 50% of donors tested. In contrast, use of IgG2, IgG4PE or Fc-disabled isotype variants of H2L5 did not result in substantial inhibition of either CD4+ or CD8+ T cell proliferation in any donors tested (FIG. 35a). The inhibitory effect of H2L5 IgG1 was further demonstrated to be due to antibody-dependent cellular cytotoxicity (ADCC) and dependent upon NK cells in the PMBC mixture (FIG. 35B-D). These results indicate that IgG4PE is the optimal antibody isotype for achieving ICOS agonist function in human cells.

Figure 28A:
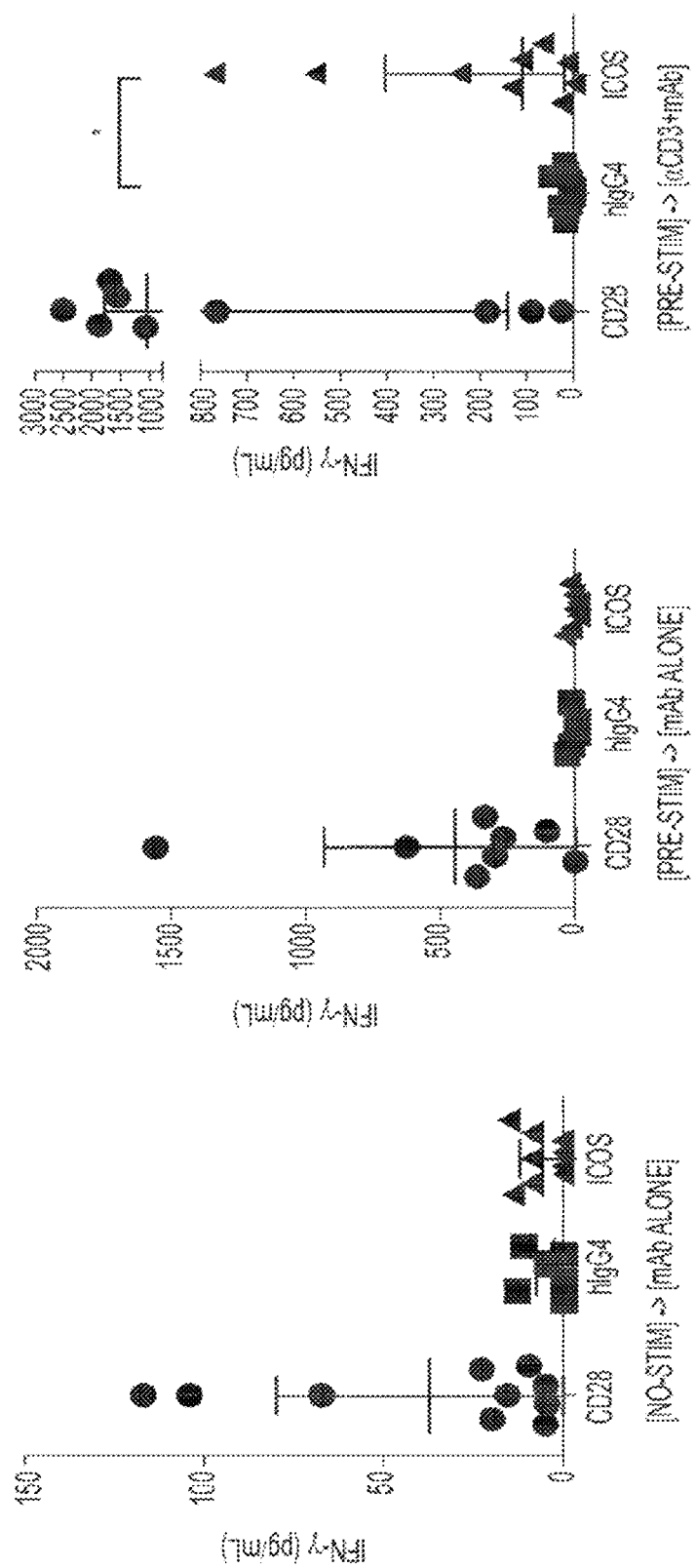
FIG. 28: H2L5 induces potent effector T cell activation and function in a TCR-dependent manner (a) [no-stim] [mAb alone] PMBC from healthy subjects treated with either anti-CD28, IgG4PE isotype control or H2L5 IgG4PE (ICOS) alone in bound format at (10 μg/mL) for 24 hrs [pre-stim] [mAb alone] PMBC prestimulated with anti-CD3 antibody followed by treatment with soluble anti-CD28, IgG4PE isotype control or H2L5 IgG4PE (ICOS) alone in bound format at (10 μg/mL) for 24 hrs [prestim] [aCD3+mAb] PMBC prestimulated with anti-CD3 antibody followed by treatment with anti-CD28, IgG4PE isotype control or H2L5 IgG4PE (ICOS) in bound format at (10 μg/mL) for 24 hrs (*P=0.0103, t=3.333 df=8) (b) quantification of soluble IFN-γ from the culture supernatant of PBMC from healthy subjects treated with (12.5 ug/mL) of bound H2L5 IgG4PE and anti-CD3 for 24 **P=0.0041, t=4.510 df=6 or 48 hrs *P=0.0375, t=2.661 df=6 (c) quantification of CD69$^+$ CD4$^+$ (*P=0.0142, t=3.416 df=6) or CD8+(**P=0.0012, t=5.734 df=6) cells in PMBC from healthy subjects treated with (12.5 ug/mL) of bound H2L5 IgG4PE and anti-CD3 for 48 hrs (d) quantification of Ki67$^+$ CD4+(*P=0.0190, t=3.809 df=4) or CD8$^+$ (*P=0.0255, t=3.474 df=4) cells healthy donor PMBC treated with (12.5 ug/mL) of bound H2L5 IgG4PE and anti-CD3 (e) quantification of RNA expression of T-Bet (TBX21) (*P=0.0156, t=2.974 df=9) and (f) Granzyme B (GZMB) (P=0.0020, t=4.292 df=9) from healthy donor CD3+ T cells following indicated treatments. (g) Quantification of IFN-γ, TNFα, IL-2 and IL-6 from the supernatant of NSCLC cancer patient PBMC treated with (10 ug/mL) of bound H2L5 IgG4PE and anti-CD3 for 72 hrs. (h) Quantification of IFN-γ from disseminated NSCLC patient tumors treated with anti-CD3 and H2L5 IgG4PE (10 μg/mL) for 24 hrs. (#) P=0.0100 ($) **P=<0.0001 (&) *P=0.002, F=15.8, df=20 (a-h) Each symbol represents an individual donor sample, horizontal lines represent median values, error bars represent interquartile range. All statistical tests were two-tailed, unpaired t-tests.
Figure 28B:
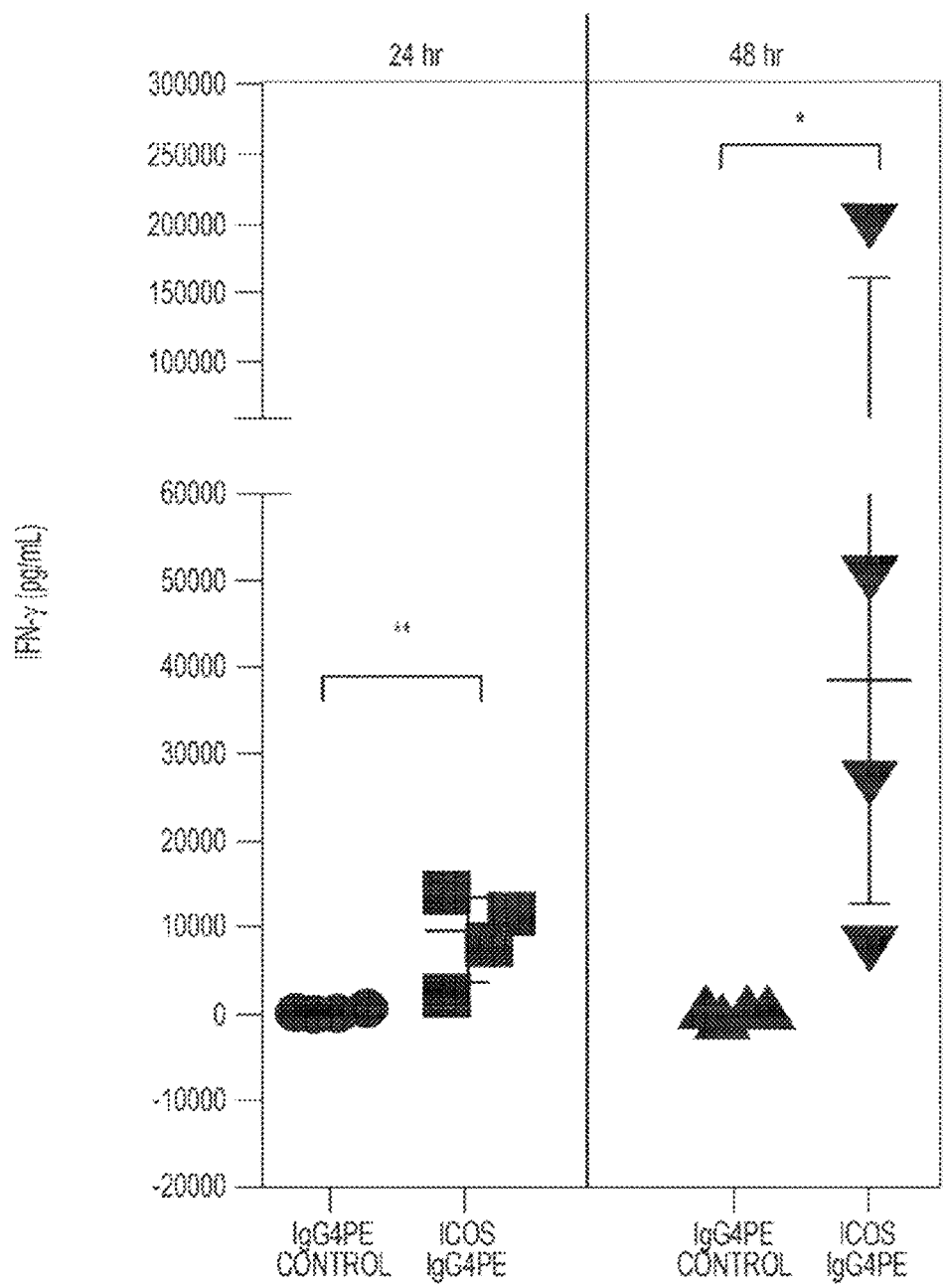
Figure 28D:
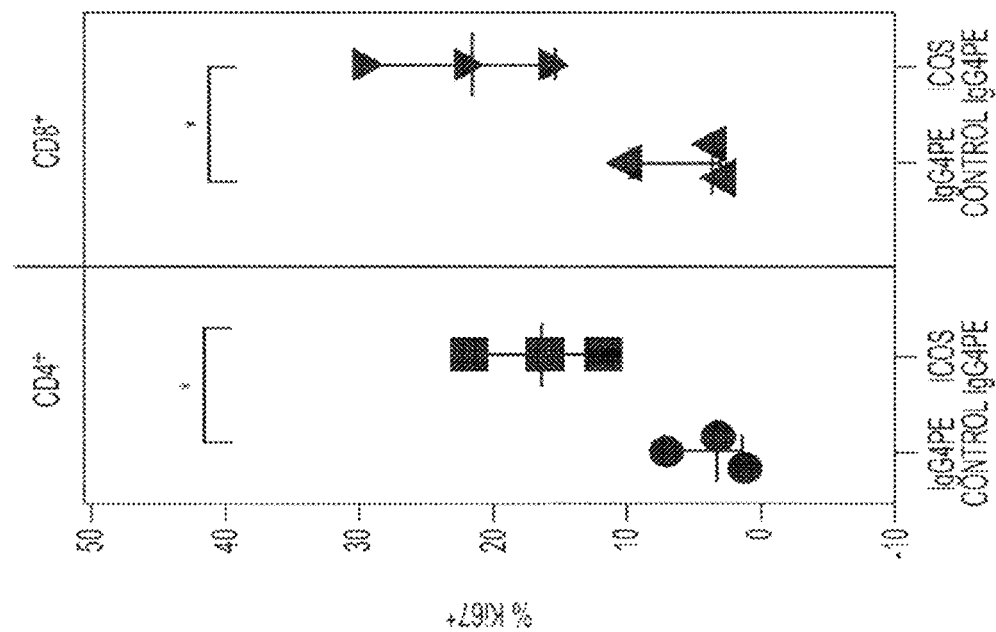
Figure 28C:
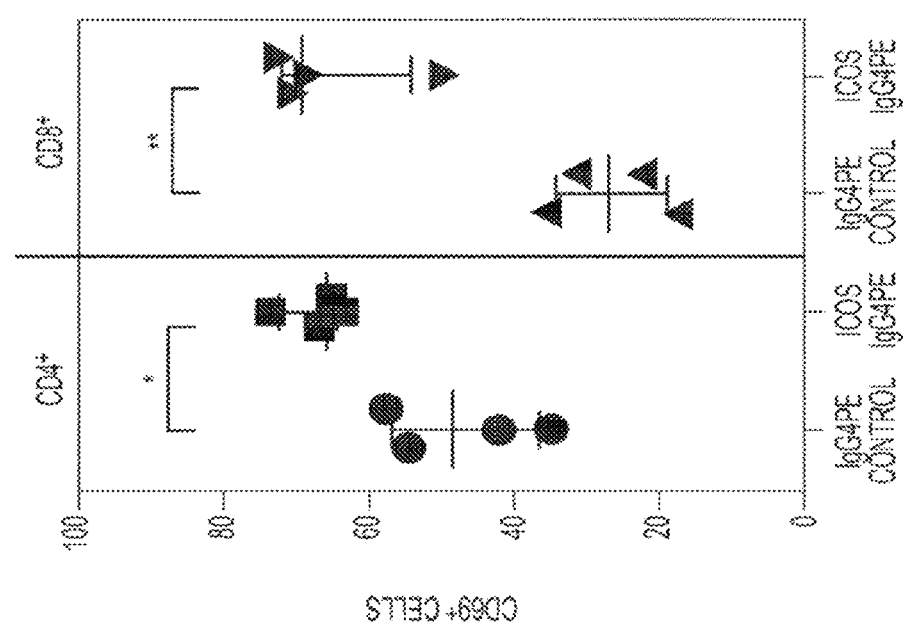
Figure 28F:
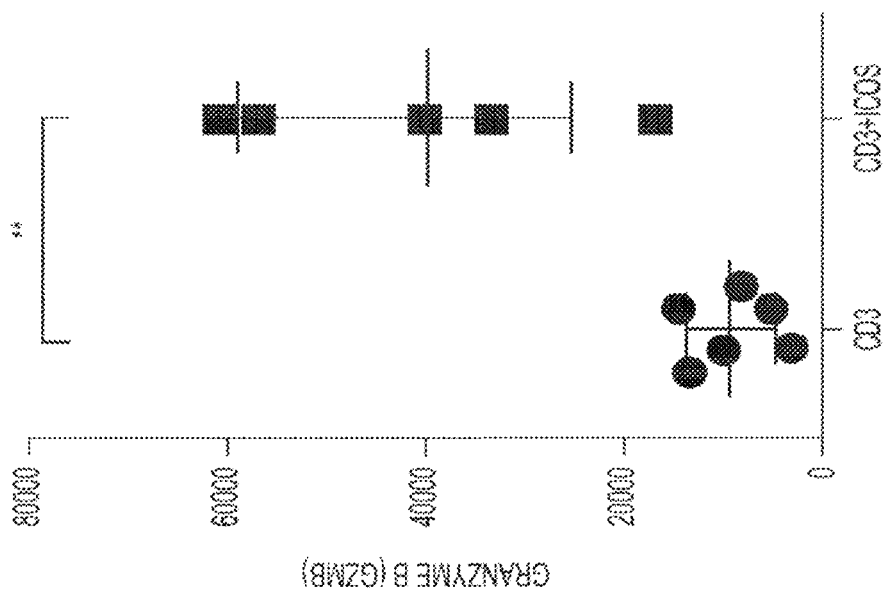
Figure 28E:
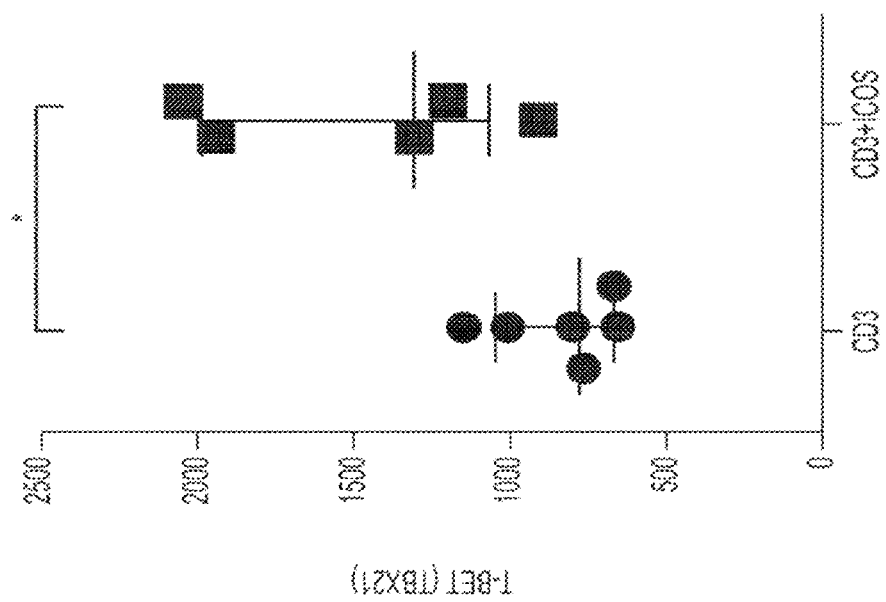
Figure 28G:
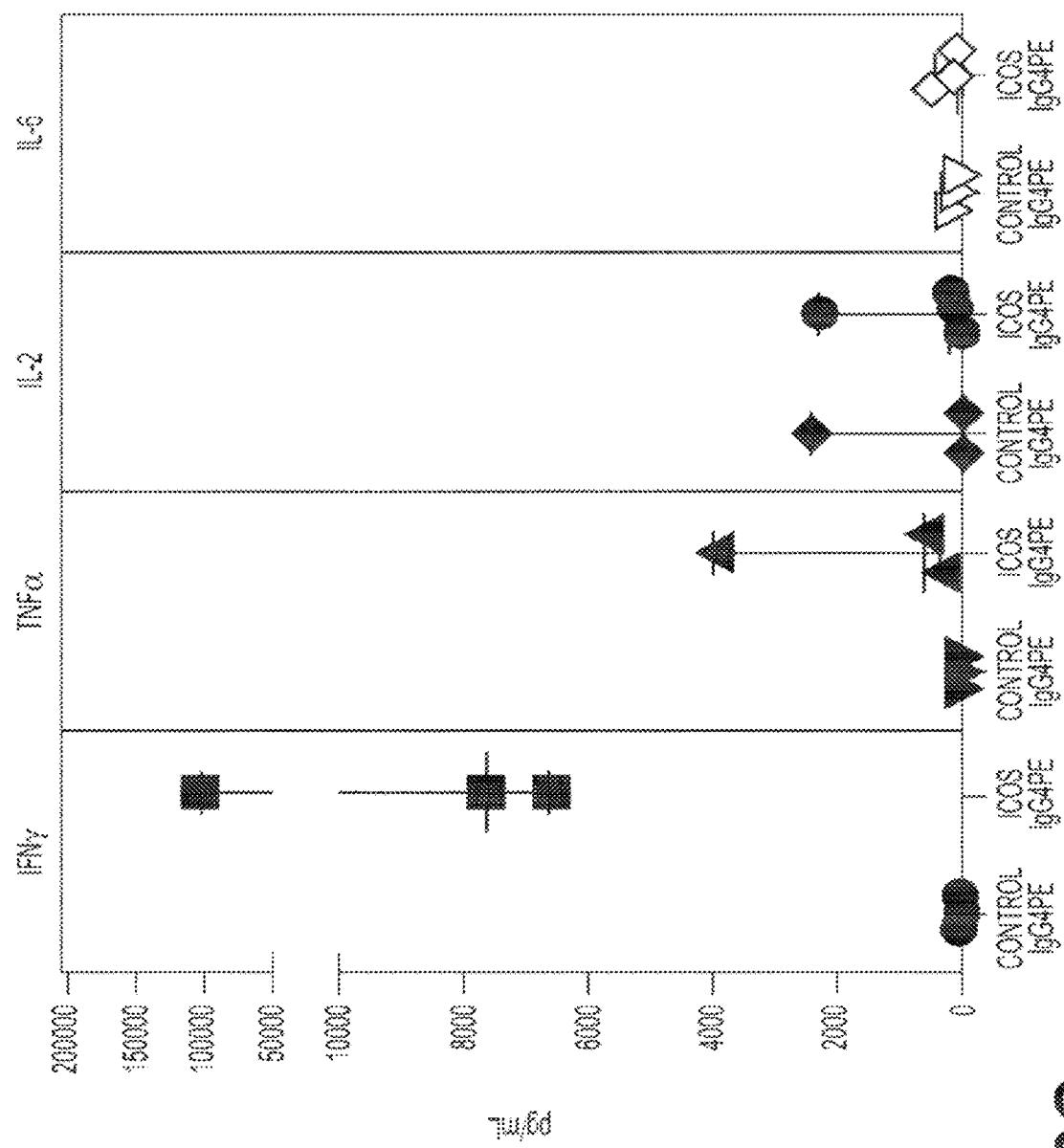
Figure 28H:
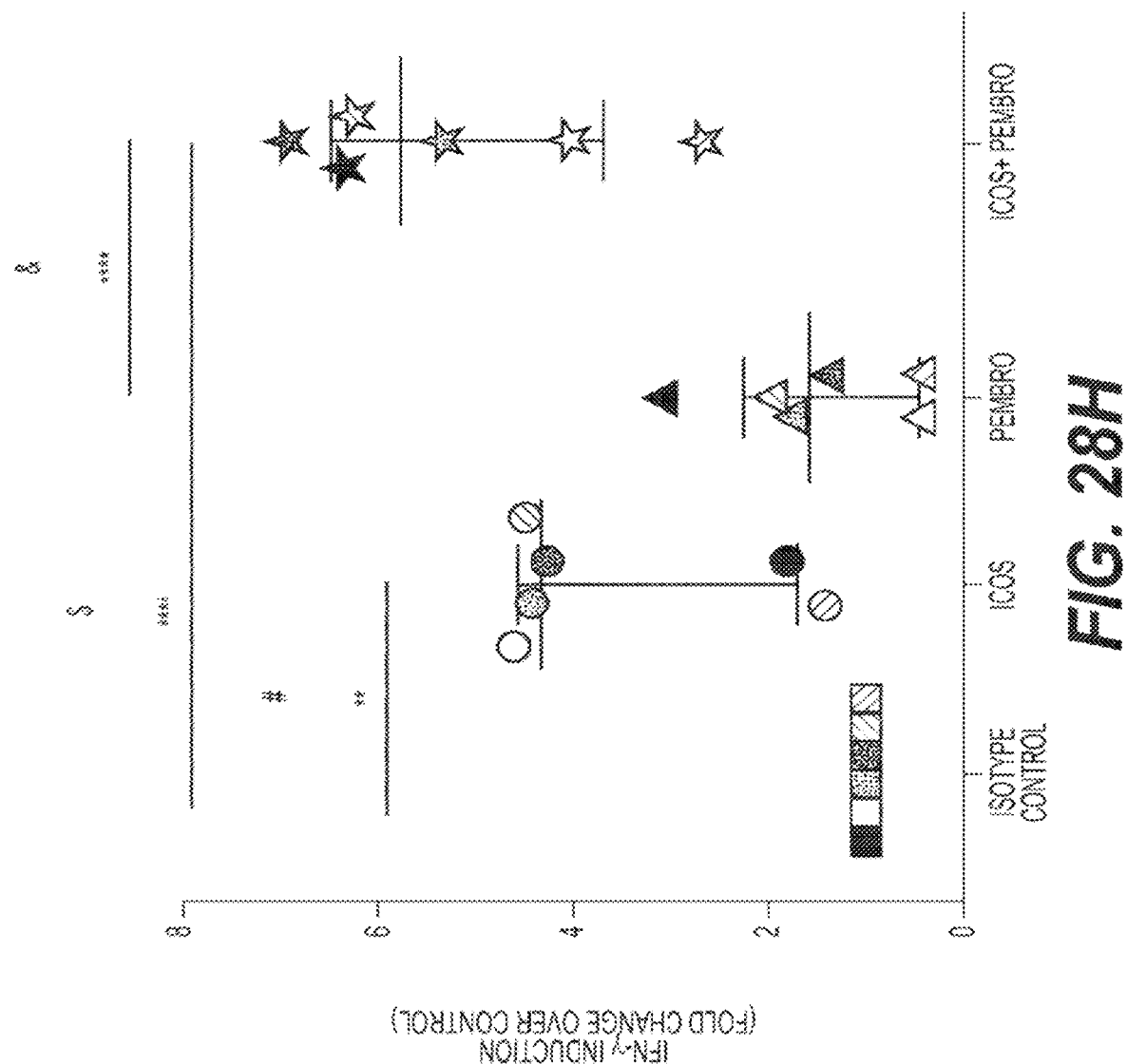

H2L5 Induces Potent Effector T Cell Activation and Function in a TCR-Dependent Manner The ability of H2L5 to co-stimulate T cells was further evaluated in assays wherein H2L5 was administered either alone or in combination with an anti-CD3 antibody in primary human PBMC. Three different incubation conditions were evaluated: 1) overnight culture of PBMC (naïve) followed by incubation of H2L5 for 24 hours; 2) overnight culture of PBMC in the presence of immobilized anti-CD3 (0.3 µg/mL) to stimulate signaling through the TCR followed by incubation with H2L5 for 24 hours, and; 3) overnight culture of PBMC in the presence of immobilized anti-CD3 (0.3 µg/mL) to stimulate signaling through the TCR followed by incubation with H2L5 and anti-CD3 for 24 hours. As a positive control, an agonist CD28 mAb was added to each condition. Under these assay conditions, H2L5 antibody was only able to induce IFN-γ when PBMC were first activated then incubated with both H2L5 and anti-CD3 (assay system 3) (FIG. 28A). These results indicate that H2L5 is not a super-agonist and co-stimulation through the TCR is required for productive H2L5 agonist function. To determine the full effect of the H2L5 agonist function, an additional 4 healthy donor PBMC samples were tested to determine the ability of H2L5 to induce T cell activation, proliferation and cytokine production. The functional effects of H2L5 were evaluated with concurrent TCR engagement via anti-human CD3. Cytokine analysis from the cell culture supernatants showed that H2L5 antibody induced $T_{H1}$, $T_{H2}$ and $T_{H17}$ cytokines IFN-γ, TNF-α, IL-17a, IL-10, IL-6 and to a lesser extent IL-2, IL-5 and IL-13 (FIG. 28B and FIG. 41). H2L5 also significantly increased CD4+ and CD8+ T cell activation (FIG. 28C) as well as proliferation (FIG. 28D). In isolated human CD3+ T cells, treatment with H2L5 also led to significant increase in the expression of the $T_{H1}$ transcription factor TBX21 (T-Bet) (FIG. 28E) as well as GZMB (FIG. 28F). PBMC were also isolated from patients with cancers including non-small cell lung carcinoma (NSCLC), head and neck and melanoma and treated with H2L5 antibody. H2L5 induced significant IFN-γ production in all but one cancer PBMC sample tested, whereas more modest increases in IL-2, TNF-α and IL-6 were observed in a proportion of the donors tested (FIG. 28G). H2L5 antibody was further tested alone or in combination with Pembrolizumab in a modified allogeneic human MLR assay where combination treatment resulted in increased IFNγ levels as compared to either agent alone, in ⅔ of the donor pairs tested. Additionally, primary resected tumors from 6 patients with NSCLC were dissociated and expanded in IL-2 supplemented RPMI media. The expanded TIL were then treated with anti-CD3 and H2L5 antibody alone or in combination with Pembrolizumab. While treatment with H2L5 alone resulted in a significant increase in IFN-γ in 4/6 of the NSCLC tumor samples tested, the combination of H2L5 and Pembrolizumab resulted in a significant increase in IFN-γ as compared to Pembrolizumab alone and an increase in ⅚ samples as compared to H2L5 treatment alone (FIG. 28H).

Figure 29A:
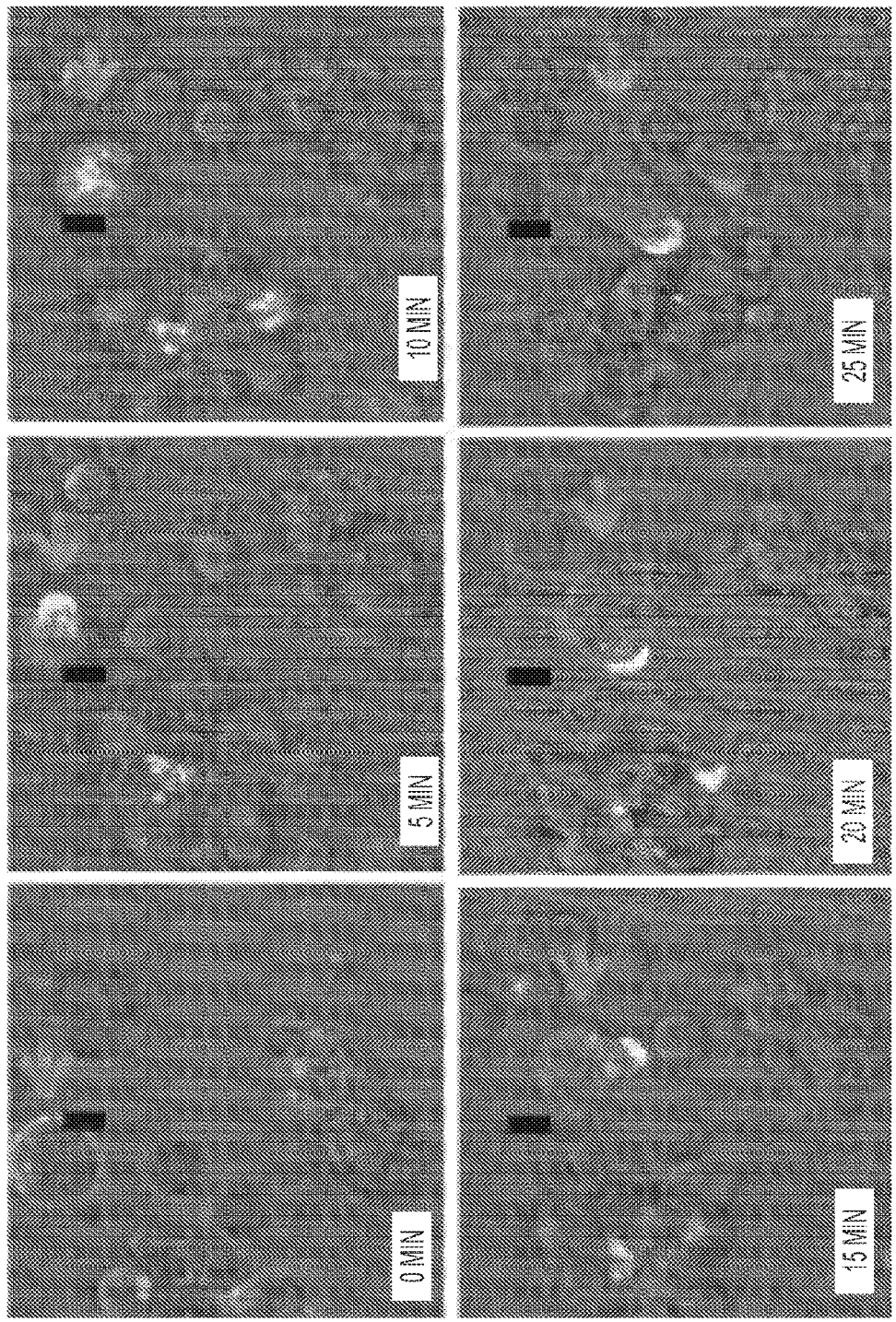
Figure 29B:
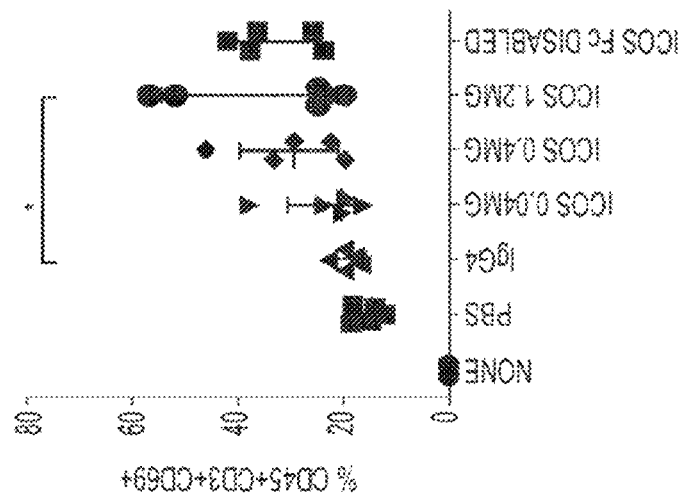
Figure 29C:
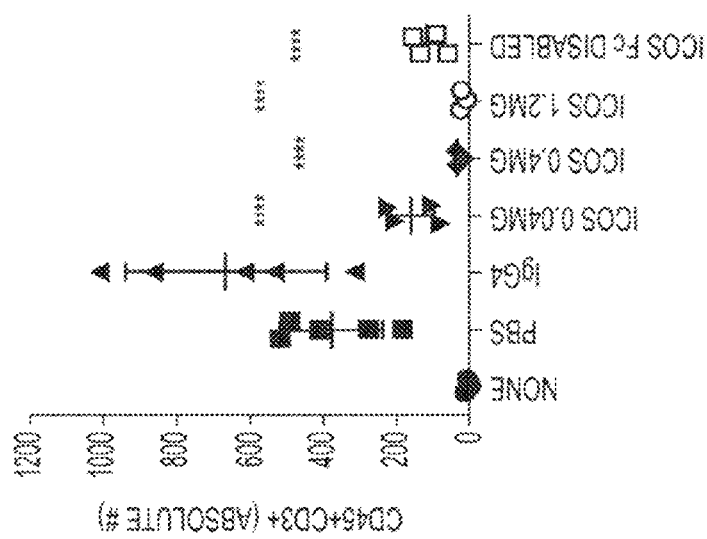
Figure 29D:
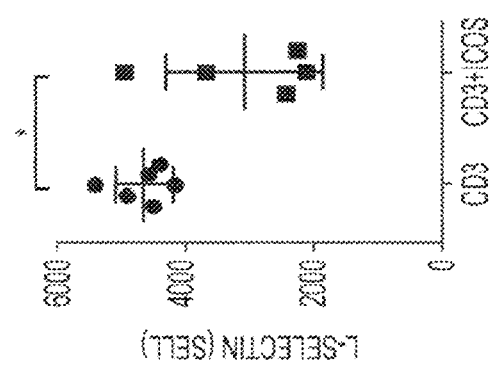
Figure 29G:
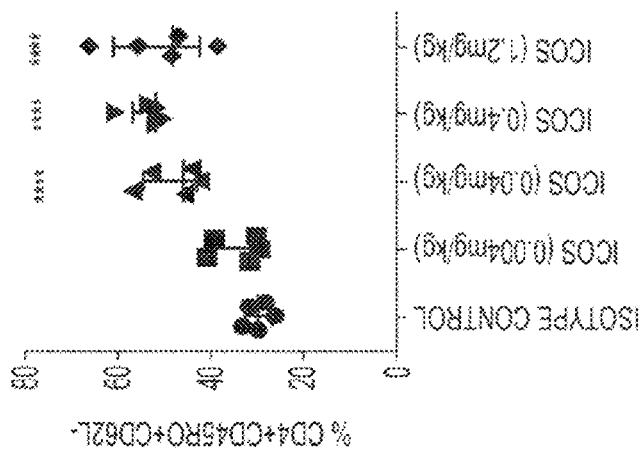
Figure 29F:
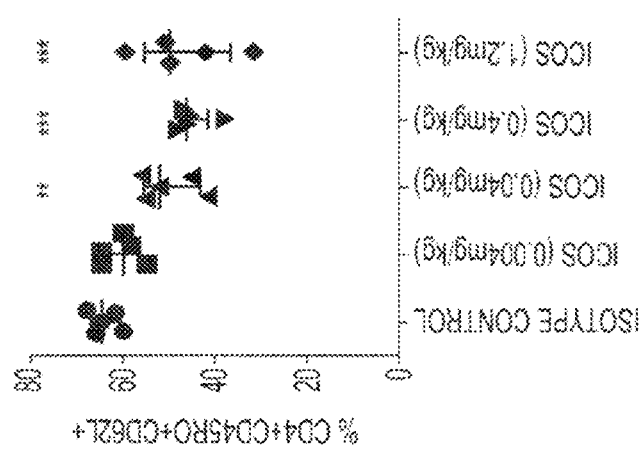
Figure 29E:
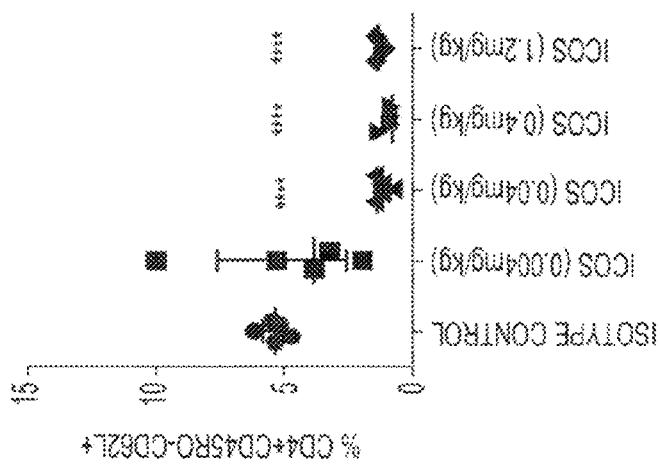
Figure 29J:
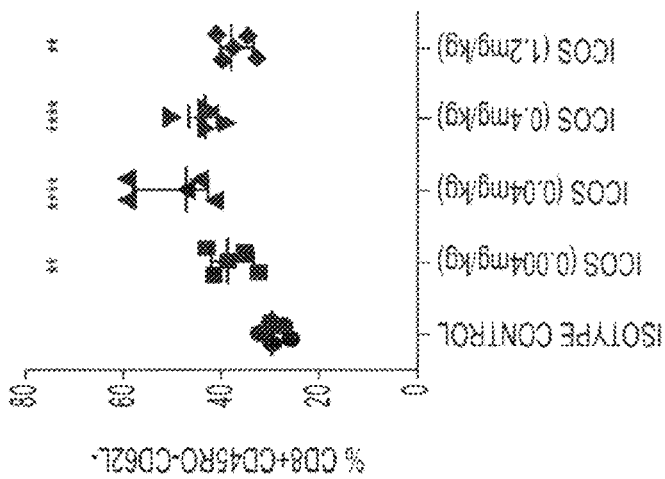
Figure 29I:
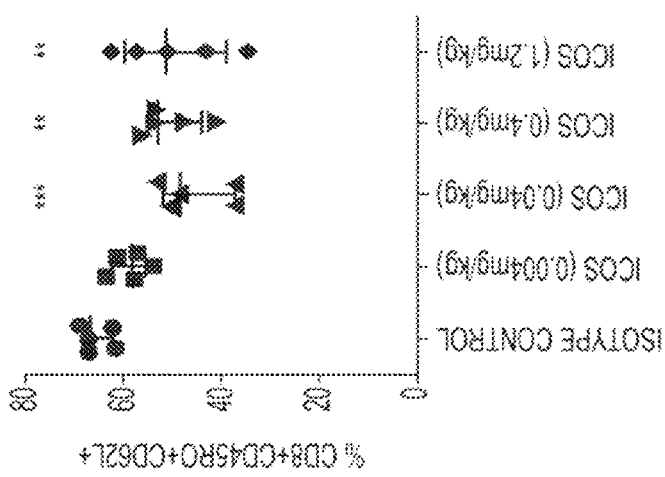
Figure 29H:
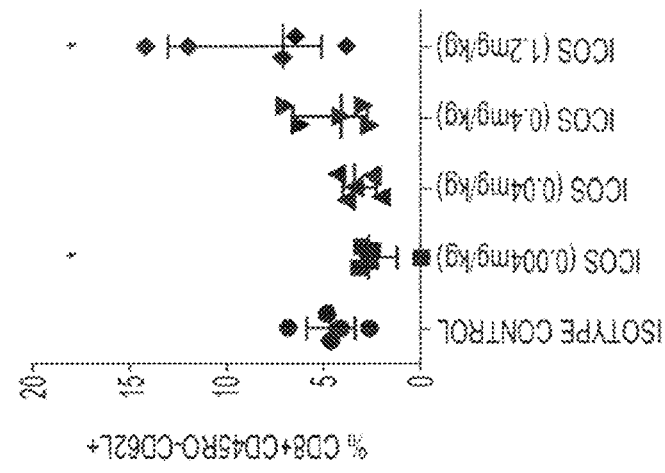

H2L5 Induces T Cell Mobilization and Effector Memory T Cell Migration to Peripheral Tissue H2L5 mAb was fluorescently labelled to image the kinetics of H2L5 cell localization and cell mobilization in a time-course following binding to primary human CD3+ T cells. Strikingly, it was found that the H2L5 mAb:ICOS receptor complex rapidly polarized following binding. The caps containing H2L5 mAb:ICOS receptor were crescent shaped foci resembling an immune synapse on the surface of T cells. In instances where T cells were in cell:cell contact, H2L5 accumulated at the point of contact (FIG. 36). Additional studies using co-cultures of human dendritic and T cells demonstrated that H2L5 mAb:ICOS complexes were rapidly co-localized to the polarized caps of activated T cells as well as the subsequent immune synapses formed upon T cell binding to dendritic cells (FIG. 29A). H2L5 activated cells rapidly polarized and mobilized towards neighbouring dendritic cells (FIG. 29A). These results indicate that ICOS induces human T cell mobilization and is co-located at the immune synapse following T cell activation. A significant decrease in SELL (L-Selectin) expression was observed on human T cells upon H2L5 treatment, similar to our finding in murine T cells in response to 7E.17G9 treatment (FIG. 29B). H2L5 was also evaluated in a human PBMC engrafted NSG mouse model. This model induces a Graft-versus-Host Disease response and has been used to study effector and memory T cell activity[22]. In the blood of H2L5 treated mice, the number of human T cells decreased in a dose-dependent manner (FIG. 29C), while a corresponding increase in T cell activation was observed (FIG. 29D). The Fc-disabled version of the H2L5 antibody showed similar, albeit weaker, trends than H2L5 IgG4PE suggesting that the disappearance of cells was not due to antibody-induced cell depletion but was likely an effect of T cell redistribution out of the blood (FIG. 29C,D). Consistent with this hypothesis, H2L5 induced a dose-dependent decrease in naive (FIG. 29E) and $T_{CM}$ CD4+ cells (FIG. 29F) and an increase in $T_{EM}$ cells in the spleen (FIG. 29G) of mice with human PBMC. Similar effects were also observed with CD8+ T cells (FIG. 29I,J) in addition to an increase in CD8+CD45RO−CD62L+ cells, potentially indicating terminally differentiated effector cells in addition to naive cells (FIG. 29H). These findings show that the human ICOS mAb H2L5 induces similar $T_{EM}$ cell expansion and functional induction as was observed with the murine ICOS agonist mAb in the syngeneic tumor models.

Discussion

Here we describe the immunological activity and antitumor potential of an anti-ICOS agonist antibody. We show that ICOS activation with both murine and human-specific agonist antibodies induces significant activation and clonal expansion of both CD4+ and CD8+ effector memory T cells. These $T_{EM}$ cells have increased effector function through increased expression of $T_{H1}$ cytokines such as IFN-γ as well as increased production of cytotoxic factors such as Granzyme B. ICOS antibody-activated $T_{EM}$ cells displayed increased tissue-homing to tumors with significant accumulation and infiltration resulting in antitumor responses. Prior reports using ICOS$^{−/−}$ and ICOS-L$^{−/−}$ mice as well as blocking antibodies to ICOS-L have demonstrated the importance of ICOS for the expansion, survival and function of both CD4+ and CD8+ $T_{EM}$ cells in mice[5, 23-25]. Additionally, patients with common variable immune deficiency (CVID) which is characterized by a homozygous loss of ICOS have been found to have fewer memory T cells, specifically those which are CD62L$^{low}$ [26]. These studies point to the critical importance of ICOS for this population of memory T cells, a finding that has been confirmed by our studies using agonist antibodies targeting ICOS.

Effector memory T cells are characterized in part by their propensity for homing to peripheral tissues and exclusion from lymph nodes through down regulation of CD62L[27]. Interestingly, ICOS has been previously implicated in the direct down regulation of CD62L in a mouse model of $T_{H2}$-mediated airway inflammation. In this model, ICOS$^{−/−}$ mice had significantly less CD4+ cell accumulation in the lungs and instead had increased lymph node homing in part through the inability to down regulate CD62L[28]. Functionally, $T_{EM}$ cells proliferate less and are skewed towards greater effector cytokine production, such as IL-4 and IFN-γ[27, 29]. Here we show that in both murine and human immune model systems, ICOS agonist antibody treatment induces down regulation of CD62L expression and increased homing to peripheral tissues. In both systems ICOS agonist treatment resulted in the preferential induction of IFN-γ which is associated with $T_{EM}$ cells as opposed to the limited induction of IL-2 which is more commonly associated with $T_{CM}$ cells[27]. Interestingly, ICOS agonist treatment also demonstrated a skewing towards a $T_{H1}$ phenotype with increased expression of the $T_{H1}$ chemokine receptors CCR5, CXCR3 and CXCR6[30] in the tumors of treated mice, while the chemokine gene CX3CR1 which is important for $T_{H2}$ recruitment and survival[31] was the most down regulated gene in ICOS treated tumors from both the EMT6 and CT26 tumor models. The clonality and degree of T cell infiltration in tumors has recently been shown to be an important positive predictor for immunotherapy outcomes in cancer[32]. Our findings demonstrate that an ICOS agonist antibody induces de novo clonal $T_{EM}$ cell expansion and tumor infiltration, implicating this approach as an attractive option for patients with cancer, both alone and in combination with other immunotherapy agents. A rational combination partner suggested by the results of this study is a PD-1/PDL-1 blocking antibody. ICOS agonist antibody treatment significantly induced PD-1 and PDL-1 expression in tumors of treated mice, indicating a possible resistance mechanism to ICOS agonist treatment. Consistent with this hypothesis, the combination of ICOS agonist and PD-1 blocking antibody in mice resulted in significantly increased TIL, T cell function and antitumor responses compared to either agent alone. Similar to the combinatorial activity observed in mice, the human ICOS agonist H2L5 in combination with the PD-1 blocking antibody Pembrolizumab showed increased cytokine production relative to either agent alone in ex vivo human immune cell assays.

Here we have provided the first comprehensive report of the immunological activity of an anti-human ICOS agonist antibody. We show that the optimal isotype for achieving agonist function against human ICOS is an engineered form of IgG4 that incorporates the mutations S228P and L235E (EU numbering) relative to the native human IgG4. These specific amino acid changes stabilize the native IgG4 hinge to de-risk heterogeneous exchange with native IgG4[33, 34] and decrease binding to activating FcγR and C1q thereby diminishing the cytotoxic potential of H2L5 that could result in depletion of ICOS-positive T cells through antibody-dependent or complement-dependent mechanisms, respectively. Moreover, the IgG4PE isoform retains functional binding to the inhibitory FcγR, FcγRIIb, important for modulating agonist activity against several stimulatory immune receptors[19, 21, 34-36], which may also be essential for optimal ICOS agonist activity and associated antitumor effects in humans. The novel ICOS agonist antibody described here offers a unique opportunity to provide therapeutic benefit specifically in patients with the greatest need, such as those with low baseline levels of immune infiltrate. These so-called "cold tumors" are not responsive to CTLA4 and PD-1/PDL-1 immune checkpoint antibodies alone where an ICOS agonist may boost the quantity and/or function of the infiltrate in these tumors.

REFERENCES

1. Hutloff, A., et al. ICOS is an inducible T-cell co-stimulator structurally and functionally related to CD28. *Nature* 397(6716), 263-266. (1999).
2. Fazilleau N. et al. Lymphoid reservoirs of antigen-specific memory T helper cells. *Nat Immunol.* 8(7):753-61. (2007).
3. Paulos, C. M. et al. The inducible costimulator (ICOS) is critical for the development of human Th17 cells. Sci Transl Med. 2(55), 55ra78. (2010).
4. Sharpe, A. H. and Freeman, G J. The B7-CD28 Superfamily. *Nat. Rev Immunol.* 2(2), 116-26. (2002)
5. Burmeister Y. et al. ICOS controls the pool size of effector-memory and regulatory T cells. *J Immunol.* 180 (2), 774-82. (2008).
6. Guedan, S. et al. ICOS-based chimeric antigen receptors program bipolar TH17/TH1 cells. *Blood* 124(7), 1070-80. (2014).
7. Bentebibel, S. E. et al. Induction of ICOS+CXCR3+ CXCR5+ TH cells correlates with antibody responses to influenza vaccination. *Sci Transl Med.* 5(176), 176ra32. (2013).
8. Ara, G. et al. Potent activity of soluble B7RP-1-Fc in therapy of murine tumors in syngeneic hosts. *Int. J Cancer.* 103(4); 501-7 (2003).
9. Fu, T., He, Q., Sharma, P. The ICOS/ICOS-L pathway is required for optimal antitumor responses mediated by anti-CTLA-4 therapy. *Cancer Res.* 71(16), 5445-54. (2011).
10. Fan X, et al. Engagement of the ICOS pathway markedly enhances efficacy of CTLA-4 blockade in cancer immunotherapy. *J Exp Med.* 211(4):715-25. (2014).
11. Liakou, C. I. et al. CTLA-4 blockade increases IFN-gamma producing CD4+ICOS[hi] cells to shift the ratio of effector to regulatory T cells in cancer patients. *Proc Natl Acad Sci USA.* 105(39), 14987-92. (2008).
12. Di Giacomo, A. M. et al. Long-term survival and immunological parameters in metastatic melanoma patients who respond to ipilimumab 10 mg/kg within an expanded access program. *Cancer Immunol Immunother.* 62(6); 1021-8. (2013).
13. Carthon, B. C. et al. Preoperative CTLA-4 blockade: Tolerability and immune monitoring in the setting of a presurgical clinical trial. *Clin Cancer Res.* 16(10), 2861-71. (2010).
14. Vonderheide, R. H. et al. Tremelimumab in combination with exemestane in patients with advanced breast cancer and treatment-associated modulation of inducible costimulator expression on patient T cells. *Clin Cancer Res.* 16(13), 3485-94. (2010).
15. Bromley S K1, Mempel T R, Luster A D. Orchestrating the orchestrators: chemokines in control of T cell traffic. *Nat Immunol.* (9):970-80. (2008).
16. Yao, S. et al. B7-H2 is a costimulatory ligand for CD28 in human. *Immunity* 34(5), 729-40. (2011).
17. Chattopadhyay, K. et al. Structural basis of inducible costimulator ligand costimulatory function: determination of the cell surface oligomeric state and functional mapping of the receptor binding site of the protein. *J Immunol.* 177(6), 3920-9. (2006).
18. Okamoto, N. et al. PI3-kinase and MAP-kinase signaling cascades in AILIM/ICOS- and CD28-costimulated T-cells have distinct functions between cell proliferation and IL-10 production. *Biochem Biophys Res Commun.* 310(3), 691-702. (2003).
19. Dahal, L. N. et al. FcγR requirements leading to successful immunotherapy. *Immunol Rev.* 268(1), 104-22. (2015).
20. Bartholomew, M. et al. Functional analysis of the effects of a fully humanized anti-CD4 antibody on resting and activated human T cells. *Immunology* 85(1), 41-8 (1995).
21. Bartholomaeus, P. et al. Cell contact-dependent priming and Fc interaction with CD32+ immune cells contribute to the TGN1412-triggered cytokine response. *J Immunol.* 192(5), 2091-8. (2014).
22. van Rijn R. S. et al. A new xenograft model for graft-versus-host disease by intravenous transfer of human peripheral blood mononuclear cells in RAG2$^{-/-}$ γc$^{-/-}$ double-mutant mice. *Blood* 102: 2522-2531. (2003)
23. Mahajan S. et al. The role of ICOS in the development of CD4 T cell help and the reactivation of memory T cells. *Eur J Immunol.* 7(7):1796-808. (2007).
24. Schenk A. D et al. Effector functions of donor-reactive CD8 memory T cells are dependent on ICOS induced during division in cardiac grafts. *Am J Transplant.* (1): 64-73. (2009).
25. Moore T. V. et al. *Protective effector memory CD4 T cells depend on ICOS for survival. PLoS One.* February 18; 6(2):e16529 (2011).

26. Takahashi N. et al. Impaired CD4 and CD8 effector function and decreased memory T cell populations in ICOS-deficient patients. *J Immunol.* 182(9):5515-27. (2009).
27. Sallusto F. et al. Two subsets of memory T lymphocytes with distinct homing potentials and effector functions. *Nature.* 401(6754):708-12. (1999).
28. Moore T. V. et al. Inducible costimulator controls migration of T cells to the lungs via down-regulation of CCR7 and CD62L. *Am J Respir Cell Mol Biol.* 45(4):843-50. (2011).
29. Hengel R. L. et al. Cutting edge: L-selectin (CD62L) expression distinguishes small resting memory CD4+ T cells that preferentially respond to recall antigen. *J Immunol.* 170(1):28-32. (2003)
30. Griffith J. W, Sokol C. L and Luster A. D. Chemokines and chemokine receptors: positioning cells for host defense and immunity. *Annu Rev Immunol.* 32:659-702. (2014).
31. Mionnet C. et al. CX3CR1 is required for airway inflammation by promoting T helper cell survival and maintenance in inflamed lung. *Nat Med.* 16(11):1305-12. (2010).
32. Tumeh P. C. et al. PD-1 blockade induces responses by inhibiting adaptive immune resistance. *Nature.* 515 (7528):568-71. (2014).
33. Aalberse, R. C and Schuurman, J. IgG4 Breaking the Rules. *Immunology* 105.1, 9-19. (2002).
34. Schuurman J. and Parren P. W. Editorial overview: Special section: New concepts in antibody therapeutics: What's in store for antibody therapy? *Curr Opin Immunol.* (2016)
35. White A. L. et al. Interaction with FcγRIIB is critical for the agonistic activity of anti-CD40 monoclonal antibody. *J Immunol.* 187(4):1754-63. (2011).
36. Hussain K. et al. Upregulation of FcγRIIb on monocytes is necessary to promote the superagonist activity of TGN1412. *Blood.* 125(1):102-10. (2015)
37. Dahan R. et al. Therapeutic Activity of Agonistic, Human Anti-CD40 Monoclonal Antibodies Requires Selective FcγR Engagement. *Cancer Cell.* 29(6):820-31. (2016)

The results described herein in Example 5 were obtained with the following materials and methods.

Humanized H2L5

Antibody

H2L5 is a humanized variant of the murine monoclonal antibody clone 422.2 obtained from the lab of Daniel Olive, Institut Paoli-Calmettes, INSERM (Marseille, France). The 422.2 murine monoclonal antibody was generated using standard hybridoma technology by immunizing 2 BALB/c mice 4 times (intraperitoneally) biweekly, with recombinant human ICOS-Fc. The recombinant protein used human IgG1 as the Fc tag and was produced at the Olive lab using COS7 cells.

Cell Lines and Primary Cell Cultures

Ba/F3-ICOS cells were obtained from the lab of Daniel Olive, Institut Paoli-Calmettes, INSERM (Marseille, France) and cultured in murine IL-3 (R&D Systems), Geneticin (ThermoFisher) and 10% FBS supplemented Dulbecco's Modified Eagle's Medium (DMEM). All patient material was obtained with the appropriate informed written consent for each donor and in accordance with the GSK human biological sample management (HBSM) policy and SOP. Whole blood in sodium heparin tubes (BD Biosciences) and surgically resected tumor tissues from cancer patients were obtained from Avaden Biosciences (Seattle) shipped overnight by post.

The human biological samples in this study were sourced ethically and their research use was in accord with the terms of the informed consents. Primary T cells or PBMC from healthy human donors were purified from whole blood collected in sodium heparin tubes at the GSK on-site blood donation units with appropriate consent and in accordance with the GSK HBSM policy. PBMC were isolated by density gradient centrifugation through Histopaque. Further isolation of T-cells was performed by negative isolation using Dynabeads™ Untouched™ Human T cell kit (Life Technologies) or RosetteSep human CD4 or CD8 T cell enrichment kits (StemCell) for binding and functional assays where indicated. Isolated T cells were pre-activated with plate-bound anti-CD3 (clone OKT3, eBioscience) and anti-CD28 (clone CD28.2, eBioscience) for 48-96 hrs to up regulate ICOS expression.

Mice, Tumor Challenge and Treatment

All studies were conducted in accordance with the GSK Policy on the Care, Welfare and Treatment of Laboratory Animals and were reviewed the Institutional Animal Care and Use Committee either at GSK or by the ethical review process at the institution where the work was performed. 6-8 week old female BALB/c mice (Harlan/Envigo) were utilized for in vivo studies in a fully accredited AAALAC facility.

$5.0 \times 10^4$ cells/mouse CT26 mouse colon carcinoma or $1 \times 10^5$ EMT6 mouse mammary carcinoma (ATCC) tumor cells were inoculated sub-cutaneously into the right flank. Palpable tumors were measured using a digital caliper with tumor volume calculated as $0.52 \times \text{Length} \times \text{Width}^2$. Mice (n=10/treatment group) were randomized when the tumors reached 100 mm$^3$ and received the mouse anti-ICOS (clone 7E.17G9) and/or mouse anti-PD1 (clone RMP1-14) antibodies or saline via intraperitoneal injection twice weekly starting on randomization day for a total of 6 doses. Tumor measurement of greater than 2,000 mm$^3$ for an individual mouse and/or development of open ulcerations resulted in mice being removed from study. In order to evaluate the expression of ICOS following treatment with anti-PD-1 monoclonal antibodies, mice bearing CT26 tumors (100 mm3), were dosed twice a week with isotype control (IgG2a 200 μg) or anti-PD-1 (RMP1-14, 200 μg) and harvested on day 3, 7 and 10 following the first dose. Mice collected on day 3, 7 and 10 received 1, 2 and 3 doses respectively.

Binding Studies

The binding affinity and kinetics of H2L5 IgG4PE binding to rabbit Fc-tagged recombinant human or cynomolgus ICOS (generated in-house) was determined using a Biacore™ T200 (GE Healthcare™). The ICOS binding data was fitted to a 1:1 kinetics model using the T200 data analysis software. Cell surface binding of H2L5IgG4PE to both freshly isolated unactivated and CD3/CD28 activated CD4+ and CD8+ T cells was determined via detection of anti-human IgG, kappa light chain FITC (Sigma) binding to H2L5 IgG4PE by flow cytometry.

Antibodies

The following anti-human antibodies were used for flow cytometry analysis, CD4 (RPA-T4, BD Biosciences), CD8 (RPA-T8, Biolegend), CD69 (FN50, Biolegend), OX40 (ACT-35, eBioscience), Ki67 (B56, BD Biosciences), ICOS (ISA3, eBioscience), p-AKT (S473, #4060 and T308,

13038), totalAkt (#9272), pGSK3-a (#5558), total GSK3-a (#12456), pS6 (5235/236, #2211 and 5240/244, #5364), total S6 (#2317), and pERK (#9101) (all from Cell Signaling Technology) for Western Blots. The following anti-mouse antibodies were used for flow cytometry analysis: CD3 (145-2C11, BD Biosciences), CD4 (RM4-5, BD Biosciences), CD8 (53-6.7, BD Biosciences), CD25 (PC61, BD Biosciences), CD44 (IM7, Biolegend), CD62L (MEL14, BD Biosciences), Foxp3 (Fjk-16s, eBioscience), ICOS (C398.4a, Biolegend), Ki67 (16A8, Biolegend). Apoptotis was measured using Annexin V kit with 7-AAD (Biolegend). For flow cytometry analysis from the human PMBC mouse model the following antibodies were used: CD45 (HI30, BD Biosciences), CD3 (UCHT1, Biolegend), CD4 (SK3, BD Biosciences), CD45RO (UCHL1, Biolegend), CD62L (SK11, BD Biosciences).

ADCC Assays

Whole PBMC or NK depleted PBMC were activated with plate-bound anti-CD3 and anti-CD28 antibodies. Cells were incubated with anti-ICOS antibodies (H2L5 IgG1, H2L5 IgG4PE and H2L5 Fc-disabled) or control antibodies at 10 µg/mL final concentration for 24 hours. Cells were stained with anti-CD8 and CD4 antibodies followed by incubation with NIR Live/Dead dye. Stained cells were analyzed by flow cytometry (FACSCanto, BD Biosciences) to determine the level of T-cell killing based on NIR Live/Dead cell dye staining.

In the FcγRIIIa engagement reporter bioassay (Promega), anti-CD3/CD28 pre-activated CD4$^+$ T cells were incubated with the anti-ICOS and control antibodies for 45 minutes prior to the addition of Jurkat-FcγRIIIA-NFAT-luciferase effector cells at an E:T cell ratio of 6:1. ONE-GLO luciferase reagent was added to each well after 6 hrs of treatment and luminescence intensity measured to determine engagement between the target CD4$^+$ T cells and the effector cells on an Envision plate reader (Perkin Elmer).

Functional Assays

H2L5 IgG4PE was tested in human PBMC assays either in a plate-bound format with concurrent CD3 stimulation using freshly isolated PBMC or in a soluble format in CD3/CD28 pre-stimulated PBMC as described earlier. For PBMC from cancer patients, an overnight rest step was included before treatment with plate bound anti-CD3 and ICOS agonist antibodies or its isotype controls. 10 µg/mL soluble Pembrolizumab was used in in vitro assays to study effects of combination. Cytokine concentrations in supernatants from these assays were measured using human special order multiplex meso-scale detection kits (Meso Scale Discovery). Human monocytes were isolated from whole blood of healthy human donors, using CD14 MicroBeads (Miltenyi Biotec) for the T cell-monocyte mixed culture assays. T cell and monocytes were donor matched. CD3/CD28 pre-stimulated T cells and monocytes were mixed at 2:1 ratio in AIM-V serum-free media and cultured together with anti-CD3 dynabeads (Life Technologies), 100 IU of recombinant human IL-2 and 100 ng/ml of M-CSF (Peprotech) prior to incubating with soluble H2L5 IgG4PE or other control antibodies at 37° C. for 4 days. 20 µg/mL human Fc block (B564220) (BD biosciences) or anti-CD32 mAb (MCA1075EL, Clone AT10) (AbD serotec) were used to test the role of FcγR cross linking.

For the mixed lymphocyte reaction (MLR) assays, monocytes (Lonza, Switzerland) were grown in GM-CSF and IL-4 (Pepro Tech) supplemented LGM-3 media (Lonza) for 9 days for differentiating into mDCs and TNFα (R&D Systems) for an additional day before use in the MLR assay. The mDC-T cell (1:10 ratio) mix was treated with 10 µg/mL soluble H2L5 IgG4PE Fc-disabled or the isotype control antibodies either in the presence of anti-CD3 beads at a 1:10 bead to cell ratio (Life Technologies) or CEFT peptide mix (0.02 µg/mL) (JPT Peptide Technologies) for 4 days before collecting the supernatants for cytokine analysis by MSD. Primary patient tumors were dissociated using GentleMACS (Miltenyi Biotec) tissue dissociator. TIL were expanded in IL-2 supplemented RPMI media (Baldan et al., 2015) before treating with anti-CD3 plus anti-ICOS agonist antibody.

In the cytokine release assay, overnight rested PMBC were incubated with immobilized H2L5 IgG4PE (10 µg/mL) in the absence of anti-CD3 costimulation for 24 hrs. In other assay conditions, PMBC were pre-stimulated overnight with immobilized anti-CD3 (0.3 µg/mL) and then incubated in a secondary stimulation for 24 hrs with immobilized H2L5 IgG4PE (up to 10 µg/mL) in the presence or absence of immobilized anti-CD3 (0.6 µg/mL). Cytokine concentrations in supernatants were measured by multiplex bead-based assays.

For PBMC assays testing different H2L5 isotypes, anonymized leukocyte cones from healthy donors were obtained from the National Blood Service at Southampton General Hospital, UK and used within 4 hours. Use of human samples was approved by local ethical committees in accordance with the Declaration of Helsinki. PMBC were isolated by density gradient centrifugation (Lymphoprep) and cultured in RPMI medium 1640 (Life Technologies) supplemented with glutamine (2 mM), sodium pyruvate (1 mM), penicillin, and streptomycin (100 IU/mL) at 37° C. in 5% $CO_2$.

Proliferation assays were performed as detailed previously[35]. Briefly, fresh PMBC were labelled with 1 µM carboxyfluorescein succinimidyl ester (CFSE) and cultured at high density ($1 \times 10^7$/mL) for 48 hours prior to antibody stimulations. For the PBMC stimulation, cells were transferred into round-bottomed 96-well plates at $1 \times 10^5$ per well and stimulated with 1 ug/ml OKT3 (plate-bound) and 5ug/ml (soluble) H2L5 mAbs. On day 6, cells were labelled with anti-CD8-e450 (SK-1, eBioscience) and anti-CD4-APC (RPA-T4, Insight Biotechnology), and proliferation assessed by CFSE dilution on a FACSCantoII flow cytometer (BD Biosciences). NK depletion was performed using CD56 micro beads (Miltenyi Biotec) according to the manufacturer's instructions post 48 hours high density culture.

Human T Cell Gene Expression

Peripheral blood was obtained from healthy volunteer donors (n=6) at the Upper Providence Blood Donation Unit in accord with the terms of the informed consents and GSK Policy. T cells were purified by Immunomagnetic negative selection from whole blood using RosetteSep™ Human T Cell Enrichment Cocktail (Stemcell Technologies, 15061) and were routinely more than 95% CD3 as determined by flow cytometry. The cells were re-suspended ($5 \times 10^6$ cells/ml) in AIM-V culture media (Gibco, 12055-091) and incubated in 96-well plates (Falcon, BD351172) that were sequentially pre-coated with 0.6 µg/ml of mouse anti-human CD3 mAb (eBioscience, 16-0037-85) and 10 µg/ml of anti-human ICOS or corresponding isotype control mAbs-mouse IgG2aκ (eBioscience, 16-4724-85) and IgG4PE. After 24 hours of incubation at 37° C. and 5% $CO_2$, cells were pelleted, suspended in RLT buffer (Qiagen), and stored at –80° C. for RNA isolation. Total RNA was extracted using the RNeasy Mini QIAcube Kit (Qiagen, 74116). RNA expression levels were determined by NanoString nCounter Analysis System. 50 ng of RNA was used in each reaction for gene signature using NanoString Human PanCancer Immune profiling CodeSet according to the manufacturer's instruction. Raw data was normalized using built-in positive controls and house-keeping genes (nCounter Expression Data Analysis Guide, NanoString). Heat map was generated using ArrayStudio (OmicSoft) and Graph for single gene expression was generated by GraphPad Prism (GraphPad Software).

Confocal Microscopy

CD3-stimulated T cells were treated with 3 µg/mL cold labeled antibody (H2L5 IgG4PE) on ice for 1 hr. Cells were then washed in cold buffer and held on ice. 200 µl of dendritic cells (at 1×10$^6$/ml) were plated in 8 well chamber coverslips and allowed to attach at RT for 1 hour. Coverslips were then placed on ice, the media removed and the H2L5 IgG4PE treated T cells (200 µl at 1×10$^6$) added and allowed to settle on ice for 15 minutes. Coverslips were then moved to the heated (37 deg C.) incubation chamber and imaged every 5 minutes with a 20× lens on a ZEISS LSM 780 confocal to create the time lapse images following antibody labeled ICOS receptor movement over time.

ICOS-L Competition Assay

MSD plates were incubated overnight at 4° C. with 10 µg/mL recombinant ICOS protein (R&D Systems) diluted in PBS. Plates were washed and blocked before adding isotype control or H2L5 IgG4PE in a7-point dose curve. After overnight incubation and washes, the plates were incubated with 1 µg/mL human ICOS ligand (B7-H2) (R&D Systems) followed by incubation with 10 µg/mL biotinylated anti-human ICOS ligand (B7-H2) (R&D Systems) antibody. Sulfo-tagged streptavidin at 10 µg/mL in Diluent 100 was used for detection of the biotinylated ligand. All incubations were at room temperature for one hour on a plate shaker unless otherwise noted. The plates were read immediately following MSD Read buffer addition on a MSD MESO Quick Plex SQ 120 and data analyzed on MSD workbench software (Meso Scale Discovery).

Human PBMC Mouse Model

Adult immunodeficient NSG (NOD/SCID/IL-2Rγnull) mice (Jackson Labs) were injected with human PBMC by intravenous injection via the tail vein. 1-3 days post human PBMC injection; mice were administered isotype control or anti-human ICOS antibodies at doses ranging from 0.004 mg/kg to 1.2 mg/kg by intraperitoneal injection twice weekly for 3 weeks. Spleens and whole blood were collected post-euthanization at 24 hrs post 2$^{nd}$ or 4$^{th}$-dose of antibodies. Splenocytes were isolated by mechanical dissociation followed by RBC lysis with LCK lysis buffer (Lonza) and antibody staining whereas whole blood was stained with the appropriate antibodies before RBC lysis with FACSlyse (BD Biosciences). All samples were evaluated by flow cytometry on FACScanto (BD) as described below.

Immunofluorescence Studies

Un-stimulated and CD3/CD28 stimulated T cells were Fc blocked and then treated with 6 µg/mL cold labeled antibody (anti-ICOS or IgG4PE isotype control) on ice for 1 hr. Cells were washed in cold buffer and transferred to 37° C. for various times (0, 5, 15, 30 minutes and 1 hr) to allow protein trafficking before fixing with freshly prepared 4% paraformaldehyde (Sigma). Samples post 1 hr and 2 hrs of the initial pulse at 37° C. were re-pulsed with Alexa Fluor 647 labeled anti-ICOS for 30 minutes at 37° C., washed and fixed in paraformaldehyde. The cells were transferred to Poly-L-lysine coated coverslips for 15 minutes and then mounted on slides in ProLong Gold with DAPI (Invitrogen). Analysis of the samples was performed using a ZEISS LSM510 Meta Confocal microscope with a 63× oil immersion lens.

Western Blotting

Ba/F3-ICOS cells were treated with H2L5 IgG4PE or an isotype control for up to 48 hrs. CD4+ T cells were pre-stimulated with CD3/CD28 Dynabeads® (ThermoFisher) at a cell-to-bead ratio of 1:20 for 48 hours, allowed to rest in the absence of stimulation for 24 hours, and then treated with isotype control antibody or H2L5 IgG4PE (10 µg/mL) in the presence of plate-bound anti-CD3 antibody. Cells were lysed with cell lysis buffer (Cell Signaling Technologies) containing protease and phosphatase inhibitors (Roche). 25-30 µg of protein was run on 4-12% Bis-Tris gels (Invitrogen) and transferred onto nitrocellulose membranes (Invitrogen). Membranes were blocked using LI-COR Odyssey Blocking Buffer and subsequently immunoblotted using the primary and secondary antibodies and scanned on a LI-COR Odyssey imaging system.

FACS Analysis

Non-specific binding on activated T-cells were blocked by incubation with human or mouse Fc block (Miltenyi Biotec) as appropriate prior to the incubation with detection antibodies to cell surface markers conjugated to different fluorophores on ice for 30 minutes. For intracellular staining, the cells were fixed and permeabilized using the Transcription Factor Buffer set (BD biosciences). After compensation, data were acquired on FACS Canto II or Fortessa (BD biosciences) and analyzed with FACSDiva (BD) or Flowjo (Treestar) software.

Statistical Analysis

One way ANOVA or Student's t-tests were used as specified in the figure legend. Data were analyzed with GraphPad Prism software (GraphPad) and p values of <0.05 were considered to be statistically significant. (* P value ≤0.05;  P value ≤0.01; * P value ≤0.005; ****P value <0.0001).

Example 6: ICOS Agonism Induces Potent Immune Activation and Anti-Tumor Response in Non-Clinical Models Inducible T cell costimulator (ICOS) is a costimulatory receptor that is upregulated on activated CD4 and CD8 T cells and plays an important role in T cell survival, differentiation, regulation of memory and regulatory T cell pools and humoral responses (Hutloff, A et al. (1999) ICOS is an inducible T-cell co-stimulator structurally and functionally related to CD28. Nature 397(6716), 263-266; Burmeister Y et al. (2008) ICOS controls the pool size of effector-memory and regulatory T cells. J Immunol. 180(2), 774-82). Pre-clinically, augmenting signaling through the ICOS pathway has been reported to induce anti-tumor activity and enhance responses to CTLA4 blockade (Ng Tang D et al. Increased frequency of ICOS+ CD4 T cells as a pharmacodynamic biomarker for anti-CTLA-4 therapy. Cancer Immunol Res 2013; 1:229-34)

Non-clinical data evaluating ICOS agonist antibody activity in human and mouse model systems using different species-specific antibodies is presented herein. H2L5 IgG4PE is a selective anti-human ICOS agonist antibody. In mice, an ICOS surrogate antibody was utilized in immune competent mouse tumor models to evaluate anti-tumor activity of an ICOS antibody alone and in combination with other immuno-modulatory antibodies.

FIG. 42A shows an example of gating strategy and ICOS expression on Foxp3+ and Foxp3-CD4 T cells populations in NSCLC tumor. ICOS median fluorescence intensity (MFI) was measured by flow cytometry from ICOS+ T cell populations in blood (FIG. 42B) and tumor infiltrating lymphocytes (TIL) (FIG. 42C) from human tumors evaluated by flow cytometry within 24-36 hrs of sampling from patients. Comparable expression on both Treg and non-Treg CD4+ TIL supports the rationale of using a non-depleting antibody to target ICOS for agonistic activity.

FIG. 43A shows that H2L5 hIgG4PE binds to naïve and CD3/CD28 activated CD4 and CD8 T cells. A Baf3 cell line stably over-expressing ICOS and treated with H2L5 hIgG4PE for 1, 6 and 24 hrs showed downstream signaling through AKT and GSK3/p phosphorylation (FIG. 43B).

FIGS. 44A-44B show that PBMC from healthy human donors (FIG. 44A) or cancer patients (FIG. 44B) treated with H2L5 hIgG4PE in the presence of anti-CD3 antibody for 24-72 hrs showed an increase in T cell activation by flow cytometry. FIG. 44C shows gene expression changes induced by H2L5 hIgG4PE in the presence of anti-CD3 antibody from healthy human T cells. Fold change with anti-CD3+anti-ICOS Ab compared to anti-CD3 alone showed a strong increase in activation and cytotoxicity markers while a modest increase in Foxp3 expression was observed.

FIGS. 45A-45B show that PBMC from cancer patients treated with H2L5 hIgG4PE in the presence of anti-CD3 antibody for 72 hrs showed an increase in secretion of pro-inflammatory cytokines in the media (FIG. 45A) and T cell proliferation as measured by Ki67+ T cells by flow cytometry (FIG. 45B).

As shown in FIGS. 46A-46B, mice implanted with EMT6 murine mammary carcinoma (FIG. 46A) and CT26 murine colon carcinoma (FIG. 46B) treated bi-weekly with 6 doses of 10 or 100 μg/mouse of anti-mouse ICOS antibody showed anti-tumor activity including complete tumor regressions in 10-50% of mice depending on dose and model.

Figure 47A:
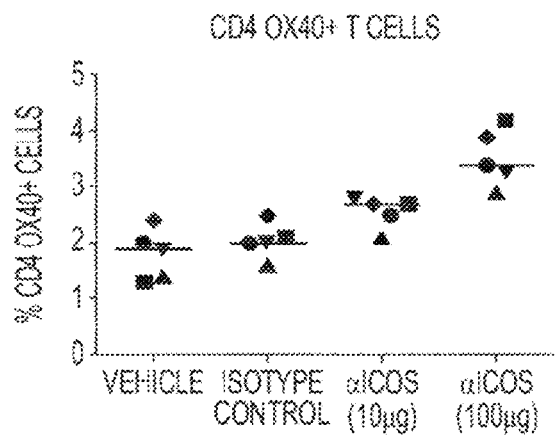
Figure 47B:
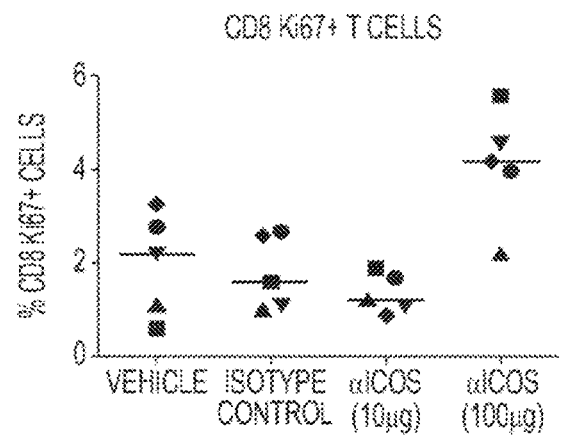
Figure 47C:
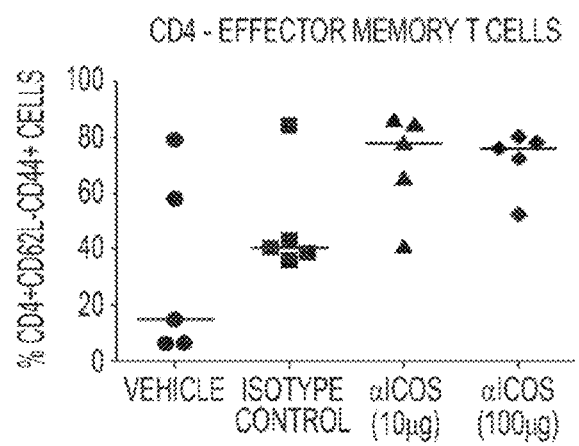
Figure 47D:
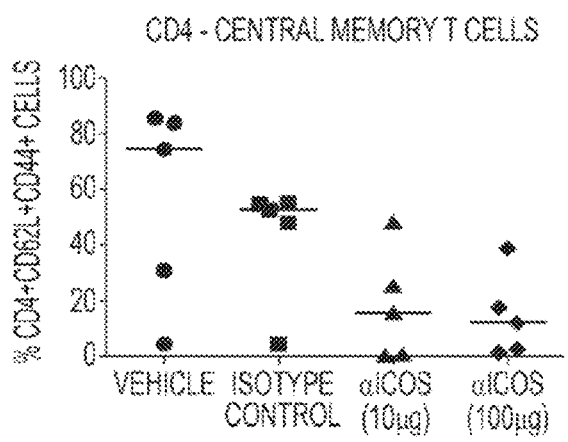

FIGS. 47A-47C show that spleens from Balb/c mice harboring EMT6 tumors treated with 3 doses of 10 or 100 μg/mouse of anti-mouse ICOS antibody had increased T cell activation (FIG. 47A), proliferation (FIG. 47B) and effector memory population and a decreased central memory population (FIG. 47C).

As shown in FIGS. 48A-48B, RNA from EMT6 tumors analyzed using TCR sequencing (FIG. 48A) and Nanostring (FIG. 48B) mouse pancancer immune panel showed greater TIL and a robust IFNγ gene signature.

As shown in FIGS. 49A-49B, significant IFNγ induction was observed with H2L5 hIgG4PE alone and in combination with pembrolizumab in TIL expanded from freshly dissociated NSCLC samples (FIG. 49A) and in Mixed Lymphocyte reaction (MLR) with CEFT peptide mix (FIG. 49B).

FIGS. 50A-50B show that a combination of ICOS and PD1 mouse surrogate antibodies showed synergistic effect on mouse survival in CT26 (FIG. 50A) and EMT6 (FIG. 50B) murine tumor models respectively.

FIGS. 51A-51B show gene expression analysis of CT26 mouse tumors treated with either anti-PD1 or anti-ICOS or the combination of the two antibodies, which show an increase in immune cells and related genes (FIG. 51A) and Granzyme B expression (FIG. 51B). FIG. 51C shows that serum from the same mice showed a significant increase in IFNγ levels in the combination group compared to the either monotherapy groups.

FIG. 52A shows ICOS, ICOS-L and PD-L1 abundance in tumors of various histologies based on RNA-Seq data from TCGA (The Cancer Genome Atlas). FIG. 52B shows IHC based analysis of tumor tissues providing correlation of ICOS with PD-L1, CD4, CD8 and Foxp3.

The invention claimed is:

1. A method for increasing T cell sensitivity to an ICOS agonist in a human having cancer or chronic infection, the method comprising administering to the human an anti-PD1 antibody and the ICOS agonist, wherein the anti-PD-1 antibody increases T cell sensitivity to the ICOS agonist in said human.

2. The method of claim 1, wherein the anti-PD-1 antibody is selected from pembrolizumab and nivolumab.

3. The method of claim 1, wherein the ICOS agonist is an agonist antibody directed to ICOS.

4. The method of claim 3, wherein the agonist antibody directed to ICOS comprises CDRH1 as set forth in SEQ ID NO:1; CDRH2 as set forth in SEQ ID NO:2; CDRH3 as set forth in SEQ ID NO:3; CDRL1 as set forth in SEQ ID NO:4; CDRL2 as set forth in SEQ ID NO:5 and CDRL3 as set forth in SEQ ID NO:6.

5. The method of claim 1, wherein said human has cancer.

6. The method of claim 5, wherein said cancer is selected from head and neck cancer, breast cancer, lung cancer, colon cancer, ovarian cancer, prostate cancer, gliomas, glioblastoma, astrocytomas, glioblastoma multiforme, Bannayan-Zonana syndrome, Cowden disease, Lhermitte-Duclos disease, inflammatory breast cancer, Wilm's tumor, Ewing's sarcoma, Rhabdomyosarcoma, ependymoma, medulloblastoma, kidney cancer, liver cancer, melanoma, pancreatic cancer, sarcoma, osteosarcoma, giant cell tumor of bone, thyroid cancer, Lymphoblastic T cell leukemia, Chronic myelogenous leukemia, Chronic lymphocytic leukemia, Hairy-cell leukemia, Acute lymphoblastic leukemia, Acute myelogenous leukemia (AML), Chronic neutrophilic leukemia, Acute lymphoblastic T cell leukemia, plasmacytoma, Immunoblastic large cell leukemia, Mantle cell leukemia, Multiple myeloma, Megakaryoblastic leukemia, Acute megakaryocytic leukemia, promyelocytic leukemia, Erythroleukemia, malignant lymphoma, Hodgkin's lymphoma, Non-Hodgkin's lymphoma, Lymphoblastic T cell lymphoma, Burkitt's lymphoma, follicular lymphoma, neuroblastoma, bladder cancer, urothelial cancer, vulval cancer, cervical cancer, endometrial cancer, renal cancer, mesothelioma, esophageal cancer, salivary gland cancer, hepatocellular cancer, gastric cancer, nasopharyngeal cancer, buccal cancer, cancer of the mouth, GIST (gastrointestinal stromal tumor), and testicular cancer.

7. The method of claim 5, wherein said cancer is selected from the group consisting of head and neck cancer, gastric cancer, melanoma, renal cell carcinoma (RCC), esophageal cancer, non-small cell lung carcinoma, prostate cancer, colorectal cancer, ovarian cancer and pancreatic cancer.

8. The method of claim 1, further comprising administering at least one additional anti-neoplastic agent and/or at least one immunostimulatory agent to said human.

9. The method of claim 1, further comprising administering an anti-CTLA4 antibody.

10. The method of claim 9, wherein the anti-CTLA4 antibody is ipilimumab.

* * * * *

SEQUENCE LISTING

```
<160> NUMBER OF SEQ ID NOS: 8

<210> SEQ ID NO 1
<211> LENGTH: 5
<212> TYPE: PRT
<213> ORGANISM: Mus musculus

<400> SEQUENCE: 1

Asp Tyr Ala Met His
1               5

<210> SEQ ID NO 2
<211> LENGTH: 17
<212> TYPE: PRT
<213> ORGANISM: Mus musculus

<400> SEQUENCE: 2

Leu Ile Ser Ile Tyr Ser Asp His Thr Asn Tyr Asn Gln Lys Phe Gln
1               5                   10                  15

Gly

<210> SEQ ID NO 3
<211> LENGTH: 12
<212> TYPE: PRT
<213> ORGANISM: Mus musculus

<400> SEQUENCE: 3

Asn Asn Tyr Gly Asn Tyr Gly Trp Tyr Phe Asp Val
1               5                   10
```

-continued

```
<210> SEQ ID NO 4
<211> LENGTH: 10
<212> TYPE: PRT
<213> ORGANISM: Mus musculus

<400> SEQUENCE: 4

Ser Ala Ser Ser Ser Val Ser Tyr Met His
1               5                   10

<210> SEQ ID NO 5
<211> LENGTH: 7
<212> TYPE: PRT
<213> ORGANISM: Mus musculus

<400> SEQUENCE: 5

Asp Thr Ser Lys Leu Ala Ser
1               5

<210> SEQ ID NO 6
<211> LENGTH: 9
<212> TYPE: PRT
<213> ORGANISM: Mus musculus

<400> SEQUENCE: 6

Phe Gln Gly Ser Gly Tyr Pro Tyr Thr
1               5

<210> SEQ ID NO 7
<211> LENGTH: 121
<212> TYPE: PRT
<213> ORGANISM: Artificial Sequence
<220> FEATURE:
<223> OTHER INFORMATION: Artificially Synthesized Sequence

<400> SEQUENCE: 7

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
                20                  25                  30

Ala Met His Trp Val Arg Gln Ala Pro Gly Gln Gly Leu Glu Trp Met
            35                  40                  45

Gly Leu Ile Ser Ile Tyr Ser Asp His Thr Asn Tyr Asn Gln Lys Phe
        50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Gly Arg Asn Asn Tyr Gly Asn Tyr Gly Trp Tyr Phe Asp Val Trp Gly
            100                 105                 110

Gln Gly Thr Thr Val Thr Val Ser Ser
        115                 120

<210> SEQ ID NO 8
<211> LENGTH: 106
<212> TYPE: PRT
<213> ORGANISM: Artificial Sequence
<220> FEATURE:
<223> OTHER INFORMATION: Artificially Synthesized Sequence

<400> SEQUENCE: 8

Glu Ile Val Leu Thr Gln Ser Pro Ala Thr Leu Ser Leu Ser Pro Gly
1               5                   10                  15
```

-continued

```
Glu Arg Ala Thr Leu Ser Cys Ser Ala Ser Ser Val Ser Tyr Met
            20              25              30

His Trp Tyr Gln Gln Lys Pro Gly Gln Ala Pro Arg Leu Leu Ile Tyr
        35              40              45

Asp Thr Ser Lys Leu Ala Ser Gly Ile Pro Ala Arg Phe Ser Gly Ser
    50              55              60

Gly Ser Gly Thr Asp Tyr Thr Leu Thr Ile Ser Ser Leu Glu Pro Glu
65              70              75              80

Asp Phe Ala Val Tyr Tyr Cys Phe Gln Gly Ser Gly Tyr Pro Tyr Thr
            85              90              95

Phe Gly Gln Gly Thr Lys Leu Glu Ile Lys
            100             105
```